(12) United States Patent
Vitalis et al.

(10) Patent No.: US 11,643,454 B2
(45) Date of Patent: *May 9, 2023

(54) P97 FUSION PROTEINS

(71) Applicant: Bioasis Technologies, Inc., Gulford, CT (US)

(72) Inventors: Timothy Z. Vitalis, Vancouver (CA); Reinhard Gabathuler, Montreal (CA)

(73) Assignee: BIOASIS TECHNOLOGIES, INC., Richmond (CA)

( * ) Notice: Subject to any disclaimer, the term of this patent is extended or adjusted under 35 U.S.C. 154(b) by 343 days.

This patent is subject to a terminal disclaimer.

(21) Appl. No.: 16/271,838

(22) Filed: Feb. 10, 2019

(65) Prior Publication Data
US 2019/0315837 A1 Oct. 17, 2019

Related U.S. Application Data

(63) Continuation of application No. 15/116,388, filed as application No. PCT/US2015/014230 on Feb. 3, 2015, now abandoned.

(60) Provisional application No. 61/935,253, filed on Feb. 3, 2014.

(51) Int. Cl.
| A61K 39/00 | (2006.01) |
| C07K 14/79 | (2006.01) |
| C07K 16/32 | (2006.01) |
| A61K 39/395 | (2006.01) |

(52) U.S. Cl.
CPC ........ *C07K 14/79* (2013.01); *A61K 39/39558* (2013.01); *C07K 16/32* (2013.01); *A61K 2039/505* (2013.01); *C07K 2317/515* (2013.01); *C07K 2317/732* (2013.01); *C07K 2319/10* (2013.01); *C07K 2319/74* (2013.01)

(58) Field of Classification Search
CPC ............................................. A61K 2039/505
See application file for complete search history.

(56) References Cited

U.S. PATENT DOCUMENTS

| 4,391,904 A | 7/1983 | Litman et al. |
| 4,394,448 A | 7/1983 | Szoka, Jr. et al. |
| 4,399,216 A | 8/1983 | Axel et al. |
| 4,683,195 A | 7/1987 | Mullis et al. |
| 4,683,202 A | 7/1987 | Mullis |
| 4,704,362 A | 11/1987 | Itakura et al. |
| 4,766,075 A | 8/1988 | Goeddel et al. |
| 4,784,950 A | 11/1988 | Hagen et al. |
| 4,800,159 A | 1/1989 | Mullis et al. |
| 4,801,542 A | 1/1989 | Murray et al. |
| 4,866,042 A | 9/1989 | Neuwelt |
| 4,935,349 A | 6/1990 | McKnight et al. |
| 4,946,778 A | 8/1990 | Ladner et al. |
| 5,091,513 A | 2/1992 | Huston et al. |
| 5,132,405 A | 7/1992 | Huston et al. |
| 5,186,941 A | 2/1993 | Callahan et al. |
| 5,672,683 A | 9/1997 | Friden et al. |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,798,239 A | 8/1998 | Wilson et al. |
| 5,844,093 A | 12/1998 | Kettleborough et al. |
| 5,932,211 A | 8/1999 | Wilson et al. |
| 5,962,012 A | 10/1999 | Lin et al. |
| 5,981,194 A | 11/1999 | Jefferies et al. |
| 6,015,557 A | 1/2000 | Tobinick et al. |
| 6,165,464 A | 12/2000 | Hudziak et al. |
| 6,177,077 B1 | 1/2001 | Tobinick |
| 6,261,595 B1 | 7/2001 | Stanley et al. |
| 6,387,371 B1 | 5/2002 | Hudziak et al. |
| 6,399,063 B1 | 6/2002 | Hudziak et al. |
| 6,419,934 B1 | 7/2002 | Tobinick |
| 6,419,944 B2 | 7/2002 | Tobinick |
| 6,455,494 B1 | 9/2002 | Jefferies et al. |
| 6,537,549 B2 | 3/2003 | Tobinick |
| 6,537,785 B1 | 3/2003 | Canfield |
| 6,596,541 B2 | 7/2003 | Murphy et al. |
| 6,765,087 B1 | 7/2004 | Casterman et al. |
| 6,838,254 B1 | 1/2005 | Hamers et al. |
| 6,982,089 B2 | 1/2006 | Tobinick |
| 7,132,511 B2 | 11/2006 | Carr et al. |

(Continued)

FOREIGN PATENT DOCUMENTS

| EP | 2399586 A1 * | 12/2011 | ..... C12Y 302/01076 |
| GB | 2188637 | 10/1987 | |

(Continued)

OTHER PUBLICATIONS

Yu et al. (PLoS One. 2012; 7 (3): e33340; pp. 1-15).*
Chang et al. (Structure. Jan. 7, 2014; 22 (1): 9-21).*
Chen et al. (Adv. Drug Deliv. Rev. Oct. 15, 2013; 65 (10): 1357-69; author manuscript; pp. 1-32).*
Boado et al. (Mol. Pharm. Feb. 1, 2010; 7 (1): 237-44).*
Oh et al. (Cancer Lett. Feb. 8, 2009; 274 (1): 33-9).*
Altenhofer, S. et al., "The NOX toolbox: validating the role of NADPH oxidases in physiology and disease," Cellular and Molecular Life Sciences, 69(14):2327-2343 (Jul. 2012). Epub May 31, 2012.
Aktas, Y. et al., "Development and brain delivery of chitosan-PEG nanoparticles functionalized with the monoclonal antibody OX26," Bioconjugate Chem,16(6):1503-1511 (2005).

(Continued)

*Primary Examiner* — Stephen L Rawlings
(74) *Attorney, Agent, or Firm* — Locke Lord LLP; Nicholas J. DiCeglie, Jr.

(57) ABSTRACT

Provided are p97 (melanotransferrin)-trastuzumab fusion proteins and related methods of use thereof, for instance, to facilitate delivery of trastuzumab across the blood-brain barrier (BBB) and/or improve tissue penetration of the antibody in CNS and peripheral tissues, and thereby treat and/or diagnose HER2-positive cancers, including those of the central nervous system (CNS).

3 Claims, 13 Drawing Sheets

Specification includes a Sequence Listing.

(56) References Cited

U.S. PATENT DOCUMENTS

| | | | |
|---|---|---|---|
| 7,138,371 B2 | 11/2006 | DeFrees et al. | |
| 7,179,617 B2 | 2/2007 | DeFrees et al. | |
| 7,214,658 B2 | 5/2007 | Tobinick | |
| 7,244,592 B2 | 7/2007 | Hoogenboom et al. | |
| 7,247,301 B2 | 7/2007 | van de Winkel et al. | |
| 7,462,697 B2 | 12/2008 | Couto et al. | |
| 7,595,378 B2 | 9/2009 | van de Winkel et al. | |
| 7,700,554 B2 | 4/2010 | Beliveau et al. | |
| 7,723,484 B2 | 5/2010 | Beidler et al. | |
| 7,939,072 B2 | 5/2011 | Yarden et al. | |
| 7,960,516 B2 | 6/2011 | Matheus et al. | |
| 8,546,319 B2 | 10/2013 | Starr et al. | |
| 8,722,019 B2 * | 5/2014 | Jefferies | C07K 16/18 424/9.34 |
| 9,150,846 B2 | 10/2015 | Hutchison et al. | |
| 9,161,992 B2 | 10/2015 | Jefferies et al. | |
| 9,364,567 B2 | 6/2016 | Vitalis et al. | |
| 9,850,472 B2 | 12/2017 | Hutchison et al. | |
| 9,932,565 B2 | 4/2018 | Vitalis et al. | |
| 9,993,530 B2 | 6/2018 | Vitalis et al. | |
| 10,058,610 B2 | 8/2018 | Jeffries et al. | |
| 2002/0059032 A1 * | 5/2002 | Camara Y. Ferrer | C12N 15/1089 702/20 |
| 2002/0119095 A1 | 8/2002 | Gabathuler et al. | |
| 2003/0072761 A1 | 4/2003 | LeBowitz | |
| 2003/0129186 A1 | 7/2003 | Beliveau et al. | |
| 2004/0055022 A1 | 3/2004 | Cheng et al. | |
| 2004/0137557 A1 | 7/2004 | DeFrees et al. | |
| 2005/0026823 A1 | 2/2005 | Zankel et al. | |
| 2005/0158296 A1 | 7/2005 | Starr et al. | |
| 2007/0167365 A1 | 7/2007 | Beliveau et al. | |
| 2008/0014188 A1 | 1/2008 | Zankel et al. | |
| 2008/0152645 A1 | 6/2008 | Pardridge et al. | |
| 2009/0226421 A1 | 9/2009 | Parren et al. | |
| 2010/0129359 A1 | 5/2010 | Tobinick | |
| 2010/0183581 A1 | 7/2010 | Beliveau et al. | |
| 2010/0297120 A1 | 11/2010 | Beliveau et al. | |
| 2010/0303797 A1 | 12/2010 | Starr et al. | |
| 2011/0093962 A1 | 4/2011 | Heidbrink et al. | |
| 2011/0142763 A1 | 6/2011 | Zankel et al. | |
| 2011/0318323 A1 | 12/2011 | Zhu et al. | |
| 2012/0003202 A1 | 1/2012 | Calias et al. | |
| 2012/0107302 A1 | 5/2012 | Berry et al. | |
| 2013/0058873 A1 * | 3/2013 | Jefferies | A61K 39/3955 424/9.4 |
| 2013/0108548 A1 | 5/2013 | Vlieghe et al. | |
| 2013/0183368 A1 | 7/2013 | Hutchison et al. | |
| 2013/0236442 A1 | 9/2013 | Lee et al. | |
| 2014/0105880 A1 | 4/2014 | Starr et al. | |
| 2014/0178350 A1 | 6/2014 | Vitalis et al. | |
| 2014/0322132 A1 | 10/2014 | Vitalis et al. | |
| 2015/0056218 A1 | 2/2015 | Jefferies et al. | |
| 2015/0093399 A1 | 4/2015 | Jefferies | |
| 2016/0053237 A1 | 2/2016 | Jefferies et al. | |
| 2016/0324937 A1 | 11/2016 | Vitalis et al. | |
| 2016/0347821 A1 | 12/2016 | Vitalis et al. | |
| 2017/0049897 A1 * | 2/2017 | Jefferies | C12N 15/1137 |
| 2017/0204386 A1 | 7/2017 | Vitalis et al. | |
| 2018/0021445 A1 | 1/2018 | Starr et al. | |
| 2019/0002852 A1 | 1/2019 | Vitalis et al. | |
| 2019/0008929 A1 | 1/2019 | Jefferies et al. | |
| 2019/0022244 A1 | 1/2019 | Vitalis et al. | |
| 2019/0192683 A1 * | 6/2019 | Jefferies | A61P 35/00 |

FOREIGN PATENT DOCUMENTS

| | | | |
|---|---|---|---|
| WO | WO 89/04663 | 6/1989 | |
| WO | WO 93/11161 | 6/1993 | |
| WO | WO 94/01463 | 1/1994 | |
| WO | WO 94/13804 | 6/1994 | |
| WO | WO 98/23646 | 6/1998 | |
| WO | WO 2000/050636 | 8/2000 | |
| WO | WO-0050636 A1 * | 8/2000 | C12N 15/1089 |
| WO | WO 2001/059459 | 8/2001 | |
| WO | WO 2001/083722 | 8/2001 | |
| WO | WO 2002/013843 | 2/2002 | |
| WO | WO 2002/013873 | 2/2002 | |
| WO | WO 2003/009815 | 2/2003 | |
| WO | WO 2003/057179 | 7/2003 | |
| WO | WO 2004/078215 | 9/2004 | |
| WO | WO 2005/034979 | 4/2005 | |
| WO | WO 2006/079372 | 8/2006 | |
| WO | WO 2008/022349 | 2/2008 | |
| WO | WO 2008/118013 | 10/2008 | |
| WO | WO 2009/019314 | 2/2009 | |
| WO | WO 2011/044542 | 4/2011 | |
| WO | WO 2011/131693 | 10/2011 | |
| WO | WO 2011/163649 | 12/2011 | |
| WO | WO 2013/006706 | 1/2013 | |
| WO | WO 2014/022738 | 2/2013 | |
| WO | WO 2014/022515 | 2/2014 | |
| WO | WO 2014/064258 | 5/2014 | |
| WO | WO 2015/031673 | 3/2015 | |
| WO | WO 2015/117121 | 8/2015 | |
| WO | WO 2015/126729 | 8/2015 | |
| WO | WO 2015/168521 | 11/2015 | |
| WO | WO 2017/123928 | 7/2017 | |

OTHER PUBLICATIONS

Asano, N. et al., "In vitro inhibition and intracellular enhancement of lysosomal α-galactosidase a activity in Fabry lymphoblasts by 1-deoxygalactonojirimycin and its derivatives," Eur. J. Biochem., 267(13):4179-4186 (2000).
Begley, D. J. et al., "Lysosomal storage diseases and the blood-brain barrier," Current Pharmaceutical Design, 14(16):1566-1580 (2008).
Bickel, U. et al., "Pharmacologic effects in vivo in brain by vector-mediated peptide drug delivery," Proc. Natl. Acad. Sci. USA, 90(7):2618-2622 (1993).
Bickel, U. et al., "In vivo demonstration of subcellular localization of anti-transferrin receptor monoclonal antibody-colloidal gold conjugate in brain capillary endothelium," Journal of Histochemistry and Cytochemistry 42(11):1493-1497 (1994).
Bickel, U. et al., "In vivo cleavability of a disulfide-based chimeric opioid peptide in rat brain," Bioconjugate Chem, 6(2):211-218 (1995).
Bickel, U. et al., "Delivery of peptides and proteins through the blood-brain barrier," Advanced Drug Delivery Review, 46(1-3):247-279 (2001).
Bielicki, J. et al., "Human liver iduronate-2-sulfatase purification characterization and catalytic properties," Biochemical Journal, 271(1):75-86 (Oct. 1990).
Bielicki, J. et al., "Recombinant human iduronate-2-sulphatase: correction of mucopolysaccharidosis-type II fibroblasts and characterization of the purified enzyme," Biochemical Journal. 289(Pt. 1):241-246 (1993).
Blattler, W. A. et al., "New heterobifunctional protein cross-linking reagent that forms an acid-labile link," Biochem., 24:1517-1524 (1985).
Boado, R. J. et al., "Cloning and expression in Pichia pastoris of a genetically engineered single chain antibody against the rat transferrin receptor," Journal of Drug Targeting, 8(6):403-412 (2000).
Braulke et al., "Sorting of lysosomal proteins," Biochimica et Biophysica Acta, 1793:605-614 (2009).
Broadwell, R. D. et al., "Transcytosis of protein through the mammalian cerebral epithelium and endothelium. III. Receptor-mediated transcytosis through the blood-brain barrier of blood-borne transferrin and antibody against the transferrin receptor." Experimental Neurology. 142(1):47-65.
Caldas et al. (Mol. Immunol. May 2003; 39 (15): 941-952).
Carter, P. et al., "Humanization of an anti-p185$^{HER2}$ antibody for human cancer therapy," Proc. Natl. Acad. Sci. USA, 89:4285-4289 (1992).
Casset et al. (Biochem. Biophys. Res. Commun. Jul. 18, 2003; 307 (1): 198-205).
Chien et al. (Proc. Natl. Acad. Sci. USA. Jul. 1989; 86 (14): 5532-5536).

(56) References Cited

OTHER PUBLICATIONS

Cerletti, A. et al., "Endocytosis and transcytosis of an immunoliposome-based brain drug delivery system," Journal of Drug Targeting, 8(6):435-446 (2000).

Chen, Q. et al., "Efficient Synthesis of Doxorubicin Melanotransferrin p97 Conjugates Through SMCC Linker," Synthetic Communications, 34(13):2407-2414 (2004).

Chen, C.-H. B. et al., "Aptamer-based endocytosis of a lysosomal enzyme," Proceedings of the National Academy of Sciences, 105(41):15908-15913 (2008).

Co, M. S. et al., "Humanized antibodies for antiviral therapy," Proc. Natl. Acad. Sci. USA, 88(7):2869-2873 (1991).

Co, M. S. et al. "Chimeric and humanized antibodies with specificity for the CD33 antigen," J. Immunol., 148(4):1149-1154 (1992).

Costantino, L. et al., "Is there a clinical future for polymeric nanoparticles as brain-targeting drug delivery agents?", Drug Discovery Today, 17(7-8):367-378 (Apr. 2012). Epub Nov. 7, 2011.

Daniele, A. et al., "Uptake of recombinant iduronate-2-sulfatase into neuronal and glial cells in vitro," Biochimica et Biophysica Acta., 1588(3):203-209 (2002).

Deguchi, Y. et al., "Retention of biologic activity of human epidermal growth factor following conjugation to a blood-brain barrier drug delivery vector via an extended poly (ethylene glycol) linker," Bioconjugate Chem.. 10(1):32-37 (1999).

Delabarre, B. et al., "Central Pore Residues Mediate the p97/VCP activity required for ERAD," Molecular Cell, 22(4):451-462 (2006).

Demeule, M. et al., "High transcytosis of melanotransferrin (P97) across the blood-brain barrier," Journal of Neurochemistry, 83:924-933 (2002).

Demeule, M. et al., "Regulation of plasminogen activation: A role for melantransferrin (p97) in cell migration," Blood, 102(5):1723-1731 (2003).

Di Natale, P. et al., "Iduronate sulfatase from human placenta," Biochimica et Biophysica Acta, 839(3):258-261 (May 1985).

De Pascalis et al. (J. Immunol. 2002; 169 (6): 3076-3084).

Dorr, R. T. et al., "In vitro rat myocyte cardiotoxicity model for antitumor antibiotics using adenosine triphosphate/protein ratios," Cancer Research, 48:5222-5227 (1988).

Friden, P. M., "Anti-transferrin receptor antibody and antibody-drug conjugates cross the blood-brain barrier," Proc. Natl. Acad. Sci. USA, 88(11):4771-4775 (1991).

Froissart, R. et al., "Processing of iduronate 2-sulphatase in human fibroblasts," Biochem. J., 309:425-430 (1995).

Gabathuler, Reinhard; "A natural solution to deliver medicine to brain"; Poster presented at the Drug Delivery & Formulation Summit; Apr. 2015; retrieved from http://www.ddfsummit.com/wp-content/uploads/2015/04/Reinhard-Gabathuler.pdf on Mar. 15, 2018.

Gabathuler, R. et al., "Incorporation of transcend (melanotransferrin or MTf) in a therapeutic antibody allows its transport across the blood-brain barrier for the treatment of brain disorders," Society for Neuroscience Abstract Viewer and Itinerary Planner, vol. 42 (2012), XP8173954, & 42nd Annual Meeting of the Society for Neuroscience, New Orleans, LA, USA, Oct. 13-17, 2012.

Gabathuler, R. et al., "BT2111, a new anticancer agent composed of trastuzumab and transcend a vector for brain delivery for the treatment of metastatic Her2+ breast cancer," [Abstract]. In: Proceedings of the AACR-NCI-EORTC International Conference: Molecular Targets and Cancer Therapeutics:, Oct. 19-23, 2013; Boston, MA. Philadelphia (PA): AACR; Mol. Cancer Ther. 2013: 12/11 Suppl) : Abstract nr A247.

Geuze, H. J. et al., "Possible Pathways for Lysosomal Enzyme Delivery," Journal of Cell Biology, 101:2253-2262 (1985).

Gosk, S. et al., "Targeting anti-transferrin receptor antibody (OX26) and OX26-conjugated liposomes to brain capillary endothelial cells using in situ perfusion," Journal of Cerebral Blood Flow & Metabolism. 24(11):1193-1204 (2004).

Grubb, J. H. et al., "Chemically modified β-glucuronidase crosses blood-brain barrier and clears neuronal storage in murine mucopolysaccharidosis VII," Proceedings of the National Academy of Sciences 105(7):2616-2621 (2008).

Giusti et al. (Proc. Natl. Acad. Sci. USA. May 1987; 84 (9): 2926-2930).

Holliger, P. et al., "'Diabodies': Small bivalent and bispecific antibody fragments," Proc. Natl. Acad. Sci., 90:6444-6448 (1993).

Holm et al. (Mol. Immunol. Feb. 2007; 44 (6): 1075-1084).

Hu, S. et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res., 56:3055-3061 (1996).

Huston, J. S. et al., "Protein engineering of antibody binding sites: recovery of specific activity in an anti-digoxin single-chain Fv analogue produced in *Escherichia coli*," Proc. Natl. Acad. Sci. USA, 85(16):5879-5883 (1988).

Huwyler, J. et al., "Receptor mediated delivery of daunomycin using immunoliposomes: pharmacokinetics and tissue distribution in the rat," Journal of Phamacology & Experimental Therapeutics. 282(3):1541-1546 (1997).

Inoue, T. et al., "Predictive in vitro cardiotoxicity and hepatotoxicity screening system using neonatal rat heart cells and rat hepatocytes," AATEX 14, Special Issue, Proc. 6th World Congress on Alternatives & Animal Use in the Life Sciences. pp. 457-462 (Aug. 21-25, 2007).

Jefferies, W. A. et al., "Transferrin receptor on endothelium of brain capillaries," Nature, 312:162-163 (1984).

Jefferies, W. A. et al., "Analysis of lymphopoletic stem cells with a monoclonal antibody to the rat transferrin receptor," Immunology, 54(2):333-341 (1985).

Jolly, R. D. et al., "Lysosomal storage diseases of animals: an essay in comparative pathology," Veterinary Pathology Online, 34:527-548 (1997).

Kakkis, E. et al., "Successful induction of immune tolerance to enzyme replacement therapy in canine mucopolysaccharidosis I," Proceedings of the National Academy of Sciences, 101(3):829-834 (2004).

Kakkis, P. E. P., "Overexpression of the human lysosomal enzyme alpha-L-iduronidase in CHO cells," Protein Expression and Purification, 5(3):225-232 (1994).

Kang, Y. S. et al., "Pharmacokinetics and organ clearance of a 3'-biotinylated, internaly [32P]-labeled phosphodiester oligodeoxynucleotide coupled to a neutral avidin/monoclonal antibody conjugate," Drug Metabolism and Disposition. 23(1):55-59 (1995).

Kang, Y. S. et al., "Stability of the disulfide bond in an avidin-biotin linked chimeric peptide during in vivo transcytosis through brain endothelial cells," Journal of Drug Targeting, 8(6):425-434 (2000).

Kang, Y. S. et al., "Use of neutral avidin improves pharmacokinetics and brain delivery of biotin bound to an avidin-monoclonal antibody conjugate," Journal of Pharmacology & Experimental Therapeutics. 269(1):344-350 (1994).

Karkan, D. et al., "A unique carrier for delivery of therapeutic compounds beyond the blood-brain barrier," PLOS One, 3(6):E2469. 1-E2469.14 (2008).

King, T. P. et al., "Preparation of protein conjugates via intermolecular hydrazone linkage," Biochem, 25(19):5774-5779 (1986).

Kurihara, A. et al., "Aβ1-40 Peptide radiopharmaceuticals for brain amyloid imaing: III-Inchelation, conjugation to poly(ethylene glycol)-biotin linkers, and autoradiography with Alzheimer's disease brain sections." Bioconjunate Chem. 11:380-386 (2000).

Mahapatro, A. et al., "Biodegradable nanoparticles are excellent vehicle for site directed in-vivo delivery of drugs and vaccines," Journal of Nanobiotechnology, 9(1):55 (2011).

Maccallum et al. (J. Mol. Biol. Oct. 11, 1996; 262 (5): 732-745).

Millat, G. et al., "IDS transfer from overexpressing cells to IDS-deficient cells," Experimental Cell Research, 230(2):362-367 (Feb. 1997).

Moos, T. et al., "Restricted transport of anti-transferrin receptor antibody (OX26) through the blood-brain barrier in the rat," Journal of Neurochemistry, 79(1):119-129 (2001).

Muraszoko, K. et al., "Pharmacokinetics and toxicology of immunotoxins administered into the subarachnoid space in nonhuman primates and rodents," Cancer Research, 53(16):3752-3757 (1993).

(56) References Cited

OTHER PUBLICATIONS

Muruganandam, A. et al., "Selection of phage-displayed llama single-domain antibodies that transmigrate across human blood-brain barrier endothelium," FASEB Journal, 16(2):240-242 (2001).
Pardridge, W. M., "Drug transport across the blood-brain barrier," Journal of Cerebral Blood Flow & Metabolism, 32(11):1959-1972 (2012).
Pardridge, W. M. et al., "Transport of human recombinant brain-derived neurotrophic factor (BDNF) through the rat blood-brain barrier in vivo using vector-mediated peptide drug delivery," Pharmaceutical Research. 11(50:738-746 (1994).
Parenti, G., "Treating lysosomal storage diseases with pharmacological chaperones: from concept to clinics," EMBO Mol. Med., 1:268-279 (2009).
Qian, Z. M. et al., "Targeted drug delivery via the transferrin receptor-mediated endocytosis pathway," Pharmacol. Rev., 54(4):561-587 (2002).
Queen, C. et al., "A humanized antibody that binds to the interleukin 2 receptor," Proc. Natl. Acad. Sci. USA, 86:10029-10033 (1988).
Richardson, D. R. et al., "The uptake of iron and transferrin by the human malignant melanoma cell," Biochimica et Biophysica Acta, 1053:1-12 (1990).
Rudikoff et al. (Proc. Natl. Acad. Sci. USA. 1982; 79: 1979-1983).
Robinson, L. J. et al., "NSF is required for transport from early to late endosomes," Journal of Cell Science, 110:2079-2087 (1997).
Rose, T. M. et al., "Primary Structure of the Human Melanoma-Associated Antigen P97 (Melanotransferrin) Deduced from the MRNA Sequence," Proc. Natl. Acad. Sci. USA, 83(5):1261-1265 (1986).
Saito, Y. et al., "Vector-mediated delivery of $^{125}$I-labeled beta-amyloid peptide Aβ1-40 through the blood-brain barrier and binding to Alzheimer's disease amytoid of the Aβ1-40/vector complex," Proc. Natl Acad Sci USA 92(22):10227-10231 (1995).
Sala, R. et al., "The Human Melanoma Associated Protein Melanotransferrin Promotes Endothelial Cell Migration and Angiogenesis in vivo," European Journal of Cell Biology, 81(11):599-607 (2002).
Sands, M. S., "Biodistribution, kinetics, and efficacy of highly phosphorylated and non-phosphorylated beta-glucuronidase in the murine model of mucopolysaccharidosis VII," Journal of Biological Chemistry. 276(46):43160-43165 (2001).
Sato, K. et al., "Reshaping a human antibody to inhibit the interleukin 6-dependent tumor cell growth," Cancer Res., 53:851-856 (1993).
Shao, W. et al., "Inhibition of human tumor xenograft growth in nude mice by a conjugate of monoclonal antibody LA22 to epidermal growth factor receptor with anti-tumor antibiotics mitomycin C." Biochemical and Biophysical Research Communications. 2006. 349:816-824.
Shi, N. et al., "Noninvasive gene targeting to the brain," Proc. Natl. Acad. Sci. USA, 97(13):7567-7572 (2000).
Skarlatos, S. et al., "Transport of [125]transferrin through the rat blood-brain barrier," Brain Research, 683(2):164-171 (1995).
Song, B. W. et al., "Enhanced neuroprotective effects of basic fibroblast growth factor in regional brain ischemia after conjugation to a blood-brain barrier delivery vector," Journal of Pharmacology and Experimental Therapeutics. 301(2):605-610 (2002).
Srinivasachar, K. et al., "New protein cross-linking reagents that are cleaved by mild acid," Biochem. 28:2501-2509 (1989).
Stefano, J. E. et al., "In vitro and in vivo evaluation of a non-carbohydrate targeting platform for lysosomal proteins," Journal of Controlled Release, 135:113-118 (2009).
Thom, G. et al., "A peptide derived from melanotransferrin delivers a protein-based interleukin I receptor antagonist across the BBB and ameliorates neuropathic pain in a preclinical model", Journal of Cerebral Blood Flow and Metabolism. 0(00). 1-15. (2018).
Thomas, F. C. et al., "Uptake of ANG1005, a novel paclitaxel derivative, through the blood-brain barrier into brain and experimental brain metastases of breast cancer," Pharmaceutical Research, 26(11):2486-2494 (2009).
Vajdos et al. (J. Mol. Biol. Jul. 5, 2002; 320 (2): 415-428).
Winkler et al. (J. Immunol. Oct. 15, 2000; 165 (8): 4505-4514).
Woodbury, R. G. et al., "Identification of a cell surface protein, p. 97, in human melanomas and certain other neoplasms," Proc. Natl. Acad. Sci. USA, 77(4):2183-2187 (1980).
Wu, D. et al., "Pharmacokinetics and brain uptake of biotinylated basic fibroblast growth factor conjugated to a blood-brain barrier drug delivery system," Journal of Drug Targeting, 10(3):239-245 (2002).
Wu, D. et al., "Central nervous system pharmacologic effect in conscious rate after intravenous injection of a biotinylated vasoactive intestinal peptide analog coupled to a blood-brain barrier drug delivery system." Journal of Pharmacology and Experimental Therapeutics. 279(1):77-83 (1996).
Wu et al. (J. Mol. Biol. Nov. 19, 1999; 294 (1): 151-162).
Wu, D. et al., "Pharmacokinetics and blood-brain transport of [3H]-biotinylated phosphorothioate oligodeoxynucleotide conjugated to a vector-mediated drug delivery system," Journal of Pharmacology and Experimental Therapeutics. 276(1):206-211 (1996).
Yang, J. et al., "Deletion of the GPI pre-anchor sequence in human p97—a general approach for generating the soluble form of GPI-linked proteins," Protein Expression and Purification, 34(1):28-48 (2004).
Yoshikawa, T. et al., "Biotin delivery to brain with a covalent conjugate of avidin and a monoclonal antibody to the transferrin receptor," Journal of Pharmacology and Experimental Therapeutics, 263(2):897-903 (1992).
Zhang, Y. et al., "Conjugation of brain-derived neurotrophic factor to a blood-brain barrier drug targeting system enables neuroprotection in regional brain ischemia following intravenous injection of the neurotrophin." Brain Research 889(1-2):49-56 (2001).

\* cited by examiner

SEQUENCE LISTING

<160> NUMBER OF SEQ ID NOS: 138

<210> SEQ ID NO 1
<211> LENGTH: 738
<212> TYPE: PRT
<213> ORGANISM: Homo sapiens

<400> SEQUENCE: 1

Met Arg Gly Pro Ser Gly Ala Leu Trp Leu Leu Ala Leu Arg Thr
1               5                   10                  15

Val Leu Gly Gly Met Glu Val Arg Trp Cys Ala Thr Ser Asp Pro Glu
                20                  25                  30

Gln His Lys Cys Gly Asn Met Ser Glu Ala Phe Arg Glu Ala Gly Ile
            35                  40                  45

Gln Pro Ser Leu Leu Cys Val Arg Gly Thr Ser Ala Asp His Cys Val
        50                  55                  60

Gln Leu Ile Ala Ala Gln Glu Ala Asp Ala Ile Thr Leu Asp Gly Gly
65                  70                  75                  80

Ala Ile Tyr Glu Ala Gly Lys Glu His Gly Leu Lys Pro Val Val Gly
                85                  90                  95

Glu Val Tyr Asp Gln Glu Val Gly Thr Ser Tyr Tyr Ala Val Ala Val
                100                 105                 110

Val Arg Arg Ser Ser His Val Thr Ile Asp Thr Leu Lys Gly Val Lys
            115                 120                 125

Ser Cys His Thr Gly Ile Asn Arg Thr Val Gly Trp Asn Val Pro Val
        130                 135                 140

Gly Tyr Leu Val Glu Ser Gly Arg Leu Ser Val Met Gly Cys Asp Val
145                 150                 155                 160

Leu Lys Ala Val Ser Asp Tyr Phe Gly Gly Ser Cys Val Pro Gly Ala
                165                 170                 175

Gly Glu Thr Ser Tyr Ser Glu Ser Leu Cys Arg Leu Cys Arg Gly Asp
                180                 185                 190

Ser Ser Gly Glu Gly Val Cys Asp Lys Ser Pro Leu Glu Arg Tyr Tyr
            195                 200                 205

Asp Tyr Ser Gly Ala Phe Arg Cys Leu Ala Glu Gly Ala Gly Asp Val
        210                 215                 220

Ala Phe Val Lys His Ser Thr Val Leu Glu Asn Thr Asp Gly Lys Thr
225                 230                 235                 240

Leu Pro Ser Trp Gly Gln Ala Leu Leu Ser Gln Asp Phe Glu Leu Leu
                245                 250                 255

Cys Arg Asp Gly Ser Arg Ala Asp Val Thr Glu Trp Arg Gln Cys His
                260                 265                 270

Leu Ala Arg Val Pro Ala His Ala Val Val Val Arg Ala Asp Thr Asp
            275                 280                 285

```
Gly Gly Leu Ile Phe Arg Leu Leu Asn Glu Gly Gln Arg Leu Phe Ser
290                 295                 300
His Glu Gly Ser Ser Phe Gln Met Phe Ser Ser Glu Ala Tyr Gly Gln
305                 310                 315                 320
Lys Asp Leu Leu Phe Lys Asp Ser Thr Ser Glu Leu Val Pro Ile Ala
                325                 330                 335
Thr Gln Thr Tyr Glu Ala Trp Leu Gly His Glu Tyr Leu His Ala Met
            340                 345                 350
Lys Gly Leu Leu Cys Asp Pro Asn Arg Leu Pro Pro Tyr Leu Arg Trp
        355                 360                 365
Cys Val Leu Ser Thr Pro Glu Ile Gln Lys Cys Gly Asp Met Ala Val
370                 375                 380
Ala Phe Arg Arg Gln Arg Leu Lys Pro Glu Ile Gln Cys Val Ser Ala
385                 390                 395                 400
Lys Ser Pro Gln His Cys Met Glu Arg Ile Gln Ala Glu Gln Val Asp
                405                 410                 415
Ala Val Thr Leu Ser Gly Glu Asp Ile Tyr Thr Ala Gly Lys Thr Tyr
            420                 425                 430
Gly Leu Val Pro Ala Ala Gly Glu His Tyr Ala Pro Glu Asp Ser Ser
        435                 440                 445
Asn Ser Tyr Tyr Val Val Ala Val Val Arg Arg Asp Ser Ser His Ala
450                 455                 460
Phe Thr Leu Asp Glu Leu Arg Gly Lys Arg Ser Cys His Ala Gly Phe
465                 470                 475                 480
Gly Ser Pro Ala Gly Trp Asp Val Pro Val Gly Ala Leu Ile Gln Arg
                485                 490                 495
Gly Phe Ile Arg Pro Lys Asp Cys Asp Val Leu Thr Ala Val Ser Glu
            500                 505                 510
Phe Phe Asn Ala Ser Cys Val Pro Val Asn Asn Pro Lys Asn Tyr Pro
        515                 520                 525
Ser Ser Leu Cys Ala Leu Cys Val Gly Asp Glu Gln Gly Arg Asn Lys
530                 535                 540
Cys Val Gly Asn Ser Gln Glu Arg Tyr Tyr Gly Tyr Arg Gly Ala Phe
545                 550                 555                 560
Arg Cys Leu Val Glu Asn Ala Gly Asp Val Ala Phe Val Arg His Thr
                565                 570                 575
Thr Val Phe Asp Asn Thr Asn Gly His Asn Ser Glu Pro Trp Ala Ala
            580                 585                 590
Glu Leu Arg Ser Glu Asp Tyr Glu Leu Leu Cys Pro Asn Gly Ala Arg
        595                 600                 605
Ala Glu Val Ser Gln Phe Ala Ala Cys Asn Leu Ala Gln Ile Pro Pro
610                 615                 620
His Ala Val Met Val Arg Pro Asp Thr Asn Ile Phe Thr Val Tyr Gly
625                 630                 635                 640
Leu Leu Asp Lys Ala Gln Asp Leu Phe Gly Asp His Asn Lys Asn
                645                 650                 655
Gly Phe Lys Met Phe Asp Ser Ser Asn Tyr His Gly Gln Asp Leu Leu
            660                 665                 670
Phe Lys Asp Ala Thr Val Arg Ala Val Pro Val Gly Glu Lys Thr Thr
        675                 680                 685
Tyr Arg Gly Trp Leu Gly Leu Asp Tyr Val Ala Ala Leu Glu Gly Met
690                 695                 700
```

```
Ser Ser Gln Gln Cys Ser Gly Ala Ala Ala Pro Ala Pro Gly Ala Pro
705                 710                 715                 720

Leu Leu Pro Leu Leu Pro Ala Leu Ala Ala Arg Leu Leu Pro Pro
            725                 730                 735

Ala Leu

<210> SEQ ID NO 2
<211> LENGTH: 692
<212> TYPE: PRT
<213> ORGANISM: Homo sapiens

<400> SEQUENCE: 2

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
                20                  25                  30

Leu Leu Cys Val Arg Gly Thr Ser Ala Asp His Cys Val Gln Leu Ile
            35                  40                  45

Ala Ala Gln Glu Ala Asp Ala Ile Thr Leu Asp Gly Gly Ala Ile Tyr
        50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335
```

```
Leu Cys Asp Pro Asn Arg Leu Pro Pro Tyr Leu Arg Trp Cys Val Leu
                340                 345                 350

Ser Thr Pro Glu Ile Gln Lys Cys Gly Asp Met Ala Val Ala Phe Arg
        355                 360                 365

Arg Gln Arg Leu Lys Pro Glu Ile Gln Cys Val Ser Ala Lys Ser Pro
    370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415

Pro Ala Ala Gly Glu His Tyr Ala Pro Glu Asp Ser Ser Asn Ser Tyr
                420                 425                 430

Tyr Val Val Ala Val Val Arg Arg Asp Ser Ser His Ala Phe Thr Leu
                435                 440                 445

Asp Glu Leu Arg Gly Lys Arg Ser Cys His Ala Gly Phe Gly Ser Pro
                450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
                500                 505                 510

Cys Ala Leu Cys Val Gly Asp Glu Gln Gly Arg Asn Lys Cys Val Gly
                515                 520                 525

Asn Ser Gln Glu Arg Tyr Tyr Gly Tyr Arg Gly Ala Phe Arg Cys Leu
                530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
                580                 585                 590

Ser Gln Phe Ala Ala Cys Asn Leu Ala Gln Ile Pro Pro His Ala Val
                595                 600                 605

Met Val Arg Pro Asp Thr Asn Ile Phe Thr Val Tyr Gly Leu Leu Asp
                610                 615                 620

Lys Ala Gln Asp Leu Phe Gly Asp Asp His Asn Lys Asn Gly Phe Lys
625                 630                 635                 640

Met Phe Asp Ser Ser Asn Tyr His Gly Gln Asp Leu Leu Phe Lys Asp
                645                 650                 655

Ala Thr Val Arg Ala Val Pro Val Gly Glu Lys Thr Thr Tyr Arg Gly
                660                 665                 670

Trp Leu Gly Leu Asp Tyr Val Ala Ala Leu Glu Gly Met Ser Ser Gln
                675                 680                 685

Gln Cys Ser Gly
        690

<210> SEQ ID NO 3
<211> LENGTH: 11
<212> TYPE: PRT
<213> ORGANISM: Homo sapiens

<400> SEQUENCE: 3

Trp Cys Ala Thr Ser Asp Pro Glu Gln His Lys
1               5                   10
```

```
<210> SEQ ID NO 4
<211> LENGTH: 11
<212> TYPE: PRT
<213> ORGANISM: Homo sapiens

<400> SEQUENCE: 4

Arg Ser Ser His Val Thr Ile Asp Thr Leu Lys
1               5                   10

<210> SEQ ID NO 5
<211> LENGTH: 13
<212> TYPE: PRT
<213> ORGANISM: Homo sapiens

<400> SEQUENCE: 5

Ser Ser His Val Thr Ile Asp Thr Leu Lys Gly Val Lys
1               5                   10

<210> SEQ ID NO 6
<211> LENGTH: 14
<212> TYPE: PRT
<213> ORGANISM: Homo sapiens

<400> SEQUENCE: 6

Leu Cys Arg Gly Asp Ser Ser Gly Glu Gly Val Cys Asp Lys
1               5                   10

<210> SEQ ID NO 7
<211> LENGTH: 16
<212> TYPE: PRT
<213> ORGANISM: Homo sapiens

<400> SEQUENCE: 7

Gly Asp Ser Ser Gly Glu Gly Val Cys Asp Lys Ser Pro Leu Glu Arg
1               5                   10                  15

<210> SEQ ID NO 8
<211> LENGTH: 9
<212> TYPE: PRT
<213> ORGANISM: Homo sapiens

<400> SEQUENCE: 8

Tyr Tyr Asp Tyr Ser Gly Ala Phe Arg
1               5

<210> SEQ ID NO 9
<211> LENGTH: 7
<212> TYPE: PRT
<213> ORGANISM: Homo sapiens

<400> SEQUENCE: 9

Ala Asp Val Thr Glu Trp Arg
1               5

<210> SEQ ID NO 10
<211> LENGTH: 9
<212> TYPE: PRT
<213> ORGANISM: Homo sapiens

<400> SEQUENCE: 10

Val Pro Ala His Ala Val Val Val Arg
1               5
```

```
<210> SEQ ID NO 11
<211> LENGTH: 10
<212> TYPE: PRT
<213> ORGANISM: Homo sapiens

<400> SEQUENCE: 11

Ala Asp Thr Asp Gly Gly Leu Ile Phe Arg
1               5                   10

<210> SEQ ID NO 12
<211> LENGTH: 9
<212> TYPE: PRT
<213> ORGANISM: Homo sapiens

<400> SEQUENCE: 12

Cys Gly Asp Met Ala Val Ala Phe Arg
1               5

<210> SEQ ID NO 13
<211> LENGTH: 11
<212> TYPE: PRT
<213> ORGANISM: Homo sapiens

<400> SEQUENCE: 13

Leu Lys Pro Glu Ile Gln Cys Val Ser Ala Lys
1               5                   10

<210> SEQ ID NO 14
<211> LENGTH: 12
<212> TYPE: PRT
<213> ORGANISM: Homo sapiens

<400> SEQUENCE: 14

Asp Ser Ser His Ala Phe Thr Leu Asp Glu Leu Arg
1               5                   10

<210> SEQ ID NO 15
<211> LENGTH: 13
<212> TYPE: PRT
<213> ORGANISM: Homo sapiens

<400> SEQUENCE: 15

Ser Glu Asp Tyr Glu Leu Leu Cys Pro Asn Gly Ala Arg
1               5                   10

<210> SEQ ID NO 16
<211> LENGTH: 15
<212> TYPE: PRT
<213> ORGANISM: Homo sapiens

<400> SEQUENCE: 16

Ala Gln Asp Leu Phe Gly Asp Asp His Asn Lys Asn Gly Phe Lys
1               5                   10                  15

<210> SEQ ID NO 17
<211> LENGTH: 40
<212> TYPE: PRT
<213> ORGANISM: Homo sapiens

<400> SEQUENCE: 17

Phe Ser Ser Glu Ala Tyr Gly Gln Lys Asp Leu Leu Phe Lys Asp Ser
1               5                   10                  15

Thr Ser Glu Leu Val Pro Ile Ala Thr Gln Thr Tyr Gly Ala Trp Leu
                20                  25                  30
```

Gly His Glu Tyr Leu His Ala Met
        35                  40

<210> SEQ ID NO 18
<211> LENGTH: 221
<212> TYPE: PRT
<213> ORGANISM: Homo sapiens

<400> SEQUENCE: 18

Glu Arg Ile Gln Ala Glu Gln Val Asp Ala Val Thr Leu Ser Gly Glu
1               5                   10                  15

Asp Ile Tyr Thr Ala Gly Lys Thr Tyr Gly Leu Val Pro Ala Ala Gly
            20                  25                  30

Glu His Tyr Ala Pro Glu Asp Ser Asn Ser Tyr Tyr Val Val Ala
        35                  40                  45

Val Val Arg Arg Asp Ser Ser His Ala Phe Thr Leu Asp Glu Leu Arg
50                  55                  60

Gly Lys Arg Ser Cys His Ala Gly Phe Gly Ser Pro Ala Gly Trp Asp
65                  70                  75                  80

Val Pro Val Gly Ala Leu Ile Gln Arg Gly Phe Ile Arg Pro Lys Asp
                85                  90                  95

Cys Asp Val Leu Thr Ala Val Ser Glu Phe Phe Asn Ala Ser Cys Val
            100                 105                 110

Pro Val Asn Asn Pro Lys Asn Tyr Pro Ser Ser Leu Cys Ala Leu Cys
        115                 120                 125

Val Gly Asp Glu Gln Gly Arg Asn Lys Cys Val Gly Asn Ser Gln Glu
130                 135                 140

Arg Tyr Tyr Gly Tyr Arg Gly Ala Phe Arg Cys Leu Val Glu Asn Ala
145                 150                 155                 160

Gly Asp Val Ala Phe Val Arg His Thr Thr Val Phe Asp Asn Thr Asn
                165                 170                 175

Gly His Asn Ser Glu Pro Trp Ala Ala Glu Leu Arg Ser Glu Asp Tyr
            180                 185                 190

Glu Leu Leu Cys Pro Asn Gly Ala Arg Ala Glu Val Ser Gln Phe Ala
        195                 200                 205

Ala Cys Asn Leu Ala Gln Ile Pro Pro His Ala Val Met
210                 215                 220

<210> SEQ ID NO 19
<211> LENGTH: 32
<212> TYPE: PRT
<213> ORGANISM: Homo sapiens

<400> SEQUENCE: 19

Val Arg Pro Asp Thr Asn Ile Phe Thr Val Tyr Gly Leu Leu Asp Lys
1               5                   10                  15

Ala Gln Asp Leu Phe Gly Asp Asp His Asn Lys Asn Gly Phe Lys Met
            20                  25                  30

<210> SEQ ID NO 20
<211> LENGTH: 564
<212> TYPE: PRT
<213> ORGANISM: Homo sapiens

<400> SEQUENCE: 20

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser

```
                20                  25                  30
Leu Leu Cys Val Arg Gly Thr Ser Ala Asp His Cys Val Gln Leu Ile
            35                  40                  45
Ala Ala Gln Glu Ala Asp Ala Ile Thr Leu Asp Gly Ala Ile Tyr
    50                  55                  60
Glu Ala Gly Lys Glu His Gly Leu Lys Pro Val Val Gly Glu Val Tyr
65                  70                  75                  80
Asp Gln Glu Val Gly Thr Ser Tyr Tyr Ala Val Ala Val Arg Arg
                85                  90                  95
Ser Ser His Val Thr Ile Asp Thr Leu Lys Gly Val Lys Ser Cys His
            100                 105                 110
Thr Gly Ile Asn Arg Thr Val Gly Trp Asn Val Pro Val Gly Tyr Leu
            115                 120                 125
Val Glu Ser Gly Arg Leu Ser Val Met Gly Cys Asp Val Leu Lys Ala
            130                 135                 140
Val Ser Asp Tyr Phe Gly Gly Ser Cys Val Pro Gly Ala Gly Glu Thr
145                 150                 155                 160
Ser Tyr Ser Glu Ser Leu Cys Arg Leu Cys Arg Gly Asp Ser Ser Gly
                165                 170                 175
Glu Gly Val Cys Asp Lys Ser Pro Leu Glu Arg Tyr Tyr Asp Tyr Ser
            180                 185                 190
Gly Ala Phe Arg Cys Leu Ala Glu Gly Ala Gly Asp Val Ala Phe Val
            195                 200                 205
Lys His Ser Thr Val Leu Glu Asn Thr Asp Gly Lys Thr Leu Pro Ser
            210                 215                 220
Trp Gly Gln Ala Leu Leu Ser Gln Asp Phe Glu Leu Leu Cys Arg Asp
225                 230                 235                 240
Gly Ser Arg Ala Asp Val Thr Glu Trp Arg Gln Cys His Leu Ala Arg
                245                 250                 255
Val Pro Ala His Ala Val Val Val Arg Ala Asp Thr Asp Gly Gly Leu
            260                 265                 270
Ile Phe Arg Leu Leu Asn Glu Gly Gln Arg Leu Phe Ser His Glu Gly
            275                 280                 285
Ser Ser Phe Gln Met Phe Ser Ser Glu Ala Tyr Gly Gln Lys Asp Leu
            290                 295                 300
Leu Phe Lys Asp Ser Thr Ser Glu Leu Val Pro Ile Ala Thr Gln Thr
305                 310                 315                 320
Tyr Glu Ala Trp Leu Gly His Glu Tyr Leu His Ala Met Lys Gly Leu
                325                 330                 335
Leu Cys Asp Pro Asn Arg Leu Pro Pro Tyr Leu Arg Trp Cys Val Leu
            340                 345                 350
Ser Thr Pro Glu Ile Gln Lys Cys Gly Asp Met Ala Val Ala Phe Arg
            355                 360                 365
Arg Gln Arg Leu Lys Pro Glu Ile Gln Cys Val Ser Ala Lys Ser Pro
            370                 375                 380
Gln His Cys Met Glu Arg Ile Gln Ala Glu Gln Val Asp Ala Val Thr
385                 390                 395                 400
Leu Ser Gly Glu Asp Ile Tyr Thr Ala Gly Lys Thr Tyr Gly Leu Val
                405                 410                 415
Pro Ala Ala Gly Glu His Tyr Ala Pro Glu Asp Ser Ser Asn Ser Tyr
            420                 425                 430
Tyr Val Val Ala Val Val Arg Arg Asp Ser Ser His Ala Phe Thr Leu
            435                 440                 445
```

```
Asp Glu Leu Arg Gly Lys Arg Ser Cys His Ala Gly Phe Gly Ser Pro
    450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
        515                 520                 525

Asn Ser Gln Glu Arg Tyr Tyr Gly Tyr Arg Gly Ala Phe Arg Cys Leu
    530                 535                 540

Val Glu Asn Ala Gly Asp Val Ala Phe Val Arg His Thr Thr Val Phe
545                 550                 555                 560

Asp Asn Thr Asn
```

<210> SEQ ID NO 21
<211> LENGTH: 22
<212> TYPE: PRT
<213> ORGANISM: Homo sapiens

<400> SEQUENCE: 21

```
Gly His Asn Ser Glu Pro Trp Ala Ala Glu Leu Arg Ser Glu Asp Tyr
1               5                   10                  15

Glu Leu Leu Cys Pro Asn
                20
```

<210> SEQ ID NO 22
<211> LENGTH: 51
<212> TYPE: PRT
<213> ORGANISM: Homo sapiens

<400> SEQUENCE: 22

```
Gly Ala Arg Ala Glu Val Ser Gln Phe Ala Ala Cys Asn Leu Ala Gln
1               5                   10                  15

Ile Pro Pro His Ala Val Met Val Arg Pro Asp Thr Asn Ile Phe Thr
            20                  25                  30

Val Tyr Gly Leu Leu Asp Lys Ala Gln Asp Leu Phe Gly Asp Asp His
        35                  40                  45

Asn Lys Asn
    50
```

<210> SEQ ID NO 23
<211> LENGTH: 53
<212> TYPE: PRT
<213> ORGANISM: Homo sapiens

<400> SEQUENCE: 23

```
Gly Phe Lys Met Phe Asp Ser Ser Asn Tyr His Gly Gln Asp Leu Leu
1               5                   10                  15

Phe Lys Asp Ala Thr Val Arg Ala Val Pro Val Gly Glu Lys Thr Thr
            20                  25                  30

Tyr Arg Gly Trp Leu Gly Leu Asp Tyr Val Ala Ala Leu Glu Gly Met
        35                  40                  45

Ser Ser Gln Gln Cys
    50
```

<210> SEQ ID NO 24
<211> LENGTH: 586
<212> TYPE: PRT
<213> ORGANISM: Homo sapiens

<400> SEQUENCE: 24

```
Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
        355                 360                 365

Arg Gln Arg Leu Lys Pro Glu Ile Gln Cys Val Ser Ala Lys Ser Pro
    370                 375                 380
```

```
Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
            405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
        435                 440                 445

Asp Glu Leu Arg Gly Lys Arg Ser Cys His Ala Gly Phe Gly Ser Pro
    450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
            485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
        515                 520                 525

Asn Ser Gln Glu Arg Tyr Tyr Gly Tyr Arg Gly Ala Phe Arg Cys Leu
    530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
            565                 570                 575

Ser Glu Asp Tyr Glu Leu Leu Cys Pro Asn
            580                 585

<210> SEQ ID NO 25
<211> LENGTH: 637
<212> TYPE: PRT
<213> ORGANISM: Homo sapiens

<400> SEQUENCE: 25

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
            85                  90                  95

Ser Ser His Val Thr Ile Asp Thr Leu Lys Gly Val Lys Ser Cys His
        100                 105                 110

Thr Gly Ile Asn Arg Thr Val Gly Trp Asn Val Pro Val Gly Tyr Leu
    115                 120                 125

Val Glu Ser Gly Arg Leu Ser Val Met Gly Cys Asp Val Leu Lys Ala
130                 135                 140

Val Ser Asp Tyr Phe Gly Gly Ser Cys Val Pro Gly Ala Gly Glu Thr
            145                 150                 155                 160

Ser Tyr Ser Glu Ser Leu Cys Arg Leu Cys Arg Gly Asp Ser Ser Gly
        165                 170                 175
```

```
Glu Gly Val Cys Asp Lys Ser Pro Leu Glu Arg Tyr Asp Tyr Ser
            180                 185                 190

Gly Ala Phe Arg Cys Leu Ala Glu Gly Ala Gly Asp Val Ala Phe Val
            195                 200                 205

Lys His Ser Thr Val Leu Glu Asn Thr Asp Gly Lys Thr Leu Pro Ser
            210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
            275                 280                 285

Ser Ser Phe Gln Met Phe Ser Ser Glu Ala Tyr Gly Gln Lys Asp Leu
            290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
            355                 360                 365

Arg Gln Arg Leu Lys Pro Glu Ile Gln Cys Val Ser Ala Lys Ser Pro
            370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
            435                 440                 445

Asp Glu Leu Arg Gly Lys Arg Ser Cys His Ala Gly Phe Gly Ser Pro
450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
            530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
            580                 585                 590
```

```
Ser Gln Phe Ala Ala Cys Asn Leu Ala Gln Ile Pro Pro His Ala Val
            595                 600                 605

Met Val Arg Pro Asp Thr Asn Ile Phe Thr Val Tyr Gly Leu Leu Asp
    610                 615                 620

Lys Ala Gln Asp Leu Phe Gly Asp Asp His Asn Lys Asn
625                 630                 635

<210> SEQ ID NO 26
<211> LENGTH: 73
<212> TYPE: PRT
<213> ORGANISM: Homo sapiens

<400> SEQUENCE: 26

Gly His Asn Ser Glu Pro Trp Ala Ala Glu Leu Arg Ser Glu Asp Tyr
1               5                   10                  15

Glu Leu Leu Cys Pro Asn Gly Ala Arg Ala Glu Val Ser Gln Phe Ala
            20                  25                  30

Ala Cys Asn Leu Ala Gln Ile Pro Pro His Ala Val Met Val Arg Pro
        35                  40                  45

Asp Thr Asn Ile Phe Thr Val Tyr Gly Leu Leu Asp Lys Ala Gln Asp
    50                  55                  60

Leu Phe Gly Asp Asp His Asn Lys Asn
65                  70

<210> SEQ ID NO 27
<211> LENGTH: 126
<212> TYPE: PRT
<213> ORGANISM: Homo sapiens

<400> SEQUENCE: 27

Gly His Asn Ser Glu Pro Trp Ala Ala Glu Leu Arg Ser Glu Asp Tyr
1               5                   10                  15

Glu Leu Leu Cys Pro Asn Gly Ala Arg Ala Glu Val Ser Gln Phe Ala
            20                  25                  30

Ala Cys Asn Leu Ala Gln Ile Pro Pro His Ala Val Met Val Arg Pro
        35                  40                  45

Asp Thr Asn Ile Phe Thr Val Tyr Gly Leu Leu Asp Lys Ala Gln Asp
    50                  55                  60

Leu Phe Gly Asp Asp His Asn Lys Asn Gly Phe Lys Met Phe Asp Ser
65                  70                  75                  80

Ser Asn Tyr His Gly Gln Asp Leu Leu Phe Lys Asp Ala Thr Val Arg
                85                  90                  95

Ala Val Pro Val Gly Glu Lys Thr Thr Tyr Arg Gly Trp Leu Gly Leu
            100                 105                 110

Asp Tyr Val Ala Ala Leu Glu Gly Met Ser Ser Gln Gln Cys
        115                 120                 125

<210> SEQ ID NO 28
<211> LENGTH: 104
<212> TYPE: PRT
<213> ORGANISM: Homo sapiens

<400> SEQUENCE: 28

Gly Ala Arg Ala Glu Val Ser Gln Phe Ala Ala Cys Asn Leu Ala Gln
1               5                   10                  15

Ile Pro Pro His Ala Val Met Val Arg Pro Asp Thr Asn Ile Phe Thr
            20                  25                  30

Val Tyr Gly Leu Leu Asp Lys Ala Gln Asp Leu Phe Gly Asp Asp His
```

```
                   35                  40                  45
Asn Lys Asn Gly Phe Lys Met Phe Asp Ser Asn Tyr His Gly Gln
 50                  55                  60

Asp Leu Leu Phe Lys Asp Ala Thr Val Arg Ala Val Pro Val Gly Glu
65                  70                  75                  80

Lys Thr Thr Tyr Arg Gly Trp Leu Gly Leu Asp Tyr Val Ala Ala Leu
                 85                  90                  95

Glu Gly Met Ser Ser Gln Gln Cys
            100

<210> SEQ ID NO 29
<211> LENGTH: 450
<212> TYPE: PRT
<213> ORGANISM: Homo sapiens

<400> SEQUENCE: 29

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 30
<211> LENGTH: 450
<212> TYPE: PRT
<213> ORGANISM: Artificial sequence
<220> FEATURE:
<223> OTHER INFORMATION: Modified Trastuzumab Sequence

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
            195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Trp Pro Pro Val
385                 390                 395                 400

Leu Asp Ser Asp Gly Ser Phe Phe Leu Thr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 31
<211> LENGTH: 240
<212> TYPE: PRT
<213> ORGANISM: Homo sapiens

<400> SEQUENCE: 31

Asn Thr Lys Val Asp Lys Lys Val Glu Pro Lys Ser Cys Asp Lys Thr
1               5                   10                  15

His Thr Cys Pro Pro Cys Pro Ala Pro Glu Leu Leu Gly Gly Pro Ser
            20                  25                  30

Val Phe Leu Phe Pro Pro Lys Pro Lys Asp Thr Leu Met Ile Ser Arg
        35                  40                  45

Thr Pro Glu Val Thr Cys Val Val Val Asp Val Ser His Glu Asp Pro
    50                  55                  60

Glu Val Lys Phe Asn Trp Tyr Val Asp Gly Val Glu Val His Asn Ala
65                  70                  75                  80

Lys Thr Lys Pro Arg Glu Glu Gln Tyr Asn Ser Thr Tyr Arg Val Val
                85                  90                  95

Ser Val Leu Thr Val Leu His Gln Asp Trp Leu Asn Gly Lys Glu Tyr
            100                 105                 110

Lys Cys Lys Val Ser Asn Lys Ala Leu Pro Ala Pro Ile Glu Lys Thr
        115                 120                 125

```
Ile Ser Lys Ala Lys Gly Gln Pro Arg Glu Pro Gln Val Tyr Thr Leu
            130                 135                 140

Pro Pro Ser Arg Asp Glu Leu Thr Lys Asn Gln Val Ser Leu Thr Cys
145                 150                 155                 160

Leu Val Lys Gly Phe Tyr Pro Ser Asp Ile Ala Val Glu Trp Glu Ser
                165                 170                 175

Asn Gly Gln Pro Glu Asn Asn Tyr Lys Thr Thr Pro Pro Val Leu Asp
            180                 185                 190

Ser Asp Gly Ser Phe Phe Leu Tyr Ser Lys Leu Thr Val Asp Lys Ser
            195                 200                 205

Arg Trp Gln Gln Gly Asn Val Phe Ser Cys Ser Val Met His Glu Ala
            210                 215                 220

Leu His Asn His Tyr Thr Gln Lys Ser Leu Ser Leu Ser Pro Gly Lys
225                 230                 235                 240

<210> SEQ ID NO 32
<211> LENGTH: 227
<212> TYPE: PRT
<213> ORGANISM: Homo sapiens

<400> SEQUENCE: 32

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 33
<211> LENGTH: 240
<212> TYPE: PRT
```

<213> ORGANISM: Artificial Sequence
<220> FEATURE:
<223> OTHER INFORMATION: Modified Trastuzumab Sequence

<400> SEQUENCE: 33

```
Asn Thr Lys Val Asp Lys Lys Val Glu Pro Lys Ser Cys Asp Lys Thr
1               5                   10                  15

His Thr Cys Pro Pro Cys Pro Ala Pro Glu Leu Leu Gly Gly Pro Ser
            20                  25                  30

Val Phe Leu Phe Pro Pro Lys Pro Lys Asp Thr Leu Met Ile Ser Arg
        35                  40                  45

Thr Pro Glu Val Thr Cys Val Val Val Asp Val Ser His Glu Asp Pro
    50                  55                  60

Glu Val Lys Phe Asn Trp Tyr Val Asp Gly Val Glu Val His Asn Ala
65                  70                  75                  80

Lys Thr Lys Pro Arg Glu Glu Gln Tyr Asn Ser Thr Tyr Arg Val Val
                85                  90                  95

Ser Val Leu Thr Val Leu His Gln Asp Trp Leu Asn Gly Lys Glu Tyr
            100                 105                 110

Lys Cys Lys Val Ser Asn Lys Ala Leu Pro Ala Pro Ile Glu Lys Thr
        115                 120                 125

Ile Ser Lys Ala Lys Gly Gln Pro Arg Glu Pro Gln Val Tyr Thr Leu
    130                 135                 140

Pro Pro Ser Arg Asp Glu Leu Thr Lys Asn Gln Val Ser Leu Thr Cys
145                 150                 155                 160

Leu Val Lys Gly Phe Tyr Pro Ser Asp Ile Ala Val Glu Trp Glu Ser
                165                 170                 175

Asn Gly Gln Pro Glu Asn Asn Tyr Lys Thr Trp Pro Pro Val Leu Asp
            180                 185                 190

Ser Asp Gly Ser Phe Phe Leu Thr Ser Lys Leu Thr Val Asp Lys Ser
        195                 200                 205

Arg Trp Gln Gln Gly Asn Val Phe Ser Cys Ser Val Met His Glu Ala
    210                 215                 220

Leu His Asn His Tyr Thr Gln Lys Ser Leu Ser Leu Ser Pro Gly Lys
225                 230                 235                 240
```

<210> SEQ ID NO 34
<211> LENGTH: 227
<212> TYPE: PRT
<213> ORGANISM: Artificial Sequence
<220> FEATURE:
<223> OTHER INFORMATION: Modified Trastuzumab Sequence

<400> SEQUENCE: 34

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Trp Pro Pro
                165                 170                 175

Val Leu Asp Ser Asp Gly Ser Phe Phe Leu Thr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 35
<211> LENGTH: 450
<212> TYPE: PRT
<213> ORGANISM: Artificial Sequence
<220> FEATURE:
<223> OTHER INFORMATION: Modified Trastuzumab Sequence

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Tyr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 36
<211> LENGTH: 214
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 1142
<212> TYPE: PRT
<213> ORGANISM: Artificial Sequence
<220> FEATURE:
<223> OTHER INFORMATION: p97-trastuzumab heavy chain fusion protein

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

-continued

```
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
                435                 440                 445
Gly Lys Gly Met Glu Val Arg Trp Cys Ala Thr Ser Asp Pro Glu Gln
450                 455                 460
His Lys Cys Gly Asn Met Ser Glu Ala Phe Arg Glu Ala Gly Ile Gln
465                 470                 475                 480
Pro Ser Leu Leu Cys Val Arg Gly Thr Ser Ala Asp His Cys Val Gln
                485                 490                 495
Leu Ile Ala Ala Gln Glu Ala Asp Ala Ile Thr Leu Asp Gly Gly Ala
            500                 505                 510
Ile Tyr Glu Ala Gly Lys Glu His Gly Leu Lys Pro Val Val Gly Glu
                515                 520                 525
Val Tyr Asp Gln Glu Val Gly Thr Ser Tyr Tyr Ala Val Ala Val Val
    530                 535                 540
Arg Arg Ser Ser His Val Thr Ile Asp Thr Leu Lys Gly Val Lys Ser
545                 550                 555                 560
Cys His Thr Gly Ile Asn Arg Thr Val Gly Trp Asn Val Pro Val Gly
                565                 570                 575
Tyr Leu Val Glu Ser Gly Arg Leu Ser Val Met Gly Cys Asp Val Leu
            580                 585                 590
Lys Ala Val Ser Asp Tyr Phe Gly Gly Ser Cys Val Pro Gly Ala Gly
            595                 600                 605
Glu Thr Ser Tyr Ser Glu Ser Leu Cys Arg Leu Cys Arg Gly Asp Ser
            610                 615                 620
Ser Gly Glu Gly Val Cys Asp Lys Ser Pro Leu Glu Arg Tyr Tyr Asp
625                 630                 635                 640
Tyr Ser Gly Ala Phe Arg Cys Leu Ala Glu Gly Ala Gly Asp Val Ala
                645                 650                 655
Phe Val Lys His Ser Thr Val Leu Glu Asn Thr Asp Gly Lys Thr Leu
                660                 665                 670
Pro Ser Trp Gly Gln Ala Leu Leu Ser Gln Asp Phe Glu Leu Leu Cys
            675                 680                 685
Arg Asp Gly Ser Arg Ala Asp Val Thr Glu Trp Arg Gln Cys His Leu
    690                 695                 700
```

```
Ala Arg Val Pro Ala His Ala Val Val Arg Ala Asp Thr Asp Gly
705                 710                 715                 720

Gly Leu Ile Phe Arg Leu Leu Asn Glu Gly Gln Arg Leu Phe Ser His
            725                 730                 735

Glu Gly Ser Ser Phe Gln Met Phe Ser Ser Glu Ala Tyr Gly Gln Lys
            740                 745                 750

Asp Leu Leu Phe Lys Asp Ser Thr Ser Glu Leu Val Pro Ile Ala Thr
            755                 760                 765

Gln Thr Tyr Glu Ala Trp Leu Gly His Glu Tyr Leu His Ala Met Lys
            770                 775                 780

Gly Leu Leu Cys Asp Pro Asn Arg Leu Pro Pro Tyr Leu Arg Trp Cys
785                 790                 795                 800

Val Leu Ser Thr Pro Glu Ile Gln Lys Cys Gly Asp Met Ala Val Ala
            805                 810                 815

Phe Arg Arg Gln Arg Leu Lys Pro Glu Ile Gln Cys Val Ser Ala Lys
            820                 825                 830

Ser Pro Gln His Cys Met Glu Arg Ile Gln Ala Glu Gln Val Asp Ala
            835                 840                 845

Val Thr Leu Ser Gly Glu Asp Ile Tyr Thr Ala Gly Lys Thr Tyr Gly
850                 855                 860

Leu Val Pro Ala Ala Gly Glu His Tyr Ala Pro Glu Asp Ser Ser Asn
865                 870                 875                 880

Ser Tyr Tyr Val Val Ala Val Val Arg Arg Asp Ser Ser His Ala Phe
            885                 890                 895

Thr Leu Asp Glu Leu Arg Gly Lys Arg Ser Cys His Ala Gly Phe Gly
            900                 905                 910

Ser Pro Ala Gly Trp Asp Val Pro Val Gly Ala Leu Ile Gln Arg Gly
            915                 920                 925

Phe Ile Arg Pro Lys Asp Cys Asp Val Leu Thr Ala Val Ser Glu Phe
            930                 935                 940

Phe Asn Ala Ser Cys Val Pro Val Asn Asn Pro Lys Asn Tyr Pro Ser
945                 950                 955                 960

Ser Leu Cys Ala Leu Cys Val Gly Asp Glu Gln Gly Arg Asn Lys Cys
            965                 970                 975

Val Gly Asn Ser Gln Glu Arg Tyr Tyr Gly Tyr Arg Gly Ala Phe Arg
            980                 985                 990

Cys Leu Val Glu Asn Ala Gly Asp Val Ala Phe Val Arg His Thr Thr
            995                 1000                1005

Val Phe Asp Asn Thr Asn Gly His Asn Ser Glu Pro Trp Ala Ala
    1010                1015                1020

Glu Leu Arg Ser Glu Asp Tyr Glu Leu Leu Cys Pro Asn Gly Ala
    1025                1030                1035

Arg Ala Glu Val Ser Gln Phe Ala Ala Cys Asn Leu Ala Gln Ile
    1040                1045                1050

Pro Pro His Ala Val Met Val Arg Pro Asp Thr Asn Ile Phe Thr
    1055                1060                1065

Val Tyr Gly Leu Leu Asp Lys Ala Gln Asp Leu Phe Gly Asp Asp
    1070                1075                1080

His Asn Lys Asn Gly Phe Lys Met Phe Asp Ser Ser Asn Tyr His
    1085                1090                1095

Gly Gln Asp Leu Leu Phe Lys Asp Ala Thr Val Arg Ala Val Pro
    1100                1105                1110

Val Gly Glu Lys Thr Thr Tyr Arg Gly Trp Leu Gly Leu Asp Tyr
```

Val Ala Ala Leu Glu Gly Met Ser Ser Gln Gln Cys Ser Gly
    1130            1135            1140

<210> SEQ ID NO 38
<211> LENGTH: 1157
<212> TYPE: PRT
<213> ORGANISM: Artificial Sequence
<220> FEATURE:
<223> OTHER INFORMATION: p97-trastuzumab heavy chain fusion protein

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr

-continued

```
               340                 345                 350
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Gly Ser Gly Gly Gly Gly
    450                 455                 460

Ser Gly Met Glu Val Arg Trp Cys Ala Thr Ser Asp Pro Glu Gln His
465                 470                 475                 480

Lys Cys Gly Asn Met Ser Glu Ala Phe Arg Glu Ala Gly Ile Gln Pro
                485                 490                 495

Ser Leu Leu Cys Val Arg Gly Thr Ser Ala Asp His Cys Val Gln Leu
            500                 505                 510

Ile Ala Ala Gln Glu Ala Asp Ala Ile Thr Leu Asp Gly Gly Ala Ile
        515                 520                 525

Tyr Glu Ala Gly Lys Glu His Gly Leu Lys Pro Val Val Gly Glu Val
    530                 535                 540

Tyr Asp Gln Glu Val Gly Thr Ser Tyr Tyr Ala Val Ala Val Val Arg
545                 550                 555                 560

Arg Ser Ser His Val Thr Ile Asp Thr Leu Lys Gly Val Lys Ser Cys
                565                 570                 575

His Thr Gly Ile Asn Arg Thr Val Gly Trp Asn Val Pro Val Gly Tyr
            580                 585                 590

Leu Val Glu Ser Gly Arg Leu Ser Val Met Gly Cys Asp Val Leu Lys
        595                 600                 605

Ala Val Ser Asp Tyr Phe Gly Gly Ser Cys Val Pro Gly Ala Gly Glu
    610                 615                 620

Thr Ser Tyr Ser Glu Ser Leu Cys Arg Leu Cys Arg Gly Asp Ser Ser
625                 630                 635                 640

Gly Glu Gly Val Cys Asp Lys Ser Pro Leu Glu Arg Tyr Tyr Asp Tyr
                645                 650                 655

Ser Gly Ala Phe Arg Cys Leu Ala Glu Gly Ala Gly Asp Val Ala Phe
            660                 665                 670

Val Lys His Ser Thr Val Leu Glu Asn Thr Asp Gly Lys Thr Leu Pro
        675                 680                 685

Ser Trp Gly Gln Ala Leu Leu Ser Gln Asp Phe Glu Leu Leu Cys Arg
    690                 695                 700

Asp Gly Ser Arg Ala Asp Val Thr Glu Trp Arg Gln Cys His Leu Ala
705                 710                 715                 720

Arg Val Pro Ala His Ala Val Val Arg Ala Asp Thr Asp Gly Gly
                725                 730                 735

Leu Ile Phe Arg Leu Leu Asn Glu Gly Gln Arg Leu Phe Ser His Glu
            740                 745                 750

Gly Ser Ser Phe Gln Met Phe Ser Ser Glu Ala Tyr Gly Gln Lys Asp
        755                 760                 765
```

Leu Leu Phe Lys Asp Ser Thr Ser Glu Leu Val Pro Ile Ala Thr Gln
770                 775                 780

Thr Tyr Glu Ala Trp Leu Gly His Glu Tyr Leu His Ala Met Lys Gly
785                 790                 795                 800

Leu Leu Cys Asp Pro Asn Arg Leu Pro Pro Tyr Leu Arg Trp Cys Val
                805                 810                 815

Leu Ser Thr Pro Glu Ile Gln Lys Cys Gly Asp Met Ala Val Ala Phe
                820                 825                 830

Arg Arg Gln Arg Leu Lys Pro Glu Ile Gln Cys Val Ser Ala Lys Ser
                835                 840                 845

Pro Gln His Cys Met Glu Arg Ile Gln Ala Glu Gln Val Asp Ala Val
            850                 855                 860

Thr Leu Ser Gly Glu Asp Ile Tyr Thr Ala Gly Lys Thr Tyr Gly Leu
865                 870                 875                 880

Val Pro Ala Ala Gly Glu His Tyr Ala Pro Glu Asp Ser Ser Asn Ser
                885                 890                 895

Tyr Tyr Val Val Ala Val Arg Arg Asp Ser Ser His Ala Phe Thr
                900                 905                 910

Leu Asp Glu Leu Arg Gly Lys Arg Ser Cys His Ala Gly Phe Gly Ser
                915                 920                 925

Pro Ala Gly Trp Asp Val Pro Val Gly Ala Leu Ile Gln Arg Gly Phe
            930                 935                 940

Ile Arg Pro Lys Asp Cys Asp Val Leu Thr Ala Val Ser Glu Phe Phe
945                 950                 955                 960

Asn Ala Ser Cys Val Pro Val Asn Asn Pro Lys Asn Tyr Pro Ser Ser
                965                 970                 975

Leu Cys Ala Leu Cys Val Gly Asp Glu Gln Gly Arg Asn Lys Cys Val
                980                 985                 990

Gly Asn Ser Gln Glu Arg Tyr Tyr Gly Tyr Arg Gly Ala Phe Arg Cys
                995                 1000                1005

Leu Val Glu Asn Ala Gly Asp Val Ala Phe Val Arg His Thr Thr
        1010                1015                1020

Val Phe Asp Asn Thr Asn Gly His Asn Ser Glu Pro Trp Ala Ala
        1025                1030                1035

Glu Leu Arg Ser Glu Asp Tyr Glu Leu Leu Cys Pro Asn Gly Ala
        1040                1045                1050

Arg Ala Glu Val Ser Gln Phe Ala Ala Cys Asn Leu Ala Gln Ile
        1055                1060                1065

Pro Pro His Ala Val Met Val Arg Pro Asp Thr Asn Ile Phe Thr
        1070                1075                1080

Val Tyr Gly Leu Leu Asp Lys Ala Gln Asp Leu Phe Gly Asp Asp
        1085                1090                1095

His Asn Lys Asn Gly Phe Lys Met Phe Asp Ser Ser Asn Tyr His
        1100                1105                1110

Gly Gln Asp Leu Leu Phe Lys Asp Ala Thr Val Arg Ala Val Pro
        1115                1120                1125

Val Gly Glu Lys Thr Thr Tyr Arg Gly Trp Leu Gly Leu Asp Tyr
        1130                1135                1140

Val Ala Ala Leu Glu Gly Met Ser Ser Gln Gln Cys Ser Gly
        1145                1150                1155

<210> SEQ ID NO 39
<211> LENGTH: 931

```
<212> TYPE: PRT
<213> ORGANISM: Artificial Sequence
<220> FEATURE:
<223> OTHER INFORMATION: p97-trastuzumab heavy chain fusion protein

<400> SEQUENCE: 39

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
        355                 360                 365

Arg Gln Arg Leu Lys Pro Glu Ile Gln Cys Val Ser Ala Lys Ser Pro
    370                 375                 380
```

```
Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
        405                 410                 415

Pro Ala Ala Gly Glu His Tyr Ala Pro Glu Asp Ser Ser Asn Ser Tyr
            420                 425                 430

Tyr Val Ala Val Val Arg Arg Asp Ser Ser His Ala Phe Thr Leu
        435                 440                 445

Asp Glu Leu Arg Gly Lys Arg Ser Cys His Ala Gly Phe Gly Ser Pro
        450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
            485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
        515                 520                 525

Asn Ser Gln Glu Arg Tyr Tyr Gly Tyr Arg Gly Ala Phe Arg Cys Leu
530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
            565                 570                 575

Ser Glu Asp Tyr Glu Leu Leu Cys Pro Asn Gly Ala Arg Ala Glu Val
        580                 585                 590

Ser Gln Phe Ala Ala Cys Asn Leu Ala Gln Ile Pro Pro His Ala Val
    595                 600                 605

Met Val Arg Pro Asp Thr Asn Ile Phe Thr Val Tyr Gly Leu Leu Asp
        610                 615                 620

Lys Ala Gln Asp Leu Phe Gly Asp Asp His Asn Lys Asn Gly Phe Lys
625                 630                 635                 640

Met Phe Asp Ser Ser Asn Tyr His Gly Gln Asp Leu Leu Phe Lys Asp
            645                 650                 655

Ala Thr Val Arg Ala Val Pro Val Gly Glu Lys Thr Thr Tyr Arg Gly
            660                 665                 670

Trp Leu Gly Leu Asp Tyr Val Ala Ala Leu Glu Gly Met Ser Ser Gln
        675                 680                 685

Gln Cys Gly Asn Thr Lys Val Asp Lys Lys Val Glu Pro Lys Ser Cys
    690                 695                 700

Asp Lys Thr His Thr Cys Pro Pro Cys Pro Ala Pro Glu Leu Leu Gly
705                 710                 715                 720

Gly Pro Ser Val Phe Leu Phe Pro Pro Lys Pro Lys Asp Thr Leu Met
            725                 730                 735

Ile Ser Arg Thr Pro Glu Val Thr Cys Val Val Val Asp Val Ser His
        740                 745                 750

Glu Asp Pro Glu Val Lys Phe Asn Trp Tyr Val Asp Gly Val Glu Val
        755                 760                 765

His Asn Ala Lys Thr Lys Pro Arg Glu Glu Gln Tyr Asn Ser Thr Tyr
    770                 775                 780

Arg Val Val Ser Val Leu Thr Val Leu His Gln Asp Trp Leu Asn Gly
785                 790                 795                 800

Lys Glu Tyr Lys Cys Lys Val Ser Asn Lys Ala Leu Pro Ala Pro Ile
```

805                 810                 815

Glu Lys Thr Ile Ser Lys Ala Lys Gly Gln Pro Arg Glu Pro Gln Val
            820                 825                 830

Tyr Thr Leu Pro Pro Ser Arg Asp Glu Leu Thr Lys Asn Gln Val Ser
            835                 840                 845

Leu Thr Cys Leu Val Lys Gly Phe Tyr Pro Ser Asp Ile Ala Val Glu
            850                 855                 860

Trp Glu Ser Asn Gly Gln Pro Glu Asn Tyr Lys Thr Thr Pro Pro
865                 870                 875                 880

Val Leu Asp Ser Asp Gly Ser Phe Phe Leu Tyr Ser Lys Leu Thr Val
            885                 890                 895

Asp Lys Ser Arg Trp Gln Gln Gly Asn Val Phe Ser Cys Ser Val Met
            900                 905                 910

His Glu Ala Leu His Asn His Tyr Thr Gln Lys Ser Leu Ser Leu Ser
            915                 920                 925

Pro Gly Lys
    930

<210> SEQ ID NO 40
<211> LENGTH: 946
<212> TYPE: PRT
<213> ORGANISM: Artificial Sequence
<220> FEATURE:
<223> OTHER INFORMATION: p97-trastuzumab heavy chain fusion protein

<400> SEQUENCE: 40

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
            35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
            115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
            195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp

-continued

```
            225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
                275                 280                 285

Ser Ser Phe Gln Met Phe Ser Ser Glu Ala Tyr Gly Gln Lys Asp Leu
            290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
            355                 360                 365

Arg Gln Arg Leu Lys Pro Glu Ile Gln Cys Val Ser Ala Lys Ser Pro
    370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
        435                 440                 445

Asp Glu Leu Arg Gly Lys Arg Ser Cys His Ala Gly Phe Gly Ser Pro
    450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
        515                 520                 525

Asn Ser Gln Glu Arg Tyr Tyr Gly Tyr Arg Gly Ala Phe Arg Cys Leu
    530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
            580                 585                 590

Ser Gln Phe Ala Ala Cys Asn Leu Ala Gln Ile Pro Pro His Ala Val
        595                 600                 605

Met Val Arg Pro Asp Thr Asn Ile Phe Thr Val Tyr Gly Leu Leu Asp
    610                 615                 620

Lys Ala Gln Asp Leu Phe Gly Asp Asp His Asn Lys Asn Gly Phe Lys
625                 630                 635                 640

Met Phe Asp Ser Ser Asn Tyr His Gly Gln Asp Leu Leu Phe Lys Asp
                645                 650                 655
```

```
Ala Thr Val Arg Ala Val Pro Val Gly Glu Lys Thr Thr Tyr Arg Gly
            660                 665                 670

Trp Leu Gly Leu Asp Tyr Val Ala Leu Glu Gly Met Ser Ser Gln
        675                 680                 685

Gln Cys Gly Gly Gly Gly Ser Gly Gly Gly Ser Gly Gly Gly
    690                 695                 700

Gly Ser Asn Thr Lys Val Asp Lys Lys Val Glu Pro Lys Ser Cys Asp
705                 710                 715                 720

Lys Thr His Thr Cys Pro Pro Cys Pro Ala Pro Glu Leu Leu Gly Gly
                725                 730                 735

Pro Ser Val Phe Leu Phe Pro Pro Lys Pro Lys Asp Thr Leu Met Ile
                740                 745                 750

Ser Arg Thr Pro Glu Val Thr Cys Val Val Val Asp Val Ser His Glu
                755                 760                 765

Asp Pro Glu Val Lys Phe Asn Trp Tyr Val Asp Gly Val Glu Val His
                770                 775                 780

Asn Ala Lys Thr Lys Pro Arg Glu Glu Gln Tyr Asn Ser Thr Tyr Arg
785                 790                 795                 800

Val Val Ser Val Leu Thr Val Leu His Gln Asp Trp Leu Asn Gly Lys
                805                 810                 815

Glu Tyr Lys Cys Lys Val Ser Asn Lys Ala Leu Pro Ala Pro Ile Glu
                820                 825                 830

Lys Thr Ile Ser Lys Ala Lys Gly Gln Pro Arg Glu Pro Gln Val Tyr
                835                 840                 845

Thr Leu Pro Pro Ser Arg Asp Glu Leu Thr Lys Asn Gln Val Ser Leu
                850                 855                 860

Thr Cys Leu Val Lys Gly Phe Tyr Pro Ser Asp Ile Ala Val Glu Trp
865                 870                 875                 880

Glu Ser Asn Gly Gln Pro Glu Asn Asn Tyr Lys Thr Thr Pro Pro Val
                885                 890                 895

Leu Asp Ser Asp Gly Ser Phe Phe Leu Tyr Ser Lys Leu Thr Val Asp
                900                 905                 910

Lys Ser Arg Trp Gln Gln Gly Asn Val Phe Ser Cys Ser Val Met His
                915                 920                 925

Glu Ala Leu His Asn His Tyr Thr Gln Lys Ser Leu Ser Leu Ser Pro
                930                 935                 940

Gly Lys
945

<210> SEQ ID NO 41
<211> LENGTH: 918
<212> TYPE: PRT
<213> ORGANISM: Artificial Sequence
<220> FEATURE:
<223> OTHER INFORMATION: p97-trastuzumab heavy chain fusion protein

<400> SEQUENCE: 41

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
                20                  25                  30

Leu Leu Cys Val Arg Gly Thr Ser Ala Asp His Cys Val Gln Leu Ile
            35                  40                  45

Ala Ala Gln Glu Ala Asp Ala Ile Thr Leu Asp Gly Gly Ala Ile Tyr
    50                  55                  60
```

```
Glu Ala Gly Lys Glu His Gly Leu Lys Pro Val Val Gly Glu Val Tyr
 65                  70                  75                  80

Asp Gln Glu Val Gly Thr Ser Tyr Tyr Ala Val Ala Val Val Arg Arg
                 85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
        355                 360                 365

Arg Gln Arg Leu Lys Pro Glu Ile Gln Cys Val Ser Ala Lys Ser Pro
370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
        435                 440                 445

Asp Glu Leu Arg Gly Lys Arg Ser Cys His Ala Gly Phe Gly Ser Pro
450                 455                 460

Ala Gly Trp Asp Val Pro Val Gly Ala Leu Ile Gln Arg Gly Phe Ile
465                 470                 475                 480
```

```
Arg Pro Lys Asp Cys Asp Val Leu Thr Ala Val Ser Glu Phe Phe Asn
            485                 490                 495
Ala Ser Cys Val Pro Val Asn Asn Pro Lys Asn Tyr Pro Ser Ser Leu
        500                 505                 510
Cys Ala Leu Cys Val Gly Asp Glu Gln Gly Arg Asn Lys Cys Val Gly
    515                 520                 525
Asn Ser Gln Glu Arg Tyr Tyr Gly Tyr Arg Gly Ala Phe Arg Cys Leu
530                 535                 540
Val Glu Asn Ala Gly Asp Val Ala Phe Val Arg His Thr Thr Val Phe
545                 550                 555                 560
Asp Asn Thr Asn Gly His Asn Ser Glu Pro Trp Ala Ala Glu Leu Arg
                565                 570                 575
Ser Glu Asp Tyr Glu Leu Leu Cys Pro Asn Gly Ala Arg Ala Glu Val
            580                 585                 590
Ser Gln Phe Ala Ala Cys Asn Leu Ala Gln Ile Pro Pro His Ala Val
        595                 600                 605
Met Val Arg Pro Asp Thr Asn Ile Phe Thr Val Tyr Gly Leu Leu Asp
    610                 615                 620
Lys Ala Gln Asp Leu Phe Gly Asp Asp His Asn Lys Asn Gly Phe Lys
625                 630                 635                 640
Met Phe Asp Ser Ser Asn Tyr His Gly Gln Asp Leu Leu Phe Lys Asp
                645                 650                 655
Ala Thr Val Arg Ala Val Pro Val Gly Glu Lys Thr Thr Tyr Arg Gly
            660                 665                 670
Trp Leu Gly Leu Asp Tyr Val Ala Ala Leu Glu Gly Met Ser Ser Gln
        675                 680                 685
Gln Cys Gly Asp Lys Thr His Thr Cys Pro Pro Cys Pro Ala Pro Glu
    690                 695                 700
Leu Leu Gly Gly Pro Ser Val Phe Leu Phe Pro Pro Lys Pro Lys Asp
705                 710                 715                 720
Thr Leu Met Ile Ser Arg Thr Pro Glu Val Thr Cys Val Val Val Asp
                725                 730                 735
Val Ser His Glu Asp Pro Glu Val Lys Phe Asn Trp Tyr Val Asp Gly
            740                 745                 750
Val Glu Val His Asn Ala Lys Thr Lys Pro Arg Glu Glu Gln Tyr Asn
        755                 760                 765
Ser Thr Tyr Arg Val Val Ser Val Leu Thr Val Leu His Gln Asp Trp
    770                 775                 780
Leu Asn Gly Lys Glu Tyr Lys Cys Lys Val Ser Asn Lys Ala Leu Pro
785                 790                 795                 800
Ala Pro Ile Glu Lys Thr Ile Ser Lys Ala Lys Gly Gln Pro Arg Glu
                805                 810                 815
Pro Gln Val Tyr Thr Leu Pro Pro Ser Arg Asp Glu Leu Thr Lys Asn
            820                 825                 830
Gln Val Ser Leu Thr Cys Leu Val Lys Gly Phe Tyr Pro Ser Asp Ile
        835                 840                 845
Ala Val Glu Trp Glu Ser Asn Gly Gln Pro Glu Asn Asn Tyr Lys Thr
    850                 855                 860
Thr Pro Pro Val Leu Asp Ser Asp Gly Ser Phe Phe Leu Tyr Ser Lys
865                 870                 875                 880
Leu Thr Val Asp Lys Ser Arg Trp Gln Gln Gly Asn Val Phe Ser Cys
                885                 890                 895
Ser Val Met His Glu Ala Leu His Asn His Tyr Thr Gln Lys Ser Leu
```

-continued

```
                    900                 905                 910

Ser Leu Ser Pro Gly Lys
        915

<210> SEQ ID NO 42
<211> LENGTH: 933
<212> TYPE: PRT
<213> ORGANISM: Artificial Sequence
<220> FEATURE:
<223> OTHER INFORMATION: p97-trastuzumab heavy chain fusion protein

<400> SEQUENCE: 42

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
```

```
                 340                 345                 350
Ser Thr Pro Glu Ile Gln Lys Cys Gly Asp Met Ala Val Ala Phe Arg
            355                 360                 365

Arg Gln Arg Leu Lys Pro Glu Ile Gln Cys Val Ser Ala Lys Ser Pro
        370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
        435                 440                 445

Asp Glu Leu Arg Gly Lys Arg Ser Cys His Ala Gly Phe Gly Ser Pro
        450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
        515                 520                 525

Asn Ser Gln Glu Arg Tyr Tyr Gly Tyr Arg Gly Ala Phe Arg Cys Leu
        530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
            580                 585                 590

Ser Gln Phe Ala Ala Cys Asn Leu Ala Gln Ile Pro Pro His Ala Val
        595                 600                 605

Met Val Arg Pro Asp Thr Asn Ile Phe Thr Val Tyr Gly Leu Leu Asp
        610                 615                 620

Lys Ala Gln Asp Leu Phe Gly Asp Asp His Asn Lys Asn Gly Phe Lys
625                 630                 635                 640

Met Phe Asp Ser Ser Asn Tyr His Gly Gln Asp Leu Leu Phe Lys Asp
                645                 650                 655

Ala Thr Val Arg Ala Val Pro Val Gly Glu Lys Thr Thr Tyr Arg Gly
            660                 665                 670

Trp Leu Gly Leu Asp Tyr Val Ala Ala Leu Glu Gly Met Ser Ser Gln
        675                 680                 685

Gln Cys Gly Gly Gly Gly Ser Gly Gly Gly Ser Gly Gly Gly
        690                 695                 700

Gly Ser Asp Lys Thr His Thr Cys Pro Pro Cys Pro Ala Pro Glu Leu
705                 710                 715                 720

Leu Gly Gly Pro Ser Val Phe Leu Phe Pro Pro Lys Pro Lys Asp Thr
                725                 730                 735

Leu Met Ile Ser Arg Thr Pro Glu Val Thr Cys Val Val Val Asp Val
            740                 745                 750

Ser His Glu Asp Pro Glu Val Lys Phe Asn Trp Tyr Val Asp Gly Val
        755                 760                 765
```

```
Glu Val His Asn Ala Lys Thr Lys Pro Arg Glu Gln Tyr Asn Ser
    770                 775                 780

Thr Tyr Arg Val Val Ser Val Leu Thr Val Leu His Gln Asp Trp Leu
785                 790                 795                 800

Asn Gly Lys Glu Tyr Lys Cys Lys Val Ser Asn Lys Ala Leu Pro Ala
                805                 810                 815

Pro Ile Glu Lys Thr Ile Ser Lys Ala Lys Gly Gln Pro Arg Glu Pro
                820                 825                 830

Gln Val Tyr Thr Leu Pro Pro Ser Arg Asp Glu Leu Thr Lys Asn Gln
                835                 840                 845

Val Ser Leu Thr Cys Leu Val Lys Gly Phe Tyr Pro Ser Asp Ile Ala
850                 855                 860

Val Glu Trp Glu Ser Asn Gly Gln Pro Glu Asn Asn Tyr Lys Thr Thr
865                 870                 875                 880

Pro Pro Val Leu Asp Ser Asp Gly Ser Phe Phe Leu Tyr Ser Lys Leu
                885                 890                 895

Thr Val Asp Lys Ser Arg Trp Gln Gln Gly Asn Val Phe Ser Cys Ser
                900                 905                 910

Val Met His Glu Ala Leu His Asn His Tyr Thr Gln Lys Ser Leu Ser
                915                 920                 925

Leu Ser Pro Gly Lys
    930

<210> SEQ ID NO 43
<211> LENGTH: 932
<212> TYPE: PRT
<213> ORGANISM: Artificial Sequence
<220> FEATURE:
<223> OTHER INFORMATION: p97-trastuzumab heavy chain fusion protein

<400> SEQUENCE: 43

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
                20                  25                  30

Leu Leu Cys Val Arg Gly Thr Ser Ala Asp His Cys Val Gln Leu Ile
            35                  40                  45

Ala Ala Gln Glu Ala Asp Ala Ile Thr Leu Asp Gly Gly Ala Ile Tyr
        50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
                100                 105                 110

Thr Gly Ile Asn Arg Thr Val Gly Trp Asn Val Pro Val Gly Tyr Leu
            115                 120                 125

Val Glu Ser Gly Arg Leu Ser Val Met Gly Cys Asp Val Leu Lys Ala
130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
                180                 185                 190
```

```
Gly Ala Phe Arg Cys Leu Ala Glu Gly Ala Gly Asp Val Ala Phe Val
            195                 200                 205

Lys His Ser Thr Val Leu Glu Asn Thr Asp Gly Lys Thr Leu Pro Ser
            210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
            245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
            275                 280                 285

Ser Ser Phe Gln Met Phe Ser Ser Glu Ala Tyr Gly Gln Lys Asp Leu
            290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                    325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
            355                 360                 365

Arg Gln Arg Leu Lys Pro Glu Ile Gln Cys Val Ser Ala Lys Ser Pro
            370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                    405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
            435                 440                 445

Asp Glu Leu Arg Gly Lys Arg Ser Cys His Ala Gly Phe Gly Ser Pro
            450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
            485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
            530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                    565                 570                 575

Ser Glu Asp Tyr Glu Leu Leu Cys Pro Asn Gly Ala Arg Ala Glu Val
            580                 585                 590

Ser Gln Phe Ala Ala Cys Asn Leu Ala Gln Ile Pro Pro His Ala Val
            595                 600                 605
```

```
Met Val Arg Pro Asp Thr Asn Ile Phe Thr Val Tyr Gly Leu Leu Asp
610                 615                 620

Lys Ala Gln Asp Leu Phe Gly Asp His Asn Lys Asn Gly Phe Lys
625                 630                 635                 640

Met Phe Asp Ser Ser Asn Tyr His Gly Gln Asp Leu Leu Phe Lys Asp
                    645                 650                 655

Ala Thr Val Arg Ala Val Pro Val Gly Glu Lys Thr Thr Tyr Arg Gly
                660                 665                 670

Trp Leu Gly Leu Asp Tyr Val Ala Ala Leu Glu Gly Met Ser Ser Gln
                675                 680                 685

Gln Cys Ser Gly Asn Thr Lys Val Asp Lys Val Glu Pro Lys Ser
690                 695                 700

Cys Asp Lys Thr His Thr Cys Pro Pro Cys Pro Ala Pro Glu Leu Leu
705                 710                 715                 720

Gly Gly Pro Ser Val Phe Leu Phe Pro Pro Lys Pro Lys Asp Thr Leu
                725                 730                 735

Met Ile Ser Arg Thr Pro Glu Val Thr Cys Val Val Val Asp Val Ser
                740                 745                 750

His Glu Asp Pro Glu Val Lys Phe Asn Trp Tyr Val Asp Gly Val Glu
                755                 760                 765

Val His Asn Ala Lys Thr Lys Pro Arg Glu Glu Gln Tyr Asn Ser Thr
770                 775                 780

Tyr Arg Val Val Ser Val Leu Thr Val Leu His Gln Asp Trp Leu Asn
785                 790                 795                 800

Gly Lys Glu Tyr Lys Cys Lys Val Ser Asn Lys Ala Leu Pro Ala Pro
                805                 810                 815

Ile Glu Lys Thr Ile Ser Lys Ala Lys Gly Gln Pro Arg Glu Pro Gln
                820                 825                 830

Val Tyr Thr Leu Pro Pro Ser Arg Asp Glu Leu Thr Lys Asn Gln Val
                835                 840                 845

Ser Leu Thr Cys Leu Val Lys Gly Phe Tyr Pro Ser Asp Ile Ala Val
                850                 855                 860

Glu Trp Glu Ser Asn Gly Gln Pro Glu Asn Asn Tyr Lys Thr Trp Pro
865                 870                 875                 880

Pro Val Leu Asp Ser Asp Gly Ser Phe Phe Leu Thr Ser Lys Leu Thr
                885                 890                 895

Val Asp Lys Ser Arg Trp Gln Gln Gly Asn Val Phe Ser Cys Ser Val
                900                 905                 910

Met His Glu Ala Leu His Asn His Tyr Thr Gln Lys Ser Leu Ser Leu
                915                 920                 925

Ser Pro Gly Lys
    930

<210> SEQ ID NO 44
<211> LENGTH: 947
<212> TYPE: PRT
<213> ORGANISM: Artificial Sequence
<220> FEATURE:
<223> OTHER INFORMATION: p97-trastuzumab heavy chain fusion protein

<400> SEQUENCE: 44

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
                20                  25                  30
```

```
Leu Leu Cys Val Arg Gly Thr Ser Ala Asp His Cys Val Gln Leu Ile
         35                  40                  45

Ala Ala Gln Glu Ala Asp Ala Ile Thr Leu Asp Gly Gly Ala Ile Tyr
 50                  55                  60

Glu Ala Gly Lys Glu His Gly Leu Lys Pro Val Val Gly Val Tyr
 65              70                  75                      80

Asp Gln Glu Val Gly Thr Ser Tyr Tyr Ala Val Ala Val Arg Arg
                 85                  90                  95

Ser Ser His Val Thr Ile Asp Thr Leu Lys Gly Val Lys Ser Cys His
             100                 105                 110

Thr Gly Ile Asn Arg Thr Val Gly Trp Asn Val Pro Val Gly Tyr Leu
             115                 120                 125

Val Glu Ser Gly Arg Leu Ser Val Met Gly Cys Asp Val Leu Lys Ala
 130                 135                 140

Val Ser Asp Tyr Phe Gly Gly Ser Cys Val Pro Gly Ala Gly Glu Thr
 145                 150                 155                 160

Ser Tyr Ser Glu Ser Leu Cys Arg Leu Cys Arg Gly Asp Ser Ser Gly
                 165                 170                 175

Glu Gly Val Cys Asp Lys Ser Pro Leu Glu Arg Tyr Tyr Asp Tyr Ser
             180                 185                 190

Gly Ala Phe Arg Cys Leu Ala Glu Gly Ala Gly Asp Val Ala Phe Val
             195                 200                 205

Lys His Ser Thr Val Leu Glu Asn Thr Asp Gly Lys Thr Leu Pro Ser
 210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                 245                 250                 255

Val Pro Ala His Ala Val Val Arg Ala Asp Thr Asp Gly Gly Leu
             260                 265                 270

Ile Phe Arg Leu Leu Asn Glu Gly Gln Arg Leu Phe Ser His Glu Gly
             275                 280                 285

Ser Ser Phe Gln Met Phe Ser Ser Glu Ala Tyr Gly Gln Lys Asp Leu
 290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                 325                 330                 335

Leu Cys Asp Pro Asn Arg Leu Pro Pro Tyr Leu Arg Trp Cys Val Leu
             340                 345                 350

Ser Thr Pro Glu Ile Gln Lys Cys Gly Asp Met Ala Val Ala Phe Arg
             355                 360                 365

Arg Gln Arg Leu Lys Pro Glu Ile Gln Cys Val Ser Ala Lys Ser Pro
 370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                 405                 410                 415

Pro Ala Ala Gly Glu His Tyr Ala Pro Glu Asp Ser Ser Asn Ser Tyr
             420                 425                 430

Tyr Val Val Ala Val Val Arg Arg Asp Ser Ser His Ala Phe Thr Leu
 435                 440                 445

Asp Glu Leu Arg Gly Lys Arg Ser Cys His Ala Gly Phe Gly Ser Pro
```

```
                450             455             460
Ala Gly Trp Asp Val Pro Val Gly Ala Leu Ile Gln Arg Gly Phe Ile
465                 470             475                 480

Arg Pro Lys Asp Cys Asp Val Leu Thr Ala Val Ser Glu Phe Phe Asn
                485             490                 495

Ala Ser Cys Val Pro Val Asn Asn Pro Lys Asn Tyr Pro Ser Ser Leu
                500             505             510

Cys Ala Leu Cys Val Gly Asp Glu Gln Gly Arg Asn Lys Cys Val Gly
            515             520             525

Asn Ser Gln Glu Arg Tyr Tyr Gly Tyr Arg Gly Ala Phe Arg Cys Leu
        530             535             540

Val Glu Asn Ala Gly Asp Val Ala Phe Val Arg His Thr Thr Val Phe
545             550             555                 560

Asp Asn Thr Asn Gly His Asn Ser Glu Pro Trp Ala Ala Glu Leu Arg
                565             570             575

Ser Glu Asp Tyr Glu Leu Leu Cys Pro Asn Gly Ala Arg Ala Glu Val
            580             585             590

Ser Gln Phe Ala Ala Cys Asn Leu Ala Gln Ile Pro Pro His Ala Val
        595             600             605

Met Val Arg Pro Asp Thr Asn Ile Phe Thr Val Tyr Gly Leu Leu Asp
    610             615             620

Lys Ala Gln Asp Leu Phe Gly Asp Asp His Asn Lys Asn Gly Phe Lys
625             630             635                 640

Met Phe Asp Ser Ser Asn Tyr His Gly Gln Asp Leu Leu Phe Lys Asp
                645             650             655

Ala Thr Val Arg Ala Val Pro Val Gly Glu Lys Thr Thr Tyr Arg Gly
            660             665             670

Trp Leu Gly Leu Asp Tyr Val Ala Ala Leu Glu Gly Met Ser Ser Gln
        675             680             685

Gln Cys Ser Gly Gly Gly Gly Ser Gly Gly Gly Ser Gly Gly
    690             695             700

Gly Gly Ser Asn Thr Lys Val Asp Lys Lys Val Glu Pro Lys Ser Cys
705             710             715                 720

Asp Lys Thr His Thr Cys Pro Pro Cys Pro Ala Pro Glu Leu Leu Gly
                725             730             735

Gly Pro Ser Val Phe Leu Phe Pro Pro Lys Pro Lys Asp Thr Leu Met
            740             745             750

Ile Ser Arg Thr Pro Glu Val Thr Cys Val Val Val Asp Val Ser His
        755             760             765

Glu Asp Pro Glu Val Lys Phe Asn Trp Tyr Val Asp Gly Val Glu Val
    770             775             780

His Asn Ala Lys Thr Lys Pro Arg Glu Glu Gln Tyr Asn Ser Thr Tyr
785             790             795                 800

Arg Val Val Ser Val Leu Thr Val Leu His Gln Asp Trp Leu Asn Gly
                805             810             815

Lys Glu Tyr Lys Cys Lys Val Ser Asn Lys Ala Leu Pro Ala Pro Ile
            820             825             830

Glu Lys Thr Ile Ser Lys Ala Lys Gly Gln Pro Arg Glu Pro Gln Val
        835             840             845

Tyr Thr Leu Pro Pro Ser Arg Asp Glu Leu Thr Lys Asn Gln Val Ser
    850             855             860

Leu Thr Cys Leu Val Lys Gly Phe Tyr Pro Ser Asp Ile Ala Val Glu
865             870             875                 880
```

-continued

Trp Glu Ser Asn Gly Gln Pro Glu Asn Asn Tyr Lys Thr Trp Pro Pro
            885                 890                 895

Val Leu Asp Ser Asp Gly Ser Phe Phe Leu Thr Ser Lys Leu Thr Val
            900                 905                 910

Asp Lys Ser Arg Trp Gln Gln Gly Asn Val Phe Ser Cys Ser Val Met
            915                 920                 925

His Glu Ala Leu His Asn His Tyr Thr Gln Lys Ser Leu Ser Leu Ser
            930                 935                 940

Pro Gly Lys
945

<210> SEQ ID NO 45
<211> LENGTH: 919
<212> TYPE: PRT
<213> ORGANISM: Artificial Sequence
<220> FEATURE:
<223> OTHER INFORMATION: p97-trastuzumab heavy chain fusion protein

<400> SEQUENCE: 45

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

```
Ser Ser Phe Gln Met Phe Ser Glu Ala Tyr Gly Gln Lys Asp Leu
    290                 295                 300
Leu Phe Lys Asp Ser Thr Ser Glu Leu Val Pro Ile Ala Thr Gln Thr
305                 310                 315                 320
Tyr Glu Ala Trp Leu Gly His Glu Tyr Leu His Ala Met Lys Gly Leu
                325                 330                 335
Leu Cys Asp Pro Asn Arg Leu Pro Pro Tyr Leu Arg Trp Cys Val Leu
                340                 345                 350
Ser Thr Pro Glu Ile Gln Lys Cys Gly Asp Met Ala Val Ala Phe Arg
            355                 360                 365
Arg Gln Arg Leu Lys Pro Glu Ile Gln Cys Val Ser Ala Lys Ser Pro
    370                 375                 380
Gln His Cys Met Glu Arg Ile Gln Ala Glu Gln Val Asp Ala Val Thr
385                 390                 395                 400
Leu Ser Gly Glu Asp Ile Tyr Thr Ala Gly Lys Thr Tyr Gly Leu Val
                405                 410                 415
Pro Ala Ala Gly Glu His Tyr Ala Pro Glu Asp Ser Ser Asn Ser Tyr
                420                 425                 430
Tyr Val Val Ala Val Val Arg Arg Asp Ser Ser His Ala Phe Thr Leu
            435                 440                 445
Asp Glu Leu Arg Gly Lys Arg Ser Cys His Ala Gly Phe Gly Ser Pro
    450                 455                 460
Ala Gly Trp Asp Val Pro Val Gly Ala Leu Ile Gln Arg Gly Phe Ile
465                 470                 475                 480
Arg Pro Lys Asp Cys Asp Val Leu Thr Ala Val Ser Glu Phe Phe Asn
                485                 490                 495
Ala Ser Cys Val Pro Val Asn Asn Pro Lys Asn Tyr Pro Ser Ser Leu
                500                 505                 510
Cys Ala Leu Cys Val Gly Asp Glu Gln Gly Arg Asn Lys Cys Val Gly
            515                 520                 525
Asn Ser Gln Glu Arg Tyr Tyr Gly Tyr Arg Gly Ala Phe Arg Cys Leu
    530                 535                 540
Val Glu Asn Ala Gly Asp Val Ala Phe Val Arg His Thr Thr Val Phe
545                 550                 555                 560
Asp Asn Thr Asn Gly His Asn Ser Glu Pro Trp Ala Ala Glu Leu Arg
                565                 570                 575
Ser Glu Asp Tyr Glu Leu Leu Cys Pro Asn Gly Ala Arg Ala Glu Val
                580                 585                 590
Ser Gln Phe Ala Ala Cys Asn Leu Ala Gln Ile Pro Pro His Ala Val
            595                 600                 605
Met Val Arg Pro Asp Thr Asn Ile Phe Thr Val Tyr Gly Leu Leu Asp
    610                 615                 620
Lys Ala Gln Asp Leu Phe Gly Asp Asp His Asn Lys Asn Gly Phe Lys
625                 630                 635                 640
Met Phe Asp Ser Ser Asn Tyr His Gly Gln Asp Leu Leu Phe Lys Asp
                645                 650                 655
Ala Thr Val Arg Ala Val Pro Val Gly Glu Lys Thr Thr Tyr Arg Gly
                660                 665                 670
Trp Leu Gly Leu Asp Tyr Val Ala Ala Leu Glu Gly Met Ser Ser Gln
            675                 680                 685
Gln Cys Ser Gly Asp Lys Thr His Thr Cys Pro Pro Cys Pro Ala Pro
    690                 695                 700
```

```
Glu Leu Leu Gly Gly Pro Ser Val Phe Leu Phe Pro Pro Lys Pro Lys
705                 710                 715                 720

Asp Thr Leu Met Ile Ser Arg Thr Pro Glu Val Thr Cys Val Val Val
            725                 730                 735

Asp Val Ser His Glu Asp Pro Glu Val Lys Phe Asn Trp Tyr Val Asp
        740                 745                 750

Gly Val Glu Val His Asn Ala Lys Thr Lys Pro Arg Glu Glu Gln Tyr
    755                 760                 765

Asn Ser Thr Tyr Arg Val Val Ser Val Leu Thr Val Leu His Gln Asp
770                 775                 780

Trp Leu Asn Gly Lys Glu Tyr Lys Cys Lys Val Ser Asn Lys Ala Leu
785                 790                 795                 800

Pro Ala Pro Ile Glu Lys Thr Ile Ser Lys Ala Lys Gly Gln Pro Arg
            805                 810                 815

Glu Pro Gln Val Tyr Thr Leu Pro Pro Ser Arg Asp Glu Leu Thr Lys
        820                 825                 830

Asn Gln Val Ser Leu Thr Cys Leu Val Lys Gly Phe Tyr Pro Ser Asp
    835                 840                 845

Ile Ala Val Glu Trp Glu Ser Asn Gly Gln Pro Glu Asn Asn Tyr Lys
850                 855                 860

Thr Trp Pro Pro Val Leu Asp Ser Asp Gly Ser Phe Phe Leu Thr Ser
865                 870                 875                 880

Lys Leu Thr Val Asp Lys Ser Arg Trp Gln Gln Gly Asn Val Phe Ser
            885                 890                 895

Cys Ser Val Met His Glu Ala Leu His Asn His Tyr Thr Gln Lys Ser
        900                 905                 910

Leu Ser Leu Ser Pro Gly Lys
        915

<210> SEQ ID NO 46
<211> LENGTH: 934
<212> TYPE: PRT
<213> ORGANISM: Artificial Sequence
<220> FEATURE:
<223> OTHER INFORMATION: p97-trastuzumab heavy chain fusion protein

<400> SEQUENCE: 46

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140
```

```
Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
            165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
            195                 200                 205

Lys His Ser Thr Val Leu Glu Asn Thr Asp Gly Lys Thr Leu Pro Ser
            210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
            245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
            275                 280                 285

Ser Ser Phe Gln Met Phe Ser Ser Glu Ala Tyr Gly Gln Lys Asp Leu
            290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
            325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
            355                 360                 365

Arg Gln Arg Leu Lys Pro Glu Ile Gln Cys Val Ser Ala Lys Ser Pro
            370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
            405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
            435                 440                 445

Asp Glu Leu Arg Gly Lys Arg Ser Cys His Ala Gly Phe Gly Ser Pro
450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
            485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
            530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
```

```
                        565                 570                 575
Ser Glu Asp Tyr Glu Leu Leu Cys Pro Asn Gly Ala Arg Ala Glu Val
                580                 585                 590

Ser Gln Phe Ala Ala Cys Asn Leu Ala Gln Ile Pro Pro His Ala Val
                595                 600                 605

Met Val Arg Pro Asp Thr Asn Ile Phe Thr Val Tyr Gly Leu Leu Asp
610                 615                 620

Lys Ala Gln Asp Leu Phe Gly Asp His Asn Lys Asn Gly Phe Lys
625                 630                 635                 640

Met Phe Asp Ser Ser Asn Tyr His Gly Gln Asp Leu Leu Phe Lys Asp
                645                 650                 655

Ala Thr Val Arg Ala Val Pro Val Gly Glu Lys Thr Thr Tyr Arg Gly
                660                 665                 670

Trp Leu Gly Leu Asp Tyr Val Ala Ala Leu Glu Gly Met Ser Ser Gln
                675                 680                 685

Gln Cys Ser Gly Gly Gly Gly Ser Gly Gly Gly Ser Gly Gly
                690                 695                 700

Gly Gly Ser Asp Lys Thr His Thr Cys Pro Pro Cys Pro Ala Pro Glu
705                 710                 715                 720

Leu Leu Gly Gly Pro Ser Val Phe Leu Phe Pro Pro Lys Pro Lys Asp
                725                 730                 735

Thr Leu Met Ile Ser Arg Thr Pro Glu Val Thr Cys Val Val Val Asp
                740                 745                 750

Val Ser His Glu Asp Pro Glu Val Lys Phe Asn Trp Tyr Val Asp Gly
                755                 760                 765

Val Glu Val His Asn Ala Lys Thr Lys Pro Arg Glu Glu Gln Tyr Asn
770                 775                 780

Ser Thr Tyr Arg Val Val Ser Val Leu Thr Val Leu His Gln Asp Trp
785                 790                 795                 800

Leu Asn Gly Lys Glu Tyr Lys Cys Lys Val Ser Asn Lys Ala Leu Pro
                805                 810                 815

Ala Pro Ile Glu Lys Thr Ile Ser Lys Ala Lys Gly Gln Pro Arg Glu
                820                 825                 830

Pro Gln Val Tyr Thr Leu Pro Pro Ser Arg Asp Glu Leu Thr Lys Asn
                835                 840                 845

Gln Val Ser Leu Thr Cys Leu Val Lys Gly Phe Tyr Pro Ser Asp Ile
                850                 855                 860

Ala Val Glu Trp Glu Ser Asn Gly Gln Pro Glu Asn Asn Tyr Lys Thr
865                 870                 875                 880

Trp Pro Pro Val Leu Asp Ser Asp Gly Ser Phe Phe Leu Thr Ser Lys
                885                 890                 895

Leu Thr Val Asp Lys Ser Arg Trp Gln Gln Gly Asn Val Phe Ser Cys
                900                 905                 910

Ser Val Met His Glu Ala Leu His Asn His Tyr Thr Gln Lys Ser Leu
                915                 920                 925

Ser Leu Ser Pro Gly Lys
    930

<210> SEQ ID NO 47
<211> LENGTH: 4
<212> TYPE: PRT
<213> ORGANISM: Artificial Sequence
<220> FEATURE:
<223> OTHER INFORMATION: Peptide linker
```

```
<400> SEQUENCE: 47

Gly Ser Gly Ser
1

<210> SEQ ID NO 48
<211> LENGTH: 4
<212> TYPE: PRT
<213> ORGANISM: Artificial Sequence
<220> FEATURE:
<223> OTHER INFORMATION: Peptide linker

<400> SEQUENCE: 48

Gly Gly Ser Gly
1

<210> SEQ ID NO 49
<211> LENGTH: 4
<212> TYPE: PRT
<213> ORGANISM: Artificial Sequence
<220> FEATURE:
<223> OTHER INFORMATION: Peptide linker

<400> SEQUENCE: 49

Gly Gly Gly Ser
1

<210> SEQ ID NO 50
<211> LENGTH: 5
<212> TYPE: PRT
<213> ORGANISM: Artificial Sequence
<220> FEATURE:
<223> OTHER INFORMATION: Peptide Linker

<400> SEQUENCE: 50

Gly Gly Gly Gly Ser
1               5

<210> SEQ ID NO 51
<211> LENGTH: 4
<212> TYPE: PRT
<213> ORGANISM: Artificial Sequence
<220> FEATURE:
<223> OTHER INFORMATION: Peptide linker

<400> SEQUENCE: 51

Gly Asn Gly Asn
1

<210> SEQ ID NO 52
<211> LENGTH: 4
<212> TYPE: PRT
<213> ORGANISM: Artificial Sequence
<220> FEATURE:
<223> OTHER INFORMATION: Peptide linker

<400> SEQUENCE: 52

Gly Gly Asn Gly
1

<210> SEQ ID NO 53
<211> LENGTH: 4
<212> TYPE: PRT
<213> ORGANISM: Artificial Sequence
<220> FEATURE:
<223> OTHER INFORMATION: Peptide linker

<400> SEQUENCE: 53
```

```
Gly Gly Gly Asn
1

<210> SEQ ID NO 54
<211> LENGTH: 5
<212> TYPE: PRT
<213> ORGANISM: Artificial Sequence
<220> FEATURE:
<223> OTHER INFORMATION: Peptide linker

<400> SEQUENCE: 54

Gly Gly Gly Gly Asn
1               5

<210> SEQ ID NO 55
<211> LENGTH: 15
<212> TYPE: PRT
<213> ORGANISM: Artificial Sequence
<220> FEATURE:
<223> OTHER INFORMATION: Peptide linker

<400> SEQUENCE: 55

Gly Gly Gly Gly Ser Gly Gly Gly Gly Ser Gly Gly Gly Gly Ser
1               5                   10                  15

<210> SEQ ID NO 56
<211> LENGTH: 4
<212> TYPE: PRT
<213> ORGANISM: Artificial Sequence
<220> FEATURE:
<223> OTHER INFORMATION: Thrombin cleavable linker

<400> SEQUENCE: 56

Gly Arg Gly Asp
1

<210> SEQ ID NO 57
<211> LENGTH: 6
<212> TYPE: PRT
<213> ORGANISM: Artificial Sequence
<220> FEATURE:
<223> OTHER INFORMATION: Thrombin cleavable linker

<400> SEQUENCE: 57

Gly Arg Gly Asp Asn Pro
1               5

<210> SEQ ID NO 58
<211> LENGTH: 5
<212> TYPE: PRT
<213> ORGANISM: Artificial Sequence
<220> FEATURE:
<223> OTHER INFORMATION: Thrombin cleavable linker

<400> SEQUENCE: 58

Gly Arg Gly Asp Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Thrombin cleavable linker

<400> SEQUENCE: 59
```

Gly Arg Gly Asp Ser Pro Lys
1               5

<210> SEQ ID NO 60
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 60

Ala Ala Pro Val
1

<210> SEQ ID NO 61
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 61

Ala Ala Pro Leu
1

<210> SEQ ID NO 62
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 62

Ala Ala Pro Phe
1

<210> SEQ ID NO 63
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 63

Ala Ala Pro Ala
1

<210> SEQ ID NO 64
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 64

Ala Tyr Leu Val
1

<210> SEQ ID NO 65
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (3)..(3)
<223> OTHER INFORMATION: Xaa = Any amino acid

```
<220> FEATURE:
<221> NAME/KEY: VARIANT
<222> LOCATION: (6)..(6)
<223> OTHER INFORMATION: Xaa = Any amino acid

<400> SEQUENCE: 65

Gly Pro Xaa Gly Pro Xaa
1               5

<210> SEQ ID NO 66
<211> LENGTH: 4
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (4)..(4)
<223> OTHER INFORMATION: Xaa = Any amino acid

<400> SEQUENCE: 66

Leu Gly Pro Xaa
1

<210> SEQ ID NO 67
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (6)..(6)
<223> OTHER INFORMATION: Xaa = Any amino acid

<400> SEQUENCE: 67

Gly Pro Ile Gly Pro Xaa
1               5

<210> SEQ ID NO 68
<211> LENGTH: 5
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (5)..(5)
<223> OTHER INFORMATION: Xaa = Any amino acid

<400> SEQUENCE: 68

Ala Pro Gly Leu Xaa
1               5

<210> SEQ ID NO 69
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 69

Pro Leu Gly Pro Asp Arg Xaa
1               5
```

```
<210> SEQ ID NO 70
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 70

Pro Leu Gly Leu Leu Gly Xaa
1               5

<210> SEQ ID NO 71
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 71

Pro Gln Gly Ile Ala Gly Trp
1               5

<210> SEQ ID NO 72
<211> LENGTH: 5
<212> TYPE: PRT
<213> ORGANISM: Artificial Sequence
<220> FEATURE:
<223> OTHER INFORMATION: Collagenase cleavable linker

<400> SEQUENCE: 72

Pro Leu Gly Cys His
1               5

<210> SEQ ID NO 73
<211> LENGTH: 6
<212> TYPE: PRT
<213> ORGANISM: Artificial Sequence
<220> FEATURE:
<223> OTHER INFORMATION: Collagenase cleavable linker

<400> SEQUENCE: 73

Pro Leu Gly Leu Tyr Ala
1               5

<210> SEQ ID NO 74
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 74

Pro Leu Ala Leu Trp Ala Arg
1               5

<210> SEQ ID NO 75
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 75

Pro Leu Ala Tyr Trp Ala Arg
```

```
1               5

<210> SEQ ID NO 76
<211> LENGTH: 7
<212> TYPE: PRT
<213> ORGANISM: Artificial Sequence
<220> FEATURE:
<223> OTHER INFORMATION: Stromelysin cleavable linker

<400> SEQUENCE: 76

Pro Tyr Ala Tyr Tyr Met Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Gelatinase cleavable linker

<400> SEQUENCE: 77

Pro Leu Gly Met Tyr Ser Arg
1               5

<210> SEQ ID NO 78
<211> LENGTH: 4
<212> TYPE: PRT
<213> ORGANISM: Artificial Sequence
<220> FEATURE:
<223> OTHER INFORMATION: Angiotensin converting enzyme cleavable linker

<400> SEQUENCE: 78

Gly Asp Lys Pro
1

<210> SEQ ID NO 79
<211> LENGTH: 5
<212> TYPE: PRT
<213> ORGANISM: Artificial Sequence
<220> FEATURE:
<223> OTHER INFORMATION: Angiotensin converting enzyme cleavable linker

<400> SEQUENCE: 79

Gly Ser Asp Lys Pro
1               5

<210> SEQ ID NO 80
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 80

Ala Leu Ala Leu
1

<210> SEQ ID NO 81
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 81

Gly Phe Leu Gly
1
```

<210> SEQ ID NO 82
<211> LENGTH: 1171
<212> TYPE: PRT
<213> ORGANISM: Artificial Sequence
<220> FEATURE:
<223> OTHER INFORMATION: TZM heavy chain - linker - p97 fusion protein

<400> SEQUENCE: 82

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365
```

-continued

```
Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Gly Gly Gly Ser Gly Gly Gly Gly Ser
465                 470                 475                 480

Gly Met Glu Val Arg Trp Cys Ala Thr Ser Asp Pro Glu Gln His Lys
                485                 490                 495

Cys Gly Asn Met Ser Glu Ala Phe Arg Glu Ala Gly Ile Gln Pro Ser
            500                 505                 510

Leu Leu Cys Val Arg Gly Thr Ser Ala Asp His Cys Val Gln Leu Ile
        515                 520                 525

Ala Ala Gln Glu Ala Asp Ala Ile Thr Leu Asp Gly Gly Ala Ile Tyr
    530                 535                 540

Glu Ala Gly Lys Glu His Gly Leu Lys Pro Val Val Gly Glu Val Tyr
545                 550                 555                 560

Asp Gln Glu Val Gly Thr Ser Tyr Tyr Ala Val Ala Val Val Arg Arg
                565                 570                 575

Ser Ser His Val Thr Ile Asp Thr Leu Lys Gly Val Lys Ser Cys His
            580                 585                 590

Thr Gly Ile Asn Arg Thr Val Gly Trp Asn Val Pro Val Gly Tyr Leu
        595                 600                 605

Val Glu Ser Gly Arg Leu Ser Val Met Gly Cys Asp Val Leu Lys Ala
    610                 615                 620

Val Ser Asp Tyr Phe Gly Gly Ser Cys Val Pro Gly Ala Gly Glu Thr
625                 630                 635                 640

Ser Tyr Ser Glu Ser Leu Cys Arg Leu Cys Arg Gly Asp Ser Ser Gly
                645                 650                 655

Glu Gly Val Cys Asp Lys Ser Pro Leu Glu Arg Tyr Tyr Asp Tyr Ser
            660                 665                 670

Gly Ala Phe Arg Cys Leu Ala Glu Gly Ala Gly Asp Val Ala Phe Val
        675                 680                 685

Lys His Ser Thr Val Leu Glu Asn Thr Asp Gly Lys Thr Leu Pro Ser
    690                 695                 700

Trp Gly Gln Ala Leu Leu Ser Gln Asp Phe Glu Leu Leu Cys Arg Asp
705                 710                 715                 720

Gly Ser Arg Ala Asp Val Thr Glu Trp Arg Gln Cys His Leu Ala Arg
                725                 730                 735

Val Pro Ala His Ala Val Val Val Arg Ala Asp Thr Asp Gly Gly Leu
            740                 745                 750

Ile Phe Arg Leu Leu Asn Glu Gly Gln Arg Leu Phe Ser His Glu Gly
        755                 760                 765

Ser Ser Phe Gln Met Phe Ser Ser Glu Ala Tyr Gly Gln Lys Asp Leu
    770                 775                 780
```

```
Leu Phe Lys Asp Ser Thr Ser Glu Leu Val Pro Ile Ala Thr Gln Thr
785                 790                 795                 800

Tyr Glu Ala Trp Leu Gly His Glu Tyr Leu His Ala Met Lys Gly Leu
            805                 810                 815

Leu Cys Asp Pro Asn Arg Leu Pro Pro Tyr Leu Arg Trp Cys Val Leu
        820                 825                 830

Ser Thr Pro Glu Ile Gln Lys Cys Gly Asp Met Ala Val Ala Phe Arg
    835                 840                 845

Arg Gln Arg Leu Lys Pro Glu Ile Gln Cys Val Ser Ala Lys Ser Pro
850                 855                 860

Gln His Cys Met Glu Arg Ile Gln Ala Glu Gln Val Asp Ala Val Thr
865                 870                 875                 880

Leu Ser Gly Glu Asp Ile Tyr Thr Ala Gly Lys Thr Tyr Gly Leu Val
            885                 890                 895

Pro Ala Ala Gly Glu His Tyr Ala Pro Glu Asp Ser Ser Asn Ser Tyr
            900                 905                 910

Tyr Val Val Ala Val Arg Arg Asp Ser Ser His Ala Phe Thr Leu
            915                 920                 925

Asp Glu Leu Arg Gly Lys Arg Ser Cys His Ala Gly Phe Gly Ser Pro
930                 935                 940

Ala Gly Trp Asp Val Pro Val Gly Ala Leu Ile Gln Arg Gly Phe Ile
945                 950                 955                 960

Arg Pro Lys Asp Cys Asp Val Leu Thr Ala Val Ser Glu Phe Phe Asn
            965                 970                 975

Ala Ser Cys Val Pro Val Asn Asn Pro Lys Asn Tyr Pro Ser Ser Leu
            980                 985                 990

Cys Ala Leu Cys Val Gly Asp Glu Gln Gly Arg Asn Lys Cys Val Gly
        995                 1000                1005

Asn Ser Gln Glu Arg Tyr Tyr Gly Tyr Arg Gly Ala Phe Arg Cys
    1010                1015                1020

Leu Val Glu Asn Ala Gly Asp Val Ala Phe Val Arg His Thr Thr
    1025                1030                1035

Val Phe Asp Asn Thr Asn Gly His Asn Ser Glu Pro Trp Ala Ala
    1040                1045                1050

Glu Leu Arg Ser Glu Asp Tyr Glu Leu Leu Cys Pro Asn Gly Ala
    1055                1060                1065

Arg Ala Glu Val Ser Gln Phe Ala Ala Cys Asn Leu Ala Gln Ile
    1070                1075                1080

Pro Pro His Ala Val Met Val Arg Pro Asp Thr Asn Ile Phe Thr
    1085                1090                1095

Val Tyr Gly Leu Leu Asp Lys Ala Gln Asp Leu Phe Gly Asp Asp
    1100                1105                1110

His Asn Lys Asn Gly Phe Lys Met Phe Asp Ser Ser Asn Tyr His
    1115                1120                1125

Gly Gln Asp Leu Leu Phe Lys Asp Ala Thr Val Arg Ala Val Pro
    1130                1135                1140

Val Gly Glu Lys Thr Thr Tyr Arg Gly Trp Leu Gly Leu Asp Tyr
    1145                1150                1155

Val Ala Ala Leu Glu Gly Met Ser Ser Gln Gln Cys Ser
    1160                1165                1170

<210> SEQ ID NO 83
<211> LENGTH: 234
<212> TYPE: PRT
```

<213> ORGANISM: Homo sapiens

<400> SEQUENCE: 83

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 84
<211> LENGTH: 493
<212> TYPE: PRT
<213> ORGANISM: Artificial Sequence
<220> FEATURE:
<223> OTHER INFORMATION: p97 fragment - linker - TZM heavy chain fusion protein

<400> SEQUENCE: 84

```
Met Glu Thr Asp Thr Leu Leu Leu Trp Val Leu Leu Leu Trp Val Pro
1               5                   10                  15

Gly Ser Thr Gly Asp Ser Ser His Ala Phe Thr Leu Asp Glu Leu Arg
            20                  25                  30

Tyr Gly Gly Gly Ser Gly Gly Gly Ser Glu Val Gln Leu Val
        35                  40                  45

Glu Ser Gly Gly Gly Leu Val Gln Pro Gly Gly Ser Leu Arg Leu Ser
50                  55                  60

Cys Ala Ala Ser Gly Phe Asn Ile Lys Asp Thr Tyr Ile His Trp Val
65                  70                  75                  80

Arg Gln Ala Pro Gly Lys Gly Leu Glu Trp Val Ala Arg Ile Tyr Pro
                85                  90                  95

Thr Asn Gly Tyr Thr Arg Tyr Ala Asp Ser Val Lys Gly Arg Phe Thr
```

```
            100                 105                 110
Ile Ser Ala Asp Thr Ser Lys Asn Thr Ala Tyr Leu Gln Met Asn Ser
        115                 120                 125

Leu Arg Ala Glu Asp Thr Ala Val Tyr Tyr Cys Ser Arg Trp Gly Gly
        130                 135                 140

Asp Gly Phe Tyr Ala Met Asp Tyr Trp Gly Gln Gly Thr Leu Val Thr
145                 150                 155                 160

Val Ser Ser Ala Ser Thr Lys Gly Pro Ser Val Phe Pro Leu Ala Pro
                165                 170                 175

Ser Ser Lys Ser Thr Ser Gly Gly Thr Ala Ala Leu Gly Cys Leu Val
            180                 185                 190

Lys Asp Tyr Phe Pro Glu Pro Val Thr Val Ser Trp Asn Ser Gly Ala
        195                 200                 205

Leu Thr Ser Gly Val His Thr Phe Pro Ala Val Leu Gln Ser Ser Gly
        210                 215                 220

Leu Tyr Ser Leu Ser Ser Val Val Thr Val Pro Ser Ser Ser Leu Gly
225                 230                 235                 240

Thr Gln Thr Tyr Ile Cys Asn Val Asn His Lys Pro Ser Asn Thr Lys
                245                 250                 255

Val Asp Lys Lys Val Glu Pro Lys Ser Cys Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
        290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
        370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
        450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 85
<211> LENGTH: 234
<212> TYPE: PRT
<213> ORGANISM: Homo sapiens
```

<400> SEQUENCE: 85

| Met | Glu | Thr | Asp | Thr | Leu | Leu | Leu | Trp | Val | Leu | Leu | Leu | Trp | Val | Pro |
|---|---|---|---|---|---|---|---|---|---|---|---|---|---|---|---|
| 1 | | | | 5 | | | | | 10 | | | | | 15 | |

Gly Ser Thr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
                100                 105                 110

Thr Thr Pro Pro Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 86
<211> LENGTH: 492
<212> TYPE: PRT
<213> ORGANISM: Artificial Sequence
<220> FEATURE:
<223> OTHER INFORMATION: TZM heavy chain - llinker - p97 fragment fusion
      protein

<400> SEQUENCE: 86

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Ile Lys Asp Thr Tyr Ile His Trp Val Arg Gln Ala Pro Gly Lys Gly
        50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Asp Gly Phe Tyr Ala Met Asp
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys Gly Gly Gly Ser Gly Gly Gly Gly Gly Ser
465                 470                 475                 480

Asp Ser Ser His Ala Phe Thr Leu Asp Glu Leu Arg
                485                 490

<210> SEQ ID NO 87
<211> LENGTH: 234
<212> TYPE: PRT
<213> ORGANISM: Homo sapiens

<400> SEQUENCE: 87

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 88
<211> LENGTH: 1177
<212> TYPE: PRT
<213> ORGANISM: Artificial Sequence
<220> FEATURE:
<223> OTHER INFORMATION: TZM heavy chain - linker - p97 fusion protein

<400> SEQUENCE: 88

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
```

```
             115                 120                 125
Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
    450                 455                 460

Ser Leu Ser Pro Gly Lys Gly Gly Gly Ser Gly Gly Gly Gly Ser
465                 470                 475                 480

Gly Gly Gly Gly Ser Gly Met Glu Val Arg Trp Cys Ala Thr Ser Asp
                485                 490                 495

Pro Glu Gln His Lys Cys Gly Asn Met Ser Glu Ala Phe Arg Glu Ala
                500                 505                 510

Gly Ile Gln Pro Ser Leu Leu Cys Val Arg Gly Thr Ser Ala Asp His
                515                 520                 525

Cys Val Gln Leu Ile Ala Ala Gln Glu Ala Asp Ala Ile Thr Leu Asp
    530                 535                 540
```

```
Gly Gly Ala Ile Tyr Glu Ala Gly Lys Glu His Gly Leu Lys Pro Val
545                 550                 555                 560

Val Gly Glu Val Tyr Asp Gln Glu Val Gly Thr Ser Tyr Tyr Ala Val
                565                 570                 575

Ala Val Val Arg Arg Ser Ser His Val Thr Ile Asp Thr Leu Lys Gly
            580                 585                 590

Val Lys Ser Cys His Thr Gly Ile Asn Arg Thr Val Gly Trp Asn Val
        595                 600                 605

Pro Val Gly Tyr Leu Val Glu Ser Gly Arg Leu Ser Val Met Gly Cys
    610                 615                 620

Asp Val Leu Lys Ala Val Ser Asp Tyr Phe Gly Gly Ser Cys Val Pro
625                 630                 635                 640

Gly Ala Gly Glu Thr Ser Tyr Ser Glu Ser Leu Cys Arg Leu Cys Arg
                645                 650                 655

Gly Asp Ser Ser Gly Glu Gly Val Cys Asp Lys Ser Pro Leu Glu Arg
            660                 665                 670

Tyr Tyr Asp Tyr Ser Gly Ala Phe Arg Cys Leu Ala Glu Gly Ala Gly
        675                 680                 685

Asp Val Ala Phe Val Lys His Ser Thr Val Leu Glu Asn Thr Asp Gly
    690                 695                 700

Lys Thr Leu Pro Ser Trp Gly Gln Ala Leu Leu Ser Gln Asp Phe Glu
705                 710                 715                 720

Leu Leu Cys Arg Asp Gly Ser Arg Ala Asp Val Thr Glu Trp Arg Gln
                725                 730                 735

Cys His Leu Ala Arg Val Pro Ala His Ala Val Val Arg Ala Asp
            740                 745                 750

Thr Asp Gly Gly Leu Ile Phe Arg Leu Leu Asn Glu Gly Gln Arg Leu
        755                 760                 765

Phe Ser His Glu Gly Ser Ser Phe Gln Met Phe Ser Ser Glu Ala Tyr
    770                 775                 780

Gly Gln Lys Asp Leu Leu Phe Lys Asp Ser Thr Ser Glu Leu Val Pro
785                 790                 795                 800

Ile Ala Thr Gln Thr Tyr Glu Ala Trp Leu Gly His Glu Tyr Leu His
                805                 810                 815

Ala Met Lys Gly Leu Leu Cys Asp Pro Asn Arg Leu Pro Pro Tyr Leu
            820                 825                 830

Arg Trp Cys Val Leu Ser Thr Pro Glu Ile Gln Lys Cys Gly Asp Met
        835                 840                 845

Ala Val Ala Phe Arg Arg Gln Arg Leu Lys Pro Glu Ile Gln Cys Val
    850                 855                 860

Ser Ala Lys Ser Pro Gln His Cys Met Glu Arg Ile Gln Ala Glu Gln
865                 870                 875                 880

Val Asp Ala Val Thr Leu Ser Gly Glu Asp Ile Tyr Thr Ala Gly Lys
                885                 890                 895

Thr Tyr Gly Leu Val Pro Ala Ala Gly Glu His Tyr Ala Pro Glu Asp
            900                 905                 910

Ser Ser Asn Ser Tyr Tyr Val Val Ala Val Val Arg Arg Asp Ser Ser
        915                 920                 925

His Ala Phe Thr Leu Asp Glu Leu Arg Gly Lys Arg Ser Cys His Ala
    930                 935                 940

Gly Phe Gly Ser Pro Ala Gly Trp Asp Val Pro Val Gly Ala Leu Ile
945                 950                 955                 960
```

Gln Arg Gly Phe Ile Arg Pro Lys Asp Cys Asp Val Leu Thr Ala Val
            965                 970                 975

Ser Glu Phe Phe Asn Ala Ser Cys Val Pro Val Asn Asn Pro Lys Asn
            980                 985                 990

Tyr Pro Ser Ser Leu Cys Ala Leu Cys Val Gly Asp Glu Gln Gly Arg
            995                 1000                1005

Asn Lys Cys Val Gly Asn Ser Gln Glu Arg Tyr Tyr Gly Tyr Arg
        1010                1015                1020

Gly Ala Phe Arg Cys Leu Val Glu Asn Ala Gly Asp Val Ala Phe
        1025                1030                1035

Val Arg His Thr Thr Val Phe Asp Asn Thr Asn Gly His Asn Ser
        1040                1045                1050

Glu Pro Trp Ala Ala Glu Leu Arg Ser Glu Asp Tyr Glu Leu Leu
        1055                1060                1065

Cys Pro Asn Gly Ala Arg Ala Glu Val Ser Gln Phe Ala Ala Cys
        1070                1075                1080

Asn Leu Ala Gln Ile Pro Pro His Ala Val Met Val Arg Pro Asp
        1085                1090                1095

Thr Asn Ile Phe Thr Val Tyr Gly Leu Leu Asp Lys Ala Gln Asp
        1100                1105                1110

Leu Phe Gly Asp Asp His Asn Lys Asn Gly Phe Lys Met Phe Asp
        1115                1120                1125

Ser Ser Asn Tyr His Gly Gln Asp Leu Leu Phe Lys Asp Ala Thr
        1130                1135                1140

Val Arg Ala Val Pro Val Gly Glu Lys Thr Thr Tyr Arg Gly Trp
        1145                1150                1155

Leu Gly Leu Asp Tyr Val Ala Ala Leu Glu Gly Met Ser Ser Gln
        1160                1165                1170

Gln Cys Ser Gly
        1175

<210> SEQ ID NO 89
<211> LENGTH: 234
<212> TYPE: PRT
<213> ORGANISM: Homo sapiens

<400> SEQUENCE: 89

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

```
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 90
<211> LENGTH: 499
<212> TYPE: PRT
<213> ORGANISM: Artificial Sequence
<220> FEATURE:
<223> OTHER INFORMATION: TZM heavy chain - linker - p97 fragment fusion
      protein

<400> SEQUENCE: 90

Met Glu Thr Asp Thr Leu Leu Leu Trp Val Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
```

```
            260                 265                 270
Asp Thr Leu Met Ile Ser Arg Thr Pro Glu Val Thr Cys Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys Glu Ala Ala Ala Lys Glu Ala Ala Ala
465                 470                 475                 480

Lys Glu Ala Ala Ala Lys Asp Ser His Ala Phe Thr Leu Asp Glu
                485                 490                 495

Leu Arg Tyr

<210> SEQ ID NO 91
<211> LENGTH: 262
<212> TYPE: PRT
<213> ORGANISM: Artificial Sequence
<220> FEATURE:
<223> OTHER INFORMATION: TZM light chain - linker - p97 fragment fusion
      protein

<400> SEQUENCE: 91

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
```

```
                    115                 120                 125
Thr Val Ala Ala Pro Ser Val Phe Ile Phe Pro Pro Ser Asp Glu Gln
                130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys Glu Ala Ala Ala Lys Glu
225                 230                 235                 240

Ala Ala Ala Lys Glu Ala Ala Ala Lys Asp Ser Ser His Ala Phe Thr
                245                 250                 255

Leu Asp Glu Leu Arg Tyr
            260

<210> SEQ ID NO 92
<211> LENGTH: 499
<212> TYPE: PRT
<213> ORGANISM: Artificial Sequence
<220> FEATURE:
<223> OTHER INFORMATION: TZM heavy chain - linker - p97 fragment

<400> SEQUENCE: 92

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Ile Lys Asp Thr Tyr Ile His Trp Val Arg Gln Ala Pro Gly Lys Gly
        50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
                100                 105                 110

Val Tyr Tyr Cys Ser Arg Trp Gly Gly Asp Gly Phe Tyr Ala Met Asp
            115                 120                 125

Tyr Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
```

```
            210                 215                 220
Val Asn His Lys Pro Ser Asn Thr Lys Val Asp Lys Lys Val Glu Pro
225                 230                 235                 240

Pro Lys Ser Cys Asp Lys Thr His Thr Cys Pro Pro Cys Pro Ala Pro
                    245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys Glu Ala Ala Lys Glu Ala Ala Ala
465                 470                 475                 480

Lys Glu Ala Ala Ala Lys Asp Ser Ser His Ala Phe Thr Leu Asp Glu
                485                 490                 495

Leu Arg Tyr

<210> SEQ ID NO 93
<211> LENGTH: 234
<212> TYPE: PRT
<213> ORGANISM: Homo sapiens

<400> SEQUENCE: 93

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
        50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
```

```
                    85                  90                  95
Ser Leu Gln Pro Glu Asp Phe Ala Thr Tyr Tyr Cys Gln Gln His Tyr
                100                 105                 110

Thr Thr Pro Pro Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 94
<211> LENGTH: 471
<212> TYPE: PRT
<213> ORGANISM: Artificial Sequence
<220> FEATURE:
<223> OTHER INFORMATION: TZM heavy chain - linker - p97 fragment fusion
      protein

<400> SEQUENCE: 94

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

Val Thr Val Pro Ser Ser Leu Gly Thr Gln Thr Tyr Ile Cys Asn
210                 215                 220

Val Asn His Lys Pro Ser Asn Thr Lys Val Asp Lys Val Glu Pro
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 95
<211> LENGTH: 262
<212> TYPE: PRT
<213> ORGANISM: Artificial Sequence
<220> FEATURE:
<223> OTHER INFORMATION: TZM light chain - linker - p97 fragment fusion
      protein

<400> SEQUENCE: 95

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

```
Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Glu Ala Ala Ala Lys Glu
225                 230                 235                 240

Ala Ala Ala Lys Glu Ala Ala Ala Lys Asp Ser Ser His Ala Phe Thr
                245                 250                 255

Leu Asp Glu Leu Arg Tyr
            260

<210> SEQ ID NO 96
<211> LENGTH: 1151
<212> TYPE: PRT
<213> ORGANISM: Artificial Sequence
<220> FEATURE:
<223> OTHER INFORMATION: TZM heavy chain - linker - p97 fusion protein

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys Gly Gly Gly Gly Ser Gly Gly Gly Ser Gly Met Glu Val
450                 455                 460

Arg Trp Cys Ala Thr Ser Asp Pro Glu Gln His Lys Cys Gly Asn Met
465                 470                 475                 480

Ser Glu Ala Phe Arg Glu Ala Gly Ile Gln Pro Ser Leu Leu Cys Val
            485                 490                 495

Arg Gly Thr Ser Ala Asp His Cys Val Gln Leu Ile Ala Ala Gln Glu
        500                 505                 510

Ala Asp Ala Ile Thr Leu Asp Gly Gly Ala Ile Tyr Glu Ala Gly Lys
    515                 520                 525

Glu His Gly Leu Lys Pro Val Val Gly Glu Val Tyr Asp Gln Glu Val
530                 535                 540

Gly Thr Ser Tyr Tyr Ala Val Ala Val Val Arg Ser Ser His Val
545                 550                 555                 560

Thr Ile Asp Thr Leu Lys Gly Val Lys Ser Cys His Thr Gly Ile Asn
            565                 570                 575

Arg Thr Val Gly Trp Asn Val Pro Val Gly Tyr Leu Val Glu Ser Gly
        580                 585                 590

Arg Leu Ser Val Met Gly Cys Asp Val Leu Lys Ala Val Ser Asp Tyr
    595                 600                 605
```

```
Phe Gly Gly Ser Cys Val Pro Gly Ala Gly Glu Thr Ser Tyr Ser Glu
    610             615                 620

Ser Leu Cys Arg Leu Cys Arg Gly Asp Ser Ser Gly Glu Gly Val Cys
625             630                 635                 640

Asp Lys Ser Pro Leu Glu Arg Tyr Tyr Asp Tyr Ser Gly Ala Phe Arg
                645                 650                 655

Cys Leu Ala Glu Gly Ala Gly Asp Val Ala Phe Val Lys His Ser Thr
            660                 665                 670

Val Leu Glu Asn Thr Asp Gly Lys Thr Leu Pro Ser Trp Gly Gln Ala
            675                 680                 685

Leu Leu Ser Gln Asp Phe Glu Leu Leu Cys Arg Asp Gly Ser Arg Ala
            690                 695                 700

Asp Val Thr Glu Trp Arg Gln Cys His Leu Ala Arg Val Pro Ala His
705             710                 715                 720

Ala Val Val Val Arg Ala Asp Thr Asp Gly Gly Leu Ile Phe Arg Leu
                725                 730                 735

Leu Asn Glu Gly Gln Arg Leu Phe Ser His Gly Ser Ser Phe Gln
            740                 745                 750

Met Phe Ser Ser Glu Ala Tyr Gly Gln Lys Asp Leu Leu Phe Lys Asp
    755                 760                 765

Ser Thr Ser Glu Leu Val Pro Ile Ala Thr Gln Thr Tyr Glu Ala Trp
770                 775                 780

Leu Gly His Glu Tyr Leu His Ala Met Lys Gly Leu Leu Cys Asp Pro
785                 790                 795                 800

Asn Arg Leu Pro Pro Tyr Leu Arg Trp Cys Val Leu Ser Thr Pro Glu
                805                 810                 815

Ile Gln Lys Cys Gly Asp Met Ala Val Ala Phe Arg Arg Gln Arg Leu
            820                 825                 830

Lys Pro Glu Ile Gln Cys Val Ser Ala Lys Ser Pro Gln His Cys Met
            835                 840                 845

Glu Arg Ile Gln Ala Glu Gln Val Asp Ala Val Thr Leu Ser Gly Glu
    850                 855                 860

Asp Ile Tyr Thr Ala Gly Lys Thr Tyr Gly Leu Val Pro Ala Ala Gly
865                 870                 875                 880

Glu His Tyr Ala Pro Glu Asp Ser Ser Asn Ser Tyr Tyr Val Val Ala
            885                 890                 895

Val Val Arg Arg Asp Ser Ser His Ala Phe Thr Leu Asp Glu Leu Arg
            900                 905                 910

Gly Lys Arg Ser Cys His Ala Gly Phe Gly Ser Pro Ala Gly Trp Asp
            915                 920                 925

Val Pro Val Gly Ala Leu Ile Gln Arg Gly Phe Ile Arg Pro Lys Asp
    930                 935                 940

Cys Asp Val Leu Thr Ala Val Ser Glu Phe Phe Asn Ala Ser Cys Val
945                 950                 955                 960

Pro Val Asn Asn Pro Lys Asn Tyr Pro Ser Ser Leu Cys Ala Leu Cys
                965                 970                 975

Val Gly Asp Glu Gln Gly Arg Asn Lys Cys Val Gly Asn Ser Gln Glu
            980                 985                 990

Arg Tyr Tyr Gly Tyr Arg Gly Ala  Phe Arg Cys Leu Val  Glu Asn Ala
            995                 1000                1005

Gly Asp  Val Ala Phe Val Arg  His Thr Thr Val Phe  Asp Asn Thr
        1010                1015                1020

Asn Gly His Asn Ser Glu Pro  Trp Ala Ala Glu Leu  Arg Ser Glu
```

```
              1025                1030                1035

Asp  Tyr  Glu  Leu  Leu  Cys  Pro  Asn  Gly  Ala  Arg  Ala  Glu  Val  Ser
          1040                1045                1050

Gln  Phe  Ala  Ala  Cys  Asn  Leu  Ala  Gln  Ile  Pro  Pro  His  Ala  Val
     1055                1060                1065

Met  Val  Arg  Pro  Asp  Thr  Asn  Ile  Phe  Thr  Val  Tyr  Gly  Leu  Leu
     1070                1075                1080

Asp  Lys  Ala  Gln  Asp  Leu  Phe  Gly  Asp  Asp  His  Asn  Lys  Asn  Gly
          1085                1090                1095

Phe  Lys  Met  Phe  Asp  Ser  Ser  Asn  Tyr  His  Gly  Gln  Asp  Leu  Leu
     1100                1105                1110

Phe  Lys  Asp  Ala  Thr  Val  Arg  Ala  Val  Pro  Val  Gly  Glu  Lys  Thr
     1115                1120                1125

Thr  Tyr  Arg  Gly  Trp  Leu  Gly  Leu  Asp  Tyr  Val  Ala  Ala  Leu  Glu
          1130                1135                1140

Gly  Met  Ser  Ser  Gln  Gln  Cys  Ser
          1145                1150

<210> SEQ ID NO 97
<211> LENGTH: 1157
<212> TYPE: PRT
<213> ORGANISM: Artificial Sequence
<220> FEATURE:
<223> OTHER INFORMATION: TZM heavy chain - linker - p97 fusion protein

<400> SEQUENCE: 97

Glu  Val  Gln  Leu  Val  Glu  Ser  Gly  Gly  Gly  Leu  Val  Gln  Pro  Gly  Gly
1                 5                   10                  15

Ser  Leu  Arg  Leu  Ser  Cys  Ala  Ala  Ser  Gly  Phe  Asn  Ile  Lys  Asp  Thr
            20                  25                  30

Tyr  Ile  His  Trp  Val  Arg  Gln  Ala  Pro  Gly  Lys  Gly  Leu  Glu  Trp  Val
        35                  40                  45

Ala  Arg  Ile  Tyr  Pro  Thr  Asn  Gly  Tyr  Thr  Arg  Tyr  Ala  Asp  Ser  Val
    50                  55                  60

Lys  Gly  Arg  Phe  Thr  Ile  Ser  Ala  Asp  Thr  Ser  Lys  Asn  Thr  Ala  Tyr
65                  70                  75                  80

Leu  Gln  Met  Asn  Ser  Leu  Arg  Ala  Glu  Asp  Thr  Ala  Val  Tyr  Tyr  Cys
                85                  90                  95

Ser  Arg  Trp  Gly  Gly  Asp  Gly  Phe  Tyr  Ala  Met  Asp  Tyr  Trp  Gly  Gln
            100                 105                 110

Gly  Thr  Leu  Val  Thr  Val  Ser  Ser  Ala  Ser  Thr  Lys  Gly  Pro  Ser  Val
        115                 120                 125

Phe  Pro  Leu  Ala  Pro  Ser  Ser  Lys  Ser  Thr  Ser  Gly  Gly  Thr  Ala  Ala
    130                 135                 140

Leu  Gly  Cys  Leu  Val  Lys  Asp  Tyr  Phe  Pro  Glu  Pro  Val  Thr  Val  Ser
145                 150                 155                 160

Trp  Asn  Ser  Gly  Ala  Leu  Thr  Ser  Gly  Val  His  Thr  Phe  Pro  Ala  Val
                165                 170                 175

Leu  Gln  Ser  Ser  Gly  Leu  Tyr  Ser  Leu  Ser  Ser  Val  Val  Thr  Val  Pro
            180                 185                 190

Ser  Ser  Ser  Leu  Gly  Thr  Gln  Thr  Tyr  Ile  Cys  Asn  Val  Asn  His  Lys
        195                 200                 205

Pro  Ser  Asn  Thr  Lys  Val  Asp  Lys  Lys  Val  Glu  Pro  Lys  Ser  Cys  Asp
    210                 215                 220

Lys  Thr  His  Thr  Cys  Pro  Pro  Cys  Pro  Ala  Pro  Glu  Leu  Leu  Gly  Gly
```

```
            225                 230                 235                 240
        Pro Ser Val Phe Leu Phe Pro Lys Pro Lys Asp Thr Leu Met Ile
                        245                 250                 255

Ser Arg Thr Pro Glu Val Thr Cys Val Val Asp Val Ser His Glu
                        260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                        355                 360                 365

Thr Cys Leu Val Lys Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly Lys Gly Gly Gly Gly Ser Gly Gly Gly Ser Gly Gly Gly Gly
                        450                 455                 460

Ser Gly Met Glu Val Arg Trp Cys Ala Thr Ser Asp Pro Glu Gln His
        465                 470                 475                 480

Lys Cys Gly Asn Met Ser Glu Ala Phe Arg Glu Ala Gly Ile Gln Pro
                        485                 490                 495

Ser Leu Leu Cys Val Arg Gly Thr Ser Ala Asp His Cys Val Gln Leu
                        500                 505                 510

Ile Ala Ala Gln Glu Ala Asp Ala Ile Thr Leu Asp Gly Gly Ala Ile
                        515                 520                 525

Tyr Glu Ala Gly Lys Glu His Gly Leu Lys Pro Val Val Gly Glu Val
                        530                 535                 540

Tyr Asp Gln Glu Val Gly Thr Ser Tyr Tyr Ala Val Ala Val Val Arg
        545                 550                 555                 560

Arg Ser Ser His Val Thr Ile Asp Thr Leu Lys Gly Val Lys Ser Cys
                        565                 570                 575

His Thr Gly Ile Asn Arg Thr Val Gly Trp Asn Val Pro Val Gly Tyr
                        580                 585                 590

Leu Val Glu Ser Gly Arg Leu Ser Val Met Gly Cys Asp Val Leu Lys
                        595                 600                 605

Ala Val Ser Asp Tyr Phe Gly Gly Ser Cys Val Pro Gly Ala Gly Glu
                        610                 615                 620

Thr Ser Tyr Ser Glu Ser Leu Cys Arg Leu Cys Arg Gly Asp Ser Ser
        625                 630                 635                 640

Gly Glu Gly Val Cys Asp Lys Ser Pro Leu Glu Arg Tyr Tyr Asp Tyr
                        645                 650                 655
```

```
Ser Gly Ala Phe Arg Cys Leu Ala Glu Gly Ala Gly Asp Val Ala Phe
            660                 665                 670

Val Lys His Ser Thr Val Leu Glu Asn Thr Asp Gly Lys Thr Leu Pro
            675                 680                 685

Ser Trp Gly Gln Ala Leu Leu Ser Gln Asp Phe Glu Leu Leu Cys Arg
            690                 695                 700

Asp Gly Ser Arg Ala Asp Val Thr Glu Trp Arg Gln Cys His Leu Ala
705                 710                 715                 720

Arg Val Pro Ala His Ala Val Val Arg Ala Asp Thr Asp Gly Gly
                725                 730                 735

Leu Ile Phe Arg Leu Leu Asn Glu Gly Gln Arg Leu Phe Ser His Glu
            740                 745                 750

Gly Ser Ser Phe Gln Met Phe Ser Ser Glu Ala Tyr Gly Gln Lys Asp
            755                 760                 765

Leu Leu Phe Lys Asp Ser Thr Ser Glu Leu Val Pro Ile Ala Thr Gln
            770                 775                 780

Thr Tyr Glu Ala Trp Leu Gly His Glu Tyr Leu His Ala Met Lys Gly
785                 790                 795                 800

Leu Leu Cys Asp Pro Asn Arg Leu Pro Pro Tyr Leu Arg Trp Cys Val
            805                 810                 815

Leu Ser Thr Pro Glu Ile Gln Lys Cys Gly Asp Met Ala Val Ala Phe
            820                 825                 830

Arg Arg Gln Arg Leu Lys Pro Glu Ile Gln Cys Val Ser Ala Lys Ser
            835                 840                 845

Pro Gln His Cys Met Glu Arg Ile Gln Ala Glu Gln Val Asp Ala Val
            850                 855                 860

Thr Leu Ser Gly Glu Asp Ile Tyr Thr Ala Gly Lys Thr Tyr Gly Leu
865                 870                 875                 880

Val Pro Ala Ala Gly Glu His Tyr Ala Pro Glu Asp Ser Ser Asn Ser
                885                 890                 895

Tyr Tyr Val Val Ala Val Arg Arg Asp Ser Ser His Ala Phe Thr
            900                 905                 910

Leu Asp Glu Leu Arg Gly Lys Arg Ser Cys His Ala Gly Phe Gly Ser
            915                 920                 925

Pro Ala Gly Trp Asp Val Pro Val Gly Ala Leu Ile Gln Arg Gly Phe
            930                 935                 940

Ile Arg Pro Lys Asp Cys Asp Val Leu Thr Ala Val Ser Glu Phe Phe
945                 950                 955                 960

Asn Ala Ser Cys Val Pro Val Asn Asn Pro Lys Asn Tyr Pro Ser Ser
                965                 970                 975

Leu Cys Ala Leu Cys Val Gly Asp Glu Gln Gly Arg Asn Lys Cys Val
            980                 985                 990

Gly Asn Ser Gln Glu Arg Tyr Tyr Gly Tyr Arg Gly Ala Phe Arg Cys
            995                1000                1005

Leu Val Glu Asn Ala Gly Asp Val Ala Phe Val Arg His Thr Thr
            1010                1015                1020

Val Phe Asp Asn Thr Asn Gly His Asn Ser Glu Pro Trp Ala Ala
            1025                1030                1035

Glu Leu Arg Ser Glu Asp Tyr Glu Leu Leu Cys Pro Asn Gly Ala
            1040                1045                1050

Arg Ala Glu Val Ser Gln Phe Ala Ala Cys Asn Leu Ala Gln Ile
            1055                1060                1065
```

```
Pro Pro His Ala Val Met Val Arg Pro Asp Thr Asn Ile Phe Thr
1070                1075                1080

Val Tyr Gly Leu Leu Asp Lys Ala Gln Asp Leu Phe Gly Asp Asp
    1085                1090                1095

His Asn Lys Asn Gly Phe Lys Met Phe Asp Ser Ser Asn Tyr His
    1100                1105                1110

Gly Gln Asp Leu Leu Phe Lys Asp Ala Thr Val Arg Ala Val Pro
    1115                1120                1125

Val Gly Glu Lys Thr Thr Tyr Arg Gly Trp Leu Gly Leu Asp Tyr
    1130                1135                1140

Val Ala Ala Leu Glu Gly Met Ser Ser Gln Gln Cys Ser Gly
    1145                1150                1155
```

<210> SEQ ID NO 98
<211> LENGTH: 473
<212> TYPE: PRT
<213> ORGANISM: Artificial Sequence
<220> FEATURE:
<223> OTHER INFORMATION: p97 fragment - linker - TZM heavy chain fusion
      protein

<400> SEQUENCE: 98

```
Asp Ser Ser His Ala Phe Thr Leu Asp Glu Leu Arg Tyr Gly Gly Gly
1               5                   10                  15

Gly Ser Gly Gly Gly Gly Ser Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asn Ile Lys Asp Thr Tyr Ile His Trp Val Arg Gln Ala Pro
    50                  55                  60

Gly Lys Gly Leu Glu Trp Val Ala Arg Ile Tyr Pro Thr Asn Gly Tyr
65                  70                  75                  80

Thr Arg Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
        115                 120                 125

Ala Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270
```

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
        340                 345                 350

Ala Leu Pro Ala Pro Ile Glu Lys Thr Ile Ser Lys Ala Lys Gly Gln
    355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
        420                 425                 430

Tyr Ser Lys Leu Thr Val Asp Lys Ser Arg Trp Gln Gln Gly Asn Val
    435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 99
<211> LENGTH: 472
<212> TYPE: PRT
<213> ORGANISM: Artificial Sequence
<220> FEATURE:
<223> OTHER INFORMATION: p97 fragment - linker - TZM heavy chain fusion
      protein

<400> SEQUENCE: 99

Asp Ser Ser His Ala Phe Thr Leu Asp Glu Leu Arg Gly Gly Gly Gly
1               5                   10                  15

Ser Gly Gly Gly Gly Ser Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asn Ile Lys Asp Thr Tyr Ile His Trp Val Arg Gln Ala Pro Gly
    50                  55                  60

Lys Gly Leu Glu Trp Val Ala Arg Ile Tyr Pro Thr Asn Gly Tyr Thr
65                  70                  75                  80

Arg Tyr Ala Asp Ser Val Lys Gly Arg Phe Thr Ile Ser Ala Asp Thr
                85                  90                  95

Ser Lys Asn Thr Ala Tyr Leu Gln Met Asn Ser Leu Arg Ala Glu Asp
            100                 105                 110

Thr Ala Val Tyr Tyr Cys Ser Arg Trp Gly Gly Asp Gly Phe Tyr Ala
        115                 120                 125

Met Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr

-continued

```
        145                 150                 155                 160
Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
                195                 200                 205

Ser Val Val Thr Val Pro Ser Ser Ser Leu Gly Thr Gln Thr Tyr Ile
            210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Asp Glu Leu Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Lys
465                 470
```

<210> SEQ ID NO 100
<211> LENGTH: 478
<212> TYPE: PRT
<213> ORGANISM: Artificial Sequence
<220> FEATURE:
<223> OTHER INFORMATION: p97 fragment - linker - TZM heavy chain fusion protein

<400> SEQUENCE: 100

```
Asp Ser Ser His Ala Phe Thr Leu Asp Glu Leu Arg Tyr Glu Ala Ala
1               5                   10                  15

Ala Lys Glu Ala Ala Ala Lys Glu Ala Ala Ala Lys Glu Val Gln Leu
            20                  25                  30
```

Val Glu Ser Gly Gly Gly Leu Val Gln Pro Gly Gly Ser Leu Arg Leu
             35                  40                  45
Ser Cys Ala Ala Ser Gly Phe Asn Ile Lys Asp Thr Tyr Ile His Trp
 50                  55                  60
Val Arg Gln Ala Pro Gly Lys Gly Leu Glu Trp Val Ala Arg Ile Tyr
 65                  70                  75                  80
Pro Thr Asn Gly Tyr Thr Arg Tyr Ala Asp Ser Val Lys Gly Arg Phe
                 85                  90                  95
Thr Ile Ser Ala Asp Thr Ser Lys Asn Thr Ala Tyr Leu Gln Met Asn
                100                 105                 110
Ser Leu Arg Ala Glu Asp Thr Ala Val Tyr Tyr Cys Ser Arg Trp Gly
             115                 120                 125
Gly Asp Gly Phe Tyr Ala Met Asp Tyr Trp Gly Gln Gly Thr Leu Val
130                 135                 140
Thr Val Ser Ser Ala Ser Thr Lys Gly Pro Ser Val Phe Pro Leu Ala
145                 150                 155                 160
Pro Ser Ser Lys Ser Thr Ser Gly Gly Thr Ala Ala Leu Gly Cys Leu
                165                 170                 175
Val Lys Asp Tyr Phe Pro Glu Pro Val Thr Val Ser Trp Asn Ser Gly
             180                 185                 190
Ala Leu Thr Ser Gly Val His Thr Phe Pro Ala Val Leu Gln Ser Ser
             195                 200                 205
Gly Leu Tyr Ser Leu Ser Ser Val Val Thr Val Pro Ser Ser Ser Leu
         210                 215                 220
Gly Thr Gln Thr Tyr Ile Cys Asn Val Asn His Lys Pro Ser Asn Thr
225                 230                 235                 240
Lys Val Asp Lys Lys Val Glu Pro Lys Ser Cys Asp Lys Thr His Thr
                245                 250                 255
Cys Pro Pro Cys Pro Ala Pro Glu Leu Leu Gly Gly Pro Ser Val Phe
             260                 265                 270
Leu Phe Pro Pro Lys Pro Lys Asp Thr Leu Met Ile Ser Arg Thr Pro
             275                 280                 285
Glu Val Thr Cys Val Val Val Asp Val Ser His Glu Asp Pro Glu Val
290                 295                 300
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
                325                 330                 335
Leu Thr Val Leu His Gln Asp Trp Leu Asn Gly Lys Glu Tyr Lys Cys
             340                 345                 350
Lys Val Ser Asn Lys Ala Leu Pro Ala Pro Ile Glu Lys Thr Ile Ser
             355                 360                 365
Lys Ala Lys Gly Gln Pro Arg Glu Pro Gln Val Tyr Thr Leu Pro Pro
         370                 375                 380
Ser Arg Asp Glu Leu Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Asp Ser Asp
             420                 425                 430
Gly Ser Phe Phe Leu Tyr Ser Lys Leu Thr Val Asp Lys Ser Arg Trp
             435                 440                 445
Gln Gln Gly Asn Val Phe Ser Cys Ser Val Met His Glu Ala Leu His

```
                450                 455                 460
Asn His Tyr Thr Gln Lys Ser Leu Ser Leu Ser Pro Gly Lys
465                 470                 475

<210> SEQ ID NO 101
<211> LENGTH: 477
<212> TYPE: PRT
<213> ORGANISM: Artificial Sequence
<220> FEATURE:
<223> OTHER INFORMATION: p97 fragment - linker - TZM heavy chain fusion
      protein

<400> SEQUENCE: 101

Asp Ser Ser His Ala Phe Thr Leu Asp Glu Leu Arg Glu Ala Ala
1               5                   10                  15

Lys Glu Ala Ala Lys Glu Ala Ala Ala Lys Glu Val Gln Leu Val
                20                  25                  30

Glu Ser Gly Gly Gly Leu Val Gln Pro Gly Gly Ser Leu Arg Leu Ser
            35                  40                  45

Cys Ala Ala Ser Gly Phe Asn Ile Lys Asp Thr Tyr Ile His Trp Val
50                  55                  60

Arg Gln Ala Pro Gly Lys Gly Leu Glu Trp Val Ala Arg Ile Tyr Pro
65                  70                  75                  80

Thr Asn Gly Tyr Thr Arg Tyr Ala Asp Ser Val Lys Gly Arg Phe Thr
                85                  90                  95

Ile Ser Ala Asp Thr Ser Lys Asn Thr Ala Tyr Leu Gln Met Asn Ser
            100                 105                 110

Leu Arg Ala Glu Asp Thr Ala Val Tyr Tyr Cys Ser Arg Trp Gly Gly
        115                 120                 125

Asp Gly Phe Tyr Ala Met Asp Tyr Trp Gly Gln Gly Thr Leu Val Thr
130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335
```

```
Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
        370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 102
<211> LENGTH: 463
<212> TYPE: PRT
<213> ORGANISM: Artificial Sequence
<220> FEATURE:
<223> OTHER INFORMATION: p97 fragment - TZM heavy chain fusion protein

<400> SEQUENCE: 102

Asp Ser Ser His Ala Phe Thr Leu Asp Glu Leu Arg Tyr Glu Val Gln
1               5                   10                  15

Leu Val Glu Ser Gly Gly Gly Leu Val Gln Pro Gly Gly Ser Leu Arg
            20                  25                  30

Leu Ser Cys Ala Ala Ser Gly Phe Asn Ile Lys Asp Thr Tyr Ile His
        35                  40                  45

Trp Val Arg Gln Ala Pro Gly Lys Gly Leu Glu Trp Val Ala Arg Ile
    50                  55                  60

Tyr Pro Thr Asn Gly Tyr Thr Arg Tyr Ala Asp Ser Val Lys Gly Arg
65                  70                  75                  80

Phe Thr Ile Ser Ala Asp Thr Ser Lys Asn Thr Ala Tyr Leu Gln Met
                85                  90                  95

Asn Ser Leu Arg Ala Glu Asp Thr Ala Val Tyr Tyr Cys Ser Arg Trp
            100                 105                 110

Gly Gly Asp Gly Phe Tyr Ala Met Asp Tyr Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220
```

-continued

```
Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 103
<211> LENGTH: 462
<212> TYPE: PRT
<213> ORGANISM: Artificial Sequence
<220> FEATURE:
<223> OTHER INFORMATION: p97 fragment - TZM heavy chain fusion protein

<400> SEQUENCE: 103

Asp Ser Ser His Ala Phe Thr Leu Asp Glu Leu Arg Glu Val Gln Leu
1               5                   10                  15

Val Glu Ser Gly Gly Leu Val Gln Pro Gly Gly Ser Leu Arg Leu
            20                  25                  30

Ser Cys Ala Ala Ser Gly Phe Asn Ile Lys Asp Thr Tyr Ile His Trp
        35                  40                  45

Val Arg Gln Ala Pro Gly Lys Gly Leu Glu Trp Val Ala Arg Ile Tyr
    50                  55                  60

Pro Thr Asn Gly Tyr Thr Arg Tyr Ala Asp Ser Val Lys Gly Arg Phe
65                  70                  75                  80

Thr Ile Ser Ala Asp Thr Ser Lys Asn Thr Ala Tyr Leu Gln Met Asn
                85                  90                  95

Ser Leu Arg Ala Glu Asp Thr Ala Val Tyr Tyr Cys Ser Arg Trp Gly
            100                 105                 110

Gly Asp Gly Phe Tyr Ala Met Asp Tyr Trp Gly Gln Gly Thr Leu Val
        115                 120                 125
```

```
Thr Val Ser Ser Ala Ser Thr Lys Gly Pro Ser Val Phe Pro Leu Ala
    130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
    210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
    450                 455                 460

<210> SEQ ID NO 104
<211> LENGTH: 472
<212> TYPE: PRT
<213> ORGANISM: Artificial Sequence
<220> FEATURE:
<223> OTHER INFORMATION: TZM heavy chain - linker - p97 fragment fusion
      protein

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
            85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

Gly Lys Gly Gly Gly Gly Ser Gly Gly Gly Gly Ser Asp Ser Ser His
    450                 455                 460

Ala Phe Thr Leu Asp Glu Leu Arg
465                 470

<210> SEQ ID NO 105
<211> LENGTH: 473
<212> TYPE: PRT
<213> ORGANISM: Artificial Sequence
<220> FEATURE:
<223> OTHER INFORMATION: TZM heavy chain - linker - p97 fragment fusion
      protein

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
             355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys Gly Gly Gly Gly Ser Gly Gly Gly Gly Ser Asp Ser Ser His
        450                 455                 460

Ala Phe Thr Leu Asp Glu Leu Arg Tyr
465                 470

<210> SEQ ID NO 106
<211> LENGTH: 479
<212> TYPE: PRT
<213> ORGANISM: Artificial Sequence
<220> FEATURE:
<223> OTHER INFORMATION: TZM heavy chain - linker - p97 fragment fusion
      protein

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys

```
                210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys Glu Ala Ala Lys Glu Ala Ala Lys Glu Ala Ala
                450                 455                 460

Ala Lys Asp Ser Ser His Ala Phe Thr Leu Asp Glu Leu Arg Tyr
465                 470                 475

<210> SEQ ID NO 107
<211> LENGTH: 478
<212> TYPE: PRT
<213> ORGANISM: Artificial Sequence
<220> FEATURE:
<223> OTHER INFORMATION: TZM heavy chain - linker - p97 fragment fusion
      protein

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
                50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Glu Ala Ala Lys Glu Ala Ala Lys Glu Ala Ala
    450                 455                 460

Ala Lys Asp Ser Ser His Ala Phe Thr Leu Asp Glu Leu Arg
465                 470                 475

<210> SEQ ID NO 108
<211> LENGTH: 462
<212> TYPE: PRT
<213> ORGANISM: Artificial Sequence
<220> FEATURE:
<223> OTHER INFORMATION: TZM heavy chain - p97 fragment fusion protein
```

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp

```
                     405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Asp Ser Ser His Ala Phe Thr Leu Asp Glu Leu Arg
            450                 455                 460

<210> SEQ ID NO 109
<211> LENGTH: 463
<212> TYPE: PRT
<213> ORGANISM: Artificial Sequence
<220> FEATURE:
<223> OTHER INFORMATION: TZM heavy chain - p97 fragment fusion protein

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                    305                 310                 315                 320
        Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                        355                 360                 365

Thr Cys Leu Val Lys Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly Lys Asp Ser Ser His Ala Phe Thr Leu Asp Glu Leu Arg Tyr
                        450                 455                 460

<210> SEQ ID NO 110
<211> LENGTH: 227
<212> TYPE: PRT
<213> ORGANISM: Artificial Sequence
<220> FEATURE:
<223> OTHER INFORMATION: Trastuzumab FL light chain - p97 fragment
      fusion protein

<400> SEQUENCE: 110

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Asp Val Asn Thr Ala
                        20                  25                  30

Val Ala Trp Tyr Gln Gln Lys Pro Gly Lys Ala Pro Lys Leu Leu Ile
                        35                  40                  45

Tyr Ser Ala Ser Phe Leu Tyr Ser Gly Val Pro Ser Arg Phe Ser Gly
                        50                  55                  60

Ser Arg Ser Gly Thr Asp Phe Thr Leu Thr Ile Ser Ser Leu Gln Pro
        65                  70                  75                  80

Glu Asp Phe Ala Thr Tyr Tyr Cys Gln Gln His Tyr Thr Thr Pro Pro
                        85                  90                  95

Thr Phe Gly Gln Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205
```

Phe Asn Arg Gly Glu Cys Asp Ser Ser His Ala Phe Thr Leu Asp Glu
            210                 215                 220

Leu Arg Tyr
225

<210> SEQ ID NO 111
<211> LENGTH: 242
<212> TYPE: PRT
<213> ORGANISM: Artificial Sequence
<220> FEATURE:
<223> OTHER INFORMATION: Trastuzumab FL light chain - linker - p97
      fragment fusion protein

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Ala Ala Ala Lys Glu Ala Ala Ala Lys
    210                 215                 220

Glu Ala Ala Ala Lys Asp Ser Ser His Ala Phe Thr Leu Asp Glu Leu
225                 230                 235                 240

Arg Tyr

<210> SEQ ID NO 112
<211> LENGTH: 237
<212> TYPE: PRT
<213> ORGANISM: Artificial Sequence
<220> FEATURE:
<223> OTHER INFORMATION: Trastuzumab FL light chain - linker - p97
      fragment fusion protein

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala

```
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Gly Ser Gly Gly Gly Gly Ser
    210                 215                 220
Asp Ser Ser His Ala Phe Thr Leu Asp Glu Leu Arg Tyr
225                 230                 235

<210> SEQ ID NO 113
<211> LENGTH: 226
<212> TYPE: PRT
<213> ORGANISM: Artificial Sequence
<220> FEATURE:
<223> OTHER INFORMATION: Trastuzumab FL light chain - p97 fragment
      fusion protein

<400> SEQUENCE: 113

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Ser Ser His Ala Phe Thr Leu Asp Glu
    210                 215                 220

Leu Arg
225

<210> SEQ ID NO 114
<211> LENGTH: 241
<212> TYPE: PRT
<213> ORGANISM: Artificial Sequence
<220> FEATURE:
<223> OTHER INFORMATION: Trastuzumab FL light chain - linker - p97
      fragment fusion protein

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Ala Ala Ala Lys Glu Ala Ala Ala Lys
    210                 215                 220

Glu Ala Ala Ala Lys Asp Ser His Ala Phe Thr Leu Asp Glu Leu
225                 230                 235                 240

Arg

<210> SEQ ID NO 115
<211> LENGTH: 237
```

```
<212> TYPE: PRT
<213> ORGANISM: Artificial Sequence
<220> FEATURE:
<223> OTHER INFORMATION: Trastuzumab FL light chain - linker - p97
      fragment fusion protein

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Asp Ser Ser His Ala Phe Thr Leu Asp Glu Leu Arg Tyr
225                 230                 235

<210> SEQ ID NO 116
<211> LENGTH: 227
<212> TYPE: PRT
<213> ORGANISM: Artificial Sequence
<220> FEATURE:
<223> OTHER INFORMATION: p97 fragment - Trastuzumab FL light chain
      fusion protein

<400> SEQUENCE: 116

Asp Ser Ser His Ala Phe Thr Leu Asp Glu Leu Arg Tyr Asp Ile Gln
1               5                   10                  15

Met Thr Gln Ser Pro Ser Ser Leu Ser Ala Ser Val Gly Asp Arg Val
            20                  25                  30

Thr Ile Thr Cys Arg Ala Ser Gln Asp Val Asn Thr Ala Val Ala Trp
        35                  40                  45

Tyr Gln Gln Lys Pro Gly Lys Ala Pro Lys Leu Leu Ile Tyr Ser Ala
    50                  55                  60

Ser Phe Leu Tyr Ser Gly Val Pro Ser Arg Phe Ser Gly Ser Arg Ser
65                  70                  75                  80
```

Gly Thr Asp Phe Thr Leu Thr Ile Ser Ser Leu Gln Pro Glu Asp Phe
            85                  90                  95

Ala Thr Tyr Tyr Cys Gln Gln His Tyr Thr Thr Pro Pro Thr Phe Gly
        100                 105                 110

Gln Gly Thr Lys Val Glu Ile Lys Arg Thr Val Ala Ala Pro Ser Val
        115                 120                 125

Phe Ile Phe Pro Pro Ser Asp Glu Gln Leu Lys Ser Gly Thr Ala Ser
130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 117
<211> LENGTH: 242
<212> TYPE: PRT
<213> ORGANISM: Artificial Sequence
<220> FEATURE:
<223> OTHER INFORMATION: p97 fragment - linker - Trastuzumab FL light
      chain fusion protein

<400> SEQUENCE: 117

Asp Ser Ser His Ala Phe Thr Leu Asp Glu Leu Arg Tyr Glu Ala Ala
1               5                   10                  15

Ala Lys Glu Ala Ala Ala Lys Glu Ala Ala Ala Lys Asp Ile Gln Met
            20                  25                  30

Thr Gln Ser Pro Ser Ser Leu Ser Ala Ser Val Gly Asp Arg Val Thr
        35                  40                  45

Ile Thr Cys Arg Ala Ser Gln Asp Val Asn Thr Ala Val Ala Trp Tyr
    50                  55                  60

Gln Gln Lys Pro Gly Lys Ala Pro Lys Leu Leu Ile Tyr Ser Ala Ser
65                  70                  75                  80

Phe Leu Tyr Ser Gly Val Pro Ser Arg Phe Ser Gly Ser Arg Ser Gly
                85                  90                  95

Thr Asp Phe Thr Leu Thr Ile Ser Ser Leu Gln Pro Glu Asp Phe Ala
            100                 105                 110

Thr Tyr Tyr Cys Gln Gln His Tyr Thr Thr Pro Pro Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

```
Leu Ser Lys Ala Asp Tyr Glu Lys His Lys Val Tyr Ala Cys Glu Val
        210                 215                 220

Thr His Gln Gly Leu Ser Ser Pro Val Thr Lys Ser Phe Asn Arg Gly
225                 230                 235                 240

Glu Cys

<210> SEQ ID NO 118
<211> LENGTH: 237
<212> TYPE: PRT
<213> ORGANISM: Artificial Sequence
<220> FEATURE:
<223> OTHER INFORMATION: p97 fragment - linker - Trastuzumab FL light
      chain fusion protein

<400> SEQUENCE: 118

Asp Ser Ser His Ala Phe Thr Leu Asp Glu Leu Arg Tyr Gly Gly Gly
1               5                   10                  15

Gly Ser Gly Gly Gly Gly Ser Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Asn Thr Ala Val Ala Trp Tyr Gln Gln Lys Pro Gly
    50                  55                  60

Lys Ala Pro Lys Leu Leu Ile Tyr Ser Ala Ser Phe Leu Tyr Ser Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 119
<211> LENGTH: 226
<212> TYPE: PRT
<213> ORGANISM: Artificial Sequence
<220> FEATURE:
<223> OTHER INFORMATION: p97 fragment - Trastuzumab FL light chain
      fusion protein

<400> SEQUENCE: 119

Asp Ser Ser His Ala Phe Thr Leu Asp Glu Leu Arg Asp Ile Gln Met
1               5                   10                  15
```

```
Thr Gln Ser Pro Ser Ser Leu Ser Ala Ser Val Gly Asp Arg Val Thr
                 20                  25                  30

Ile Thr Cys Arg Ala Ser Gln Asp Val Asn Thr Ala Val Ala Trp Tyr
             35                  40                  45

Gln Gln Lys Pro Gly Lys Ala Pro Lys Leu Leu Ile Tyr Ser Ala Ser
 50                  55                  60

Phe Leu Tyr Ser Gly Val Pro Ser Arg Phe Ser Gly Ser Arg Ser Gly
 65                  70                  75                  80

Thr Asp Phe Thr Leu Thr Ile Ser Ser Leu Gln Pro Glu Asp Phe Ala
                 85                  90                  95

Thr Tyr Tyr Cys Gln Gln His Tyr Thr Thr Pro Pro Thr Phe Gly Gln
            100                 105                 110

Gly Thr Lys Val Glu Ile Lys Arg Thr Val Ala Ala Pro Ser Val Phe
        115                 120                 125

Ile Phe Pro Pro Ser Asp Glu Gln Leu Lys Ser Gly Thr Ala Ser Val
130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225

<210> SEQ ID NO 120
<211> LENGTH: 241
<212> TYPE: PRT
<213> ORGANISM: Artificial Sequence
<220> FEATURE:
<223> OTHER INFORMATION: p97 fragment - linker - Trastuzumab FL light
      chain fusion protein

<400> SEQUENCE: 120

Asp Ser Ser His Ala Phe Thr Leu Asp Glu Leu Arg Glu Ala Ala Ala
 1               5                  10                  15

Lys Glu Ala Ala Ala Lys Glu Ala Ala Ala Lys Asp Ile Gln Met Thr
                 20                  25                  30

Gln Ser Pro Ser Ser Leu Ser Ala Ser Val Gly Asp Arg Val Thr Ile
             35                  40                  45

Thr Cys Arg Ala Ser Gln Asp Val Asn Thr Ala Val Ala Trp Tyr Gln
 50                  55                  60

Gln Lys Pro Gly Lys Ala Pro Lys Leu Leu Ile Tyr Ser Ala Ser Phe
65                  70                  75                  80

Leu Tyr Ser Gly Val Pro Ser Arg Phe Ser Gly Ser Arg Ser Gly Thr
                 85                  90                  95

Asp Phe Thr Leu Thr Ile Ser Ser Leu Gln Pro Glu Asp Phe Ala Thr
            100                 105                 110

Tyr Tyr Cys Gln Gln His Tyr Thr Thr Pro Pro Thr Phe Gly Gln Gly
        115                 120                 125

Thr Lys Val Glu Ile Lys Arg Thr Val Ala Ala Pro Ser Val Phe Ile
130                 135                 140
```

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
            165                 170                 175

Val Asp Asn Ala Leu Gln Ser Gly Asn Ser Gln Glu Ser Val Thr Glu
        180                 185                 190

Gln Asp Ser Lys Asp Ser Thr Tyr Ser Leu Ser Ser Thr Leu Thr Leu
            195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys

<210> SEQ ID NO 121
<211> LENGTH: 236
<212> TYPE: PRT
<213> ORGANISM: Artificial Sequence
<220> FEATURE:
<223> OTHER INFORMATION: p97 fragment - linker - Trastuzumab FL light
      chain fusion protein

<400> SEQUENCE: 121

Asp Ser Ser His Ala Phe Thr Leu Asp Glu Leu Arg Gly Gly Gly Gly
1               5                   10                  15

Ser Gly Gly Gly Gly Ser Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 122

```
<211> LENGTH: 471
<212> TYPE: PRT
<213> ORGANISM: Homo sapiens

<400> SEQUENCE: 122
```

| | | | | | | | | | | | | | | |
|---|---|---|---|---|---|---|---|---|---|---|---|---|---|---|
| Met | Glu | Thr | Asp | Thr | Leu | Leu | Leu | Trp | Val | Leu | Leu | Leu | Trp | Val | Pro |
| 1 | | | | 5 | | | | | 10 | | | | | 15 | |
| Gly | Ser | Thr | Gly | Glu | Val | Gln | Leu | Val | Glu | Ser | Gly | Gly | Gly | Leu | Val |
| | | | 20 | | | | | 25 | | | | | 30 | | |
| Gln | Pro | Gly | Gly | Ser | Leu | Arg | Leu | Ser | Cys | Ala | Ala | Ser | Gly | Phe | Asn |
| | | 35 | | | | | 40 | | | | | 45 | | | |
| Ile | Lys | Asp | Thr | Tyr | Ile | His | Trp | Val | Arg | Gln | Ala | Pro | Gly | Lys | Gly |
| | 50 | | | | | 55 | | | | | 60 | | | | |
| Leu | Glu | Trp | Val | Ala | Arg | Ile | Tyr | Pro | Thr | Asn | Gly | Tyr | Thr | Arg | Tyr |
| 65 | | | | | 70 | | | | | 75 | | | | | 80 |
| Ala | Asp | Ser | Val | Lys | Gly | Arg | Phe | Thr | Ile | Ser | Ala | Asp | Thr | Ser | Lys |
| | | | | 85 | | | | | 90 | | | | | 95 | |
| Asn | Thr | Ala | Tyr | Leu | Gln | Met | Asn | Ser | Leu | Arg | Ala | Glu | Asp | Thr | Ala |
| | | | 100 | | | | | 105 | | | | | 110 | | |
| Val | Tyr | Tyr | Cys | Ser | Arg | Trp | Gly | Gly | Asp | Gly | Phe | Tyr | Ala | Met | Asp |
| | | 115 | | | | | 120 | | | | | 125 | | | |
| Tyr | Trp | Gly | Gln | Gly | Thr | Leu | Val | Thr | Val | Ser | Ser | Ala | Ser | Thr | Lys |
| | 130 | | | | | 135 | | | | | 140 | | | | |
| Gly | Pro | Ser | Val | Phe | Pro | Leu | Ala | Pro | Ser | Ser | Lys | Ser | Thr | Ser | Gly |
| 145 | | | | | 150 | | | | | 155 | | | | | 160 |
| Gly | Thr | Ala | Ala | Leu | Gly | Cys | Leu | Val | Lys | Asp | Tyr | Phe | Pro | Glu | Pro |
| | | | | 165 | | | | | 170 | | | | | 175 | |
| Val | Thr | Val | Ser | Trp | Asn | Ser | Gly | Ala | Leu | Thr | Ser | Gly | Val | His | Thr |
| | | | 180 | | | | | 185 | | | | | 190 | | |
| Phe | Pro | Ala | Val | Leu | Gln | Ser | Ser | Gly | Leu | Tyr | Ser | Leu | Ser | Ser | Val |
| | | 195 | | | | | 200 | | | | | 205 | | | |
| Val | Thr | Val | Pro | Ser | Ser | Leu | Gly | Thr | Gln | Thr | Tyr | Ile | Cys | Asn |
| | 210 | | | | | 215 | | | | | 220 | | | | |
| Val | Asn | His | Lys | Pro | Ser | Asn | Thr | Lys | Val | Asp | Lys | Lys | Val | Glu | Pro |
| 225 | | | | | 230 | | | | | 235 | | | | | 240 |
| Pro | Lys | Ser | Cys | Asp | Lys | Thr | His | Thr | Cys | Pro | Pro | Cys | Pro | Ala | Pro |
| | | | | 245 | | | | | 250 | | | | | 255 | |
| Glu | Leu | Leu | Gly | Gly | Pro | Ser | Val | Phe | Leu | Phe | Pro | Pro | Lys | Pro | Lys |
| | | | 260 | | | | | 265 | | | | | 270 | | |
| Asp | Thr | Leu | Met | Ile | Ser | Arg | Thr | Pro | Glu | Val | Thr | Cys | Val | Val | Val |
| | | 275 | | | | | 280 | | | | | 285 | | | |
| Asp | Val | Ser | His | Glu | Asp | Pro | Glu | Val | Lys | Phe | Asn | Trp | Tyr | Val | Asp |
| | 290 | | | | | 295 | | | | | 300 | | | | |
| Gly | Val | Glu | Val | His | Asn | Ala | Lys | Thr | Lys | Pro | Arg | Glu | Glu | Gln | Tyr |
| 305 | | | | | 310 | | | | | 315 | | | | | 320 |
| Asn | Ser | Thr | Tyr | Arg | Val | Val | Ser | Val | Leu | Thr | Val | Leu | His | Gln | Asp |
| | | | | 325 | | | | | 330 | | | | | 335 | |
| Trp | Leu | Asn | Gly | Lys | Glu | Tyr | Lys | Cys | Lys | Val | Ser | Asn | Lys | Ala | Leu |
| | | | 340 | | | | | 345 | | | | | 350 | | |
| Pro | Ala | Pro | Ile | Glu | Lys | Thr | Ile | Ser | Lys | Ala | Lys | Gly | Gln | Pro | Arg |
| | | 355 | | | | | 360 | | | | | 365 | | | |
| Glu | Pro | Gln | Val | Tyr | Thr | Leu | Pro | Pro | Ser | Arg | Asp | Glu | Leu | Thr | Lys |
| | 370 | | | | | 375 | | | | | 380 | | | | |
| Asn | Gln | Val | Ser | Leu | Thr | Cys | Leu | Val | Lys | Gly | Phe | Tyr | Pro | Ser | Asp |

```
385                 390                 395                 400
Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 123
<211> LENGTH: 234
<212> TYPE: PRT
<213> ORGANISM: Homo sapiens

<400> SEQUENCE: 123

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
        50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
                100                 105                 110

Thr Thr Pro Pro Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 124
<211> LENGTH: 15
<212> TYPE: PRT
<213> ORGANISM: Artificial Sequence
<220> FEATURE:
<223> OTHER INFORMATION: Linker peptide

<400> SEQUENCE: 124
```

Glu Ala Ala Ala Lys Glu Ala Ala Ala Lys Glu Ala Ala Ala Lys
1               5                   10                  15

<210> SEQ ID NO 125
<211> LENGTH: 3519
<212> TYPE: DNA
<213> ORGANISM: Artificial Sequence
<220> FEATURE:
<223> OTHER INFORMATION: TZM HC-MTf fusion protein polynucleotide

<400> SEQUENCE: 125

| | | | | | |
|---|---|---|---|---|---|
| atggagaccg | acaccctgct | gctctgggtg | ctgctgctct | gggtgcccgg | ctccaccgga | 60 |
| gaggtgcagc | tggtggagag | cggcggaggc | ctcgtgcagc | ccggcggatc | tctgcggctg | 120 |
| agctgcgccg | ctagcggctt | caacatcaag | gacacctaca | tccactgggt | gcgccaggcc | 180 |
| cccggcaagg | gcctggagtg | ggtggcccgg | atctacccca | ccaacggcta | cacccgctac | 240 |
| gccgacagcg | tgaagggccg | gttcaccatc | agcgccgaca | cctccaagaa | caccgcctac | 300 |
| ctgcagatga | acagcctgcg | cgccgaggac | accgccgtgt | actactgcag | ccgtgggggc | 360 |
| ggcgacggat | tctacgccat | ggactactgg | ggacagggca | ccctggtgac | cgtgagcagc | 420 |
| gcctctacca | agggccccag | cgtgttccct | ctggccccca | gcagcaagag | caccagcggc | 480 |
| ggaaccgccg | ccctgggctg | cctggtgaag | gactacttcc | ccgagcccgt | gaccgtgtcc | 540 |
| tggaacagcg | gcgctctgac | cagcggagtg | cacaccttcc | ctgccgtgct | gcagagcagc | 600 |
| ggcctgtact | ccctgagcag | cgtggtgacc | gtgcccagca | gcagcctggg | cacccagacc | 660 |
| tacatctgca | acgtgaacca | caagccctcc | aacaccaagg | tggacaagaa | ggtggagcct | 720 |
| aagagctgcg | acaagaccca | cacctgccct | ccctgccccg | cccccgagct | gctgggcgga | 780 |
| cccagcgtgt | tcctgttccc | tcccaagccc | aaggacaccc | tgatgatcag | ccgcaccccc | 840 |
| gaggtgacct | gcgtggtggt | ggacgtgagc | cacgaggacc | ccgaggtgaa | gttcaactgg | 900 |
| tacgtggacg | gcgtggaggt | gcacaacgcc | aagaccaagc | ctcgggagga | gcagtacaac | 960 |
| tccacctacc | gcgtggtgag | cgtgctgacc | gtgctgcacc | aggactggct | gaacggcaag | 1020 |
| gagtacaagt | gcaaggtgag | caacaaggcc | ctgcccgctc | ccatcgagaa | gaccatcagc | 1080 |
| aaggccaagg | gccagccccg | ggagcctcag | gtgtacaccc | tgcccccagc | ccgcgacgag | 1140 |
| ctgaccaaga | accaggtgag | cctgacctgc | ctggtgaagg | gcttctaccc | ctccgacatc | 1200 |
| gccgtggagt | gggagagcaa | cggccagcct | gagaacaact | acaagaccac | ccctcccgtg | 1260 |
| ctggacagcg | acggcagctt | cttcctgtac | agcaagctga | ccgtggacaa | gtcccggtgg | 1320 |
| cagcagggca | acgtgttcag | ctgcagcgtg | atgcacgagg | ccctgcacaa | ccactacacc | 1380 |
| cagaagagcc | tgagcctgag | ccccggaaag | ggtggcggag | gatctggcgg | aggcggatcc | 1440 |
| ggcatggaag | tgcgttggtg | cgccacctct | gaccccgagc | agcacaagtg | cggcaacatg | 1500 |
| tccgaggcct | tcagagaggc | cggcatccag | ccttctctgc | tgtgtgtgcg | gggcacctct | 1560 |
| gccgaccatt | gcgtgcagct | gatcgccgcc | caggaagccg | acgctatcac | actggatgga | 1620 |
| ggcgctatct | acgaggctgg | caaagagcac | ggcctgaagc | ccgtcgtggg | cgaggtgtac | 1680 |
| gatcaggaag | tgggcacctc | ctactacgcc | gtggctgtcg | tgcggagatc | ctcccacgtg | 1740 |
| accatcgaca | ccctgaaggg | cgtgaagtcc | tgccacaccg | gcatcaacag | aaccgtgggc | 1800 |
| tggaacgtgc | ccgtgggcta | cctggtggaa | tccggcagac | tgtccgtgat | gggctgcgac | 1860 |
| gtgctgaagg | ccgtgtccga | ttacttcggc | ggctcttgtg | tgcctggcgc | tggcgagaca | 1920 |
| tcctactccg | agtccctgtg | cagactgtgc | agggcgact | cttctggcga | gggcgtgtgc | 1980 |

-continued

```
gacaagtccc ctctggaacg gtactacgac tactccggcg ccttcagatg cctggctgaa    2040
ggtgctggcg acgtggcctt cgtgaagcac tccaccgtgc tggaaaacac cgacggcaag    2100
accctgcctt cttggggcca ggcactgctg tcccaggact cgagctgct gtgccgggat     2160 ggctccagag ccgatgtgac agagtggcgg cagtgccacc tggccagagt gcctgcccat    2220
gctgtggtcg tgcgcgccga tacagatggc ggcctgatct tccggctgct gaacgagggc    2280
cagcggctgt tctctcacga gggctccagc ttccagatgt tctccagcga ggcctacggc    2340
cagaaggacc tgctgttcaa ggactccacc tccgagctgg tgcctatcgc cacccagacc    2400
tatgaggctt ggctgggcca cgagtacctg cacgctatga agggactgct gtgcgacccc    2460
aaccggctgc ctccttatct gaggtggtgc gtgctgtcca ccccgagat ccagaaatgc     2520 ggcgatatgg ccgtggcctt tcggcggcag agactgaagc ctgagatcca gtgcgtgtct    2580
gccaagagcc ctcagcactg catggaacgg atccaggccg aacaggtgga cgccgtgaca    2640
ctgtccggcg aggatatcta caccgccgga aagacctacg gcctggtgcc agctgctggc    2700
gagcattacg cccctgagga ctcctccaac agctactacg tggtggcagt cgtgcgccgg    2760
gactcctctc acgcctttac cctggatgag ctgcggggca agagaagctg tcacgccggc    2820
tttggaagcc ctgccggatg ggatgtgcct gtgggcgctc tgatccagcg gggcttcatc    2880
agacccaagg actgtgatgt gctgaccgcc gtgtctgagt tcttcaacgc ctcctgtgtg    2940
cccgtgaaca accccaagaa ctaccctcc agcctgtgcg ccctgtgtgt gggagatgag     3000
cagggccgga acaaatgcgt gggcaactcc caggaaagat attacggcta cagaggcgcc    3060
ttccggtgtc tggtggaaaa cgccggggat gtggcttttg tgcggcacac caccgtgttc    3120
gacaacacca atggccacaa ctccgagcct tgggccgctg agctgagatc cgaggattac    3180
gaactgctgt gtcccaacgg cgccagggct gaggtgtccc agtttgccgc ctgtaacctg    3240
gcccagatcc ctccccacgc tgtgatggtg cgacccgaca ccaacatctt caccgtgtac    3300
ggcctgctgg acaaggccca ggatctgttc ggcgacgacc acaacaagaa cgggttcaag    3360
atgttcgact ccagcaacta ccacggacag gatctgctgt ttaaagatgc caccgtgcgg    3420
gccgtgccag tgggcgaaaa gaccacctac agaggatggc tgggactgga ctacgtggcc    3480
gccctggaag gcatgtcctc ccagcagtgt tccggctag                          3519
```

<210> SEQ ID NO 126
<211> LENGTH: 705
<212> TYPE: DNA
<213> ORGANISM: Homo sapiens

<400> SEQUENCE: 126

```
atggagaccg acaccctgct gctctgggtg ctgctgctct gggtgcccgg ctccaccgga     60
gacatccaga tgacccagag cccttccagc ctgagcgcca gcgtgggcga ccgggtgacc    120
atcacctgcc gcgctagcca ggacgtgaac accgccgtgg cctggtacca gcagaagccc    180
ggaaaggccc ccaagctgct gatctactct gctagcttcc tgtacagcgg cgtgcccagc    240
cggttcagcg gatctcgcag cggcaccgac ttcaccctga ccatcagcag cctgcagcct    300
gaggacttcg ccacctacta ctgccagcag cactacacca cgcctcccac cttcggacag    360
ggcaccaagg tggagatcaa gcggaccgtg gccgccccca gcgtgttcat cttccctccc    420
agcgacgagc agctgaagtc tggcaccgcc agcgtggtgt gcctgctgaa caacttctac    480
ccccgcgagg ccaaggtgca gtggaaggtg gacaacgccc tgcagagcgg caacagccag    540
```

```
gagagcgtga ccgagcagga ctccaaggac agcacctaca gcctgagcag caccctgacc    600
ctgagcaagg ccgactacga gaagcacaag gtgtacgcct gcgaggtgac ccaccaggga    660
ctgtctagcc ccgtgaccaa gagcttcaac cggggcgagt gctaa                    705
```

<210> SEQ ID NO 127
<211> LENGTH: 1482
<212> TYPE: DNA
<213> ORGANISM: Artificial Sequence
<220> FEATURE:
<223> OTHER INFORMATION: MTfp NH-TZM fusion protein polynucleotide

<400> SEQUENCE: 127

```
atggagaccg acaccctgct gctctgggtg ctgctgctct gggtgcccgg ctccaccgga     60
gactcctctc acgccttcac cctggacgag ctgcggtacg tggcggagg atctggcgga    120 ggcggatccg aggtgcagct ggtggagagc ggcggaggcc tcgtgcagcc cggcggatct    180
ctgcggctga gctgcgccgc tagcggcttc aacatcaagg acacctacat ccactgggtg    240
cgccaggccc ccggcaaggg cctggagtgg gtggcccgga tctaccccac caacggctac    300
acccgctacg ccgacagcgt gaagggccgg ttcaccatca gcgccgacac ctccaagaac    360
accgcctacc tgcagatgaa cagcctgcgc gccgaggaca ccgccgtgta ctactgcagc    420
cggtggggcg gcgacggatt ctacgccatg gactactggg gacagggcac cctggtgacc    480
gtgagcagcg cctctaccaa gggccccagc gtgttccctc tggcccccag cagcaagagc    540
accagcggcg gaaccgccgc cctgggctgc ctggtgaagg actacttccc cgagcccgtg    600
accgtgtcct ggaacagcgg cgctctgacc agcggagtgc acaccttccc tgccgtgctg    660
cagagcagcg gcctgtactc cctgagcagc gtggtgaccg tgcccagcag cagcctgggc    720
acccagacct acatctgcaa cgtgaaccac aagcccagca acaccaaggt ggacaagaag    780
gtggagccta gagctgcga caagacccac acctgccctc cctgccccgc ccccgagctg    840
ctgggcggac ccagcgtgtt cctgttccct cccaagccca aggacaccct gatgatcagc    900
cgcacccccg aggtgacctg cgtggtggtg gacgtgagcc acgaggaccc cgaggtgaag    960
ttcaactggt acgtggacgg cgtggaggtg cacaacgcca agaccaagcc tcgggaggag   1020
cagtacaact ccacctaccg cgtggtgagc gtgctgaccg tgctgcacca ggactggctg   1080
aacggcaagg agtacaagtg caaggtgagc aacaaggccc tgcccgctcc catcgagaag   1140
accatcagca aggccaaggg ccagccccgg gagcctcagg tgtacaccct gccccccagc   1200
cgcgacgagc tgaccaagaa ccaggtgagc ctgacctgcc tggtgaaggg cttctacccc   1260
tccgacatcg ccgtggagtg ggagagcaac ggccagcctg agaacaacta caagaccacc   1320
cctcccgtgc tggacagcga cggcagcttc ttcctgtaca gcaagctgac cgtggacaag   1380
tcccggtggc agcagggcaa cgtgttcagc tgcagcgtga tgcacgaggc cctgcacaac   1440
cactacaccc agaagagcct gagcctgagc cccggaaagt aa                      1482
```

<210> SEQ ID NO 128
<211> LENGTH: 705
<212> TYPE: DNA
<213> ORGANISM: Homo sapiens

<400> SEQUENCE: 128

```
atggagaccg acaccctgct gctctgggtg ctgctgctct gggtgcccgg ctccaccgga     60
gacatccaga tgacccagag cccttccagc ctgagcgcca gcgtgggcga ccgggtgacc    120
atcacctgcc gcgctagcca ggacgtgaac accgccgtgg cctggtacca gcagaagccc    180
```

```
ggaaaggccc ccaagctgct gatctactct gctagcttcc tgtacagcgg cgtgcccagc    240
cggttcagcg gatctcgcag cggcaccgac ttcaccctga ccatcagcag cctgcagcct    300
gaggacttcg ccacctacta ctgccagcag cactacacca cgcctcccac cttcggacag    360
ggcaccaagg tggagatcaa gcggaccgtg gccgccccca gcgtgttcat cttccctccc    420
agcgacgagc agctgaagtc tggcaccgcc agcgtggtgt gcctgctgaa caacttctac    480
ccccgcgagg ccaaggtgca gtggaaggtg gacaacgccc tgcagagcgg caacagccag    540
gagagcgtga ccgagcagga ctccaaggac agcacctaca gcctgagcag caccctgacc    600
ctgagcaagg ccgactacga gaagcacaag gtgtacgcct gcgaggtgac ccaccaggga    660
ctgtctagcc ccgtgaccaa gagcttcaac cggggcgagt gctaa                    705
```

```

<210> SEQ ID NO 129
<211> LENGTH: 1479
<212> TYPE: PRT
<213> ORGANISM: Artificial Sequence
<220> FEATURE:
<223> OTHER INFORMATION: TZM HC-MTfp fusion protein polynucleotid

<400> SEQUENCE: 129

Ala Thr Gly Gly Ala Gly Ala Cys Cys Gly Ala Cys Ala Cys Cys Cys
1               5                   10                  15

Thr Gly Cys Thr Gly Cys Thr Cys Thr Gly Gly Gly Thr Gly Cys Thr
            20                  25                  30

Gly Cys Thr Gly Cys Thr Cys Thr Gly Gly Gly Thr Gly Cys Cys Cys
        35                  40                  45

Gly Gly Cys Thr Cys Cys Ala Cys Cys Gly Gly Ala Gly Ala Gly Gly
    50                  55                  60

Thr Gly Cys Ala Gly Cys Thr Gly Gly Thr Gly Gly Ala Gly Ala Gly
65                  70                  75                  80

Cys Gly Gly Cys Gly Gly Ala Gly Gly Cys Cys Thr Cys Gly Thr Gly
                85                  90                  95

Cys Ala Gly Cys Cys Cys Gly Gly Cys Gly Gly Ala Thr Cys Thr Cys
            100                 105                 110

Thr Gly Cys Gly Gly Cys Thr Gly Ala Gly Cys Thr Gly Cys Gly Cys
        115                 120                 125

Cys Gly Cys Thr Ala Gly Cys Gly Gly Cys Thr Thr Cys Ala Ala Cys
    130                 135                 140

Ala Thr Cys Ala Ala Gly Gly Ala Cys Ala Cys Cys Thr Ala Cys Ala
145                 150                 155                 160

Thr Cys Cys Ala Cys Thr Gly Gly Gly Thr Gly Cys Gly Cys Cys Ala
                165                 170                 175

Gly Gly Cys Cys Cys Cys Cys Gly Gly Cys Ala Ala Gly Gly Gly Cys
            180                 185                 190

Cys Thr Gly Gly Ala Gly Thr Gly Gly Gly Thr Gly Gly Cys Cys Cys
        195                 200                 205

Gly Gly Ala Thr Cys Thr Ala Cys Cys Cys Cys Ala Cys Cys Ala Ala
    210                 215                 220

Cys Gly Gly Cys Thr Ala Cys Ala Cys Cys Cys Gly Cys Thr Ala Cys
225                 230                 235                 240

Gly Cys Cys Gly Ala Cys Ala Gly Cys Gly Thr Gly Ala Ala Gly Gly
                245                 250                 255

Gly Cys Cys Gly Gly Thr Thr Cys Ala Cys Cys Ala Thr Cys Ala Gly
            260                 265                 270
```

```
Cys Gly Cys Cys Gly Ala Cys Ala Cys Cys Thr Cys Ala Ala Gly
            275                 280                 285

Ala Ala Cys Ala Cys Cys Gly Cys Cys Thr Ala Cys Cys Thr Gly Cys
        290                 295                 300

Ala Gly Ala Thr Gly Ala Ala Cys Ala Gly Cys Cys Thr Gly Cys Gly
305                 310                 315                 320

Cys Gly Cys Cys Gly Ala Gly Ala Cys Ala Cys Cys Gly Cys Cys
                325                 330                 335

Gly Thr Gly Thr Ala Cys Thr Ala Cys Thr Gly Cys Ala Gly Cys Cys
            340                 345                 350

Gly Gly Thr Gly Gly Gly Cys Gly Gly Cys Gly Ala Cys Gly Gly
            355                 360                 365

Ala Thr Thr Cys Thr Ala Cys Gly Cys Cys Ala Thr Gly Gly Ala Cys
        370                 375                 380

Thr Ala Cys Thr Gly Gly Gly Ala Cys Ala Gly Gly Gly Cys Ala
385                 390                 395                 400

Cys Cys Cys Thr Gly Gly Thr Gly Ala Cys Cys Gly Thr Gly Ala Gly
                405                 410                 415

Cys Ala Gly Cys Gly Cys Cys Thr Cys Thr Ala Cys Cys Ala Ala Gly
            420                 425                 430

Gly Gly Cys Cys Cys Cys Ala Gly Cys Gly Thr Gly Thr Thr Cys Cys
            435                 440                 445

Cys Thr Cys Thr Gly Gly Cys Cys Cys Cys Ala Gly Cys Ala Gly
        450                 455                 460

Cys Ala Ala Gly Ala Gly Cys Ala Cys Cys Ala Gly Cys Gly Gly Cys
465                 470                 475                 480

Gly Gly Ala Ala Cys Cys Gly Cys Cys Gly Cys Cys Cys Thr Gly Gly
            485                 490                 495

Gly Cys Thr Gly Cys Cys Thr Gly Gly Thr Gly Ala Ala Gly Gly Ala
            500                 505                 510

Cys Thr Ala Cys Thr Thr Cys Cys Cys Cys Gly Ala Gly Cys Cys Cys
            515                 520                 525

Gly Thr Gly Ala Cys Cys Gly Thr Gly Thr Cys Thr Gly Gly Ala
            530                 535                 540

Ala Cys Ala Gly Cys Gly Gly Cys Gly Cys Thr Cys Thr Gly Ala Cys
545                 550                 555                 560

Cys Ala Gly Cys Gly Gly Ala Gly Thr Gly Cys Ala Cys Ala Cys Cys
            565                 570                 575

Thr Thr Cys Cys Cys Thr Gly Cys Cys Gly Thr Gly Cys Thr Gly Cys
            580                 585                 590

Ala Gly Ala Gly Cys Ala Gly Cys Gly Gly Cys Cys Thr Gly Thr Ala
            595                 600                 605

Cys Thr Cys Cys Cys Thr Gly Ala Gly Cys Ala Gly Cys Gly Thr Gly
            610                 615                 620

Gly Thr Gly Ala Cys Cys Gly Thr Gly Cys Cys Cys Ala Gly Cys Ala
625                 630                 635                 640

Gly Cys Ala Gly Cys Cys Thr Gly Gly Gly Cys Ala Cys Cys Ala
                645                 650                 655

Gly Ala Cys Cys Thr Ala Cys Ala Thr Cys Thr Gly Cys Ala Ala Cys
            660                 665                 670

Gly Thr Gly Ala Ala Cys Cys Ala Cys Ala Ala Gly Cys Cys Cys Thr
            675                 680                 685
```

```
Cys Cys Ala Ala Cys Ala Cys Cys Ala Ala Gly Gly Thr Gly Gly Ala
    690             695             700

Cys Ala Ala Gly Ala Ala Gly Gly Thr Gly Gly Ala Gly Cys Cys Thr
705             710             715                     720

Ala Ala Gly Ala Gly Cys Thr Gly Cys Gly Ala Cys Ala Ala Gly Ala
            725             730                 735

Cys Cys Cys Ala Cys Ala Cys Cys Thr Gly Cys Cys Thr Cys Cys
        740         745             750

Cys Thr Gly Cys Cys Cys Gly Cys Cys Cys Cys Gly Ala Gly
    755             760             765

Cys Thr Gly Cys Thr Gly Gly Gly Cys Gly Gly Ala Cys Cys Ala
    770             775             780

Gly Cys Gly Thr Gly Thr Thr Cys Cys Thr Gly Thr Thr Cys Cys Cys
785             790             795                     800

Thr Cys Cys Cys Ala Ala Gly Cys Cys Ala Ala Gly Gly Ala Cys
            805             810             815

Ala Cys Cys Cys Thr Gly Ala Thr Gly Ala Thr Cys Ala Gly Cys Cys
            820             825             830

Gly Cys Ala Cys Cys Cys Cys Gly Ala Gly Gly Thr Gly Ala Cys
        835             840             845

Cys Thr Gly Cys Gly Thr Gly Thr Gly Thr Gly Gly Ala Cys
    850             855             860

Gly Thr Gly Ala Gly Cys Ala Cys Gly Ala Gly Gly Ala Cys Cys
865             870             875             880

Cys Cys Gly Ala Gly Gly Thr Gly Ala Ala Gly Thr Thr Cys Ala Ala
            885             890             895

Cys Thr Gly Gly Thr Ala Cys Gly Thr Gly Gly Ala Cys Gly Gly Cys
        900             905             910

Gly Thr Gly Gly Ala Gly Gly Thr Gly Cys Ala Cys Ala Ala Cys Gly
        915             920             925

Cys Cys Ala Ala Gly Ala Cys Cys Ala Ala Gly Cys Cys Thr Cys Gly
    930             935             940

Gly Gly Ala Gly Gly Ala Gly Cys Ala Gly Thr Ala Cys Ala Ala Cys
945             950             955             960

Thr Cys Cys Ala Cys Cys Thr Ala Cys Cys Gly Cys Gly Thr Gly Gly
        965             970             975

Thr Gly Ala Gly Cys Gly Thr Gly Cys Thr Gly Ala Cys Cys Gly Thr
            980             985             990

Gly Cys Thr Gly Cys Ala Cys Cys Ala Gly Gly Ala Cys Thr Gly Gly
    995             1000            1005

Cys Thr Gly Ala Ala Cys Gly Gly Cys Ala Ala Gly Gly Ala Gly
    1010            1015            1020

Thr Ala Cys Ala Ala Gly Thr Gly Cys Ala Ala Gly Gly Thr Gly
    1025            1030            1035

Ala Gly Cys Ala Ala Cys Ala Ala Gly Gly Cys Cys Cys Thr Gly
    1040            1045            1050

Cys Cys Cys Gly Cys Thr Cys Cys Ala Thr Cys Gly Ala Gly
    1055            1060            1065

Ala Ala Gly Ala Cys Cys Ala Thr Cys Ala Gly Cys Ala Ala Gly
    1070            1075            1080

Gly Cys Cys Ala Ala Gly Gly Gly Cys Cys Ala Gly Cys Cys Cys
    1085            1090            1095

Cys Gly Gly Gly Ala Gly Cys Cys Thr Cys Ala Gly Gly Thr Gly
```

```
            1100                1105                1110

Thr Ala Cys Ala Cys Cys Cys Thr Gly Cys Cys Cys Cys Cys
        1115                1120                1125

Ala Gly Cys Cys Gly Cys Gly Ala Cys Gly Ala Gly Cys Thr Gly
        1130                1135                1140

Ala Cys Cys Ala Ala Gly Ala Ala Cys Cys Ala Gly Gly Thr Gly
        1145                1150                1155

Ala Gly Cys Cys Thr Gly Ala Cys Cys Thr Gly Cys Cys Thr Gly
        1160                1165                1170

Gly Thr Gly Ala Ala Gly Gly Gly Cys Thr Thr Cys Thr Ala Cys
        1175                1180                1185

Cys Cys Cys Thr Cys Cys Gly Ala Cys Ala Thr Cys Gly Cys Cys
        1190                1195                1200

Gly Thr Gly Gly Ala Gly Thr Gly Gly Ala Gly Ala Gly Cys
        1205                1210                1215

Ala Ala Cys Gly Gly Cys Cys Ala Gly Cys Cys Thr Gly Ala Gly
        1220                1225                1230

Ala Ala Cys Ala Ala Cys Thr Ala Cys Ala Ala Gly Ala Cys Cys
        1235                1240                1245

Ala Cys Cys Cys Cys Thr Cys Cys Cys Gly Thr Gly Cys Thr Gly
        1250                1255                1260

Gly Ala Cys Ala Gly Cys Gly Ala Cys Gly Gly Cys Ala Gly Cys
        1265                1270                1275

Thr Thr Cys Thr Thr Cys Cys Thr Gly Thr Ala Cys Ala Gly Cys
        1280                1285                1290

Ala Ala Gly Cys Thr Gly Ala Cys Cys Gly Thr Gly Gly Ala Cys
        1295                1300                1305

Ala Ala Gly Thr Cys Cys Cys Gly Gly Thr Gly Gly Cys Ala Gly
        1310                1315                1320

Cys Ala Gly Gly Gly Cys Ala Ala Cys Gly Thr Gly Thr Thr Cys
        1325                1330                1335

Ala Gly Cys Thr Gly Cys Ala Gly Cys Gly Thr Gly Ala Thr Gly
        1340                1345                1350

Cys Ala Cys Gly Ala Gly Gly Cys Cys Cys Thr Gly Cys Ala Cys
        1355                1360                1365

Ala Ala Cys Cys Ala Cys Thr Ala Cys Ala Cys Cys Cys Ala Gly
        1370                1375                1380

Ala Ala Gly Ala Gly Cys Cys Thr Gly Ala Gly Cys Cys Thr Gly
        1385                1390                1395

Ala Gly Cys Cys Cys Cys Gly Gly Ala Ala Ala Gly Gly Gly Thr
        1400                1405                1410

Gly Gly Cys Gly Gly Ala Gly Gly Ala Thr Cys Thr Gly Gly Cys
        1415                1420                1425

Gly Gly Ala Gly Gly Cys Gly Gly Ala Thr Cys Cys Gly Ala Cys
        1430                1435                1440

Thr Cys Cys Thr Cys Thr Cys Ala Cys Gly Cys Cys Thr Thr Cys
        1445                1450                1455

Ala Cys Cys Cys Thr Gly Gly Ala Cys Gly Ala Gly Cys Thr Gly
        1460                1465                1470

Cys Gly Gly Thr Ala Gly
        1475

<210> SEQ ID NO 130
```

```
<211> LENGTH: 705
<212> TYPE: DNA
<213> ORGANISM: Homo sapiens

<400> SEQUENCE: 130
atggagaccg acaccctgct gctctgggtg ctgctgctct gggtgcccgg ctccaccgga      60
gacatccaga tgacccagag cccttccagc ctgagcgcca gcgtgggcga ccgggtgacc     120
atcacctgcc gcgctagcca ggacgtgaac accgccgtgg cctggtacca gcagaagccc     180
ggaaaggccc ccaagctgct gatctactct gctagcttcc tgtacagcgg cgtgcccagc     240
cggttcagcg gatctcgcag cggcaccgac ttcaccctga ccatcagcag cctgcagcct     300
gaggacttcg ccacctacta ctgccagcag cactacacca cgcctcccac cttcggacag     360
ggcaccaagg tggagatcaa gcggaccgtg gccgccccca gcgtgttcat cttccctccc     420
agcgacgagc agctgaagtc tggcaccgcc agcgtggtgt gcctgctgaa caacttctac     480
ccccgcgagg ccaaggtgca gtggaaggtg gacaacgccc tgcagagcgg caacagccag     540
gagagcgtga ccgagcagga ctccaaggac agcacctaca gcctgagcag caccctgacc     600
ctgagcaagg ccgactacga gaagcacaag gtgtacgcct gcgaggtgac ccaccaggga     660
ctgtctagcc ccgtgaccaa gagcttcaac cggggcgagt gctaa                     705

<210> SEQ ID NO 131
<211> LENGTH: 3534
<212> TYPE: DNA
<213> ORGANISM: Artificial Sequence
<220> FEATURE:
<223> OTHER INFORMATION: TZM/MTf fusion protein polynucleotide

<400> SEQUENCE: 131
atggagaccg acaccctgct gctctgggtg ctgctgctct gggtgcccgg ctccaccgga      60
gaggtgcagc tggtggagag cggcggaggc ctcgtgcagc ccggcggatc tctgcggctg     120
agctgcgccg ctagcggctt caacatcaag gacacctaca tccactgggt gcgccaggcc     180
cccggcaagg gcctggagtg ggtggcccgg atctacccca ccaacggcta caccgcctac     240
gccgacagcg tgaagggccg gttcaccatc agcgccgaca cctccaagaa caccgcctac     300
ctgcagatga acagcctgcg cgccgaggac accgccgtgt actactgcag ccggtggggc     360
ggcgacggat tctacgccat ggactactgg ggacagggca ccctggtgac cgtgagcagc     420
gcctctacca agggccccag cgtgttccct ctggccccca gcagcaagag caccagcggc     480
ggaaccgccg ccctgggctg cctggtgaag gactacttcc ccgagcccgt gaccgtgtcc     540
tggaacagcg gcgctctgac cagcggagtg cacaccttcc ctgccgtgct gcagagcagc     600
ggcctgtact ccctgagcag cgtggtgacc gtgcccagca gcagcctggg cacccagacc     660
tacatctgca acgtgaacca caagccctcc aacaccaagg tggacaagaa ggtggagcct     720
aagagctgcg acaagaccca cacctgcccc cctgccccg ccccgagct gctgggcgga     780
cccagcgtgt tcctgttccc tcccaagccc aaggacaccc tgatgatcag ccgcaccccc     840
gaggtgacct gcgtggtggt ggacgtgagc cacgaggacc ccgaggtgaa gttcaactgg     900
tacgtggacg gcgtggaggt gcacaacgcc aagaccaagc tcgggagga gcagtacaac     960
tccacctacc gcgtggtgag cgtgctgacc gtgctgcacc aggactggct gaacggcaag    1020
gagtacaagt gcaaggtgag caacaaggcc ctgcccgctc ccatcgagaa gaccatcagc    1080
aaggccaagg gccagccccg ggagcctcag gtgtacaccc tgcccccag ccgcgacgag    1140
ctgaccaaga accaggtgag cctgacctgc ctggtgaagg gcttctaccc ctccgacatc    1200
```

```
gccgtggagt gggagagcaa cggccagcct gagaacaact acaagaccac ccctcccgtg   1260
ctggacagcg acggcagctt cttcctgtac agcaagctga ccgtggacaa gtcccggtgg   1320
cagcagggca acgtgttcag ctgcagcgtg atgcacgagg ccctgcacaa ccactacacc   1380
cagaagagcc tgagcctgag ccccggaaag ggaggtggcg gttctggtgg cggaggatct   1440
ggcggaggcg gatccggcat ggaagtgcgt tggtgcgcca cctctgaccc cgagcagcac   1500
aagtgcggca acatgtccga ggccttcaga gaggccggca tccagccttc tctgctgtgt   1560
gtgcgggcca cctctgccga ccattgcgtg cagctgatcg ccgcccagga agccgacgct   1620
atcacactgg atggcggcgc tatctacgag gctggcaaag agcacggcct gaagcccgtc   1680
gtgggcgagg tgtacgatca ggaagtgggc acctcctact acgccgtggc tgtcgtgcgg   1740
agatcctccc acgtgaccat cgacaccctg aagggcgtga agtcctgcca caccggcatc   1800
aacagaaccg tgggctggaa cgtgcccgtg ggctacctgg tggaatccgg cagactgtcc   1860
gtgatgggct gcgacgtgct gaaggccgtg tccgattact tcggcggctc ttgtgtgcct   1920
ggcgctggcg agacatccta ctccgagtcc ctgtgcagac tgtgcagggg cgactcttct   1980
ggcgagggcg tgtgcgacaa gtcccctctg aacggtact acgactactc cggcgccttc   2040
agatgcctgg ctgaaggtgc tggcgacgtg gccttcgtga agcactccac cgtgctggaa   2100
aacaccgacg gcaagaccct gccttcttgg ggccaggcac tgctgtccca ggacttcgag   2160
ctgctgtgcc gggatggctc cagagccgat gtgacagagt ggcggcagtg ccacctggcc   2220
agagtgcctg ctcatgctgt ggtcgtgcgc gccgatacag atggcggcct gatcttccgg   2280
ctgctgaacg agggccagcg gctgttctct cacgagggct ccagcttcca gatgttctcc   2340
agcgaggcct acggcagaa ggacctgctg ttcaaggact ccacctccga gctggtgcct   2400
atcgccaccc agacctatga ggcttggctg gccacgagt acctgcacgc tatgaaggga   2460
ctgctgtgcg accccaaccg gctgcctcct tatctgaggt ggtgcgtgct gtccaccccc   2520
gagatccaga aatgcggcga tatggccgtg gcctttcggc ggcagagact gaagcctgag   2580
atccagtgcg tgtccgccaa gagccctcag cactgcatgg aacggatcca ggccgaacag   2640
gtggacgccg tgacactgtc cggcgaggat atctacaccg ccggaaagac ctacggcctg   2700
gtgccagctg ctggcgagca ttacgcccct gaggactcct ccaacagcta ctacgtggtg   2760
gcagtcgtgc gccgggactc ctctcacgcc tttaccctgg atgagctgcg gggcaagaga   2820
agctgtcacg ccggctttgg aagccctgcc ggatgggatg tgcctgtggg cgctctgatc   2880
cagcggggct tcatcagacc caaggactgt gatgtgctga ccgccgtgtc tgagttcttc   2940
aacgcctcct gtgtgcccgt gaacaacccc aagaactacc cctccagcct gtgcgccctg   3000
tgtgtgggag atgagcaggg ccggaacaaa tgcgtgggca actcccagga agatattac   3060
ggctacagag gcgccttccg gtgtctggtg aaaacgccg gggatgtggc ttttgtgcgg   3120
cacaccaccg tgttcgacaa caccaatggc acaactccg agccttgggc cgctgagctg   3180
agatccgagg attacgaact gctgtgtccc aacggcgcca gggctgaggt gtcccagttt   3240
gccgcctgta acctgcccca gatccctccc cacgctgtga tggtgcgacc cgacaccaac   3300
atcttcaccg tgtacggcct gctggacaag gcccaggatc tgttcggcga cgaccacaac   3360
aagaacgggt tcaagatgtt cgactccagc aactaccacg acaggatct gctgtttaaa   3420
gatgccaccg tgcgggccgt gccagtgggc gaaaagacca cctacagagg atggctggga   3480
ctggactacg tggccgccct ggaaggcatg tcctcccagc agtgttccgg ctag         3534
```

<210> SEQ ID NO 132
<211> LENGTH: 705
<212> TYPE: DNA
<213> ORGANISM: Homo sapiens

<400> SEQUENCE: 132

| | | | | | |
|---|---|---|---|---|---|
| atggagaccg | acaccctgct | gctctgggtg | ctgctgctct | gggtgcccgg | ctccaccgga | 60 |
| gacatccaga | tgacccagag | cccttccagc | ctgagcgcca | gcgtgggcga | ccgggtgacc | 120 |
| atcacctgcc | gcgctagcca | ggacgtgaac | accgccgtgg | cctggtacca | gcagaagccc | 180 |
| ggaaaggccc | ccaagctgct | gatctactct | gctagcttcc | tgtacagcgg | cgtgcccagc | 240 |
| cggttcagcg | gatctcgcag | cggcaccgac | ttcaccctga | ccatcagcag | cctgcagcct | 300 |
| gaggacttcg | ccacctacta | ctgccagcag | cactacacca | cgcctcccac | cttcggacag | 360 |
| ggcaccaagg | tggagatcaa | gcggaccgtg | gccgccccca | gcgtgttcat | cttccctccc | 420 |
| agcgacgagc | agctgaagtc | tggcaccgcc | agcgtggtgt | gcctgctgaa | caacttctac | 480 |
| ccccgcgagg | ccaaggtgca | gtggaaggtg | gacaacgccc | tgcagagcgg | caacagccag | 540 |
| gagagcgtga | ccgagcagga | ctccaaggac | agcacctaca | gcctgagcag | caccctgacc | 600 |
| ctgagcaagg | ccgactacga | aagcacaag | gtgtacgcct | gcgaggtgac | ccaccaggga | 660 |
| ctgtctagcc | ccgtgaccaa | gagcttcaac | cggggcgagt | gctaa | | 705 |

<210> SEQ ID NO 133
<211> LENGTH: 1497
<212> TYPE: DNA
<213> ORGANISM: Homo sapiens

<400> SEQUENCE: 133

| | | | | | |
|---|---|---|---|---|---|
| atggagaccg | acaccctgct | gctctgggtg | ctgctgctct | gggtgcccgg | ctccaccgga | 60 |
| gaggtgcagc | tggtggagag | cggcggaggc | ctcgtgcagc | ccggcggatc | tctgcggctg | 120 |
| agctgcgccg | ctagcggctt | caacatcaag | gacacctaca | tccactgggt | gcgccaggcc | 180 |
| cccggcaagg | gcctggagtg | ggtggcccgg | atctacccca | ccaacggcta | cacccgctac | 240 |
| gccgacagcg | tgaagggccg | gttcaccatc | agcgccgaca | cctccaagaa | caccgcctac | 300 |
| ctgcagatga | acagcctgcg | cgccgaggac | accgccgtgt | actactgcag | ccggtggggc | 360 |
| ggcgacggat | tctacgccat | ggactactgg | ggacagggca | ccctggtgac | cgtgagcagc | 420 |
| gcctctacca | agggcccag | cgtgttccct | ctggcccca | gcagcaagag | caccagcggc | 480 |
| ggaaccgccg | ccctgggctg | cctggtgaag | gactacttcc | ccgagcccgt | gaccgtgtcc | 540 |
| tggaacagcg | gcgctctgac | cagcggagtg | cacaccttcc | ctgccgtgct | gcagagcagc | 600 |
| ggcctgtact | ccctgagcag | cgtggtgacc | gtgcccagca | gcagcctggg | cacccagacc | 660 |
| tacatctgca | acgtgaacca | caagccctcc | aacaccaagg | tggacaagaa | ggtggagcct | 720 |
| aagagctgcg | acaagaccca | cacctgccct | ccctgcccg | ccccgagct | gctgggcgga | 780 |
| cccagcgtgt | tcctgttccc | tcccaagccc | aaggacaccc | tgatgatcag | ccgcaccccc | 840 |
| gaggtgacct | gcgtggtggt | ggacgtgagc | cacgaggacc | ccgaggtgaa | gttcaactgg | 900 |
| tacgtggacg | gcgtggaggt | gcacaacgcc | aagaccaagc | ctcgggagga | gcagtacaac | 960 |
| tccacctacc | gcgtggtgag | cgtgctgacc | gtgctgcacc | aggactggct | gaacggcaag | 1020 |
| gagtacaagt | gcaaggtgag | caacaaggcc | ctgcccgctc | ccatcgagaa | gaccatcagc | 1080 |
| aaggccaagg | gccagccccg | ggagcctcag | gtgtacaccc | tgcccccag | ccgcgacgag | 1140 |
| ctgaccaaga | accaggtgag | cctgacctgc | ctggtgaagg | gcttctaccc | ctccgacatc | 1200 |

```
gccgtggagt gggagagcaa cggccagcct gagaacaact acaagaccac ccctcccgtg    1260
ctggacagcg acggcagctt cttcctgtac agcaagctga ccgtggacaa gtcccggtgg    1320
cagcagggca acgtgttcag ctgcagcgtg atgcacgagg ccctgcacaa ccactacacc    1380
cagaagagcc tgagcctgag ccccggaaag gaggccgctg ctaaagaggc tgccgccaaa    1440
gaagccgccg ctaaggactc ctctcacgcc ttcaccctgg acgagctgcg gtactaa      1497
```

<210> SEQ ID NO 134
<211> LENGTH: 789
<212> TYPE: DNA
<213> ORGANISM: Artificial Sequence
<220> FEATURE:
<223> OTHER INFORMATION: LC-MTfp/Fc-MTfp fusion protein polynucleotid

<400> SEQUENCE: 134

```
atggagaccg acaccctgct gctctgggtg ctgctgctct gggtgcccgg ctccaccgga     60
gacatccaga tgacccagag cccttccagc ctgagcgcca gcgtgggcga ccgggtgacc    120
atcacctgcc gcgctagcca ggacgtgaac accgccgtgg cctggtacca gcagaagccc    180
ggaaaggccc ccaagctgct gatctactct gctagcttcc tgtacagcgg cgtgcccagc    240
cggttcagcg gatctcgcag cggcaccgac ttcaccctga ccatcagcag cctgcagcct    300
gaggacttcg ccacctacta ctgccagcag cactacacca cgcctcccac cttcggacag    360
ggcaccaagg tagagatcaa gcggaccgtg gccgccccca gcgtgttcat cttccctccc    420
agcgacgagc agctgaagtc tggcaccgcc agcgtggtgt gcctgctgaa caacttctac    480
ccccgcgagg ccaaggtgca gtggaaggtg acaacgccc tgcagagcgg caacagccag    540
gagagcgtga ccgagcagga ctccaaggac agcacctaca gcctgagcag caccctgacc    600
ctgagcaagg ccgactacga aagcacaag gtgtacgcct gcgaggtgac ccaccaggga    660
ctgtctagcc ccgtgaccaa gagcttcaac cggggcgagt gcgaggccgc tgctaaagag    720
gctgccgcca aagaagccgc cgctaaggac tcctctcacg ccttcaccct ggacgagctg    780
cggtactaa                                                            789
```

<210> SEQ ID NO 135
<211> LENGTH: 1497
<212> TYPE: DNA
<213> ORGANISM: Homo sapiens

<400> SEQUENCE: 135

```
atggagaccg acaccctgct gctctgggtg ctgctgctct gggtgcccgg ctccaccgga     60
gaggtgcagc tggtggagag cggcggaggc ctcgtgcagc ccggcggatc tctgcggctg    120
agctgcgccc tagcggcttt caacatcaag gacacctaca tccactgggt gcgccaggcc    180
cccggcaagg gcctggagtg ggtggcccgg atctacccca ccaacggcta caccgcctac    240
gccgacagcg tgaagggccg gttcaccatc agcgccgaca cctccaagaa caccgcctac    300
ctgcagatga acagcctgcg cgccgaggac accgccgtgt actactgcag ccggtggggc    360
ggcgacggat tctacgccat ggactactgg ggacagggca ccctggtgac cgtgagcagc    420
gcctctacca agggccccag cgtgttccct ctggccccca gcagcaagag caccagcggg    480
ggaaccgccg ccctgggctg cctggtgaag gactacttcc ccgagcccgt gaccgtgtcc    540
tggaacagcg gcgctctgac cagcggagtg cacaccttcc ctgccgtgct gcagagcagc    600
ggcctgtact ccctgagcag cgtggtgacc gtgcccagca gcagcctggg cacccagacc    660
```

| | |
|---|---|
| tacatctgca acgtgaacca caagccctcc aacaccaagg tggacaagaa ggtggagcct | 720 |
| aagagctgcg acaagaccca cacctgccct ccctgcccg cccccgagct gctgggcgga | 780 |
| cccagcgtgt tcctgttccc tcccaagccc aaggacaccc tgatgatcag ccgcaccccc | 840 |
| gaggtgacct gcgtggtggt ggacgtgagc cacgaggacc ccgaggtgaa gttcaactgg | 900 |
| tacgtggacg gcgtggaggt gcacaacgcc aagaccaagc ctcgggagga gcagtacaac | 960 |
| tccacctacc gcgtggtgag cgtgctgacc gtgctgcacc aggactggct gaacggcaag | 1020 |
| gagtacaagt gcaaggtgag caacaaggcc ctgcccgctc ccatcgagaa gaccatcagc | 1080 |
| aaggccaagg gccagccccg ggagcctcag gtgtacaccc tgccccccag ccgcgacgag | 1140 |
| ctgaccaaga accaggtgag cctgacctgc ctggtgaagg gcttctaccc ctccgacatc | 1200 |
| gccgtggagt gggagagcaa cggccagcct gagaacaact acaagaccac ccctcccgtg | 1260 |
| ctggacagcg acggcagctt cttcctgtac agcaagctga ccgtggacaa gtcccggtgg | 1320 |
| cagcagggca acgtgttcag ctgcagcgtg atgcacgagg ccctgcacaa ccactacacc | 1380 |
| cagaagagcc tgagcctgag ccccggaaag gaggccgctg ctaaagaggc tgccgccaaa | 1440 |
| gaagccgccg ctaaggactc ctctcacgcc ttcaccctgg acgagctgcg gtactaa | 1497 |

```
<210> SEQ ID NO 136
<211> LENGTH: 705
<212> TYPE: DNA
<213> ORGANISM: Homo sapiens

<400> SEQUENCE: 136
```

| | |
|---|---|
| atggagaccg acaccctgct gctctgggtg ctgctgctct gggtgcccgg ctccaccgga | 60 |
| gacatccaga tgacccagag cccttccagc ctgagcgcca gcgtgggcga ccgggtgacc | 120 |
| atcacctgcc gcgctagcca ggacgtgaac accgccgtgg cctggtacca gcagaagccc | 180 |
| ggaaaggccc ccaagctgct gatctactct gctagcttcc tgtacagcgg cgtgcccagc | 240 |
| cggttcagcg gatctcgcag cggcaccgac ttcaccctga ccatcagcag cctgcagcct | 300 |
| gaggacttcg ccacctacta ctgccagcag cactacacca cgcctcccac cttcggacag | 360 |
| ggcaccaagg tggagatcaa gcggaccgtg gccgccccca gcgtgttcat cttccctccc | 420 |
| agcgacgagc agctgaagtc tggcaccgcc agcgtggtgt gcctgctgaa caacttctac | 480 |
| ccccgcgagg ccaaggtgca gtggaaggtg gacaacgccc tgcagagcgg caacagccag | 540 |
| gagagcgtga ccgagcagga ctccaaggac agcacctaca gcctgagcag caccctgacc | 600 |
| ctgagcaagg ccgactacga gaagcacaag gtgtacgcct gcgaggtgac ccaccaggga | 660 |
| ctgtctagcc ccgtgaccaa gagcttcaac cggggcgagt gctaa | 705 |

```
<210> SEQ ID NO 137
<211> LENGTH: 1413
<212> TYPE: DNA
<213> ORGANISM: Homo sapiens

<400> SEQUENCE: 137
```

| | |
|---|---|
| atggagaccg acaccctgct gctctgggtg ctgctgctct gggtgcccgg ctccaccgga | 60 |
| gaggtgcagc tggtggagag cggcggaggc ctcgtgcagc ccggcggatc tctgcggctg | 120 |
| agctgcgccg ctagcggctt caacatcaag gacacctaca tccactgggt gcgccaggcc | 180 |
| cccggcaagg gcctggagtg ggtggcccgg atctacccca acggcta cacccgctac | 240 |
| gccgacagcg tgaagggccg gttcaccatc agcgccgaca cctccaagaa caccgcctac | 300 |
| ctgcagatga acagcctgcg cgccgaggac accgccgtgt actactgcag ccggtggggc | 360 |

```
ggcgacggat tctacgccat ggactactgg ggacagggca ccctggtgac cgtgagcagc    420
gcctctacca agggcccag cgtgttccct ctggccccca gcagcaagag caccagcggc    480
ggaaccgccg ccctgggctg cctggtgaag gactacttcc ccgagcccgt gaccgtgtcc    540
tggaacagcg gcgctctgac cagcggagtg cacaccttcc ctgccgtgct gcagagcagc    600
ggcctgtact ccctgagcag cgtggtgacc gtgcccagca gcagcctggg cacccagacc    660
tacatctgca acgtgaacca caagccctcc aacaccaagg tggacaagaa ggtggagcct    720
aagagctgcg acaagaccca cacctgcccc cctgccccg ccccgagct gctgggcgga    780 cccagcgtgt tcctgttccc tcccaagccc aaggacaccc tgatgatcag ccgcacccc    840 gaggtgacct gcgtggtggt ggacgtgagc cacgaggacc ccgaggtgaa gttcaactgg    900
tacgtggacg gcgtggaggt gcacaacgcc aagaccaagc ctcgggagga gcagtacaac    960
tccacctacc gcgtggtgag cgtgctgacc gtgctgcacc aggactggct gaacggcaag    1020
gagtacaagt gcaaggtgag caacaaggcc ctgcccgctc ccatcgagaa gaccatcagc    1080
aaggccaagg gccagccccg ggagcctcag gtgtacaccc tgcccccag ccgcgacgag    1140 ctgaccaaga accaggtgag cctgacctgc ctggtgaagg gcttctaccc ctccgacatc    1200
gccgtggagt gggagagcaa cggccagcct gagaacaact acaagaccac ccctcccgtg    1260
ctggacagcg acggcagctt cttcctgtac agcaagctga ccgtggacaa gtcccggtgg    1320
cagcagggca acgtgttcag ctgcagcgtg atgcacgagg ccctgcacaa ccactacacc    1380
cagaagagcc tgagcctgag ccccggaaag taa                                 1413

<210> SEQ ID NO 138
<211> LENGTH: 789
<212> TYPE: DNA
<213> ORGANISM: Artificial Sequence
<220> FEATURE:
<223> OTHER INFORMATION: LC-MTfp/Fc fusion protein polynucleotide

<400> SEQUENCE: 138
atggagaccg acaccctgct gctctgggtg ctgctgctct gggtgcccgg ctccaccgga     60
gacatccaga tgacccagag ccctttccagc ctgagcgcca gcgtgggcga ccgggtgacc    120
atcacctgcc gcgctagcca ggacgtgaac accgccgtgg cctggtacca gcagaagccc    180
ggaaaggccc ccaagctgct gatctactct gctagcttcc tgtacagcgg cgtgcccagc    240
cggttcagcg gatctcgcag cggcaccgac ttcaccctga ccatcagcag cctgcagcct    300
gaggacttcg ccacctacta ctgccagcag cactacacca gcctcccac cttcggacag    360 ggcaccaagg tagagatcaa gcggaccgtg gccgccccca gcgtgttcat cttccctccc    420
agcgacgagc agctgaagtc tggcaccgcc agcgtggtgt gcctgctgaa caacttctac    480
ccccgcgagg ccaaggtgca gtggaaggtg gacaacgccc tgcagagcgg caacagccag    540
gagagcgtga ccgagcagga ctccaaggac agcacctaca gcctgagcag caccctgacc    600
ctgagcaagg ccgactacga gaagcacaag gtgtacgcct gcgaggtgac ccaccaggga    660
ctgtctagcc ccgtgaccaa gagcttcaac cggggcgagt gcgaggccgc tgctaaagag    720
gctgccgcca aagaagccgc cgctaaggac tcctctcacg ccttcaccct ggacgagctg    780
cggtactaa                                                            789
```

P97 FUSION PROTEINS

CROSS-REFERENCE TO RELATED APPLICATIONS

This application claims priority to U.S. application Ser. No. 15/116,388, filed Aug. 3, 2016, which is a national stage entry of PCT/US2015/014230 filed on Feb. 3, 2015, which is incorporated by reference in its entirety.

SEQUENCE LISTING

The Sequence Listing associated with this application is provided in text format in lieu of a paper copy, and is hereby incorporated by reference into the specification. The name of the text file containing the Sequence Listing is BIOA_008_01WO_ST25.txt. The text file is about 340 KB, was created on Feb. 3, 2015, and is being submitted electronically via EFS-Web.

BACKGROUND

Technical Field

Embodiments of the present invention relate to p97 (melanotransferrin)-trastuzumab fusion proteins and antibody fusion proteins and related methods of use thereof, for instance, to facilitate delivery of trastuzumab across the blood-brain barrier (BBB) and/or improve tissue penetration of the antibody in CNS and peripheral tissues, and thereby treat and/or diagnose HER2-positive cancers, including those of the central nervous system (CNS).

Description of the Related Art

Overcoming the difficulties of delivering therapeutic or diagnostic agents to specific regions of the brain represents a major challenge to treatment or diagnosis of many central nervous system (CNS) disorders, including those of the brain. In its neuroprotective role, the blood-brain barrier (BBB) functions to hinder the delivery of many potentially important diagnostic and therapeutic agents to the brain.

Therapeutic molecules and genes that might otherwise be effective in diagnosis and therapy do not cross the BBB in adequate amounts and often have poor tissue penetration, even in peripheral tissues. It is reported that over 95% of all therapeutic molecules do not cross the blood-brain barrier.

Accordingly, there is a need for compositions and methods that facilitate the delivery of therapeutic agents and other molecules across the blood-brain-barrier, for instance, to effectively treat certain diseases of the central nervous system (CNS) such as cancers, particularly those that have metastasized to the CNS. The present invention addresses these needs and offers other related advantages.

BRIEF SUMMARY OF THE INVENTION

Embodiments of the present invention include p97 (melanotransferrin or MTf)-trastuzumab fusion proteins, comprising a trastuzumab heavy chain and/or light chain sequence fused to a p97 sequence and an optional linker in between. In some embodiments, the fusion protein comprises a trastuzumab heavy chain sequence fused to the N-terminus of the p97 sequence. In certain embodiments, the fusion protein comprises a trastuzumab heavy chain sequence fused to the C-terminus of the p97 sequence. In some embodiments, the fusion protein comprises a truncated trastuzumab heavy chain sequence fused to the C-terminus of the p97 sequence.

In some embodiments, the truncated trastuzumab heavy chain sequence consists essentially of the heavy chain constant region or a fragment thereof and substantially or entirely lacks the heavy chain variable region. In certain embodiments, the truncated trastuzumab heavy chain sequence consists essentially of the CH1 domain or a fragment thereof, the hinge region, the CH2 domain, and the CH3 domain. In certain embodiments, the truncated trastuzumab heavy chain sequence consists essentially of the hinge region or a fragment thereof, the CH2 domain, and the CH3 domain.

In some embodiments, the fusion protein comprises (a) a heavy chain amino acid sequence set forth in SEQ ID NOs:37-46 or 96-109; (b) a heavy chain amino acid sequence at least 90% identical to a sequence set forth in SEQ ID NOs:37-46 or 96-109; (c) or a heavy chain amino acid sequence that differs from SEQ ID NOs:37-46 or 96-109 by addition, substitution, insertion, or deletion of about 1-50 amino acids. In some embodiments, the fusion protein comprises a heavy chain amino acid sequence set forth in one or more of SEQ ID NOs:37-46 or 96-109.

In some embodiments, the fusion protein comprises a trastuzumab light chain sequence fused to the N-terminus of the p97 sequence. In certain embodiments, the fusion protein comprises a trastuzumab light chain sequence fused to the C-terminus of the p97 sequence. In some embodiments, the fusion protein comprises (a) a light amino acid sequence set forth in SEQ ID NOs:110-121; (b) a light chain amino acid sequence at least 90% identical to a sequence set forth in SEQ ID NOs: 110-121; (c) or a light chain amino acid sequence that differs from SEQ ID NOs: 110-121 by addition, substitution, insertion, or deletion of about 1-50 amino acids. In some embodiments, the fusion protein comprises a light chain amino acid sequence set forth in SEQ ID NOs: 110-121.

In specific embodiments, the p97 sequence comprises, consists, or consists essentially of SEQ ID NO:2 (soluble MTf) or SEQ ID NO:14 (MTfp or MTfpep).

Also included are isolated polynucleotides, which encode a p97 fusion protein described herein. In some aspects, the isolated polynucleotides are codon-optimized for expression in a host cell. In some embodiments, the host cell is a mammalian cell, an insect cell, a yeast cell, or a bacterial cell.

Also included are recombinant host cells, comprising an isolated polynucleotide described herein, optionally where the isolated polynucleotide is operably linked to one or more regulatory elements. In certain embodiments, the recombinant host cell comprises an isolated polynucleotide that encodes a (non-fusion) trastuzumab light chain sequence, which is operably linked to one or more regulatory elements. In certain embodiments, the recombinant host cell comprises an isolated polynucleotide that encodes a (non-fusion) trastuzumab heavy chain sequence, which is operably linked to one or more regulatory elements. In certain embodiments, the recombinant host cell comprises an isolated polynucleotide that encodes a (non-fusion) trastuzumab light chain sequence, and an isolated polynucleotide that encodes a (non-fusion) trastuzumab heavy chain sequence, which are operably linked to one or more regulatory elements.

Certain embodiments relate to vectors, comprising an isolated polynucleotide, which encodes a p97 fusion protein of any of the preceding claims, which is operably linked to one or more regulatory elements. In some embodiments, the vector comprises an isolated polynucleotide that encodes a (non-fusion) trastuzumab light chain sequence, which is operably linked to one or more regulatory elements. In some embodiments, the vector comprises an isolated polynucleotide that encodes a (non-fusion) trastuzumab heavy chain sequence, which is operably linked to one or more regulatory elements. In some embodiments, the vector comprises an isolated polynucleotide that encodes a (non-fusion) trastuzumab light chain sequence, and an isolated polynucleotide that encodes a (non-fusion) trastuzumab heavy chain sequence, which are operably linked to one or more regulatory elements. Also included are recombinant host cells, comprising one or more vectors as described herein.

Some embodiments relate to p97-antibody fusion proteins that comprise two (non-fusion) trastuzumab light chain sequences, and one or two p97-trastuzumab heavy chain fusion proteins described herein, where the one or two p97-trastuzumab heavy chain fusion protein(s) comprise a trastuzumab heavy chain sequence fused to the N-terminus of a p97 sequence and an optional linker in between (see, e.g., FIGS. 1A & 1B). In some embodiments, the p97-antibody fusion protein comprises two p97-trastuzumab heavy chain fusion proteins (see, e.g., FIGS. 1A and 1E). In certain embodiments, the p97-antibody fusion protein comprises one p97-trastuzumab heavy chain fusion protein and one (non-fusion) trastuzumab heavy chain sequence (see, e.g., FIG. 1B).

Also included are p97-antibody fusion proteins that comprise one trastuzumab light chain sequence, one trastuzumab heavy chain sequence, and one p97-trastuzumab heavy chain fusion protein of any of the preceding claims, where p97-trastuzumab heavy chain fusion protein comprises a truncated trastuzumab heavy chain fused to the C-terminus of a p97 sequence and an optional linker in between (see, e.g., FIG. 1C).

In some embodiments, the p97-antibody fusion protein comprises two trastuzumab light chain sequences, and two p97-trastuzumab heavy chain fusion proteins described herein, where the p97-trastuzumab heavy chain fusion proteins comprise a trastuzumab heavy chain fused to the C-terminus of a p97 sequence and an optional linker in between (see, e.g., FIG. 1D).

In some embodiments, the p97-antibody fusion protein comprises two p97-trastuzumab light chain fusion proteins described herein, and two p97-trastuzumab heavy chain fusion proteins described herein, where the p97-trastuzumab light chain fusion proteins comprise a trastuzumab light chain fused to the N-terminus of a p97 sequence and an optional linker in between, and where the p97-trastuzumab heavy chain fusion proteins comprise a trastuzumab heavy chain fused to the N-terminus of a p97 sequence and an optional linker in between (see, e.g., FIG. 1F).

Specific examples of p97-antibody fusion proteins include those that comprise two sets of heavy and light chains, where at least one set is selected from one or more of:

a) the heavy chain of SEQ ID NO:82 and the light chain of SEQ ID NO:83;
b) the heavy chain of SEQ ID NO:84 and the light chain of SEQ ID NO:85;
c) the heavy chain of SEQ ID NO:86 and the light chain of SEQ ID NO:87;
d) the heavy chain of SEQ ID NO:88 and the light chain of SEQ ID NO:89;
e) the heavy chain of SEQ ID NO:90 and the light chain of SEQ ID NO:91;
f) the heavy chain of SEQ ID NO:92 and the light chain of SEQ ID NO:93; and
g) the heavy chain of SEQ ID NO:94 and the light chain of SEQ ID NO:95; including fragments/variants thereof of any of the foregoing. In some embodiments, the p97-antibody fusion is a homodimer that comprises two sets of a), two sets of b), two sets of c), two sets of d), two sets of e), two sets of f), or two sets of g). In some embodiments, the p97-antibody fusion is a heterodimer that comprises any combination of a)-g) above. In particular embodiments, the p97-antibody fusion is a heterodimer that comprises a first set of sets of heavy and light chains selected from a)-g) above, and a second set of trastuzumab (non-fusion) heavy and light chains, for example, SEQ ID NOs: 29-35 or 122 (heavy chains) and 36 or 123 (light chains).

Certain embodiments relate to recombinant host cells that comprises a p97-antibody fusion protein of any of the preceding claims. In certain embodiments, the host cell is a mammalian cell, an insect cell, a yeast cell, or a bacterial cell. In certain embodiments, the mammalian cell is a Chinese hamster ovary (CHO) cell or a HEK-293 cell.

Also included are pharmaceutical compositions, comprising a pharmaceutically-acceptable carrier and a p97-antibody fusion protein of any of the preceding claims.

Some embodiments include methods for the treatment of a HER2-overexpressing cancer in a subject in need thereof, comprising administering to the subject a p97-antibody fusion protein or pharmaceutical composition described herein.

In certain embodiments, the HER2-overexpressing cancer is at risk for metastasizing to the CNS of the subject. In some embodiments, the HER2-overexpressing cancer has metastasized to the CNS of the subject. In certain embodiments, the HER2-overexpressing cancer is a breast cancer, ovarian cancer, gastric cancer, or uterine cancer.

In particular embodiments, the HER2-overexpressing cancer is a HER2-overexpressing metastatic breast cancer. In certain embodiments, the HER2-overexpressing metastatic breast cancer is at risk for metastasizing to the CNS of the subject. In some embodiments, the HER2-overexpressing breast cancer has metastasized to the CNS of the subject.

In certain embodiments, the HER2-overexpressing cancer is a HER2-overexpressing metastatic gastric or gastroesophageal junction adenocarcinoma. In certain embodiments, the HER2-overexpressing metastatic gastric or gastroesophageal junction adenocarcinoma is at risk for metastasizing to the CNS of the subject. In certain embodiments, the HER2-overexpressing metastatic gastric or gastroesophageal junction adenocarcinoma has metastasized to the CNS of the subject.

In certain embodiments, the HER2-overexpressing cancer is a HER2-overexpressing uterine serous carcinoma (USC). In certain embodiments, the HER2-overexpressing USC is at risk for metastasizing to the CNS of the subject. In certain embodiments, the HER2-overexpressing USC has metastasized to the CNS of the subject.

Certain methods include administering the p97-antibody fusion protein or pharmaceutical composition as part of an adjuvant treatment for a HER2-overexpresssing breast cancer. In certain embodiments, the adjuvant treatment comprises doxorubicin, cyclophosphamide, and either paclitaxel or docetaxel. In certain embodiments, the adjuvant treatment comprises docetaxel and carboplatin.

Some methods include administering the p97-antibody fusion protein or pharmaceutical composition as a single agent following multi-modality anthracycline based therapy.

In certain embodiments, the subject is a female human.

Certain methods include administering the p97-antibody fusion protein or pharmaceutical composition by intravenous (IV) infusion.

BRIEF DESCRIPTION OF THE DRAWINGS

FIG. 1A illustrates a homodimeric antibody fusion protein composed of two trastuzumab light chains and two trastuzumab heavy chains each fused to the N-terminus of p97. FIG. 1B illustrates a heterodimeric antibody fusion protein composed of two trastuzumab light chains, one non-fused trastuzumab heavy chain, and one trastuzumab heavy chain fused to the N-terminus of p97. FIG. 1C illustrates a heterodimeric antibody fusion protein composed of one trastuzumab light chain, one non-fused trastuzumab heavy chain, and one trastuzumab heavy chain fused to the C-terminus of p97. FIGS. 1D-1E illustrate antibody fusions composed of two p97-trastuzumab heavy chain fusion proteins and two (non-fusion) trastuzumab light chains. FIG. 1F illustrates an antibody fusion composed of two p97-trastuzumab light chain fusion proteins and two 97-trastuzumab heavy chain fusion proteins. FIG. 1G illustrates an antibody fusion composed of two p97-trastuzumab light chain fusion proteins and two (non-fusion) trastuzumab heavy chain sequences.

FIG. 2A shows the results for human IgG1, FIG. 2B shows the results for TZM HC-MTf, FIG. 2C shows the results for MTfp NH-TZM, and FIG. 2D shows the results for TZM HC-MTfp (see Example 1).

DETAILED DESCRIPTION

Figure 1A:
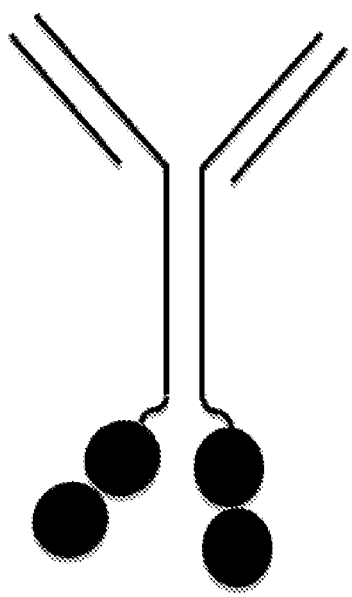
FIGS. 1A-1G illustrate the general structure of exemplary p97-antibody fusion proteins (black circles represent p97).

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (3$^{rd}$ Edition, 2000); *DNA Cloning: A Practical Approach*, vol. I & II (D. Glover, ed.); Oligonucleotide Synthesis (N. Gait, ed., 1984); Oligonucleotide Synthesis: Methods and Applications (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, 5$^{th}$ Ed. Hoboken N.J., John Wiley & Sons; B. Perbal, *A Practical Guide to Molecular Cloning* (3$^{rd}$ Edition 2010); Farrell, R., *RNA Methodologies: A Laboratory Guide for Isolation and Characterization* (3$^{rd}$ Edition 2005).

All publications, patents, and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" is intended to refer to the entity formed as a result of covalent or non-covalent attachment or linkage of an agent or other molecule, e.g., a biologically active molecule, to a p97 polypeptide or p97 sequence. One example of a conjugate polypeptide is a "fusion protein" or "fusion polypeptide," that is, a polypeptide that is created through the joining of two or more coding sequences, which originally coded for separate polypeptides; translation of the joined coding sequences results in a single, fusion polypeptide, typically with functional properties derived from each of the separate polypeptides. The terms "antibody fusion" and "antibody fusion protein" are used interchangeably herein to refer to an antibody or antibody-like molecule that comprises at least one fusion protein described herein.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., *Nucleic Acids Research.* 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "linkage," "linker," "linker moiety," or "L" is used herein to refer to a linker that can be used to separate a p97 polypeptide from an agent of interest, or to separate a first agent from another agent, for instance where two or more agents are linked to form a p97 conjugate. The linker may be physiologically stable or may include a releasable linker such as an enzymatically degradable linker (e.g., proteolytically cleavable linkers). In certain aspects, the linker may be a peptide linker, for instance, as part of a p97 fusion protein. In some aspects, the linker may be a non-peptide linker or non-proteinaceous linker. In some aspects, the linker may be particle, such as a nanoparticle.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., the absence of a fusion protein or antibody fusion of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition or a control composition, including all integers in between. As one non-limiting example, a control could compare the activity, such as the amount or rate of transport/delivery across the blood brain barrier, the rate and/or levels of distribution to central nervous system tissue, and/or the $C_{max}$ for plasma, central nervous system tissues, or any other systemic or peripheral non-central nervous system tissues, of a p97 fusion protein or antibody fusion relative to the agent/antibody alone. Other examples of comparisons and "statistically significant" amounts are described herein.

In certain embodiments, the "purity" of any given agent (e.g., a p97 conjugate such as a fusion protein or antibody fusion) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides.

A "releasable linker" includes, but is not limited to, a physiologically cleavable linker and an enzymatically degradable linker. Thus, a "releasable linker" is a linker that may undergo either spontaneous hydrolysis, or cleavage by some other mechanism (e.g., enzyme-catalyzed, acid-catalyzed, base-catalyzed, and so forth) under physiological conditions. For example, a "releasable linker" can involve an elimination reaction that has a base abstraction of a proton, (e.g., an ionizable hydrogen atom, Hα), as the driving force. For purposes herein, a "releasable linker" is synonymous with a "degradable linker." An "enzymatically degradable linkage" includes a linkage, e.g., amino acid sequence that is subject to degradation by one or more enzymes, e.g., peptidases or proteases. In particular embodiments, a releasable linker has a half life at pH 7.4, 25° C., e.g., a physiological pH, human body temperature (e.g., in vivo), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or less.

The term "reference sequence" refers generally to a nucleic acid coding sequence, or amino acid sequence, to which another sequence is being compared. All polypeptide and polynucleotide sequences described herein are included as references sequences, including those described by name and those described in the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99%, or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of a protein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (~37° C.). In certain embodiments, a p97 polypeptide or conjugate has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at about 37° C.

A "subject," as used herein, includes any animal that exhibits a symptom, or is at risk for exhibiting a symptom, which can be treated or diagnosed with a p97 fusion protein or related antibody fusion of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild type gene or gene product (e.g., a polypeptide) is that which is most frequently observed in a population and is thus arbitrarily designed the "normal" or "wild-type" form of the gene.

Fusion Proteins

Embodiments of the present invention relate generally to fusion proteins that comprise a human p97 (melanotransferrin; MTf) polypeptide sequence a trastuzumab sequence, or an antigen-binding fragment thereof, antibodies that comprise such fusion proteins (i.e., antibody fusions), polynucleotides encoding the fusion proteins, host cells and methods of producing fusion proteins/antibodies, and related compositions and methods of use thereof. Exemplary p97 polypeptide sequences and trastuzumab sequences are described below. Also described are exemplary methods and components, such as linker peptides, for coupling a p97 polypeptide sequence to a trastuzumab sequence.

p97 Sequences.

In certain embodiments, a p97 polypeptide sequence used in a composition and/or fusion protein of the invention comprises, consists essentially of, or consists of a human p97 reference sequence provided in Table 1 below. Also included are variants and fragments thereof.

TABLE 1

Exemplary p97 Sequences

| Description | Sequence | SEQ ID NO: |
|---|---|---|
| FL Human p97 | MRGPSGALWLLLALRTVLGGMEVRWCATSDPEQHKCGNMSEAFREAGIQ PSLLCVRGTSADHCVQLIAAQEADAITLDGGAIYEAGKEHGLKPVVGEV YDQEVGTSYYAVAVVRRSSHVTIDTLKGVKSCHTGINRTVGWNVPVGYL VESGRLSVMGCDVLKAVSDYFGGSCVPGAGETSYSESLCRLCRGDSSGE GVCDKSPLERYYDYSGAFRCLAEGAGDVAFVKHSTVLENTDGKTLPSWG QALLSQDFELLCRDGSRADVTEWRQCHLARVPAHAVVVRADTDGGLIFR LLNEGQRLFSHEGSSFQMFSSEAYGQKDLLFKDSTSELVPIATQTYEAW LGHEYLHAMKGLLCDPNRLPPYLRWCVLSTPEIQKCGDMAVAFRRQRLK PEIQCVSAKSPQHCMERIQAEQVDAVTLSGEDIYTAGKTYGLVPAAGEH YAPEDSSNSYYVVAVVRRDSSHAFTLDELRGKRSCHAGFGSPAGWDVPV GALIQRGFIRPKDCDVLTAVSEFFNASCVPVNNPKNYPSSLCALCVGDE QGRNKCVGNSQERYYGYRGAFRCLVENAGDVAFVRHTTVFDNTNGHNSE PWAAELRSEDYELLCPNGARAEVSQFAACNLAQIPPHAVMVRPDTNIFT VYGLLDKAQDLFGDDHNKNGFKMFDSSNYHGQDLLFKDATVRAVPVGEK TTYRGWLGLDYVAALEGMSSQQCSGAAAPAPGAPLLPLLLPALAARLLP PAL | 1 |
| Soluble Human p97 | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTISGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQCSG | 2 |
| P97 fragment | WCATSDPEQHK | 3 |
| P97 fragment | RSSHVTIDTLK | 4 |
| P97 fragment | SSHVTIDTLKGVK | 5 |
| P97 fragment | LCRGDSSGEGVCDK | 6 |
| P97 fragment | GDSSGEGVCDKSPLER | 7 |
| P97 fragment | YYDYSGAFR | 8 |
| P97 fragment | ADVTEWR | 9 |
| P97 fragment | VPAHAVVVR | 10 |
| P97 fragment | ADTDGGLIFR | 11 |
| P97 fragment | CGDMAVAFR | 12 |
| P97 fragment | LKPEIQCVSAK | 13 |
| P97 fragment | DSSHAFTLDELR | 14 |
| P97 fragment | SEDYELLCPNGAR | 15 |

TABLE 1-continued

Exemplary p97 Sequences

| Description | Sequence | SEQ ID NO: |
|---|---|---|
| P97 fragment | AQDLFGDDHNKNGFK | 16 |
| P97 fragment | FSSEAYGQKDLLFKDSTSELVPIATQTYEAWLGHEYLHAM | 17 |
| P97 fragment | ERIQAEQVDAVTLSGEDIYTAGKTYGLVPAAGEHYAPEDSSNSYYVVAV VRRDSSHAFTLDELRGKRSCHAGFGSPAGWDVPVGALIQRGFIRPKDCD VLTAVSEFFNASCVPVNNPKNYPSSLCALCVGDEQGRNKCVGNSQERYY GYRGAFRCLVENAGDVAFVRHTTVFDNTNGHNSEPWAAELRSEDYELLC PNGARAEVSQFAACNLAQIPPHAVM | 18 |
| P97 fragment | VRPDTNIFTVYGLLDKAQDLFGDDHNKNGFKM | 19 |
| P97 fragment | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTISGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTN | 20 |
| P97 fragment | GHNSEPWAAELRSEDYELLCPN | 21 |
| P97 fragment | GARAEVSQFAACNLAQIPPHAVMVRPDTNIFTVYGLLDKAQDLFGDDHN KN | 22 |
| P97 fragment | GFKMFDSSNYHGQDLLFKDATVRAVPVGEKTTYRGWLGLDYVAALEGMS SQQC | 23 |
| P97 fragment | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTISGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPN | 24 |
| P97 fragment | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTISGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN | 25 |
| P97 fragment | GHNSEPWAAELRSEDYELLCPNGARAEVSQFAACNLAQIPPHAVMVRPD TNIFTVYGLLDKAQDLFGDDHNKN | 26 |
| P97 fragment | GHNSEPWAAELRSEDYELLCPNGARAEVSQFAACNLAQIPPHAVMVRPD TNIFTVYGLLDKAQDLFGDDHNKNGFKMFDSSNYHGQDLLFKDATVRAV PVGEKTTYRGWLGLDYVAALEGMSSQQC | 27 |
| P97 fragment | GARAEVSQFAACNLAQIPPHAVMVRPDTNIFTVYGLLDKAQDLFGDDHN KNGFKMFDSSNYHGQDLLFKDATVRAVPVGEKTTYRGWLGLDYVAALEG MSSQQC | 28 |

In some embodiments, a p97 polypeptide sequence comprises a sequence having at least 70%, 75%, 80%, 85%, 90%, 95%, 96%, 97%, 98%, or 99% identity or homology, along its length, to a human p97 sequence in Table 1, or a fragment thereof.

In particular embodiments, a p97 polypeptide sequence comprises a fragment of a human p97 sequence in Table 1. In certain embodiments, a p97 polypeptide fragment is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730 or more amino acids in length, including all integers and ranges in between, and which may comprise all or a portion of the sequence of a p97 reference sequence.

In certain embodiments, a p97 polypeptide fragment is about 5-700, 5-600, 5-500, 5-400, 5-300, 5-200, 5-100, 5-50, 5-40, 5-30, 5-25, 5-20, 5-15, 5-10, 10-700, 10-600, 10-500, 10-400, 10-300, 10-200, 10-100, 10-50, 10-40, 10-30, 10-25, 10-20, 10-15, 20-700, 20-600, 20-500, 20-400, 20-300, 20-200, 20-100, 20-50, 20-40, 20-30, 20-25, 30-700, 30-600, 30-500, 30-400, 30-300, 30-200, 30-100, 30-50, 30-40, 40-700, 40-600, 40-500, 40-400, 40-300, 40-200, 40-100, 40-50, 50-700, 50-600, 50-500, 50-400, 50-300, 50-200, 50-100, 60-700, 60-600, 60-500, 60-400, 60-300, 60-200, 60-100, 60-70, 70-700, 70-600, 70-500, 70-400, 70-300, 70-200, 70-100, 70-80, 80-700, 80-600, 80-500, 80-400, 80-300, 80-200, 80-100, 80-90, 90-700, 90-600, 90-500, 90-400, 90-300, 90-200, 90-100, 100-700, 100-600, 100-500, 100-400, 100-300, 100-250, 100-200, 100-150, 200-700, 200-600, 200-500, 200-400, 200-300, or 200-250 amino acids in length, and comprises all or a portion of a p97 reference sequence.

In certain embodiments, p97 polypeptide sequences of interest include p97 amino acid sequences, subsequences, and/or variants of p97 that are effective for transporting an agent of interest across the blood brain barrier and into the central nervous system (CNS). In particular embodiments, the variant or fragment comprises the N-lobe of human p97 (residues 20-361 of SEQ ID NO:1). In specific aspects, the variant or fragment comprises an intact and functional $Fe^{3+}$-binding site.

In some embodiments, a p97 polypeptide sequence is a soluble form of a p97 polypeptide (see Yang et al., Prot Exp Purif. 34:28-48, 2004), or a fragment or variant thereof. In some aspects, the soluble p97 polypeptide has a deletion of the all or a portion of the hydrophobic domain (residues 710-738 of SEQ ID NO:1), alone or in combination with a deletion of all or a portion of the signal peptide (residues 1-19 of SEQ ID NO:1). In specific aspects, the soluble p97 polypeptide comprises or consists of SEQ ID NO:2 (residues 20-711 of SEQ ID NO:1), including variants and fragments thereof.

In some embodiments, the p97 polypeptide comprises, consists, or consists essentially of the sequence DSSHAFTLDELR (SEQ ID NO:14 or MTfp), including variants and fragments thereof. In some embodiments, the DSSHAFTLDELR (SEQ ID NO:14) peptide comprises a C-terminal tyrosine (Y).

In certain embodiments, for instance, those that employ liposomes, the p97 polypeptide sequence is a lipid soluble form of a p97 polypeptide. For instance, certain of these and related embodiments include a p97 polypeptide that comprises all or a portion of the hydrophobic domain, optionally with or without the signal peptide.

In certain other embodiments, the p97 fragment or variant is capable of specifically binding to a p97 receptor, an LRP1 receptor and/or an LRP1B receptor.

Variants and fragments of reference p97 polypeptides and other reference polypeptides are described in greater detail below.

Trastuzumab Sequences.

In certain embodiments, a trastuzumab antibody sequence used in a fusion protein of the invention comprises, consists essentially of, or consists of the trastuzumab light chain and/or heavy chain sequence(s) illustrated in Table 2 below.

TABLE 2

Exemplary Trastuzumab Sequences

| Description | Sequence | SEQ ID NO: |
|---|---|---|
| FL heavy chain (hinge underlined) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVE<u>PKSCDKTHTCPPCP</u>APELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGK | 29 |
| FL heavy chain (hinge underlined) with substituted amino acids for "hole" (bold underlined) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVE<u>PKSCDKTHTCPPCP</u>APELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTWPPVLDSDGSFFLTSKLTVDKSRWQQGNVFSCSVMHEALHNHYTQ KSLSLSPGK | 30 |

TABLE 2-continued

Exemplary Trastuzumab Sequences

| Description | Sequence | SEQ ID NO: |
|---|---|---|
| Heavy chain truncation (hinge underlined) | NTKVDKKVE<u>PKSCDKTHTCPPCP</u>APELLGGPSVFLFPPKPKDTLMISRT PEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGS FFLYSKLTVDKSRWQQGNVFSCSVMHEALHNHYTQKSLSLSPGK | 31 |
| Heavy chain truncation (partial hinge underlined) | <u>DKTHTCPPCP</u>APELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK | 32 |
| Heavy chain truncation (hinge underlined) with substituted amino acids for "hole" (bold underlined) | NTKVDKKVE<u>PKSCDKTHTCPPCP</u>APELLGGPSVFLFPPKPKDTLMISRT PEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPS RDELTKNQVSLTCLVKGFYPSDIAVEWESNGQPENNYKT<u>W</u>PPVLDSDGS FFL<u>T</u>SKLTVDKSRWQQGNVFSCSVMHEALHNHYTQKSLSLSPGK | 33 |
| Heavy chain truncation (partial hinge underlined) with substituted amino acids for "hole" (bold underlined) | <u>DKTHTCPPCP</u>APELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKT<u>W</u>PPVLDSDGSFFL<u>T</u>SKLTVDKSR WQQGNVFSCSVMHEALHNHYTQKSLSTSPGK | 34 |
| FL heavy chain (hinge underlined) with substituted amino acids for "knob" (bold underlined) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVE<u>PKSCDKTHTCPPCP</u>APELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSL<u>Y</u>CLVKGFYPSDIAVEWESNGQPEN NYKTTPPVLDSDGSF<u>AL</u>YSKLTVDKSRWQQGNVFSCSVMHEALHNHYTQ KSLSLSPGK | 35 |
| FL heavy chain with Signal Sequence (underlined) | <u>METDTLLLWVLLLWVPGSTG</u>EVQLVESGGGLVQPGGSLRLSCAASGFNI KDTYIHWVRQAPGKGLEWVARIYPTNGYTRYADSVKGRFTISADTSKNT AYLQMNSLRAEDTAVYYCSRWGGDGFYAMDYWGQGTLVTVSSASTKGPS VFPLAPSSKSTSGGTAALGCLVKDYFPEPVTVSWNSGALTSGVHTFPAV LQSSGLYSLSSVVTVPSSSLGTQTYICNVNHKPSNTKVDKKVEPPKSCD KTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRW QQGNVFSCSVMHEALHNHYTQKSLSLSPGK | 122 |
| FL Light Chain | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC | 36 |
| FL Light Chain with Signal Sequence (underlined) | <u>METDTLLLWVLLLWVPGSTG</u>DIQMTQSPSSLSASVGDRVTITCRASQDV NTAVAWYQQKPGKAPKLLIYSASFLYSGVPSRFSGSRSGTDFTLTISSL QPEDFATYYCQQHYTTPPTFGQGTKVEIKRTVAAPSVFIFPPSDEQLKS GTASVVCLLNNFYPREAKVQWKVDNALQSGNSQESVTEQDSKDSTYSLS STLTLSKADYEKHKVYACEVTHQGLSSPVTKSFNRGEC | 123 |

Also included are antigen-binding variants and fragments of the trastuzumab heavy and light chain sequences described herein. In certain embodiments, the trastuzumab antibody, antigen-binding fragment thereof, or related fusion protein or antibody fusion specifically binds to Her2/neu or an epitope or fragment thereof.

In particular embodiments, the trastuzumab heavy chain fragment(s), e.g., the Fc regions of the heavy chain fragments, are modified to increase a preferred chain combination, for example, by using knobs-into-holes (KiH) technology (see, e.g., Klein et al., mAbs. 4:6, 653-663, 2012) or other technologies, such as those described in U.S. Application No. 2012/0149876. As one example, to increase the formation of a heterodimeric antibody fusion (e.g., an antibody that comprises one p97-trastuzumab heavy chain fusion and one normal trastuzumab heavy chain; see, e.g., FIGS. 1B and 1C), one of the heavy chains can have amino acid modifications to generate the "knob" and the other heavy chain can have amino acid modifications to form the "hole". Specific, non-limiting examples of KiH modifications to trastuzumab heavy chain sequences are illustrated in Table 2 above. As another example, one heavy chain fragment could comprise a CH3 domain having amino acid modifications selected from one or more of T350V, L351Y, D399R, D399 (e.g., D399R, D399W, D399Y, D399K), S400 (e.g., S400E, S400D, S400R, S400K), F405 (e.g., F405I, F405M, F405T, F405S, F405V, F405W), Y407A, Y407I, Y407V, including combinations thereof, and the other could comprise a CH3 domain having amino acid modifications selected from one or more of T350V, T366V, T366I, T366L, T366M, N390 (e.g., N390R, N390K, N390D), K392 (e.g., K392V, K392M, K392R, K392L, K392F, K392E), F405 (e.g., F405I, F405M, F405T, F405S, F405V, F405W), K409F, K409W, and T411 (e.g., T411N, T411R, T411Q, T411K, T411D, T411E, T411W) including combinations thereof (see U.S. Application No. 2012/0149876, hereby incorporated by reference in its entirety).

The term "antigen-binding fragment" as used herein refers to a polypeptide fragment that contains at least one CDR of an immunoglobulin heavy and/or light chains that bind to the antigen of interest. In this regard, an antigen-binding fragment of the herein described antibodies may comprise 1, 2, 3, 4, 5, or all 6 CDRs of a VH and VL sequence from antibodies that bind to a therapeutic or diagnostic target.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

An antibody, antigen-binding fragment thereof, is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$.

Immunological binding properties of proteins such as trastuzumab, antigen-binding fragments thereof, and related fusion proteins and antibody fusions can be quantified using methods well known in the art (see Davies et al., *Annual Rev. Biochem.* 59:439-473, 1990). In some embodiments, a protein is said to specifically bind an antigen or epitope thereof when the equilibrium dissociation constant is about ≤$10^{-7}$ or $10^{-8}$ M. In some embodiments, the equilibrium dissociation constant of a protein may be about ≤$10^{-9}$ M or ≤$10^{-10}$ M. In certain illustrative embodiments, a protein has an affinity ($K_d$) for an antigen or target described herein (to which it specifically binds) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures-regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. See Inbar et al., *PNAS USA.* 69:2659-2662, 1972; Hochman et al., *Biochem.* 15:2706-2710, 1976; and Ehrlich et al., *Biochem.* 19:4091-4096, 1980.

In certain embodiments, single chain Fv or scFV antibodies are contemplated. For example, Kappa bodies (Ill et al., *Prot. Eng.* 10:949-57, 1997); minibodies (Martin et al., *EMBO J* 13:5305-9, 1994); diabodies (Holliger et al., *PNAS* 90: 6444-8, 1993); or Janusins (Traunecker et al., *EMBO J* 10: 3655-59, 1991; and Traunecker et al., *Int. J. Cancer Suppl.* 7:51-52, 1992), may be prepared using standard molecular biology techniques following the teachings of the present application with regard to selecting antibodies having the desired specificity.

A single chain Fv (sFv) polypeptide is a covalently linked $V_H::V_L$ heterodimer which is expressed from a gene fusion including $V_H$- and $V_L$-encoding genes linked by a peptide-encoding linker. Huston et al. (*PNAS USA.* 85(16):5879-5883, 1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio et al., *PNAS USA* 86:4220-4224, 1989; Queen et al., *PNAS USA.* 86:10029-10033, 1988; Riechmann et al., *Nature.* 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., *Cancer Res.* 53:851-856, 1993; Riechmann et al., *Nature* 332:323-327, 1988; Verhoeyen et al., *Science* 239:1534-1536, 1988; Kettleborough et al., *Protein Engineering.* 4:773-3783, 1991; Maeda et al., *Human Antibodies Hybridoma* 2:124-134, 1991; Gorman et al., *PNAS USA.* 88:4181-4185, 1991; Tempest et al., *Bio/Technology* 9:266-271, 1991; Co et al., *PNAS USA.* 88:2869-2873, 1991; Carter et al., *PNAS USA.*

89:4285-4289, 1992; and Co et al., *J Immunol.* 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

Linkers.

As noted above, certain fusion proteins may employ one or more linker groups, including peptide linkers. Such linkers can be stable linkers or releasable linkers.

For instance, for polypeptide-polypeptide conjugates, peptide linkers can separate the components by a distance sufficient to ensure that each polypeptide folds into its secondary and tertiary structures. Such a peptide linker sequence may be incorporated into the fusion protein using standard techniques described herein and well-known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180.

In certain illustrative embodiments, a peptide linker is between about 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids. In other illustrative embodiments, a peptide linker comprises about 1, 5, 10, 15, 20, 25, 30, 35, 40, 45, 50 or more amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., Gene 40:39-46, 1985; Murphy et al., PNAS USA. 83:8258-8262, 1986; U.S. Pat. Nos. 4,935,233 and 4,751,180. Particular peptide linker sequences contain Gly, Ser, and/or Asn residues. Other near neutral amino acids, such as Thr and Ala may also be employed in the peptide linker sequence, if desired.

Certain exemplary linkers include Gly, Ser and/or Asn-containing linkers, as follows: [G]$_x$, [S]$_x$, [N]$_x$, [GS]$_x$, [GGS]$_x$, [GSS]$_x$, [GSGS]$_x$(SEQ ID NO:47), [GGSG]$_x$ (SEQ ID NO:48), [GGGS]$_x$ (SEQ ID NO:49), [GGGGS]$_x$(SEQ ID NO:50), [GN]$_x$, [GGN]$_x$, [GNN]$_x$, [GNGN]$_x$(SEQ ID NO:51), [GGNG]$_x$(SEQ ID NO:52), [GGGN]$_x$(SEQ ID NO:53), [GGGGN]$_x$(SEQ ID NO:54) linkers, where $_x$ is 1, 2, 3, 4, 5, 6, 7, 8, 9, 10, 11, 12, 13, 14, 15, 16, 17, 18, 19, or 20 or more. Other combinations of these and related amino acids will be apparent to persons skilled in the art. In specific embodiments, the linker comprises or consists of a [GGGGS]$_3$ (SEQ ID NO:55) sequence, or GGGGSG-GGGSGGGGS (SEQ ID NO:55).

In specific embodiments, the linker sequence comprises a Gly3 linker sequence, which includes three glycine residues. In particular embodiments, flexible linkers can be rationally designed using a computer program capable of modeling both DNA-binding sites and the peptides themselves (Desjarlais & Berg, *PNAS.* 90:2256-2260, 1993; and *PNAS.* 91:11099-11103, 1994) or by phage display methods.

The peptide linkers may be physiologically stable or may include a releasable linker such as a physiologically degradable or enzymatically degradable linker (e.g., proteolytically cleavable linker). In certain embodiments, one or more releasable linkers can result in a shorter half-life and more rapid clearance of the conjugate. These and related embodiments can be used, for example, to enhance the solubility and blood circulation lifetime of p97 conjugates in the bloodstream, while also delivering an agent into the bloodstream (or across the BBB) that, subsequent to linker degradation, is substantially free of the p97 sequence. These aspects are especially useful in those cases where polypeptides or other agents, when permanently conjugated to a p97 sequence, demonstrate reduced activity. By using the linkers as provided herein, such antibodies can maintain their therapeutic activity when in conjugated form. In these and other ways, the properties of the p97 conjugates can be more effectively tailored to balance the bioactivity and circulating half-life of the antibodies over time.

Enzymatically degradable linkages suitable for use in particular embodiments of the present invention include, but are not limited to: an amino acid sequence cleaved by a serine protease such as thrombin, chymotrypsin, trypsin, elastase, kallikrein, or substilisin. Illustrative examples of thrombin-cleavable amino acid sequences include, but are not limited to: -Gly-Arg-Gly-Asp-(SEQ ID NO:56), -Gly-Gly-Arg-, -Gly-Arg-Gly-Asp-Asn-Pro-(SEQ ID NO:57), -Gly-Arg-Gly-Asp-Ser-(SEQ ID NO:58), -Gly-Arg-Gly-Asp-Ser-Pro-Lys-(SEQ ID NO:59), -Gly-Pro-Arg-, -Val-Pro-Arg-, and -Phe-Val-Arg-. Illustrative examples of elastase-cleavable amino acid sequences include, but are not limited to: -Ala-Ala-Ala-, -Ala-Ala-Pro-Val-(SEQ ID NO:60), -Ala-Ala-Pro-Leu-(SEQ ID NO:61), -Ala-Ala-Pro-Phe-(SEQ ID NO:62), -Ala-Ala-Pro-Ala-(SEQ ID NO:63), and -Ala-Tyr-Leu-Val-(SEQ ID NO:64).

Enzymatically degradable linkages suitable for use in particular embodiments of the present invention also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z-(SEQ ID NO:65), -Gly-Pro-, Leu-Gly-Pro-Z-(SEQ ID NO:66), -Gly-Pro-Ile-Gly-Pro-Z-(SEQ ID NO:67), and -Ala-Pro-Gly-Leu-Z-(SEQ ID NO: 68), where Y and Z are amino acids. Illustrative examples of collagenase-cleavable amino acid sequences include, but are not limited to: -Pro-Leu-Gly-Pro-D-Arg-Z-(SEQ ID NO:69), -Pro-Leu-Gly-Leu-Leu-Gly-Z-(SEQ ID NO:70), -Pro-Gln-Gly-Ile-Ala-Gly-Trp-(SEQ ID NO:71), -Pro-Leu-Gly-Cys(Me)-His-(SEQ ID NO:72), -Pro-Leu-Gly-Leu-Tyr-Ala-(SEQ ID NO:73), -Pro-Leu-Ala-Leu-Trp-Ala-Arg-(SEQ ID NO:74), and -Pro-Leu-Ala-Tyr-Trp-Ala-Arg-(SEQ ID NO:75), where Z is an amino acid. An illustrative example of a stromelysin-cleavable amino acid sequence is -Pro-Tyr-Ala-Tyr-Tyr-Met-Arg-(SEQ ID NO:76); and an example of a gelatinase-cleavable amino acid sequence is -Pro-Leu-Gly-Met-Tyr-Ser-Arg-(SEQ ID NO:77).

Enzymatically degradable linkages suitable for use in particular embodiments of the present invention also include amino acid sequences that can be cleaved by an angiotensin converting enzyme, such as, for example, -Asp-Lys-Pro-, -Gly-Asp-Lys-Pro-(SEQ ID NO:78), and -Gly-Ser-Asp-Lys-Pro-(SEQ ID NO:79).

Enzymatically degradable linkages suitable for use in particular embodiments of the present invention also include amino acid sequences that can be degraded by cathepsin B, such as, for example, -Val-Cit-, -Ala-Leu-Ala-Leu- (SEQ ID NO:80), -Gly-Phe-Leu-Gly- (SEQ ID NO:81) and -Phe-Lys-.

In some embodiments, the linker comprises, consists, or consists essentially of 125 (SEQ ID NO:124), including fragments and variants thereof.

In certain embodiments, however, any one or more of the non-peptide or peptide linkers are optional. For instance, linker sequences may not be required in a fusion protein where the first and second polypeptides have non-essential N-terminal and/or C-terminal amino acid regions that can be used to separate the functional domains and prevent steric interference.

Fusion Proteins and Antibody Fusions.

Certain embodiments relate to fusion proteins, comprising a p97 polypeptide sequence fused to a trastuzumab polypeptide sequence such as a trastuzumab heavy or light chain sequence, and antibody fusions comprising the same. An "antibody fusion" refers to an antibody or antibody-like immunoglobulin molecule that comprises one or more p97-trastuzumab fusion proteins and optionally one or more non-fusion trastuzumab sequences, i.e., trastuzumab light chain or heavy chain sequences, or variants/fragments thereof, which are not fused to a p97 sequence. In some instances, an antibody fusion comprises two light chain sequences and two heavy chain sequences, which are individually selected from any of the light/heavy chain sequences and/or fusion protein sequences described herein. In some instances, an antibody fusion comprises one light chain sequence and two heavy chain sequences, which are individually selected from any of the light/heavy chain sequences and/or fusion protein sequences described herein.

Specific, non-limiting examples of p97-trastuzumab heavy chain fusion proteins are illustrated in Table 3 below, and in Table E1 (see Examples).

TABLE 3

Exemplary p97-trastuzmab fusion protein sequences

| Description | Sequence | SEQ ID NO: |
|---|---|---|
| Trastuzumab FL heavy chain fused to N-terminus of soluble human p97 (no linker) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGK/GMEVRWCATSDPEQHKCGNMSEAFREAGIQPSLLCVRGT SADHCVQLIAAQEADAITLDGGAIYEAGKEHGLKPVVGEVYDQEVGTSY YAVAVVRRSSHVTIDTLKGVKSCHTGINRTVGWNVPVGYLVESGRLSVM GCDVLKAVSDYFGGSCVPGAGETSYSESLCRLCRGDSSGEGVCDKSPLE RYYDYSGAFRCLAEGAGDVAFVKHSTVLENTDGKTLPSWGQALLSQDFE LLCRDGSRADVTEWRQCHLARVPAHAVVVRADTDGGLIFRLLNEGQRLF SHEGSSFQMFSSEAYGQKDLLFKDSTSELVPIATQTYEAWLGHEYLHAM KGLLCDPNRLPPYLRWCVLSTPEIQKCGDMAVAFRRQRLKPEIQCVSAK SPQHCMERIQAEQVDAVTLSGEDIYTAGKTYGLVPAAGEHYAPEDSSNS YYVVAVVRRDSSHAFTLDELRGKRSCHAGFGSPAGWDVPVGALIQRGFI RPKDCDVLTAVSEFFNASCVPVNNPKNYPSSLCALCVGDEQGRNKCVGN SQERYYGYRGAFRCLVENAGDVAFVRHTTVFDNTNGHNSEPWAAELRSE DYELLCPNGARAEVSQFAACNLAQIPPHAVMVRPDTNIFTVYGLLDKAQ DLFGDDHNKNGFKMFDSSNYHGQDLLFKDATVRAVPVGEKTTYRGWLGL DYVAALEGMSSQQCSG | 37 |
| Trastuzumab FL heavy chain fused to N-terminus of soluble human p97 (linker underlined) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGKGGGGSGGGGSGGGGSGMEVRWCATSDPEQHKCGNMSEAFR EAGIQPSLLCVRGTSADHCVQLIAAQEADAITLDGGAIYEAGKEHGLKP VVGEVYDQEVGTSYYAVAVVRRSSHVTIDTLKGVKSCHTGINRTVGWNV PVGYLVESGRLSVMGCDVLKAVSDYFGGSCVPGAGETSYSESLCRLCRG DSSGEGVCDKSPLERYYDYSGAFRCLAEGAGDVAFVKHSTVLENTDGKT LPSWGQALLSQDFELLCRDGSRADVTEWRQCHLARVPAHAVVVRADTDG GLIFRLLNEGQRLFSHEGSSFQMFSSEAYGQKDLLFKDSTSELVPIATQ TYEAWLGHEYLHAMKGLLCDPNRLPPYLRWCVLSTPEIQKCGDMAVAFR RQRLKPEIQCVSAKSPQHCMERIQAEQVDAVTLSGEDIYTAGKTYGLVP | 38 |

TABLE 3-continued

Exemplary p97-trastuzmab fusion protein sequences

| Description | Sequence | SEQ ID NO: |
|---|---|---|
| | AAGEHYAPEDSSNSYYVVAVVRRDSSHAFTLDELRGKRSCHAGFGSPAG WDVPVGALIQRGFIRPKDCDVLTAVSEFFNASCVPVNNPKNYPSSLCAL CVGDEQGRNKCVGNSQERYYGYRGAFRCLVENAGDVAFVRHTTVFDNTN GHNSEPWAAELRSEDYELLCPNGARAEVSQFAACNLAQIPPHAVMVRPD TNIFTVYGLLDKAQDLFGDDHNKNGFKMFDSSNYHGQDLLFKDATVRAV PVGEKTTYRGWLGLDYVAALEGMSSQQCSG | |
| Trastuzumab truncated heavy chain fused to C-terminus of soluble human p97 (no linker) | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQCG/NTKVDKKVEPKSCDKTHTCPPCPAPELLGGPSVFLFPPKPKDT LMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPG K | 39 |
| Trastuzumab truncated heavy chain fused to C-terminus of soluble human p97 (linker underlined) | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQC<u>GGGGGSGGGGSGGGGS</u>NTKVDKKVEPKSCDKTHTCPPCPAPELLG GPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWES NGQPENNYKTTPPVLDSDGSFFLYSKLTVDKSRWQQGNVFSCSVMHEAL HNHYTQKSLSLSPGK | 40 |
| Trastuzumab partial hinge truncated heavy chain fused to C-terminus of soluble human p97 (no linker) | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQCG/DKTHTCPPCPAPELLGGPSVFLFPPKPKDTLMISRTPEVTCVV VDVSHEDPEVKFNWYVDGVEVHNAKTKPREEQYNSTYRVVSVLTVLHQD WLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKL TVDKSRWQQGNVFSCSVMHEALHNHYTQKSLSLSPGK | 41 |
| Trastuzumab partial hinge truncated heavy chain | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD | 42 |

TABLE 3-continued

Exemplary p97-trastuzmab fusion protein sequences

| Description | Sequence | SEQ ID NO: |
|---|---|---|
| fused to C-terminus of soluble human p97 (linker underlined) | VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQC<u>GGGGGSGGGGSGGGGS</u>DKTHTCPPCPAPELLGGPSVFLFPPKPKD TLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSP GK | |
| Trastuzumab truncated heavy chain with KiH "hole" variation fused to C-terminus of soluble human p97 (no linker) | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQCSG/NTKVDKKVEPKSCDKTHTCPPCPAPELLGGPSVFLFPPKPKD TLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQ VYTLPPSRDELTKNQVSLTCLVKGFYPSDIAVEWESNGQPENNYKTWPP VLDSDGSFFLTSKLTVDKSRWQQGNVFSCSVMHEALHNHYTQKSLSLSP GK | 43 |
| Trastuzumab truncated heavy chain with KiH "hole" variation fused to C-terminus of soluble human p97 (linker underlined) | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQCSG<u>GGGGSGGGGSGGGGS</u>NTKVDKKVEPKSCDKTHTCPPCPAPELL GGPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWE SNGQPENNYKTWPPVLDSDGSFFLTSKLTVDKSRWQQGNVFSCSVMHEA LHNHYTQKSLSLSPGK | 44 |
| Trastuzumab partial hinge truncated heavy chain with KiH "hole" variation fused to C-terminus of soluble human p97 (no linker) | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQCSG/DKTHTCPPCPAPELLGGPSVFLFPPKPKDTLMISRTPEVTCV VVDVSHEDPEVKFNWYVDGVEVHNAKTKPREEQYNSTYRVVSVLTVLHQ | 45 |

TABLE 3-continued

Exemplary p97-trastuzmab fusion protein sequences

| Description | Sequence | SEQ ID NO: |
|---|---|---|
| | DWLNGKEYKCKVSNKALPAPIEKTISKAKGQPREPQVYTLPPSRDELTK NQVSLTCLVKGFYPSDIAVEWESNGQPENNYKTWPPVLDSDGSFFLTSK LTVDKSRWQQGNVFSCSVMHEALHNHYTQKSLSLSPGK | |
| Trastuzumab partial hinge truncated heavy chain with KiH "hole" variation fused to C-terminus of soluble human p97 (linker underlined) | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQCSGGGGSGGGGSGGGGSDKTHTCPPCPAPELLGGPSVFLFPPKPK DTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREP QVYTLPPSRDELTKNQVSLTCLVKGFYPSDIAVEWESNGQPENNYKTWP PVLDSDGSFFLTSKLTVDKSRWQQGNVFSCSVMHEALHNHYTQKSLSLS PGK | 46 |
| TZM heavy chain: linker (underlined): MTf (bold) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGK<u>GGGGSGGGGS</u>GMEVRWCATSDPEQHKCGNMSEAFREAGIQ PSLLCVRGTSADHCVQLIAAQEADAITLDGGAIYEAGKEHGLKPVVGEV YDQEVGTSYYAVAVVRRSSHVTIDTLKGVKSCHTGINRTVGWNVPVGYL VESGRLSVMGCDVLKAVSDYFGGSCVPGAGETSYSESLCRLCRGDSSGE GVCDKSPLERYYDYSGAFRCLAEGAGDVAFVKHSTVLENTDGKTLPSWG QALLSQDFELLCRDGSRADVTEWRQCHLARVPAHAVVVRADTDGGLIFR LLNEGQRLFSHEGSSFQMFSSEAYGQKDLLFKDSTSELVPIATQTYEAW LGHEYLHAMKGLLCDPNRLPPYLRWCVLSTPEIQKCGDMAVAFRRQRLK PEIQCVSAKSPQHCMERIQAEQVDAVTLSGEDIYTAGKTYGLVPAAGEH YAPEDSSNSYYVVAVVRRDSSHAFTLDELRGKRSCHAGFGSPAGWDVPV GALIQRGFIRPKDCDVLTAVSEFFNASCVPVNNPKNYPSSLCALCVGDE QGRNKCVGNSQERYYGYRGAFRCLVENAGDVAFVRHTTVFDNTNGHNSE PWAAELRSEDYELLCPNGARAEVSQFAACNLAQIPPHAVMVRPDTNIFT VYGLLDKAQDLFGDDHNKNGFKMFDSSNYHGQDLLFKDATVRAVPVGEK TTYRGWLGLDYVAALEGMSSQQCS | 96 |
| TZM heavy chain: linker (underlined): MTf (bold) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGK<u>GGGGSGGGGSGGGGS</u>GMEVRWCATSDPEQHKCGNMSEAFR EAGIQPSLLCVRGTSADHCVQLIAAQEADAITLDGGAIYEAGKEHGLKP VVGEVYDQEVGTSYYAVAVVRRSSHVTIDTLKGVKSCHTGINRTVGWNV PVGYLVESGRLSVMGCDVLKAVSDYFGGSCVPGAGETSYSESLCRLCRG DSSGEGVCDKSPLERYYDYSGAFRCLAEGAGDVAFVKHSTVLENTDGKT LPSWGQALLSQDFELLCRDGSRADVTEWRQCHLARVPAHAVVVRADTDG GLIFRLLNEGQRLFSHEGSSFQMFSSEAYGQKDLLFKDSTSELVPIATQ TYEAWLGHEYLHAMKGLLCDPNRLPPYLRWCVLSTPEIQKCGDMAVAFR RQRLKPEIQCVSAKSPQHCMERIQAEQVDAVTLSGEDIYTAGKTYGLVP AAGEHYAPEDSSNSYYVVAVVRRDSSHAFTLDELRGKRSCHAGFGSPAG WDVPVGALIQRGFIRPKDCDVLTAVSEFFNASCVPVNNPKNYPSSLCAL CVGDEQGRNKCVGNSQERYYGYRGAFRCLVENAGDVAFVRHTTVFDNTN GHNSEPWAAELRSEDYELLCPNGARAEVSQFAACNLAQIPPHAVMVRPD TNIFTVYGLLDKAQDLFGDDHNKNGFKMFDSSNYHGQDLLFKDATVRAV PVGEKTTYRGWLGLDYVAALEGMSSQQCSG | 97 |

TABLE 3-continued

Exemplary p97-trastuzmab fusion protein sequences

| Description | Sequence | SEQ ID NO: |
|---|---|---|
| MTfp sequence (bold): linker (underlined): TZM heavy chain | DSSHAFTLDELRYGGGGSGGGGSEVQLVESGGGLVQPGGSLRLSCAASG FNIKDTYIHWVRQAPGKGLEWVARIYPTNGYTRYADSVKGRFTISADTS KNTAYLQMNSLRAEDTAVYYCSRWGGDGFYAMDYWGQGTLVTVSSASTK GPSVFPLAPSSKSTSGGTAALGCLVKDYFPEPVTVSWNSGALTSGVHTF PAVLQSSGLYSLSSVVTVPSSSLGTQTYICNVNHKPSNTKVDKKVEPKS CDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLT CLVKGFYPSDIAVEWESNGQPENNYKTTPPVLDSDGSFFLYSKLTVDKS RWQQGNVFSCSVMHEALHNHYTQKSLSLSPGK | 98 |
| MTfp sequence (bold): linker (underlined): TZM heavy chain | DSSHAFTLDELRGGGGSGGGGSEVQLVESGGGLVQPGGSLRLSCAASGF NIKDTYIHWVRQAPGKGLEWVARIYPTNGYTRYADSVKGRFTISADTSK NTAYLQMNSLRAEDTAVYYCSRWGGDGFYAMDYWGQGTLVTVSSASTKG PSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK | 99 |
| MTfp sequence (bold) w/terminal Y (bold): linker (underlined): TZM heavy chain | DSSHAFTLDELRYEAAAKEAAAKEAAAKEVQLVESGGGLVQPGGSLRLS CAASGFNIKDTYIHWVRQAPGKGLEWVARIYPTNGYTRYADSVKGRFTI SADTSKNTAYLQMNSLRAEDTAVYYCSRWGGDGFYAMDYWGQGTLVTVS SASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQD WLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKL TVDKSRWQQGNVFSCSVMHEALHNHYTQKSLSLSPGK | 100 |
| MTfp sequence (bold) w/o terminal Y: linker (underlined): TZM heavy chain | DSSHAFTLDELREAAAKEAAAKEAAAKEVQLVESGGGLVQPGGSLRLSC AASGFNIKDTYIHWVRQAPGKGLEWVARIYPTNGYTRYADSVKGRFTIS ADTSKNTAYLQMNSLRAEDTAVYYCSRWGGDGFYAMDYWGQGTLVTVSS ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLT VDKSRWQQGNVFSCSVMHEALHNHYTQKSLSLSPGK | 101 |
| MTfp sequence (bold): TZM heavy chain w/terminal Y (bold) | DSSHAFTLDELRYEVQLVESGGGLVQPGGSLRLSCAASGFNIKDTYIHW VRQAPGKGLEWVARIYPTNGYTRYADSVKGRFTISADTSKNTAYLQMNS LRAEDTAVYYCSRWGGDGFYAMDYWGQGTLVTVSSASTKGPSVFPLAPS SKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSD IAVEWESNGQPENNYKTTPPVLDSDGSFFLYSKLTVDKSRWQQGNVFSC SVMHEALHNHYTQKSLSLSPGK | 102 |
| MTfp sequence (bold) w/o terminal Y: TZM heavy chain | DSSHAFTLDELREVQLVESGGGLVQPGGSLRLSCAASGFNIKDTYIHWV RQAPGKGLEWVARIYPTNGYTRYADSVKGRFTISADTSKNTAYLQMNSL RAEDTAVYYCSRWGGDGFYAMDYWGQGTLVTVSSASTKGPSVFPLAPSS KSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCS VMHEALHNHYTQKSLSLSPGK | 103 |
| TZM heavy chain: linker (underlined): MTfp sequence without C- | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK | 104 |

TABLE 3-continued

Exemplary p97-trastuzmab fusion protein sequences

| Description | Sequence | SEQ ID NO: |
|---|---|---|
| terminal Y (bold) | GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGK<u>GGGGSGGGGS</u>DSSHAFTLDELR | |
| TZM heavy chain linker (underlined): MTfp sequence w/terminal Y (bold) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGK<u>GGGGSGGGGS</u>DSSHAFTLDELRY | 105 |
| TZM heavy chain: linker (underlined): MTfp w/terminal Y (bold) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPPKSCDKTHTCPPCPAPELLGGPSVF LFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYT QKSLSLSPGK<u>EAAAKEAAAKEAAAK</u>DSSHAFTLDELRY | 106 |
| TZM heavy chain: linker (underlined): MTfp w/o terminal Y (bold | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPPKSCDKTHTCPPCPAPELLGGPSVF LFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYT QKSLSLSPGK<u>EAAAKEAAAKEAAAK</u>DSSHAFTLDELR | 107 |
| TZM heavy chain: MTfp sequence without C-terminal Y (bold) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGKDSSHAFTLDELR | 108 |
| TZM heavy chain: MTfp sequence w/terminal Y (bold) | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSR WGGDGFYAMDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQ KSLSLSPGKDSSHAFTLDELRY | 109 |

In certain embodiments, the p97-trastuzumab fusion protein comprises, consists, or consists essentially of a trastuzumab heavy chain sequence fused to the N-terminus of a p97 sequence. In particular embodiments, the p97 sequence is human soluble p97, for example, comprising or consisting of SEQ ID NO:2, or a variant/fragment thereof. In some embodiments, the p97 sequence comprises or consists of SEQ ID NO:14, or a variant/fragment thereof. In some embodiments, the trastuzumab heavy chain sequence is selected from SEQ ID NO:29-35 or 122, or a variant/fragment thereof. Optionally, the fusion protein comprises a peptide linker in between the p97 and trastuzumab sequences. In specific embodiments, the linker is a (GGGGS)$_2$ or (GGGGS)$_3$ linker or a EAAAKEAAAKEAAAK (SEQ ID NO:124) linker. In specific embodiments, the p97-trastuzumab fusion protein comprises, consists, or consists essentially of SEQ ID NO:37 (trastuzumab heavy chain fused to the N-terminus of soluble p97) or a variant/fragment thereof. In specific embodiments, the linker is a (GGGGS)$_3$ linker, and the fusion protein optionally comprises, consists, or consists essentially of SEQ ID NO:38 (trastuzumab heavy chain fused to the N-terminus of soluble human p97, and separated by a (GGGGS)₃ linker), or a variant/fragment thereof. Other combinations will be apparent to persons skilled in the art.

In some embodiments, the p97-trastuzumab fusion protein comprises, consists, or consists essentially of a trastuzumab heavy chain sequence fused to the C-terminus of a p97 sequence. In particular embodiments, the p97 sequence is human soluble p97, for example, comprising or consisting of SEQ ID NO:2, or a variant/fragment thereof. In some embodiments, the p97 sequence comprises or consists of SEQ ID NO:14, or a variant/fragment thereof. In some embodiments, the trastuzumab heavy chain sequence is selected from SEQ ID NO:29-35 or 122, or a variant/fragment thereof. In some embodiments, the trastuzumab heavy chain sequence is a truncated sequence that comprises the polypeptide of SEQ ID NO:31-33 or 34, or a variant/fragment thereof. In specific embodiments, the p97-trastuzumab fusion protein comprises, consists, or consists essentially of SEQ ID NO:39, 41, 43, or 45 (truncated trastuzumab heavy chain fused to the C-terminus of soluble human p97), or a variant/fragment thereof. Optionally, the fusion protein comprises a peptide linker in between the p97 and trastuzumab sequences. In specific embodiments, the linker is a (GGGGS)₂ or (GGGGS)₃ linker or a EAAAKEAAAKEAAAK (SEQ ID NO:124) linker. In specific embodiments, the linker is a (GGGGS)₃ linker, and the fusion protein optionally comprises, consists, or consists essentially of SEQ ID NO:40, 42, 44 or 46 (truncated trastuzumab heavy chain fused to the C-terminus of soluble human p97, and separated by a (GGGGS)₃ linker), or a variant/fragment thereof.

In some embodiments, the p97-trastuzumab heavy chain fusion protein comprises, consists, or consists essentially of a polypeptide sequence selected from SEQ ID NOs:37-46 and 96-109, or a variant/fragment thereof.

Other combinations will be apparent to persons skilled in the art.

Also included are p97-trastuzumab light chain fusion proteins. Specific, non-limiting examples of p97-trastuzumab light chain fusion proteins are illustrated in Table 4 below, and in Table E1 (see Examples).

TABLE 4

Exemplary p97-trastuzmab fusion protein sequences

| | Sequence | SEQ ID NO: |
|---|---|---|
| Trastuzumab FL light chain fused to N-terminus of MTfp (no linker) | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGECDSSHAFTLDELRY | 110 |
| Trastuzumab FL light chain fused to N-terminus of MTfp (linker underlined) | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC<u>EAAAKEAAAKEAAAK</u>DSSHAFTLDELRY | 111 |
| Trastuzumab FL light chain fused to N-terminus of MTfp (linker underlined) | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC<u>GGGGSGGGGS</u>DSSHAFTLDELRY | 112 |
| Trastuzumab FL light chain fused to N-terminus of MTfp (no linker) | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGECDSSHAFTLDELR | 113 |
| Trastuzumab FL light chain fused to N-terminus of MTfp (linker underlined) | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC<u>EAAAKEAAAKEAAAK</u>DSSHAFTLDELR | 114 |
| Trastuzumab FL light chain fused to N-terminus of MTfp (linker underlined) | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC<u>GGGGSGGGGS</u>DSSHAFTLDELRY | 115 |

TABLE 4-continued

Exemplary p97-trastuzmab fusion protein sequences

| | Sequence | SEQ ID NO: |
|---|---|---|
| Trastuzumab FL light chain fused to C-terminus of MTfp (no linker) | DSSHAFTLDELRYDIQMTQSPSSLSASVGDRVTITCRASQDVNTAVAWY QQKPGKAPKLLIYSASFLYSGVPSRFSGSRSGTDFTLTISSLQPEDFAT YYCQQHYTTPPTFGQGTKVEIKRTVAAPSVFIFPPSDEQLKSGTASVVC LLNNFYPREAKVQWKVDNALQSGNSQESVTEQDSKDSTYSLSSTLTLSK ADYEKHKVYACEVTHQGLSSPVTKSFNRGEC | 116 |
| Trastuzumab FL light chain fused to C-terminus of MTfp (linker underlined) | DSSHAFTLDELRY<u>EAAAKEAAAKEAAAK</u>DIQMTQSPSSLSASVGDRVTI TCRASQDVNTAVAWYQQKPGKAPKLLIYSASFLYSGVPSRFSGSRSGTD FTLTISSLQPEDFATYYCQQHYTTPPTFGQGTKVEIKRTVAAPSVFIFP PSDEQLKSGTASVVCLLNNFYPREAKVQWKVDNALQSGNSQESVTEQDS KDSTYSLSSTLTLSKADYEKHKVYACEVTHQGLSSPVTKSFNRGEC | 117 |
| Trastuzumab FL light chain fused to C-terminus of MTfp (linker underlined) | DSSHAFTLDELRY<u>GGGGSGGGGS</u>DIQMTQSPSSLSASVGDRVTITCRAS QDVNTAVAWYQQKPGKAPKLLIYSASFLYSGVPSRFSGSRSGTDFTLTI SSLQPEDFATYYCQQHYTTPPTFGQGTKVEIKRTVAAPSVFIFPPSDEQ LKSGTASVVCLLNNFYPREAKVQWKVDNALQSGNSQESVTEQDSKDSTY SLSSTLTLSKADYEKHKVYACEVTHQGLSSPVTKSFNRGEC | 118 |
| Trastuzumab FL light chain fused to C-terminus of MTfp (no linker) | DSSHAFTLDELRDIQMTQSPSSLSASVGDRVTITCRASQDVNTAVAWYQ QKPGKAPKLLIYSASFLYSGVPSRFSGSRSGTDFTLTISSLQPEDFATY YCQQHYTTPPTFGQGTKVEIKRTVAAPSVFIFPPSDEQLKSGTASVVCL LNNFYPREAKVQWKVDNALQSGNSQESVTEQDSKDSTYSLSSTLTLSKA DYEKHKVYACEVTHQGLSSPVTKSFNRGEC | 119 |
| Trastuzumab FL light chain fused to C-terminus of MTfp (linker underlined) | DSSHAFTLDELR<u>EAAAKEAAAKEAAAK</u>DIQMTQSPSSLSASVGDRVTIT CRASQDVNTAVAWYQQKPGKAPKLLIYSASFLYSGVPSRFSGSRSGTDF TLTISSLQPEDFATYYCQQHYTTPPTFGQGTKVEIKRTVAAPSVFIFPP SDEQLKSGTASVVCLLNNFYPREAKVQWKVDNALQSGNSQESVTEQDSK DSTYSLSSTLTLSKADYEKHKVYACEVTHQGLSSPVTKSFNRGEC | 120 |
| Trastuzumab FL light chain fused to C-terminus of MTfp (linker underlined) | DSSHAFTLDELR<u>GGGGSGGGGS</u>DIQMTQSPSSLSASVGDRVTITCRASQ DVNTAVAWYQQKPGKAPKLLIYSASFLYSGVPSRFSGSRSGTDFTLTIS SLQPEDFATYYCQQHYTTPPTFGQGTKVEIKRTVAAPSVFIFPPSDEQL KSGTASVVCLLNNFYPREAKVQWKVDNALQSGNSQESVTEQDSKDSTYS LSSTLTLSKADYEKHKVYACEVTHQGLSSPVTKSFNRGEC | 121 |

In some embodiments, the p97-trastuzumab fusion protein comprises, consists, or consists essentially of a trastuzumab light chain sequence fused to the N-terminus of a p97 sequence. In particular embodiments, the p97 sequence is human soluble p97, for example, comprising or consisting of SEQ ID NO:2, or a variant/fragment thereof. In some embodiments, the p97 sequence comprises or consists of SEQ ID NO:14, or a variant/fragment thereof. In some embodiments, the trastuzumab light chain sequence comprises or consists of SEQ ID NO:36 or 123, or a variant/fragment thereof. In specific embodiments, the p97-trastuzumab fusion protein comprises, consists, or consists essentially of a sequence selected from SEQ ID NOs:110-115 (trastuzumab light chain fused to the N-terminus of p97pep), or a variant/fragment thereof. Optionally, the fusion protein comprises a peptide linker in between the p97 and trastuzumab sequence, for example, as illustrated in SEQ ID NO:111-112 or 114-115. In specific embodiments, the linker is a (GGGGS)$_2$ or (GGGGS)$_3$ linker or a EAAAKEAAAKEAAAK (SEQ ID NO:124) linker. Other combinations will be apparent to persons skilled in the art.

In some embodiments, the p97-trastuzumab fusion protein comprises, consists, or consists essentially of a trastuzumab light chain sequence fused to the C-terminus of a p97 sequence. In particular embodiments, the p97 sequence is human soluble p97, for example, comprising or consisting of SEQ ID NO:2, or a variant/fragment thereof. In some embodiments, the p97 sequence comprises or consists of SEQ ID NO:14, or a variant/fragment thereof. In some embodiments, the trastuzumab light chain sequence comprises or consists of SEQ ID NO:36 or 123, or a variant/fragment thereof. In specific embodiments, the p97-trastuzumab fusion protein comprises, consists, or consists essentially of SEQ ID NO:116-121 (trastuzumab light chain fused to the C-terminus of p97p), or a variant/fragment thereof. Optionally, the fusion protein comprises a peptide linker in between the p97 and trastuzumab sequences, as illustrated, for example, in SEQ ID NOs:117-118 and 120-121. In specific embodiments, the linker is a (GGGGS)$_2$ or (GGGGS)$_3$ linker or a EAAAKEAAAKEAAAK (SEQ ID NO:124) linker. Other combinations will be apparent to persons skilled in the art.

Also included are p97-antibody fusion proteins, comprising one or more p97-trastuzumab heavy or light chain fusion proteins described herein. In particular embodiments, the p97-antibody fusion protein comprises two (non-fusion) trastuzumab light chain sequences, and one or two p97-trastuzumab heavy chain fusion proteins described herein, where the one or two p97-trastuzumab heavy chain fusion protein(s) comprise a trastuzumab heavy chain sequence fused to the N-terminus of a p97 sequence and an optional linker in between. In some embodiments, the p97-antibody fusion comprises two p97-trastuzumab heavy chain fusion proteins (see, e.g., FIGS. 1A and 1E), including homodimeric antibody fusions that comprise the same p97-trastuzumab heavy chain fusion proteins. In some embodiments, the p97-antibody fusion comprises one p97-trastuzumab heavy chain fusion protein (see, e.g., FIG. 1B).

In some embodiments, the p97-antibody fusion protein comprises one or two trastuzumab light chain sequences, one trastuzumab heavy chain sequence, and one p97-trastuzumab heavy chain fusion protein described herein, where p97-trastuzumab heavy chain fusion protein comprises a trastuzumab heavy chain fused to the C-terminus of a p97 sequence and an optional linker in between. In some embodiments, the p97-antibody fusion protein comprises one trastuzumab light chain sequence, one trastuzumab heavy chain sequence, and one p97-trastuzumab heavy chain fusion protein that has a truncated trastuzumab heavy chain (see, e.g., FIG. 1C).

Figure 1B:
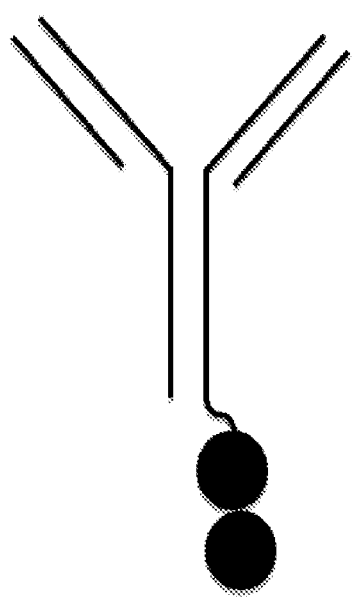
Figure 1C:
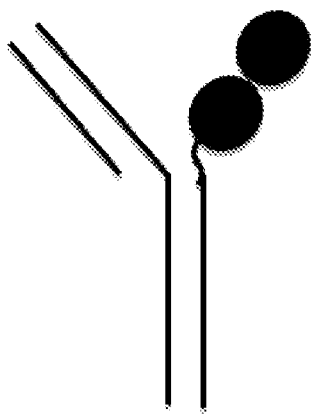
Figure 1D:
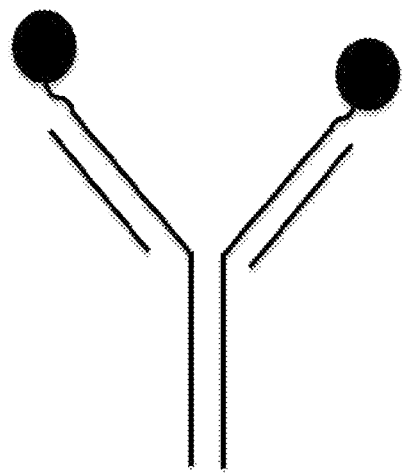

In some embodiments, the p97-antibody fusion protein comprises two trastuzumab light chain sequences, and two p97-trastuzumab heavy chain fusion proteins described herein, where the p97-trastuzumab heavy chain fusion proteins comprise a trastuzumab heavy chain fused to the C-terminus of a p97 sequence and an optional linker in between (see, e.g., FIG. 1D).

Figure 1E:
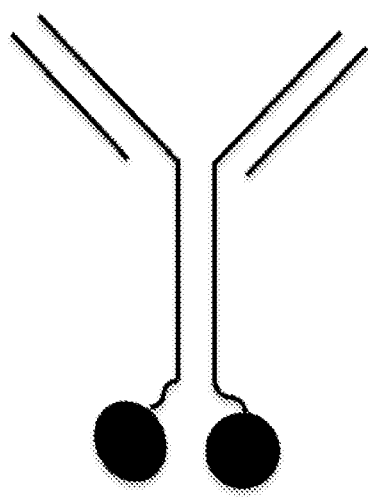
Figure 1F:
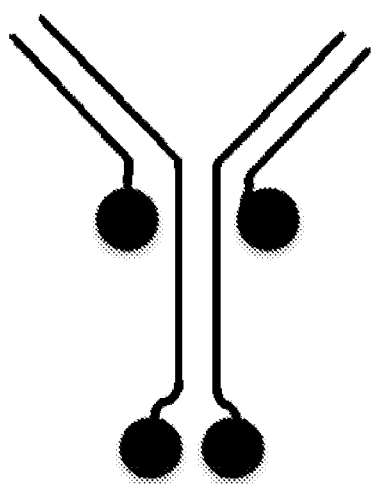

In some embodiments, the p97-antibody fusion protein comprises two p97-trastuzumab light chain fusion proteins described herein, and two p97-trastuzumab heavy chain fusion proteins described herein, where the p97-trastuzumab light chain fusion proteins comprise a trastuzumab light chain fused to the N-terminus of a p97 sequence and an optional linker in between, and where the p97-trastuzumab heavy chain fusion proteins comprise a trastuzumab heavy chain fused to the N-terminus of a p97 sequence and an optional linker in between (see, e.g., FIG. 1F).

In some embodiments, the p97-antibody fusion protein comprises one or two p97-trastuzumab light chain fusion proteins described herein, and two trastuzumab heavy chain sequences, where the one or two p97-trastuzumab light chain fusion proteins comprise a trastuzumab light chain fused to the N-terminus of a p97 sequence and an optional linker in between. In some embodiments, the p97-antibody fusion protein comprises two p97-trastuzumab light chain fusion proteins described herein (see, e.g., FIG. 1G).

In specific embodiments, the p97-antibody fusion comprises one or two sets of heavy and light chains selected from one or more of the following:

a) the heavy chain of SEQ ID NO:82 and the light chain of SEQ ID NO:83;
b) the heavy chain of SEQ ID NO:84 and the light chain of SEQ ID NO:85;
c) the heavy chain of SEQ ID NO:86 and the light chain of SEQ ID NO:87;
d) the heavy chain of SEQ ID NO:88 and the light chain of SEQ ID NO:89;
e) the heavy chain of SEQ ID NO:90 and the light chain of SEQ ID NO:91;
f) the heavy chain of SEQ ID NO:92 and the light chain of SEQ ID NO:93;
g) the heavy chain of SEQ ID NO:94 and the light chain of SEQ ID NO:95;

including fragments/variants thereof. In some embodiments, the p97-antibody fusion is a homodimer that comprises two sets of a), two sets of b), two sets of c), two sets of d), two sets of e), two sets of f), or two sets of g). In particular embodiments, the p97-antibody fusion is a heterodimer that comprises a first set of sets of heavy and light chains selected from a)-g) above, and a second set of heavy and light chains composed of any combination of the p97-trastuzumab heavy or light chains described herein (for example, a)-g) above; SEQ ID NOS:37-46, 96-109, and 110-121), and/or any of the trastuzumab (non-fusion) heavy and light chains (for example, SEQ ID NOs: 29-35 or 122 (heavy chains) and 36 or 123 (light chains)).

Figure 1G:
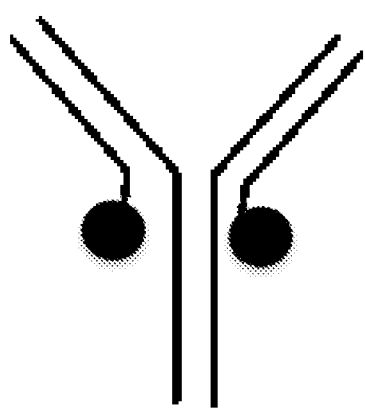
Figure 2A:
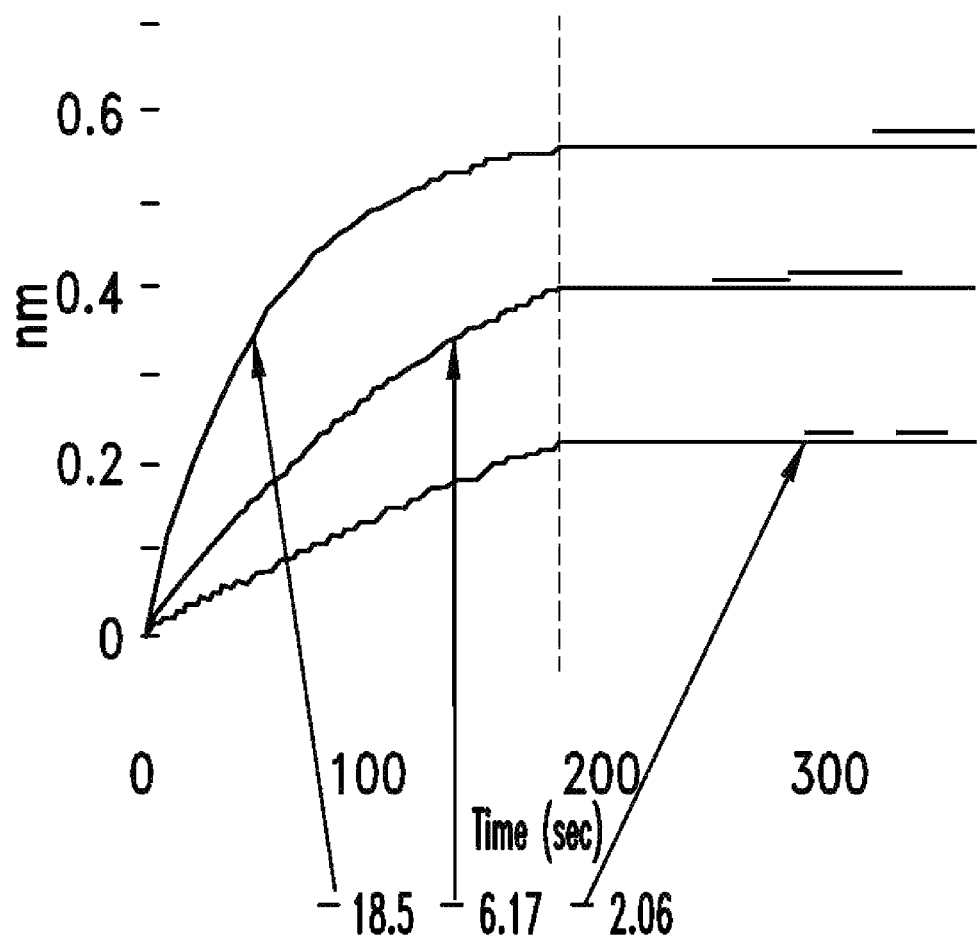
FIGS. 2A-2D shows octet analysis demonstrating the affinity of antibody fusions for Her2 relative to IgG1 control.
Figure 2B:
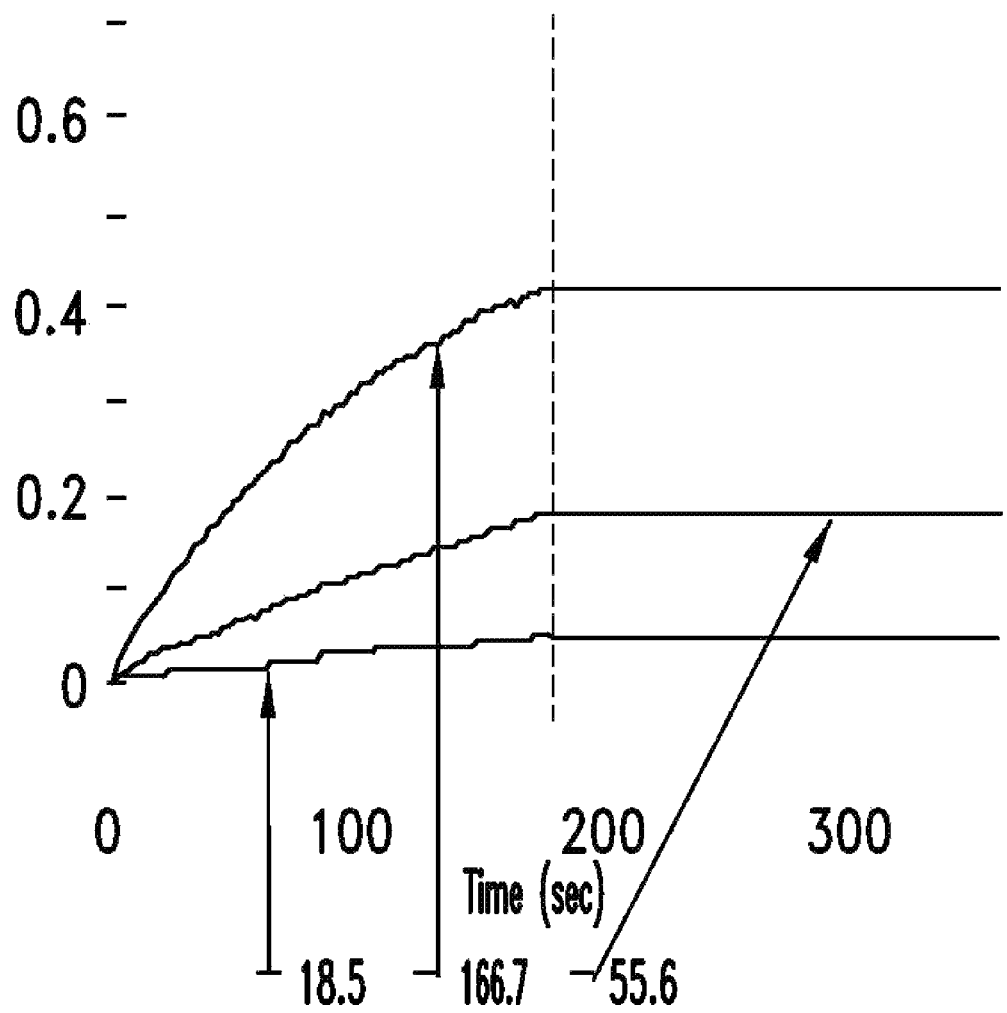
Figure 2C:
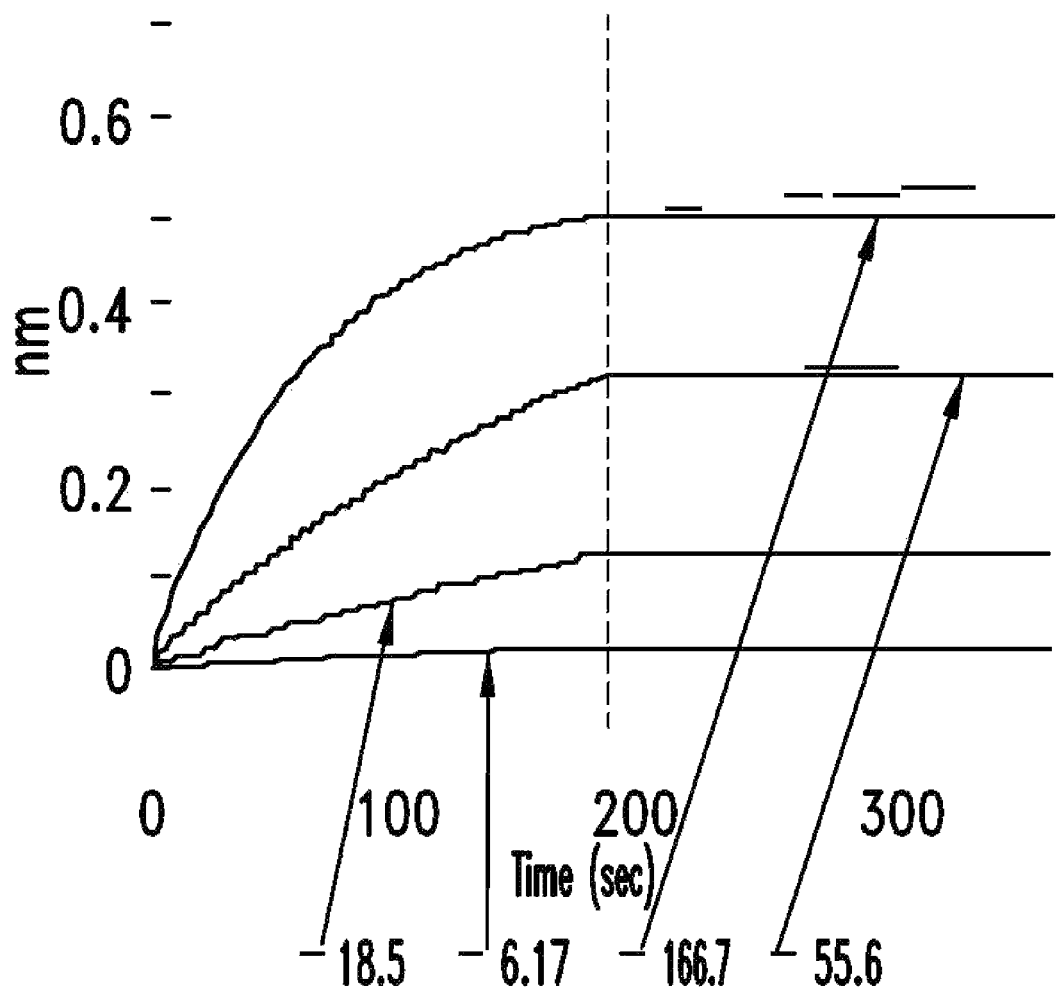
Figure 2D:
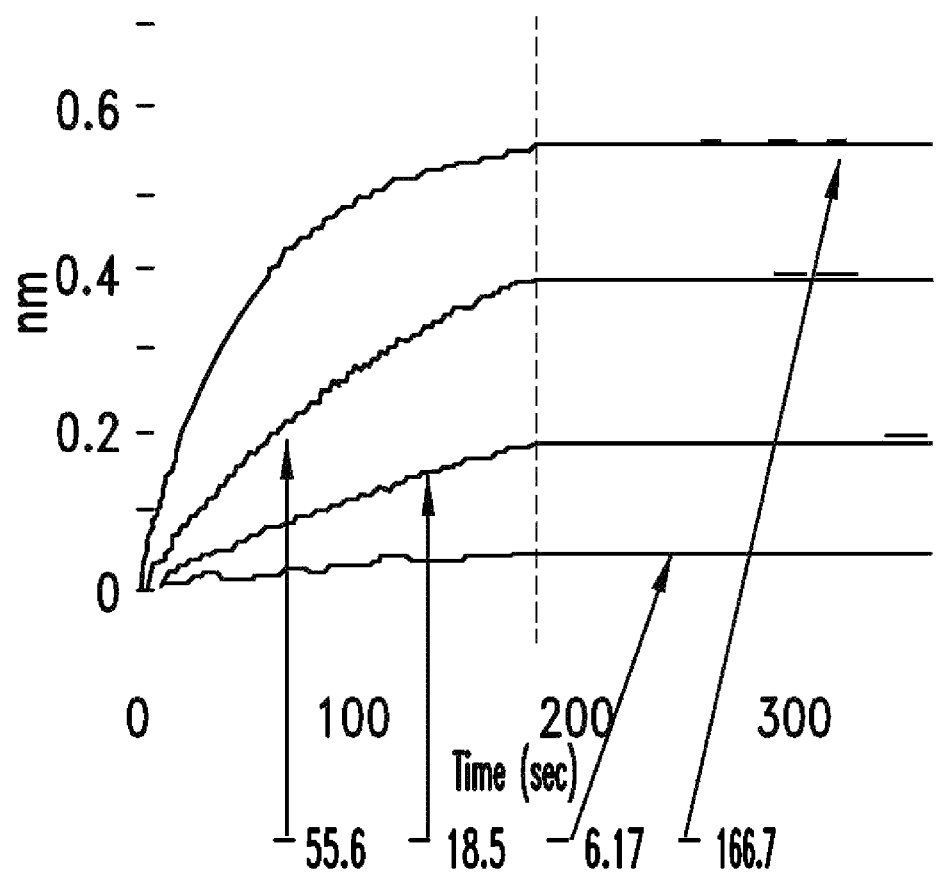

Non-limiting examples of p97-antibody fusions are illustrated in FIGS. 1A-1G. FIG. 1A illustrates an antibody fusion composed of two p97-trastuzumab heavy chain fusion proteins, and two (non-fusion) trastuzumab light chains. FIG. 1B illustrates an antibody fusion composed of one p97-trastuzumab heavy chain fusion protein, one (non-fusion) trastuzumab heavy chain, and two (non-fusion) trastuzumab light chains. FIG. 1C illustrates an antibody fusion protein composed of one p97-trastuzumab heavy chain fusion protein (having a truncated trastuzumab heavy chain), one (non-fusion) trastuzumab light chain, and one (non-fusion) trastuzumab heavy chain. FIGS. 1D and 1E illustrate antibody fusions composed of two p97-trastuzumab heavy chain fusion proteins and two (non-fusion) trastuzumab light chains. FIG. 1F illustrates an antibody fusion composed of two p97-trastuzumab light chain fusion proteins and two 97-trastuzumab heavy chain fusion proteins. FIG. 1G illustrates an antibody fusion composed of two p97-trastuzumab light chain fusion proteins and two (non-fusion) trastuzumab heavy chain sequences. In any of the antibody fusions described herein, the first set of light/heavy chains can be the same as or different from the second set of light/heavy chains.

In some embodiments, the p97-antibody fusion is a homodimer, for example, which is composed of two identical sets of heavy and/or light chains, at least one of which is a p97-trastuzumab fusion protein. In some embodiments, the p97-antibody fusion is a heterodimer, for example, which is composed of a first set of heavy and/or light chains and a second set of heavy/light chains, where the first set comprises at least one heavy and/or light chain p97-trastuzumab fusion protein and the second set comprises only trastuzumab heavy and/or light chain sequences.

Other combinations will be apparent to persons skilled in the art. Thus, any of the p97 sequences described herein can be combined with any of the trastuzumab sequences described herein, to generate a desired p97-trastuzumab light chain or heavy chain fusion protein, and any such fusion proteins can be combined with the same or different fusion protein(s) or with any of the trastuzumab heavy chain or light chain sequences to generate a desired antibody fusion.

In certain embodiments, the p97-antibody fusion protein specifically binds to the human HER2/neu receptor. In specific embodiments, the p97-antibody fusion protein specifically binds to domain IV of the extracellular segment of the human HER2/neu receptor (see Cho et al., Nature. 421:756-760, 2003). In particular embodiments, the p97-antibody fusion protein is an HER2/neu receptor antagonist.

The functional properties of the fusion proteins and antibody fusions described herein may be assessed using a variety of methods known to the skilled person, including, e.g., affinity/binding assays (for example, surface plasmon resonance, competitive inhibition assays); cytotoxicity assays, cell viability assays, cell proliferation or differentiation assays, cancer cell and/or tumor growth inhibition using in vitro or in vivo models. For instance, the fusion proteins described herein may be tested for effects on receptor internalization, in vitro and in vivo efficacy, etc., including the rate of transport across the blood-brain barrier. Such assays may be performed using well-established protocols known to the skilled person (see e.g., Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

Variant Sequences.

Certain embodiments include variants of the reference polypeptide and polynucleotide sequences described herein, whether described by name or by reference to a sequence identifier, including p97 sequences and trastuzumab sequences (see, e.g., the Sequence Listing). The wild-type or most prevalent sequences of these polypeptides are known in the art, and can be used as a comparison for the variants and fragments described herein.

A "variant" sequence, as the term is used herein, refers to a polypeptide or polynucleotide sequence that differs from a reference sequence disclosed herein by one or more substitutions, deletions (e.g., truncations), additions, and/or insertions. Certain variants thus include fragments of a reference sequence described herein. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table A below.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |

TABLE A-continued

| Amino Acids | | | Codons |
|---|---|---|---|
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Sequence Listing).

In other specific embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Sequence Listing).

In still other specific embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol*, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS* USA.

89:10915-10919, 1992). GAP uses the algorithm of Needleman and Wunsch (*J Mol Biol.* 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS* USA. 82: 488-492, 1985); Kunkel et al., (*Methods in Enzymol.* 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS* USA 89: 7811-7815, 1992; Delgrave et al., *Protein Engineering.* 6: 327-331, 1993).

Polynucleotides, Host Cells, and Methods of Production.

Certain embodiments relate to polynucleotides that encode the fusion proteins and antibody fusions described herein, and vectors that comprise such polynucleotides, for example, where the polynucleotides are operably linked to one or more regulatory elements. Also included are recombinant host cells that comprise such polynucleotides, vectors, fusion proteins, and antibody fusions, and methods of recombinant production of the foregoing.

Fusion proteins and antibody fusions may be prepared using standard techniques. Preferably, however, a fusion protein is expressed as a recombinant protein in an expression system, as described herein and known in the art. Fusion proteins can contain one or multiple copies of a p97 sequence and one or multiple copies of a trastuzumab sequence, present in any desired arrangement.

Polynucleotides and fusion polynucleotides can contain one or multiple copies of a nucleic acid encoding a p97 polypeptide sequence, and/or may contain one or multiple copies of a nucleic acid encoding a trastuzumab sequence.

For fusion proteins, DNA sequences encoding the p97 polypeptide sequence, the trastuzumab sequence of interest, and optionally a peptide linker components may be assembled separately, and then ligated into an appropriate expression vector. The 3' end of the DNA sequence encoding one polypeptide component can be ligated, with or without a peptide linker, to the 5' end of a DNA sequence encoding the other polypeptide component(s) so that the reading frames of the sequences are in frame. The ligated DNA sequences are operably linked to suitable transcriptional and/or translational regulatory elements. The regulatory elements responsible for expression of DNA are usually located only 5' to the DNA sequence encoding the first polypeptides. Similarly, stop codons required to end translation and transcription termination signals are only present 3' to the DNA sequence encoding the most C-terminal polypeptide. This permits translation into a single fusion polypeptide that retains the biological activity of both component polypeptides.

Similar techniques, mainly the arrangement of regulatory elements such as promoters, stop codons, and transcription termination signals, can be applied to the recombinant production of non-fusion proteins, for instance, non-fusion trastuzumab sequences for the production of antibodies that comprise a fusion protein described herein.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such polynucleotides are commonly referred to as "codon-optimized." Any of the polynucleotides described herein may be utilized in a codon-optimized form. In certain embodiments, a polynucleotide can be codon optimized for use in specific bacteria such as *E. coli* or yeast such as *S. cerevisiae* (see, e.g., Burgess-Brown et al., *Protein Expr Purif.* 59:94-102, 2008).

Exemplary polynucleotide sequences are provided in Table 5 below.

TABLE 5

Exemplary polynucleotide sequences

| Name | Sequence | SEQ ID NO: |
|---|---|---|
| TZM HC-MTf | Heavy Chain<br>ATGGAGACCGACACCCTGCTGCTCTGGGTGCTGCTGCTCTGGGTGCCCGGCTCCACC<br>GGAGAGGTGCAGCTGGTGGAGAGCGGCGGAGGCCTCGTGCAGCCCGGCGGATCTCTG<br>CGGCTGAGCTGCGCCGCTAGCGGCTTCAACATCAAGGACACCTACATCCACTGGGTG<br>CGCCAGGCCCCCGGCAAGGGCCTGGAGTGGGTGGCCCGGATCTACCCCACCAACGGC<br>TACACCCGCTACGCCGACAGCGTGAAGGGCCGGTTCACCATCAGCGCCGACACCTCC<br>AAGAACACCGCCTACCTGCAGATGAACAGCCTGCGCGCCGAGGACACCGCCGTGTAC<br>TACTGCAGCCGGTGGGGCGGCGACGGATTCTACGCCATGGACTACTGGGGACAGGGC<br>ACCCTGGTGACCGTGAGCAGCGCCTCTACCAAGGGCCCCAGCGTGTTCCCTCTGGCC<br>CCCAGCAGCAAGAGCACCAGCGGCGGAACCGCCGCCCTGGGCTGCCTGGTGAAGGAC<br>TACTTCCCCGAGCCCGTGACCGTGTCCTGGAACAGCGGCGCTCTGACCAGCGGAGTG<br>CACACCTTCCCTGCCGTGCTGCAGAGCAGCGGCCTGTACTCCCTGAGCAGCGTGGTG<br>ACCGTGCCCAGCAGCAGCCTGGGCACCCAGACCTACATCTGCAACGTGAACCACAAG<br>CCCTCCAACACCAAGGTGGACAAGAAGGTGGAGCCTAAGAGCTGCGACAAGACCCAC<br>ACCTGCCCTCCCTGCCCCGCCCCCGAGCTGCTGGGCGGACCCAGCGTGTTCCTGTTC<br>CCTCCCAAGCCCAAGGACACCCTGATGATCAGCCGCACCCCCGAGGTGACCTGCGTG<br>GTGGTGGACGTGAGCCACGAGGACCCCGAGGTGAAGTTCAACTGGTACGTGGACGGC<br>GTGGAGGTGCACAACGCCAAGACCAAGCCTCGGGAGGAGCAGTACAACTCCACCTAC<br>CGCGTGGTGAGCGTGCTGACCGTGCTGCACCAGGACTGGCTGAACGGCAAGGAGTAC<br>AAGTGCAAGGTGAGCAACAAGGCCCTGCCCGCTCCCATCGAGAAGACCATCAGCAAG<br>GCCAAGGGCCAGCCCCGGGAGCCTCAGGTGTACACCCTGCCCCCCAGCCGCGACGAG<br>CTGACCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACCACCCCT<br>CCCGTGCTGGACAGCGACGGCAGCTTCTTCCTGTACAGCAAGCTGACCGTGGACAAG<br>TCCCGGTGGCAGCAGGGCAACGTGTTCAGCTGCAGCGTGATGCACGAGGCCCTGCAC<br>AACCACTACACCCAGAAGAGCCTGAGCCTGAGCCCCGGAAAGGGTGGCGGAGGATCT<br>GGCGGAGGCGGATCCGGCATGGAAGTGCGTTGGTGCGCCACCTCTGACCCCGAGCAG<br>CACAAGTGCGGCAACATGTCCGAGGCCTTCAGAGAGGCCGGCATCCAGCCTTCTCTG<br>CTGTGTGTGCGGGGCACCTCTGCCGACCATTGCGTGCAGCTGATCGCCGCCAGGAA<br>GCCGACGCTATCACACTGGATGGCGGCGCTATCTACGAGGCTGGCAAAGAGCACGGC<br>CTGAAGCCCGTCGTGGGCGAGGTGTACGATCAGGAAGTGGGCACCTCCTACTACGCC<br>GTGGCTGTCGTGCGGAGATCCTCCCACGTGACCATCGACACCCTGAAGGGCGTGAAG<br>TCCTGCCACACCGGCATCAACAGAACCGTGGGCTGGAACGTGCCCGTGGGCTACCTG<br>GTGGAATCCGGCAGACTGTCCGTGATGGGCTGCGACGTGCTGAAGGCCGTGTCCGAT<br>TACTTCGGCGGCTCTTGTGTGCCTGGCGCTGGCGAGACATCCTACTCCGAGTCCCTG<br>TGCAGACTGTGCAGGGGCGACTCTTCTGGCGAGGGCGTGTGCGACAAGTCCCCTCTG<br>GAACGGTACTACGACTACTCCGGCGCCTTCAGATGCCTGGCTGAAGGTGCTGGCGAC<br>GTGGCCTTCGTGAAGCACTCCACCGTGCTGGAAAACACCGACGGCAAGACCCTGCCT<br>TCTTGGGGCCAGGCACTGCTGTCCCAGGACTTCGAGCTGCTGTGCCGGGATGGCTCC<br>AGAGCCGATGTGACAGAGTGGCGGCAGTGCCACCTGGCCAGAGTGCCTGCCCATGCT<br>GTGGTCGTGCGCGCCGATACAGATGGCGGCCTGATCTTCCGGCTGCTGAACGAGGGC<br>CAGCGGCTGTTCTCTCACGAGGGCTCCAGCTTCCAGATGTTCTCCAGCGAGGCCTAC<br>GGCCAGAAGGACCTGCTGTTCAAGGACTCCACCTCCGAGCTGGTGCCTATCGCCACC<br>CAGACCTATGAGGCTTGGCTGGGCACGAGTACCTGCACGCTATGAAGGGACTGCTG<br>TGCGACCCCAACCGGCTGCCTCCTTATCTGAGGTGGTGCGTGCTGTCCACCCCCGAG<br>ATCCAGAAATGCGGCGATATGGCCGTGGCCTTTCGGCGGCAGAGACTGAAGCCTGAG<br>ATCCAGTGCGTGTCTGCCAAGAGCCCTCAGCACTGCATGGAACGGATCCAGGCCGAA<br>CAGGTGGACGCCGTGACACTGTCCGGCGAGGATATCTACACCGCCGGAAAGACCTAC<br>GGCCTGGTGCCAGCTGCTGGCGAGCATTACGCCCCTGAGGACTCCTCCAACAGCTAC<br>TACGTGGTGGCAGTCGTGCGCCGGGACTCCTCTCACGCCTTTACCCTGGATGAGCTG<br>CGGGGCAAGAGAAGCTGTCACGCCGGCTTTGGAAGCCCTGCCGGATGGGATGTGCCT<br>GTGGGCGCTCTGATCCAGCGGGCTTCATCAGACCCAAGGACTGTGATGTGCTGACC<br>GCCGTGTCTGAGTTCTTCAACGCCTCCTGTGTGCCCGTGAACAACCCCAAGAACTAC<br>CCCTCCAGCCTGTGCGCCCTGTGTGTGGGAGATGAGCAGGGCCGGAACAAATGCGTG<br>GGCAACTCCCAGGAAAGATATTACGGCTACGAGGCGCCTTCCGGTGTCTGGTGGAA<br>AACGCCGGGGATGTGGCTTTTGTGCGGCACACCACCGTGTTCGACAACACCAATGGC<br>CACAACTCCGAGCCTTGGGCCGCTGAGCTGAGATCCGAGGATTACGAACTGCTGTGT<br>CCCAACGGCGCCAGGGCTGAGGTGTCCCAGTTTGCCGCCTGTAACCTGGCCCAGATC<br>CCTCCCCACGCTGTGATGGTGCGACCCGACACCAACATCTTCACCGTGTACGGCCTG<br>CTGGACAAGGCCCAGGATCGTTCGGCGACGACCACAACAAGAACGGGTTCAAGATG<br>TTCGACTCCAGCAACTACCACGGACAGGATCTGCTGTTTAAAGATGCCACCGTGCGG<br>GCCGTGCCAGTGGGCGAAAAGACCACCTACAGAGGATGGCTGGGACTGGACTACGTG<br>GCCGCCCTGGAAGGCATGTCCTCCCAGCAGTGTTCCGGCTAG | 125 |
| | Light Chain<br>ATGGAGACCGACACCCTGCTGCTCTGGGTGCTGCTGCTCTGGGTGCCCGGCTCCACC<br>GGAGACATCCAGATGACCCAGAGCCCTTCCAGCCTGAGCGCCAGCGTGGGCGACCGG<br>GTGACCATCACCTGCCGCGCTAGCCAGGACGTGAACACCGCCGTGGCCTGGTACCAG<br>CAGAAGCCCGGAAAGGCCCCCAAGCTGCTGATCTACTCTGCTAGCTTCCTGTACAGC<br>GGCGTGCCCAGCCGGTTCAGCGGATCTCGCAGCGGCACCGACTTCACCCTGACCATC<br>AGCAGCCTGCAGCCTGAGGACTTCGCCACCTACTACTGCCAGCAGCACTACACCACG | 126 |

TABLE 5-continued

Exemplary polynucleotide sequences

| Name | Sequence | SEQ ID NO: |
|---|---|---|
| | CCTCCCACCTTCGGACAGGGCACCAAGGTGGAGATCAAGCGGACCGTGGCCGCCCCC<br>AGCGTGTTCATCTTCCCTCCCAGCGACGAGCAGCTGAAGTCTGGCACCGCCAGCGTG<br>GTGTGCCTGCTGAACAACTTCTACCCCCGCGAGGCCAAGGTGCAGTGGAAGGTGGAC<br>AACGCCCTGCAGAGCGGCAACAGCCAGGAGAGCGTGACCGAGCAGGACTCCAAGGAC<br>AGCACCTACAGCCTGAGCAGCACCCTGACCCTGAGCAAGGCCGACTACGAGAAGCAC<br>AAGGTGTACGCCTGCGAGGTGACCCACCAGGGACTGTCTAGCCCCGTGACCAAGAGC<br>TTCAACCGGGGCGAGTGCTAA | |
| MTfp NH-TZM | Heavy Chain<br>ATGGAGACCGACACCCTGCTGCTCTGGGTGCTGCTGCTCTGGGTGCCCGGCTCCACC<br>GGAGACTCCTCTCACGCCTTCACCCTGGACGAGCTGCGGTACGGTGGCGGAGGATCT<br>GGCGGAGGCGGATCCGAGGTGCAGCTGGTGGAGAGCGGCGGAGGCCTCGTGCAGCCC<br>GGCGGATCTCTGCGGCTGAGCTGCGCCGCTAGCGGCTTCAACATCAAGGACACCTAC<br>ATCCACTGGGTGCGCCAGGCCCCCGGCAAGGGCCTGGAGTGGGTGGCCCGGATCTAC<br>CCCACCAACGGCTACACCCGCTACGCCGACAGCGTGAAGGGCCGGTTCACCATCAGC<br>GCCGACACCTCCAAGAACACCGCCTACCTGCAGATGAACAGCCTGCGCGCCGAGGAC<br>ACCGCCGTGTACTACTGCAGCCGGTGGGGCGGCGACGGATTCTACGCCATGGACTAC<br>TGGGGACAGGGCACCCTGGTGACCGTGAGCAGCGCCTCTACCAAGGGCCCCAGCGTG<br>TTCCCTCTGGCCCCCAGCAGCAAGAGCACCAGCGGCGGAACCGCCGCCCTGGGCTGC<br>CTGGTGAAGGACTACTTCCCCGAGCCCGTGACCGTGTCCTGGAACAGCGGCGCTCTG<br>ACCAGCGGAGTGCACACCTTCCCTGCCGTGCTGCAGAGCAGCGGCCTGTACTCCCTG<br>AGCAGCGTGGTGACCGTGCCCAGCAGCAGCCTGGGCACCCAGACCTACATCTGCAAC<br>GTGAACCACAAGCCCTCCAACACCAAGGTGGACAAGAAGGTGGAGCCTAAGAGCTGC<br>GACAAGACCCACACCTGCCCTCCCTGCCCCGCCCCCGAGCTGCTGGGCGGACCCAGC<br>GTGTTCCTGTTCCCTCCCAAGCCCAAGGACACCCTGATGATCAGCCGCACCCCCGAG<br>GTGACCTGCGTGGTGGTGGACGTGAGCCACGAGGACCCCGAGGTGAAGTTCAACTGG<br>TACGTGGACGGCGTGGAGGTGCACAACGCCAAGACCAAGCCTCGGGAGGAGCAGTAC<br>AACTCCACCTACCGCGTGGTGAGCGTGCTGACCGTGCTGCACCAGGACTGGCTGAAC<br>GGCAAGGAGTACAAGTGCAAGGTGAGCAACAAGGCCCTGCCCGCTCCCATCGAGAAG<br>ACCATCAGCAAGGCCAAGGGCCAGCCCCGGGAGCCTCAGGTGTACACCCTGCCCCCC<br>AGCCGCGACGAGCTGACCAAGAACCAGGTGAGCCTGACCTGCCTGGTGAAGGGCTTC<br>TACCCCTCCGACATCGCCGTGGAGTGGGAGAGCAACGGCCAGCCTGAGAACAACTAC<br>AAGACCACCCCTCCCGTGCTGGACAGCGACGGCAGCTTCTTCCTGTACAGCAAGCTG<br>ACCGTGGACAAGTCCCGGTGGCAGCAGGGCAACGTGTTCAGCTGCAGCGTGATGCAC<br>GAGGCCCTGCACAACCACTACACCCAGAAGAGCCTGAGCCTGAGCCCCGGAAAGTAA | 127 |
| | Light Chain<br>ATGGAGACCGACACCCTGCTGCTCTGGGTGCTGCTGCTCTGGGTGCCCGGCTCCACC<br>GGAGACATCCAGATGACCCAGAGCCCTTCCAGCCTGAGCGCCAGCGTGGGCGACCGG<br>GTGACCATCACCTGCCGCGCTAGCCAGGACGTGAACACCGCCGTGGCCTGGTACCAG<br>CAGAAGCCCGGAAAGGCCCCCAAGCTGCTGATCTACTCTGCTAGCTTCCTGTACAGC<br>GGCGTGCCCAGCCGGTTCAGCGGATCTCGCAGCGGCACCGACTTCACCCTGACCATC<br>AGCAGCCTGCAGCCTGAGGACTTCGCCACCTACTACTGCCAGCAGCACTACACCACG<br>CCTCCCACCTTCGGACAGGGCACCAAGGTGGAGATCAAGCGGACCGTGGCCGCCCCC<br>AGCGTGTTCATCTTCCCTCCCAGCGACGAGCAGCTGAAGTCTGGCACCGCCAGCGTG<br>GTGTGCCTGCTGAACAACTTCTACCCCCGCGAGGCCAAGGTGCAGTGGAAGGTGGAC<br>AACGCCCTGCAGAGCGGCAACAGCCAGGAGAGCGTGACCGAGCAGGACTCCAAGGAC<br>AGCACCTACAGCCTGAGCAGCACCCTGACCCTGAGCAAGGCCGACTACGAGAAGCAC<br>AAGGTGTACGCCTGCGAGGTGACCCACCAGGGACTGTCTAGCCCCGTGACCAAGAGC<br>TTCAACCGGGGCGAGTGCTAA | 128 |
| TZM HC-MTfp | Heavy Chain<br>ATGGAGACCGACACCCTGCTGCTCTGGGTGCTGCTGCTCTGGGTGCCCGGCTCCACC<br>GGAGAGGTGCAGCTGGTGGAGAGCGGCGGAGGCCTCGTGCAGCCCGGCGGATCTCTG<br>CGGCTGAGCTGCGCCGCTAGCGGCTTCAACATCAAGGACACCTACATCCACTGGGTG<br>CGCCAGGCCCCCGGCAAGGGCCTGGAGTGGGTGGCCCGGATCTACCCCACCAACGGC<br>TACACCCGCTACGCCGACAGCGTGAAGGGCCGGTTCACCATCAGCGCCGACACCTCC<br>AAGAACACCGCCTACCTGCAGATGAACAGCCTGCGCGCCGAGGACACCGCCGTGTAC<br>TACTGCAGCCGGTGGGGCGGCGACGGATTCTACGCCATGGACTACTGGGGACAGGGC<br>ACCCTGGTGACCGTGAGCAGCGCCTCTACCAAGGGCCCCAGCGTGTTCCCTCTGGCC<br>CCCAGCAGCAAGAGCACCAGCGGCGGAACCGCCGCCCTGGGCTGCCTGGTGAAGGAC<br>TACTTCCCCGAGCCCGTGACCGTGTCCTGGAACAGCGGCGCTCTGACCAGCGGAGTG<br>CACACCTTCCCTGCCGTGCTGCAGAGCAGCGGCCTGTACTCCCTGAGCAGCGTGGTG<br>ACCGTGCCCAGCAGCAGCCTGGGCACCCAGACCTACATCTGCAACGTGAACCACAAG<br>CCCTCCAACACCAAGGTGGACAAGAAGGTGGAGCCTAAGAGCTGCGACAAGACCCAC<br>ACCTGCCCTCCCTGCCCCGCCCCCGAGCTGCTGGGCGGACCCAGCGTGTTCCTGTTC<br>CCTCCCAAGCCCAAGGACACCCTGATGATCAGCCGCACCCCCGAGGTGACCTGCGTG<br>GTGGTGGACGTGAGCCACGAGGACCCCGAGGTGAAGTTCAACTGGTACGTGGACGGC<br>GTGGAGGTGCACAACGCCAAGACCAAGCCTCGGGAGGAGCAGTACAACTCCACCTAC<br>CGCGTGGTGAGCGTGCTGACCGTGCTGCACCAGGACTGGCTGAACGGCAAGGAGTAC<br>AAGTGCAAGGTGAGCAACAAGGCCCTGCCCGCTCCCATCGAGAAGACCATCAGCAAG<br>GCCAAGGGCCAGCCCCGGGAGCCTCAGGTGTACACCCTGCCCCCCAGCCGCGACGAG<br>CTGACCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACCACCCCT | 129 |

TABLE 5-continued

Exemplary polynucleotide sequences

| Name | Sequence | SEQ ID NO: |
|---|---|---|
| | CCCGTGCTGGACAGCGACGGCAGCTTCTTCCTGTACAGCAAGCTGACCGTGGACAAG<br>TCCCGGTGGCAGCAGGGCAACGTGTTCAGCTGCAGCGTGATGCACGAGGCCCTGCAC<br>AACCACTACACCCAGAAGAGCCTGAGCCTGAGCCCCGGAAAGGGTGGCGGAGGATCT<br>GGCGGAGGCGGATCCGACTCCTCTCACGCCTTCACCCTGGACGAGCTGCGGTAG | |
| | Light Chain<br>ATGGAGACCGACACCCTGCTGCTCTGGGTGCTGCTGCTCTGGGTGCCCGGCTCCACC<br>GGAGACATCCAGATGACCCAGAGCCCTTCCAGCCTGAGCGCCAGCGTGGGCGACCGG<br>GTGACCATCACCTGCCGCGCTAGCCAGGACGTGAACACCGCCGTGGCCTGGTACCAG<br>CAGAAGCCCGGAAAGGCCCCCAAGCTGCTGATCTACTCTGCTAGCTTCCTGTACAGC<br>GGCGTGCCCAGCCGGTTCAGCGGATCTCGCAGCGGCACCGACTTCACCCTGACCATC<br>AGCAGCCTGCAGCCTGAGGACTTCGCCACCTACTACTGCCAGCAGCACTACACCACG<br>CCTCCCACCTTCGGACAGGGCACCAAGGTGGAGATCAAGCGGACCGTGGCCGCCCCC<br>AGCGTGTTCATCTTCCCTCCCAGCGACGAGCAGCTGAAGTCTGGCACCGCCAGCGTG<br>GTGTGCCTGCTGAACAACTTCTACCCCCGCGAGGCCAAGGTGCAGTGGAAGGTGGAC<br>AACGCCCTGCAGAGCGGCAACAGCCAGGAGAGCGTGACCGAGCAGGACTCCAAGGAC<br>AGCACCTACAGCCTGAGCAGCACCCTGACCCTGAGCAAGGCCGACTACGAGAAGCAC<br>AAGGTGTACGCCTGCGAGGTGACCCACCAGGGACTGTCTAGCCCCGTGACCAAGAGC<br>TTCAACCGGGGCGAGTGCTAA | 130 |
| TZM/MTf | Heavy Chain<br>ATGGAGACCGACACCCTGCTGCTCTGGGTGCTGCTGCTCTGGGTGCCCGGCTCCACC<br>GGAGAGGTGCAGCTGGTGGAGAGCGGCGGAGGCCTCGTGCAGCCCGGCGGATCTCTG<br>CGGCTGAGCTGCGCCGCTAGCGGCTTCAACATCAAGGACACCTACATCCACTGGGTG<br>CGCCAGGCCCCCGGCAAGGGCCTGGAGTGGGTGGCCCGGATCTACCCCACCAACGGC<br>TACACCCGCTACGCCGACAGCGTGAAGGGCCGGTTCACCATCAGCGCCGACACCTCC<br>AAGAACACCGCCTACCTGCAGATGAACAGCCTGCGCGCCGAGGACACCGCCGTGTAC<br>TACTGCAGCCGGTGGGGCGGCGACGGATTCTACGCCATGGACTACTGGGGACAGGGC<br>ACCCTGGTGACCGTGAGCAGCGCCTCTACCAAGGGCCCCAGCGTGTTCCCTCTGGCC<br>CCCAGCAGCAAGAGCACCAGCGGCGGAACCGCCGCCCTGGGCTGCCTGGTGAAGGAC<br>TACTTCCCCGAGCCCGTGACCGTGTCCTGGAACAGCGGCGCTCTGACCAGCGGAGTG<br>CACACCTTCCCTGCCGTGCTGCAGAGCAGCGGCCTGTACTCCCTGAGCAGCGTGGTG<br>ACCGTGCCCAGCAGCAGCCTGGGCACCCAGACCTACATCTGCAACGTGAACCACAAG<br>CCCTCCAACACCAAGGTGGACAAGAAGGTGGAGCCTAAGAGCTGCGACAAGACCCAC<br>ACCTGCCCTCCCTGCCCCGCCCCCGAGCTGCTGGGCGGACCCAGCGTGTTCCTGTTC<br>CCTCCCAAGCCCAAGGACACCCTGATGATCAGCCGCACCCCCGAGGTGACCTGCGTG<br>GTGGTGGACGTGAGCCACGAGGACCCCGAGGTGAAGTTCAACTGGTACGTGGACGGC<br>GTGGAGGTGCACAACGCCAAGACCAAGCCTCGGGAGGAGCAGTACAACTCCACCTAC<br>CGCGTGGTGAGCGTGCTGACCGTGCTGCACCAGGACTGGCTGAACGGCAAGGAGTAC<br>AAGTGCAAGGTGAGCAACAAGGCCCTGCCCGCTCCCATCGAGAAGACCATCAGCAAG<br>GCCAAGGGCCAGCCCCGGGAGCCTCAGGTGTACACCCTGCCCCCCAGCCGCGACGAG<br>CTGACCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACCACCCCT<br>CCCGTGCTGGACAGCGACGGCAGCTTCTTCCTGTACAGCAAGCTGACCGTGGACAAG<br>TCCCGGTGGCAGCAGGGCAACGTGTTCAGCTGCAGCGTGATGCACGAGGCCCTGCAC<br>AACCACTACACCCAGAAGAGCCTGAGCCTGAGCCCCGGAAAGGGAGGTGGCGGTTCT<br>GGTGGCGGAGGATCTGGCGGAGGCGGATCCGGCATGGAAGTGCGTTGGTGCGCCACC<br>TCTGACCCCGAGCAGCACAAGTGCGGCAACATGTCCGAGGCCTTCAGAGAGGCCGGC<br>ATCCAGCCTTCTCTGCTGTGTGTGCGGGGCACCTCTGCCGACCATTGCGTGCAGCTG<br>ATCGCCGCCCAGGAAGCCGACGCTATCACACTGGATGGCGGCGCTATCTACGAGGCT<br>GGCAAAGAGCACGGCCTGAAGCCCGTCGTGGGCGAGGTGTACGATCAGGAAGTGGGC<br>ACCTCCTACTACGCCGTGGCTGTCGTGCGGAGATCCTCCCACGTGACCATCGACACC<br>CTGAAGGGCGTGAAGTCCTGCCACACCGGCATCAACAGAACCGTGGGCTGGAACGTG<br>CCCGTGGGCTACCTGGTGGAATCCGGCAGACTGTCCGTGATGGGCTGCGACGTGCTG<br>AAGGCCGTGTCCGATTACTTCGGCGGCTCTTGTGTGCCTGGCGCTGGCGAGACATCC<br>TACTCCGAGTCCCTGTGCAGACTGTGCAGGGGCGACTCTTCTGGCGAGGGCGTGTGC<br>GACAAGTCCCCTCTGGAACGGTACTACGACTACTCCGGCGCCTTCAGATGCCTGGCT<br>GAAGGTGCTGGCGACGTGGCCTTCGTGAAGCACTCCACCGTGCTGGAAAACACCGAC<br>GGCAAGACCCTGCCTTCTTGGGGCCAGGCACTGCTGTCCCAGGACTTCGAGCTGCTG<br>TGCCGGGATGGCTCCAGAGCCGATGTGACAGAGTGGCGGCAGTGCCACCTGGCCAGA<br>GTGCCTGCTCATGCTGTGGTCGTGCGCGCCGATACAGATGGCGGCCTGATCTTCCGG<br>CTGCTGAACGAGGGCCAGCGGCTGTTCTCTCACGAGGGCTCCAGCTTCCAGATGTTC<br>TCCAGCGAGGCCTACGCCAGAAGGACCTGCTGTTCAAGGACTCCACCTCCGAGCTG<br>GTGCCTATCGCCACCCAGACCTATGAGGCTTGGCTGGGCACGAGTACCTGCACGCT<br>ATGAAGGGACTGCTGTGTGCGACCCCAACCGGCTGCCTCCTTATCTGAGGTGGTGCGTG<br>CTGTCCACCCCGAGATCCAGAAATGCGGCGATATGGCCGTGGCCTTTCGGCGGCAG<br>AGACTGAAGCCTGAGATCCAGTGCGTGTCCGCCAAGAGCCCTCAGCACTGCATGGAA<br>CGGATCCAGGCCGAACAGGTGGACGCCGTGACACTGTCCGGCGAGGATATCTACACC<br>GCCGGAAAGACCTACGGCCTGGTGCCAGCTGCTGGCGAGCATTACGCCCCTGAGGAC<br>TCCTCCAACAGCTACTACGTGGTGGCAGTCGTGCGCCGGGACTCCTCTCACGCCTTT<br>ACCCTGGATGAGCTGCGGGGCAAGAGAAGCTGTCACGCCGGCTTTGGAAGCCCTGCC<br>GGATGGGATGTGCCTGTGGGCGCTCTGATCCAGCGGGGCTTCATCAGACCCAAGGAC<br>TGTGATGTGCTGACCGCCGTGTCTGAGTTCTTCAACGCCTCCTGTGTGCCCGTGAAC<br>AACCCCAAGAACTACCCCTCCAGCCTGTGCGCCCTGTGTGTGGGAGATGAGCAGGGC | 131 |

TABLE 5-continued

Exemplary polynucleotide sequences

| Name | Sequence | SEQ ID NO: |
|---|---|---|
| | CGGAACAAATGCGTGGGCAACTCCCAGGAAAGATATTACGGCTACAGAGGCGCCTTC CGGTGTCTGGTGGAAAACGCCGGGGATGTGGCTTTTGTGCGGCACACCACCGTGTTC GACAACACCAATGGCCACAACTCCGAGCCTTGGGCCGCTGAGCTGAGATCCGAGGAT TACGAACTGCTGTGTCCCAACGGCGCCAGGGCTGAGGTGTCCCAGTTTGCCGCCTGT AACCTGGCCCAGATCCCTCCCCACGCTGTGATGGTGCGACCCGACACCAACATCTTC ACCGTGTACGGCCTGCTGGACAAGGCCCAGGATCTGTTCGGCGACGACCACAACAAG AACGGGTTCAAGATGTTCGACTCCAGCAACTACCACGGACAGGATCTGCTGTTTAAA GATGCCACCGTGCGGGCCGTGCCAGTGGGCGAAAAGACCACCTACAGAGGATGGCTG GGACTGGACTACGTGGCCGCCCTGGAAGGCATGTCCTCCCAGCAGTGTTCCGGCTAG | |
| | Light Chain<br>ATGGAGACCGACACCCTGCTGCTCTGGGTGCTGCTGCTCTGGGTGCCCGGCTCCACC GGAGACATCCAGATGACCCAGAGCCCTTCCAGCCTGAGCGCCAGCGTGGGCGACCGG GTGACCATCACCTGCCGCGCTAGCCAGGACGTGAACACCGCCGTGGCCTGGTACCAG CAGAAGCCCGGAAAGGCCCCCAAGCTGCTGATCTACTCTGCTAGCTTCCTGTACAGC GGCGTGCCCAGCCGGTTCAGCGGATCTCGCAGCGGCACCGACTTCACCCTGACCATC AGCAGCCTGCAGCCTGAGGACTTCGCCACCTACTACTGCCAGCAGCACTACACCACG CCTCCCACCTTCGGACAGGGCACCAAGGTGGAGATCAAGCGGACCGTGGCCGCCCCC AGCGTGTTCATCTTCCCTCCCAGCGACGAGCAGCTGAAGTCTGGCACCGCCAGCGTG GTGTGCCTGCTGAACAACTTCTACCCCCGCGAGGCCAAGGTGCAGTGGAAGGTGGAC AACGCCCTGCAGAGCGGCAACAGCCAGGAGAGCGTGACCGAGCAGGACTCCAAGGAC AGCACCTACAGCCTGAGCAGCACCCTGACCCTGAGCAAGGCCGACTACGAGAAGCAC AAGGTGTACGCCTGCGAGGTGACCCACCAGGGACTGTCTAGCCCCGTGACCAAGAGC TTCAACCGGGGCGAGTGCTAA | 132 |
| LC-MTfp/Fc-MTfp | Heavy Chain<br>ATGGAGACCGACACCCTGCTGCTCTGGGTGCTGCTGCTCTGGGTGCCCGGCTCCACC GGAGAGGTGCAGCTGGTGGAGAGCGGCGGAGGCCTCGTGCAGCCCGGCGGATCTCTG CGGCTGAGCTGCGCCGCTAGCGGCTTCAACATCAAGGACACCTACATCCACTGGGTG CGCCAGGCCCCCGGCAAGGGCCTGGAGTGGGTGGCCCGGATCTACCCCACCAACGGC TACACCCGCTACGCCGACAGCGTGAAGGGCCGGTTCACCATCAGCGCCGACACCTCC AAGAACACCGCCTACCTGCAGATGAACAGCCTGCGCGCCGAGGACACCGCCGTGTAC TACTGCAGCCGGTGGGGCGGCGACGGATTCTACGCCATGGACTACTGGGGACAGGGC ACCCTGGTGACCGTGAGCAGCGCCTCTACCAAGGGCCCCAGCGTGTTCCCTCTGGCC CCCAGCAGCAAGAGCACCAGCGGCGGAACCGCCGCCCTGGGCTGCCTGGTGAAGGAC TACTTCCCCGAGCCCGTGACCGTGTCCTGGAACAGCGGCGCTCTGACCAGCGGAGTG CACACCTTCCCTGCCGTGCTGCAGAGCAGCGGCCTGTACTCCCTGAGCAGCGTGGTG ACCGTGCCCAGCAGCAGCCTGGGCACCCAGACCTACATCTGCAACGTGAACCACAAG CCCTCCAACACCAAGGTGGACAAGAAGGTGGAGCCTAAGAGCTGCGACAAGACCCAC ACCTGCCCTCCCTGCCCCGCCCCCGAGCTGCTGGGCGGACCCAGCGTGTTCCTGTTC CCTCCCAAGCCCAAGGACACCCTGATGATCAGCCGCACCCCCGAGGTGACCTGCGTG GTGGTGGACGTGAGCCACGAGGACCCCGAGGTGAAGTTCAACTGGTACGTGGACGGC GTGGAGGTGCACAACGCCAAGACCAAGCCTCGGGAGGAGCAGTACAACTCCACCTAC CGCGTGGTGAGCGTGCTGACCGTGCTGCACCAGGACTGGCTGAACGGCAAGGAGTAC AAGTGCAAGGTGAGCAACAAGGCCCTGCCCGCTCCCATCGAGAAGACCATCAGCAAG GCCAAGGGCCAGCCCCGGGAGCCTCAGGTGTACACCCTGCCCCCCAGCCGCGACGAG CTGACCAAGAACCAGGTGAGCCTGACCTGCCTGGTGAAGGGCTTCTACCCCTCCGAC ATCGCCGTGGAGTGGGAGAGCAACGGCCAGCCTGAGAACAACTACAAGACCACCCCT CCCGTGCTGGACAGCGACGGCAGCTTCTTCCTGTACAGCAAGCTGACCGTGGACAAG TCCCGGTGGCAGCAGGGCAACGTGTTCAGCTGCAGCGTGATGCACGAGGCCCTGCAC AACCACTACACCCAGAAGAGCCTGAGCCTGAGCCCCGGAAAGGAGGCCGCTGCTAAA GAGGCTGCCGCCAAAGAAGCCGCCGCTAAGGACTCCTCTCACGCCTTCACCCTGGAC GAGCTGCGGTACTAA | 133 |
| | Light Chain<br>ATGGAGACCGACACCCTGCTGCTCTGGGTGCTGCTGCTCTGGGTGCCCGGCTCCACC GGAGACATCCAGATGACCCAGAGCCCTTCCAGCCTGAGCGCCAGCGTGGGCGACCGG GTGACCATCACCTGCCGCGCTAGCCAGGACGTGAACACCGCCGTGGCCTGGTACCAG CAGAAGCCCGGAAAGGCCCCCAAGCTGCTGATCTACTCTGCTAGCTTCCTGTACAGC GGCGTGCCCAGCCGGTTCAGCGGATCTCGCAGCGGCACCGACTTCACCCTGACCATC AGCAGCCTGCAGCCTGAGGACTTCGCCACCTACTACTGCCAGCAGCACTACACCACG CCTCCCACCTTCGGACAGGGCACCAAGGTAGAGATCAAGCGGACCGTGGCCGCCCCC AGCGTGTTCATCTTCCCTCCCAGCGACGAGCAGCTGAAGTCTGGCACCGCCAGCGTG GTGTGCCTGCTGAACAACTTCTACCCCCGCGAGGCCAAGGTGCAGTGGAAGGTGGAC AACGCCCTGCAGAGCGGCAACAGCCAGGAGAGCGTGACCGAGCAGGACTCCAAGGAC AGCACCTACAGCCTGAGCAGCACCCTGACCCTGAGCAAGGCCGACTACGAGAAGCAC AAGGTGTACGCCTGCGAGGTGACCCACCAGGGACTGTCTAGCCCCGTGACCAAGAGC TTCAACCGGGGCGAGTGCGAGGCCGCTGCTAAGAGGCTGCCGCCAAAGAAGCCGCC GCTAAGGACTCCTCTCACGCCTTCACCCTGGACGAGCTGCGGTACTAA | 134 |
| LC/Fc-MTfp | Heavy Chain<br>ATGGAGACCGACACCCTGCTGCTCTGGGTGCTGCTGCTCTGGGTGCCCGGCTCCACC GGAGAGGTGCAGCTGGTGGAGAGCGGCGGAGGCCTCGTGCAGCCCGGCGGATCTCTG CGGCTGAGCTGCGCCGCTAGCGGCTTCAACATCAAGGACACCTACATCCACTGGGTG | 135 |

TABLE 5-continued

Exemplary polynucleotide sequences

| Name | Sequence | SEQ ID NO: |
|---|---|---|
| | CGCCAGGCCCCCGGCAAGGGCCTGGAGTGGGTGGCCCGGATCTACCCCACCAACGGC<br>TACACCCGCTACGCCGACAGCGTGAAGGGCCGGTTCACCATCAGCGCCGACACCTCC<br>AAGAACACCGCCTACCTGCAGATGAACAGCCTGCGCGCCGAGGACACCGCCGTGTAC<br>TACTGCAGCCGGTGGGGCGGCGACGGATTCTACGCCATGGACTACTGGGGACAGGGC<br>ACCCTGGTGACCGTGAGCAGCGCCTCTACCAAGGGCCCCAGCGTGTTCCCTCTGGCC<br>CCCAGCAGCAAGAGCACCAGCGGCGGAACCGCCGCCCTGGGCTGCCTGGTGAAGGAC<br>TACTTCCCCGAGCCCGTGACCGTGTCCTGGAACAGCGGCGCTCTGACCAGCGGAGTG<br>CACACCTTCCCTGCCGTGCTGCAGAGCAGCGGCCTGTACTCCCTGAGCAGCGTGGTG<br>ACCGTGCCCAGCAGCAGCCTGGGCACCCAGACCTACATCTGCAACGTGAACCACAAG<br>CCCTCCAACACCAAGGTGGACAAGAAGGTGGAGCCTAAGAGCTGCGACAAGACCCAC<br>ACCTGCCCTCCCTGCCCCGCCCCCGAGCTGCTGGGCGGACCCAGCGTGTTCCTGTTC<br>CCTCCCAAGCCCAAGGACACCCTGATGATCAGCCGCACCCCCGAGGTGACCTGCGTG<br>GTGGTGGACGTGAGCCACGAGGACCCCGAGGTGAAGTTCAACTGGTACGTGGACGGC<br>GTGGAGGTGCACAACGCCAAGACCAAGCCTCGGGAGGAGCAGTACAACTCCACCTAC<br>CGCGTGGTGAGCGTGCTGACCGTGCTGCACCAGGACTGGCTGAACGGCAAGGAGTAC<br>AAGTGCAAGGTGAGCAACAAGGCCCTGCCCGCTCCCATCGAGAAGACCATCAGCAAG<br>GCCAAGGGCCAGCCCCGGGAGCCTCAGGTGTACACCCTGCCCCCCAGCCGCGACGAG<br>CTGACCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACCACCCCT<br>CCCGTGCTGGACAGCGACGGCAGCTTCTTCCTGTACAGCAAGCTGACCGTGGACAAG<br>TCCCGGTGGCAGCAGGGCAACGTGTTCAGCTGCAGCGTGATGCACGAGGCCCTGCAC<br>AACCACTACACCCAGAAGAGCCTGAGCCTGAGCCCCGGAAAGGAGGCCGCTGCTAAA<br>GAGGCTGCCGCCAAAGAAGCCGCCGCTAAGGACTCCTCTCACGCCTTCACCCTGGAC<br>GAGCTGCGGTACTAA | |
| | Light Chain<br>ATGGAGACCGACACCCTGCTGCTCTGGGTGCTGCTGCTCTGGGTGCCCGGCTCCACC<br>GGAGACATCCAGATGACCCAGAGCCCTTCCAGCCTGAGCGCCAGCGTGGGCGACCGG<br>GTGACCATCACCTGCCGCGCTAGCCAGGACGTGAACACCGCCGTGGCCTGGTACCAG<br>CAGAAGCCCGGAAAGGCCCCCAAGCTGCTGATCTACTCTGCTAGCTTCCTGTACAGC<br>GGCGTGCCCAGCCGGTTCAGCGGATCTCGCAGCGGCACCGACTTCACCCTGACCATC<br>AGCAGCCTGCAGCCTGAGGACTTCGCCACCTACTACTGCCAGCAGCACTACACCACG<br>CCTCCCACCTTCGGACAGGGCACCAAGGTGGAGATCAAGCGGACCGTGGCCGCCCCC<br>AGCGTGTTCATCTTCCCTCCCAGCGACGAGCAGCTGAAGTCTGGCACCGCCAGCGTG<br>GTGTGCCTGCTGAACAACTTCTACCCCCGCGAGGCCAAGGTGCAGTGGAAGGTGGAC<br>AACGCCCTGCAGAGCGGCAACAGCCAGGAGAGCGTGACCGAGCAGGACTCCAAGGAC<br>AGCACCTACAGCCTGAGCAGCACCCTGACCCTGAGCAAGGCCGACTACGAGAAGCAC<br>AAGGTGTACGCCTGCGAGGTGACCCACCAGGGACTGTCTAGCCCCGTGACCAAGAGC<br>TTCAACCGGGGCGAGTGCTAA | 136 |
| LC-MTfp/Fc | Heavy Chain<br>ATGGAGACCGACACCCTGCTGCTCTGGGTGCTGCTGCTCTGGGTGCCCGGCTCCACC<br>GGAGAGGTGCAGCTGGTGGAGAGCGGCGGAGGCCTCGTGCAGCCCGGCGGATCTCTG<br>CGGCTGAGCTGCGCCGCTAGCGGCTTCAACATCAAGGACACCTACATCCACTGGGTG<br>CGCCAGGCCCCCGGCAAGGGCCTGGAGTGGGTGGCCCGGATCTACCCCACCAACGGC<br>TACACCCGCTACGCCGACAGCGTGAAGGGCCGGTTCACCATCAGCGCCGACACCTCC<br>AAGAACACCGCCTACCTGCAGATGAACAGCCTGCGCGCCGAGGACACCGCCGTGTAC<br>TACTGCAGCCGGTGGGGCGGCGACGGATTCTACGCCATGGACTACTGGGGACAGGGC<br>ACCCTGGTGACCGTGAGCAGCGCCTCTACCAAGGGCCCCAGCGTGTTCCCTCTGGCC<br>CCCAGCAGCAAGAGCACCAGCGGCGGAACCGCCGCCCTGGGCTGCCTGGTGAAGGAC<br>TACTTCCCCGAGCCCGTGACCGTGTCCTGGAACAGCGGCGCTCTGACCAGCGGAGTG<br>CACACCTTCCCTGCCGTGCTGCAGAGCAGCGGCCTGTACTCCCTGAGCAGCGTGGTG<br>ACCGTGCCCAGCAGCAGCCTGGGCACCCAGACCTACATCTGCAACGTGAACCACAAG<br>CCCTCCAACACCAAGGTGGACAAGAAGGTGGAGCCTAAGAGCTGCGACAAGACCCAC<br>ACCTGCCCTCCCTGCCCCGCCCCCGAGCTGCTGGGCGGACCCAGCGTGTTCCTGTTC<br>CCTCCCAAGCCCAAGGACACCCTGATGATCAGCCGCACCCCCGAGGTGACCTGCGTG<br>GTGGTGGACGTGAGCCACGAGGACCCCGAGGTGAAGTTCAACTGGTACGTGGACGGC<br>GTGGAGGTGCACAACGCCAAGACCAAGCCTCGGGAGGAGCAGTACAACTCCACCTAC<br>CGCGTGGTGAGCGTGCTGACCGTGCTGCACCAGGACTGGCTGAACGGCAAGGAGTAC<br>AAGTGCAAGGTGAGCAACAAGGCCCTGCCCGCTCCCATCGAGAAGACCATCAGCAAG<br>GCCAAGGGCCAGCCCCGGGAGCCTCAGGTGTACACCCTGCCCCCCAGCCGCGACGAG<br>CTGACCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACCACCCCT<br>CCCGTGCTGGACAGCGACGGCAGCTTCTTCCTGTACAGCAAGCTGACCGTGGACAAG<br>TCCCGGTGGCAGCAGGGCAACGTGTTCAGCTGCAGCGTGATGCACGAGGCCCTGCAC<br>AACCACTACACCCAGAAGAGCCTGAGCCTGAGCCCCGGAAAGTAA | 137 |
| | Light Chain<br>ATGGAGACCGACACCCTGCTGCTCTGGGTGCTGCTGCTCTGGGTGCCCGGCTCCACC<br>GGAGACATCCAGATGACCCAGAGCCCTTCCAGCCTGAGCGCCAGCGTGGGCGACCGG<br>GTGACCATCACCTGCCGCGCTAGCCAGGACGTGAACACCGCCGTGGCCTGGTACCAG<br>CAGAAGCCCGGAAAGGCCCCCAAGCTGCTGATCTACTCTGCTAGCTTCCTGTACAGC<br>GGCGTGCCCAGCCGGTTCAGCGGATCTCGCAGCGGCACCGACTTCACCCTGACCATC<br>AGCAGCCTGCAGCCTGAGGACTTCGCCACCTACTACTGCCAGCAGCACTACACCACG | 138 |

TABLE 5-continued

Exemplary polynucleotide sequences

| Name | Sequence | SEQ ID NO: |
|---|---|---|
| | CCTCCCACCTTCGGACAGGGCACCAAGGTAGAGATCAAGCGGACCGTGGCCGCCCCC<br>AGCGTGTTCATCTTCCCTCCCAGCGACGAGCAGCTGAAGTCTGGCACCGCCAGCGTG<br>GTGTGCCTGCTGAACAACTTCTACCCCCGCGAGGCCAAGGTGCAGTGGAAGGTGGAC<br>AACGCCCTGCAGAGCGGCAACAGCCAGGAGAGCGTGACCGAGCAGGACTCCAAGGAC<br>AGCACCTACAGCCTGAGCAGCACCCTGACCCTGAGCAAGGCCGACTACGAGAAGCAC<br>AAGGTGTACGCCTGCGAGGTGACCCACCAGGGACTGTCTAGCCCCGTGACCAAGAGC<br>TTCAACCGGGGCGAGTGCGAGGCCGCTGCTAAAGAGGCTGCCGCCAAAGAAGCCGCC<br>GCTAAGGACTCCTCTCACGCCTTCACCCTGGACGAGCTGCGGTACTAA | |

Thus, in certain embodiments, a polynucleotide that encodes a fusion protein or antibody fusion described herein, or a portion thereof, comprises one or more polynucleotide sequences from Table 5 (e.g., SEQ ID NOS:125-138), or a fragment/variant thereof.

In some embodiments, one or more nucleic acids or vectors encoding a subject p97 polypeptide, a trastuzumab polypeptide (e.g., light chain polypeptide, heavy chain polypeptide), and/or a p97-trastuzumab fusion protein are introduced directly into a host cell, and the cell is incubated under conditions sufficient to induce expression of the encoded polypeptide(s). Therefore, according to certain related embodiments, there is provided a recombinant host cell which comprises a polynucleotide or a fusion polynucleotide that encodes one or more fusion proteins described herein, optionally in combination with other (non-fusion) components of an antibody, and which optionally comprises additional heterologous polynucleotide sequences.

Expression of a fusion protein or antibody fusion in the host cell may be achieved by culturing the recombinant host cells (containing the polynucleotide(s)) under appropriate conditions. Following production by expression, the polypeptide(s), fusion proteins, and/or antibody fusions may be isolated and/or purified using any suitable technique, and then used as desired. The term "host cell" is used to refer to a cell into which has been introduced, or which is capable of having introduced into it, a nucleic acid sequence encoding one or more of the polypeptides described herein, and which further expresses or is capable of expressing a selected gene of interest, such as a gene encoding any herein described polypeptide. The term includes the progeny of the parent cell, whether or not the progeny are identical in morphology or in genetic make-up to the original parent, so long as the selected gene is present. Host cells may be chosen for certain characteristics, for instance, the expression of aminoacyl tRNA synthetase(s) that can incorporate unnatural amino acids into the polypeptide.

Systems for cloning and expression of a protein in a variety of different host cells are well known. Suitable host cells include mammalian cells, bacteria, yeast, and baculovirus systems. Mammalian cell lines available in the art for expression of a heterologous polypeptide include Chinese hamster ovary (CHO) cells, HeLa cells, baby hamster kidney cells, HEK-293 cells, NSO mouse melanoma cells and many others. Additional examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS* USA 77:4216 (1980)); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

A common, preferred bacterial host is *E. coli*. The expression of proteins in prokaryotic cells such as *E. coli* is well established in the art. For a review, see for example Pluckthun, A. *Bio/Technology*. 9:545-551 (1991). Expression in eukaryotic cells in culture is also available to those skilled in the art as an option for recombinant production of polypeptides (see Ref, *Curr. Opinion Biotech.* 4:573-576, 1993; and Trill et al., *Curr. Opinion Biotech.* 6:553-560, 1995). In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in Ion and ompT proteases for improved target protein stability. Also included are expression host strains carrying plasmids encoding tRNAs rarely used in *E. coli*, such as Rosetta™ (DE3) and Rosetta 2 (DE3) strains. Cell lysis and sample handling may also be improved using reagents such as Benzonase® nuclease and BugBuster® Protein Extraction Reagent. For cell culture, auto-inducing media can improve the efficiency of many expression systems, including high-throughput expression systems. Media of this type (e.g., Overnight Express™ Autoinduction System) gradually elicit protein expression through metabolic shift without the addition of artificial inducing agents such as IPTG. Particular embodiments employ hexahistidine tags (such as His•Tag® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology*. 22:877-882, 2004).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing, which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the fusion protein or antibody fusion of interest.

For long-term, high-yield production of recombinant proteins, stable expression is generally preferred. For example, cell lines that stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which, successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 and CHO-based systems.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can grow on serum free medium (see, e.g., Rosser et al., *Protein Expr. Purif.* 40:237-43, 2005; and U.S. Pat. No. 6,210,922).

The protein(s) produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HyperD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

Also included are methods of concentrating recombinantly produced proteins, e.g., antibodies. Examples include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the fusion proteins or antibody fusion proteins have a purity of at least about 90%, as measured according to routine techniques in the art. In certain embodiments, such as diagnostic compositions or certain therapeutic compositions, the fusion proteins or antibody fusions have a purity of at least about 95%. In specific embodiments, such as therapeutic or pharmaceutical compositions, the fusion proteins or antibody fusions have a purity of at least about 97% or 98% or 99%. In other embodiments, such as when being used as reference or research reagents, fusion proteins or antibody fusions can be of lesser purity, and may have a purity of at least about 50%, 60%, 70%, or 80%. Purity can be measured overall or in relation to selected components, such as other proteins, e.g., purity on a protein basis.

In certain embodiments, as noted above, the compositions described here are about substantially endotoxin free, including, for example, about 95% endotoxin free, preferably about 99% endotoxin free, and more preferably about 99.99% endotoxin free. The presence of endotoxins can be detected according to routine techniques in the art, as described herein. In specific embodiments, the fusion proteins or antibody fusions are made from a eukaryotic cell such as a mammalian or human cell in substantially serum free media.

Methods of Use Pharmaceutical Compositions

Certain embodiments relate to methods of using the p97-trastuzumab fusion proteins and/or related antibody fusion proteins described herein. Examples of such methods include methods of treatment and methods of diagnosis, the latter including, for instance, the medical imaging of certain organs/tissues, such as those of the central nervous system. Specific embodiments include methods of treating and/or diagnosing disorders or conditions of the central nervous system (CNS), or disorders or conditions having a CNS component. Also included are pharmaceutical compositions comprising the p97-trastuzumab fusion proteins and/or related antibody fusion proteins described herein.

Accordingly, certain embodiments include methods of treating a subject in need thereof, comprising administering a p97-trastuzumab fusion protein or antibody fusion protein described herein. In particular embodiments, the methods comprise administering a p97-antibody fusion protein, which comprises one or more p97-trastuzumab fusion proteins described herein (e.g., as at least one component of the antibody or antibody-like molecule), and optionally other non-fusion antibody components (e.g., non-fusion light chain(s), non-fusion heavy chain(s)). Also included are methods of delivering such molecules to the nervous system (e.g., central nervous system tissues) of a subject, comprising administering to the subject a p97-trastuzumab fusion protein or antibody fusion described herein.

In some embodiments, the methods increase the rate and/or amount of delivery of the trastuzumab antibody (or antigen-binding fragment thereof) to the central nervous system tissues of the subject, relative, for example, to delivery by a composition that comprises the trastuzumab antibody (or antigen-binding fragment thereof) alone. In certain embodiments, the methods reduce the distribution of trastuzumab antibody (or antigen-binding fragment thereof) to heart tissues of the subject, relative, for example, to distribution by a composition that comprises the trastuzumab antibody (or antigen-binding fragment thereof) alone, and thereby reduces the cardiotoxicity associated with trastuzumab.

In some instances, a subject has a disease, disorder, or condition that is associated with the central nervous system (CNS) or that has a CNS component, where increased delivery of the trastuzumab antibody (or antigen-binding fragment thereof) across the blood brain barrier to CNS tissues relative to peripheral tissues can improve treatment, for instance, by increasing the tissue concentration of the antibody in the CNS, and/or by reducing side-effects associated with exposure of the antibody to peripheral tissues/organs.

Certain embodiments include the treatment of various cancers. "Cancer" relates generally to a class of diseases or conditions in which a group of cells display one or more of uncontrolled growth (i.e., division beyond normal limits), invasion (i.e., intrusion on and destruction of adjacent tissues), and/or metastasis (i.e., spread to other locations in the body via lymph or blood). These malignant properties of cancers differentiate them from benign cancers, which are self-limited, and typically do not invade or metastasize. Included are cancers of the central nervous system (CNS), or neurological cancers, such as brain cancers.

In some instances, the neurological cancer is a metastatic brain cancer. Examples of cancers that can metastasize to the brain include, without limitation, breast cancers, lung cancers, genitourinary tract cancers, gastrointestinal tract cancers (e.g., colorectal cancers, pancreatic carcinomas), osteosarcomas, melanomas, head and neck cancers, prostate cancers (e.g., prostatic adenocarcinomas), and lymphomas. Certain embodiments thus include methods for treating, inhibiting or preventing metastasis of a cancer by administering to a patient a therapeutically effective amount of a fusion protein described herein (e.g., in an amount that, following administration, inhibits, prevents or delays metastasis of a cancer in a statistically significant manner, i.e., relative to an appropriate control as will be known to those skilled in the art). In particular embodiments, the subject has a cancer that is at risk for but has not yet metastasized to the central nervous system, including one or more of the above-described cancers, among others known in the art.

In some aspects, the subject has a cancer associated with expression of Her2/neu. In particular aspects, subject has a Her2/neu-expressing or Her2/neu-overexpressing cancer. Hence, certain embodiments include methods for the treatment of a HER2-overexpressing cancer in a subject in need thereof, comprising administering to the subject a (e.g., therapeutically-effective amount of a) p97-antibody fusion protein (described herein) or a pharmaceutical composition comprising the same. In some embodiments, the HER2-overexpressing cancer is at risk for metastasizing to the CNS of the subject. In particular embodiments, the HER2-overexpressing cancer has metastasized to the CNS of the subject. In some aspects, the antibody fusion is administered in an amount that inhibits, prevents, or delays the progression and/or metastasis of the cancer in a statistically significant manner (i.e., relative to an appropriate control as will be known to those skilled in the art). Included are amounts that inhibit, prevent, or delay the progression and/or metastasis into tissues of the CNS, and those that inhibit, prevent, or delay progression and/or metastasis within tissues of the CNS.

In certain aspects, the HER2-overexpressing cancer is a breast cancer, ovarian cancer, gastric cancer, or uterine cancer. In particular aspects, the HER2-overexpressing cancer is a metastatic breast cancer, metastatic ovarian cancer, metastatic gastric cancer, or metastatic or aggressive form of uterine cancer.

In some aspects, the HER2-overexpressing cancer is a HER2-overexpressing breast cancer, such as a HER2-overexpressing metastatic breast cancer. In certain instances, the HER2-overexpressing metastatic breast cancer is at risk for metastasizing to the CNS of the subject. In certain instances, the HER2-overexpressing metastatic breast cancer has already metastasized to the CNS of the subject. In some instances, the p97-antibody fusion is administered with paclitaxel for first-line treatment of HER2-overexpressing metastatic breast cancer. In particular instances, the p97-antibody fusion is administered as a single agent for treatment of HER2-overexpressing metastatic breast cancer in patients who have received one or more chemotherapy regimens for metastatic disease.

Certain embodiments include administering the p97-antibody fusion or pharmaceutical composition as part of an adjuvant treatment for HER2-overexpresssing breast cancer. In some aspects, the adjuvant treatment comprises doxorubicin, cyclophosphamide, and either paclitaxel or docetaxel. In some aspects, the adjuvant treatment comprises docetaxel and carboplatin. Certain aspects include administering the p97-antibody fusion or pharmaceutical composition as a single agent following multi-modality anthracycline based therapy.

In some aspects, the HER2-overexpressing cancer is a HER2-overexpressing metastatic gastric or gastroesophageal junction adenocarcinoma. In some instances, the HER2-overexpressing metastatic gastric or gastroesophageal junction adenocarcinoma is at risk for metastasizing to the CNS of the subject. In certain instances, the HER2-overexpressing metastatic gastric or gastroesophageal junction adenocarcinoma has already metastasized to the CNS of the subject. In some instances, the p97-antibody fusion is administered in combination with cisplatin and capecitabine or 5-fluorouracil, optionally where the subject or patient has not received prior treatment for metastatic disease.

In certain aspects, the HER2-overexpressing uterine cancer is a HER2-overexpressing uterine serous carcinoma (USC) (see, e.g., Santin et al., *Int J Gynaecol Obstet.* 102:128-31, 2008). USC, also known as uterine papillary serous carcinoma (UPSC) and uterine serous adenocarcinoma, is a form of endometrial cancer that typically arises in postmenopausal women. In some instances, the HER2-overexpressing USC is at risk for metastasizing to the CNS of the subject. In certain instances, the HER2-overexpressing USC has already metastasized to the CNS of the subject.

Methods for identifying subjects with one or more of the diseases or conditions described herein are known in the art.

Also included are methods for imaging an organ or tissue component in a subject, comprising (a) administering to the subject a composition comprising a fusion protein or antibody fusion described herein, which is conjugated to a detectable entity, and (b) visualizing the detectable entity in the subject, organ, or tissue.

In particular embodiments, the organ or tissue compartment comprises the central nervous system (e.g., brain, brainstem, spinal cord). In specific embodiments, the organ or tissue compartment comprises the brain or a portion thereof, for instance, the parenchyma of the brain.

A variety of methods can be employed to visualize the detectable entity in the subject, organ, or tissue. Exemplary non-invasive methods include radiography, such as fluoroscopy and projectional radiographs, CT-scanning or CAT-scanning (computed tomography (CT) or computed axial tomography (CAT)), whether employing X-ray CT-scanning, positron emission tomography (PET), or single photon emission computed tomography (SPECT), and certain types of magnetic resonance imaging (MRI), especially those that utilize contrast agents, including combinations thereof.

Merely by way of example, PET can be performed with positron-emitting contrast agents or radioisotopes such as $^{18}$F, SPECT can be performed with gamma-emitting contrast agents or radioisotopes such as $^{201}$Tl, $^{99m}$TC, $^{123}$I, and $^{67}$Ga, and MRI can be performed with contrast agents or radioisotopes such as $^{3}$H, $^{13}$C, $^{19}$F, $^{17}$O, $^{23}$Na, $^{31}$P, and $^{129}$Xe, and Gd (gadolidinium; chelated organic Gd (III) complexes). Any one or more of these exemplary contrast agents or radioisotopes can be conjugated to or otherwise incorporated into a p97 polypeptide and administered to a subject for imaging purposes. For instance, p97 polypeptides can be directly labeled with one or more of these radioisotopes, or conjugated to molecules (e.g., small molecules) that comprise one or more of these radioisotopic contrast agents, or any others described herein.

For in vivo use, for instance, for the treatment of human disease, medical imaging, or testing, the fusion proteins or antibody fusions described herein are generally incorporated into a pharmaceutical composition prior to administration. A pharmaceutical composition comprises one or more of the fusion proteins or antibody fusions described herein in combination with a physiologically-acceptable, pharmaceutically-acceptable, or pharmaceutical grade carrier or excipient.

To prepare a pharmaceutical composition, an effective or desired amount of one or more fusion protein or antibody fusions is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of fusion proteins or antibody fusions described herein, in pure form or in an appropriate pharmaceutical composition, can be carried out via any of the accepted modes of administration of agents for serving similar utilities. The pharmaceutical compositions can be prepared by combining a fusion protein or antibody fusion-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, intradermal, subcutaneous or topical. Preferred modes of administration depend upon the nature of the condition to be treated or prevented. Particular embodiments include administration by IV infusion.

Carriers can include, for example, pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In certain aspects, a fusion protein or antibody fusion is bound to or encapsulated within a particle, e.g., a nanoparticle, bead, lipid formulation, lipid particle, or liposome, e.g., immunoliposome. The fusion proteins or antibody fusions may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents, such as cytotoxic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described conjugate in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will typically contain a therapeutically effective amount of a fusion protein or antibody fusion described herein, for treatment of a disease or condition of interest.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a fusion protein or antibody fusion such that a suitable dosage will be obtained. Typically, this amount is at least 0.01% of the agent of interest in the composition. When intended for oral administration, this amount may be varied to be between 0.1 and about 70% of the weight of the composition. Certain oral pharmaceutical compositions contain between about 4% and about 75% of the agent of interest. In certain embodiments, pharmaceutical compositions and preparations according to the present invention are prepared so that a parenteral dosage unit contains between 0.01 to 10% by weight of the agent of interest prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the conjugate or agent and thereby assists in the delivery of the compound. Suitable agents that may act in this capacity include monoclonal or polyclonal antibodies, one or more proteins or a liposome.

The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the fusion proteins or antibody fusions against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the conjugate so as to facilitate dissolution or homogeneous suspension of the conjugate in the aqueous delivery system.

The compositions may be administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., ~0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g).

Compositions described herein may also be administered simultaneously with, prior to, or after administration of one or more other therapeutic agents, as described herein. For instance, in one embodiment, the conjugate is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

In certain embodiments, the compositions disclosed herein may be administered in conjunction with any number of chemotherapeutic or cytotoxic agents. Examples of chemotherapeutic or cytotoxic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.RTM.; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Such combination therapy may include administration of a single pharmaceutical dosage formulation, which contains a compound of the invention (i.e., fusion protein, antibody fusion protein) and one or more additional active agents, as well as administration of compositions comprising conjugates of the invention and each active agent in its own separate pharmaceutical dosage formulation. For example, a fusion protein or antibody fusion as described herein and the other active agent can be administered to the patient together in a single oral dosage composition such as a tablet or capsule, or each agent administered in separate oral dosage formulations. Similarly, a fusion protein or antibody fusion as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising fusion proteins or antibody fusions and one or more additional active agents can be administered at essentially the same time, i.e., concurrently, or at separately staggered times, i.e., sequentially and in any order; combination therapy is understood to include all these regimens.

The various embodiments described herein can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

Binding of p97-Trastuzumab Fusion Proteins to Human Her2/Neu

Human p97 (MTf)-trastuzumab fusion constructs were prepared and tested for activity. The amino acid sequences of the MTf-trastuzumab fusion constructs are shown in Table E1 below.

TABLE E1

| Name | Heavy and Light Chain Sequences | SEQ ID NO |
|---|---|---|
| TZM HC-MTf Homodimer (C-terminal TZM heavy chain MTf; See FIG. 1A for general structure) | Heavy Chain<br>Signal sequence (italics): TZM heavy chain: linker (underlined): MTf (bold)<br>*METDTLLLWVLLLWVPGS*TGEVQLVESGGGLVQPGGSLRLSCAASGFNIKDT<br>YIHWVRQAPGKGLEWVARIYPTNGYTRYADSVKGRFTISADTSKNTAYLQMN<br>SLRAEDTAVYYCSRWGGDGFYAMDYWGQGTLVTVSSASTKGPSVFPLAPSSK<br>STSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSLSLSP<br>GK<u>GGGGSGGGGS</u>GMEVRWCATSDPEQHKCGNMSEAFREAGIQPSLLCVRGTS<br>ADHCVQLIAAQEADAITLDGGAIYEAGKEHGLKPVVGEVYDQEVGTSYYAVA<br>VVRRSSHVTIDTLKGVKSCHTGINRTVGWNVPVGYLVESGRLSVMGCDVLKA<br>VSDYFGGSCVPGAGETSYSESLCRLCRGDSSGEGVCDKSPLERYYDYSGAFR<br>CLAEGAGDVAFVKHSTVLENTDGKTLPSWGQALLSQDFELLCRDGSRADVTE<br>WRQCHLARVPAHAVVVRADTDGGLIFRLLNEGQRLFSHEGSSFQMFSSEAYG<br>QKDLLFKDSTSELVPIATQTYEAWLGHEYLHAMKGLLCDPNRLPPYLRWCVL<br>STPEIQKCGDMAVAFRRQRLKPEIQCVSAKSPQHCMERIQAEQVDAVTLSGE<br>DIYTAGKTYGLVPAAGEHYAPEDSSNSYYVVAVVRRDSSHAFTLDELRGKRS<br>CHAGFGSPAGWDVPVGALIQRGFIRPKDCDVLTAVSEFFNASCVPVNNPKNY<br>PSSLCALCVGDEQGRNKCVGNSQERYYGYRGAFRCLVENAGDVAFVRHTTVF<br>DNTNGHNSEPWAAELRSEDYELLCPNGARAEVSQFAACNLAQIPPHAVMVRP<br>DTNIFTVYGLLDKAQDLFGDDHNKNGFKMFDSSNYHGQDLLFKDATVRAVPV<br>GEKTTYRGWLGLDYVAALEGMSSQQCS | 82 |
| | Light Chain<br>Signal sequence (italics) : TZM light chain<br>*METDTLLLWVLLLWVPGS*TGDIQMTQSPSSLSASVGDRVTITCRASQDVNTA<br>VAWYQQKPGKAPKLLIYSASFLYSGVPSRFSGSRSGTDFTLTISSLQPEDFA<br>TYYCQQHYTTPPTFGQGTKVEIKRTVAAPSVFIFPPSDEQLKSGTASVVCLL<br>NNFYPREAKVQWKVDNALQSGNSQESVTEQDSKDSTYSLSSTLTLSKADYEK<br>HKVYACEVTHQGLSSPVTKSFNRGEC | 83 |
| MTfp NH-TZM (N-terminal MTfp TZM heavy chain; see FIG. 1D for general structure) | Heavy Chain<br>Signal sequence (italics): MTfp sequence (bold): linker (underlined): TZM heavy chain<br>*METDTLLLWVLLLWVPGS*TGDSSHAFTLDELRY<u>GGGGSGGGGS</u>EVQLVESGG<br>GLVQPGGSLRLSCAASGFNIKDTYIHWVRQAPGKGLEWVARIYPTNGYTRYA<br>DSVKGRFTISADTSKNTAYLQMNSLRAEDTAVYYCSRWGGDGFYAMDYWGQG<br>TLVTVSSASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNV<br>FSCSVMHEALHNHYTQKSLSLSPGK | 84 |

TABLE E1-continued

| Name | Heavy and Light Chain Sequences | SEQ ID NO |
|---|---|---|
| | Light Chain<br>Signal sequence (italics): TZM light chain<br>*METDTLLLWVLLLWVPGSTG*DIQMTQSPSSLSASVGDRVTITCRASQDVNTA<br>VAWYQQKPGKAPKLLIYSASFLYSGVPSRFSGSRSGTDFTLTISSLQPEDFA<br>TYYCQQHYTTPPTFGQGTKVEIKRTVAAPSVFIFPPSDEQLKSGTASVVCLL<br>NNFYPREAKVQWKVDNALQSGNSQESVTEQDSKDSTYSLSSTLTLSKADYEK<br>HKVYACEVTHQGLSSPVTKSFNRGEC | 85 |
| TZM HC-MTfp (C-terminal TZM heavy chain MTfp; see FIG. 1E for general structure) | Heavy Chain<br>Signal sequence (italics): TZM heavy chain: linker (underlined): MTfp sequence without C-terminal Y (bold)<br>*METDTLLLWVLLLWVPGSTG*EVQLVESGGGLVQPGGSLRLSCAASGFNIKDT<br>YIHWVRQAPGKGLEWVARIYPTNGYTRYADSVKGRFTISADTSKNTAYLQMN<br>SLRAEDTAVYYCSRWGGDGFYAMDYWGQGTLVTVSSASTKGPSVFPLAPSSK<br>STSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSLSLSP<br>GK<u>GGGGSGGGGS</u>DSSHAFTLDELR | 86 |
| | Light Chain<br>Signal sequence (italics): TZM light chain<br>*METDTLLLWVLLLWVPGSTG*DIQMTQSPSSLSASVGDRVTITCRASQDVNTA<br>VAWYQQKPGKAPKLLIYSASFLYSGVPSRFSGSRSGTDFTLTISSLQPEDFA<br>TYYCQQHYTTPPTFGQGTKVEIKRTVAAPSVFIFPPSDEQLKSGTASVVCLL<br>NNFYPREAKVQWKVDNALQSGNSQESVTEQDSKDSTYSLSSTLTLSKADYEK<br>HKVYACEVTHQGLSSPVTKSFNRGEC | 87 |
| TZM/MTf Homodimer (C-terminal TZM heavy chain MTf; see FIG. 1A for general structure) | Heavy Chain<br>Signal sequence (italics): TZM heavy chain: linker (underlined): MTf (bold)<br>*METDTLLLWVLLLWVPGSTG*EVQLVESGGGLVQPGGSLRLSCAASGFNIKDT<br>YIHWVRQAPGKGLEWVARIYPTNGYTRYADSVKGRFTISADTSKNTAYLQMN<br>SLRAEDTAVYYCSRWGGDGFYAMDYWGQGTLVTVSSASTKGPSVFPLAPSSK<br>STSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSLSLSP<br>GK<u>GGGGSGGGGSGGGGS</u>GMEVRWCATSDPEQHKCGNMSEAFREAGIQPSLLC<br>VRGTSADHCVQLIAAQEADAITLDGGAIYEAGKEHGLKPVVGEVYDQEVGTS<br>YYAVAVVRRSSHVTIDTLKGVKSCHTGINRTVGWNVPVGYLVESGRLSVMGC<br>DVLKAVSDYFGGSCVPGAGETSYSESLCRLCRGDSSGEGVCDKSPLERYYDY<br>SGAFRCLAEGAGDVAFVKHSTVLENTDGKTLPSWGQALLSQDFELLCRDGSR<br>ADVTEWRQCHLARVPAHAVVRADTDGGLIFRLLNEGQRLFSHEGSSFQMFS<br>SEAYGQKDLLFKDSTSELVPIATQTYEAWLGHEYLHAMKGLLCDPNRLPPYL<br>RWCVLSTPEIQKCGDMAVAFRRQRLKPEIQCVSAKSPQHCMERIQAEQVDAV<br>TLSGEDIYTAGKTYGLVPAAGEHYAPEDSSNSYYVVAVVRRDSSHAFTLDEL<br>RGKRSCHAGFGSPAGWDVPVGALIQRGFIRPKDCDVLTAVSEFFNASCVPVN<br>NPKNYPSSLCALCVGDEQGRNKCVGNSQERYYGYRGAFRCLVENAGDVAFVR<br>HTTVFDNTNGHNSEPWAAELRSEDYELLCPNGARAEVSQFAACNLAQIPPHA<br>VMVRPDTNIFTVYGLLDKAQDLFGDDHNKNGFKMFDSSNYHGQDLLFKDATV<br>RAVPVGEKTTYRGWLGLDYVAALEGMSSQQCSG | 88 |
| | Light Chain<br>Signal sequence: TZM light chain<br>*METDTLLLWVLLLWVPGSTG*DIQMTQSPSSLSASVGDRVTITCRASQDVNTA<br>VAWYQQKPGKAPKLLIYSASFLYSGVPSRFSGSRSGTDFTLTISSLQPEDFA<br>TYYCQQHYTTPPTFGQGTKVEIKRTVAAPSVFIFPPSDEQLKSGTASVVCLL<br>NNFYPREAKVQWKVDNALQSGNSQESVTEQDSKDSTYSLSSTLTLSKADYEK<br>HKVYACEVTHQGLSSPVTKSFNRGEC | 89 |
| LC-MTfp/Fc-MTfp (C-terminal TZM light chain MTfp/C-terminal TZM heavy chain MTfp; see FIG. | Heavy Chain<br>Signal sequence (italics): TZM heavy chain: linker (underlined): Mtfp (bold)<br>*METDTLLLWVLLLWVPGSTG*EVQLVESGGGLVQPGGSLRLSCAASGFNIKDT<br>YIHWVRQAPGKGLEWVARIYPTNGYTRYADSVKGRFTISADTSKNTAYLQMN<br>SLRAEDTAVYYCSRWGGDGFYAMDYWGQGTLVTVSSASTKGPSVFPLAPSSK<br>STSGGTAALGCLVKDYFPEPVTVSWNSGALTSGVHTFPAVLQSSGLYSLSSV<br>VTVPSSSLGTQTYICNVNHKPSNTKVDKKVEPPKSCDKTHTCPPCPAPELLG<br>GPSVFLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTISKAK | 90 |

TABLE E1-continued

| Name | Heavy and Light Chain Sequences | SEQ ID NO |
|---|---|---|
| 1F for general structure) | GQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLS<br>PGK<u>EAAAKEAAAKEAAAK</u>DSSHAFTLDELRY | |
| | Light Chain<br>Signal sequence (italics): TZM light chain: linker (underlined): Mtfp (bold)<br>*METDTLLLWVLLLWVPGSTG*DIQMTQSPSSLSASVGDRVTITCRASQDVNTA<br>VAWYQQKPGKAPKLLIYSASFLYSGVPSRFSGSRSGTDFTLTISSLQPEDFA<br>TYYCQQHYTTPPTFGQGTKVEIKRTVAAPSVFIFPPSDEQLKSGTASVVCLL<br>NNFYPREAKVQWKVDNALQSGNSQESVTEQDSKDSTYSLSSTLTLSKADYEK<br>HKVYACEVTHQGLSSPVTKSFNRGEC<u>EAAAKEAAAKKAAAK</u>DSSHAFTLDEL<br>RY | 91 |
| LC/Fc-MTfp (TZM light chain/C-terminal TZM heavy chain MTfp; see FIG. 1E for general structure) | Heavy Chain<br>Signal sequence (italics): TZM heavy chain: linker (underlined): Mtfp (bold)<br>*METDTLLLWVLLLWVPGSTG*EVQLVESGGGLVQPGGSLRLSCAASGFNIKDT<br>YIHWVRQAPGKGLEWVARIYPTNGYTRYADSVKGRFTISADTSKNTAYLQMN<br>SLRAEDTAVYYCSRWGGDGFYAMDYWGQGTLVTVSSASTKGPSVFPLAPSSK<br>STSGGTAALGCLVKDYFPEPVTVSWNSGALTSGVHTFPAVLQSSGLYSLSSV<br>VTVPSSSLGTQTYICNVNHKPSNTKVDKKVEPPKSCDKTHTCPPCPAPELLG<br>GPSVFLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLS<br>PGK<u>EAAAKEAAAKEAAAK</u>DSSHAFTLDELRY | 92 |
| | Light Chain<br>Signal sequence (italics): TZM heavy chain<br>*METDTLLLWVLLLWVPGSTG*DIQMTQSPSSLSASVGDRVTITCRASQDVNTA<br>VAWYQQKPGKAPKLLIYSASFLYSGVPSRFSGSRSGTDFTLTISSLQPEDFA<br>TYYCQQHYTTPPTFGQGTKVEIKRTVAAPSVFIFPPSDEQLKSGTASVVCLL<br>NNFYPREAKVQWKVDNALQSGNSQESVTEQDSKDSTYSLSSTLTLSKADYEK<br>HKVYACEVTHQGLSSPVTKSFNRGEC | 93 |
| LC-MTfp/Fc (C-terminal TZM light chain MTfp/ TZM heavy chain; see FIG. 1G for general structure) | Heavy Chain<br>Signal sequence (italics): TZM heavy chain: linker: MTfp<br>*METDTLLLWVLLLWVPGSTG*EVQLVESGGGLVQPGGSLRLSCAASGFNIKDT<br>YIHWVRQAPGKGLEWVARIYPTNGYTRYADSVKGRFTISADTSKNTAYLQMN<br>SLRAEDTAVYYCSRWGGDGFYAMDYWGQGTLVTVSSASTKGPSVFPLAPSSK<br>STSGGTAALGCLVKDYFPEPVTVSWNSGALTSGVHTFPAVLQSSGLYSLSSV<br>VTVPSSSLGTQTYICNVNHKPSNTKVDKKVEPPKSCDKTHTCPPCPAPELLG<br>GPSVFLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLS<br>PGK | 94 |
| | Light Chain<br>Signal sequence (italics): TZM light chain<br>*METDTLLLWVLLLWVPGSTG*DIQMTQSPSSLSASVGDRVTITCRASQDVNTA<br>VAWYQQKPGKAPKLLIYSASFLYSGVPSRFSGSRSGTDFTLTISSLQPEDFA<br>TYYCQQHYTTPPTFGQGTKVEIKRTVAAPSVFIFPPSDEQLKSGTASVVCLL<br>NNFYPREAKVQWKVDNALQSGNSQESVTEQDSKDSTYSLSSTLTLSKADYEK<br>HKVYACEVTHQGLSSPVTKSFNRGEC<u>EAAAKEAAAKKAAAK</u>DSSHAFTLDEL<br>RY | 95 |

TZM - Trastuzumab
MTf - p97
MTfp - p97 fragment
HC - Heavy Chain
LC - Light Chain In vitro binding assays were performed to measure the binding of MTf-trastuzumab fusion constructs to His-tagged human Her2/Neu protein (Her2-His). Her2-His was loaded onto penta-His biosensor at a concentration of 20 µg/mL and dipped into TZM HC-MTf, MTfp NH-TZM, and TZM HC-MTfp fusion proteins (see Table E1) and a human IgG1 control at varying concentrations.

The results of octet analysis in FIGS. 2A-2D and Table E2 (below) demonstrate the affinity of the MTf-trastuzumab fusions for Her2.

TABLE E2

| Loading Sample ID | Sample ID | $K_D$ (M) | $K_{on}$ (1/Ms) | $K_{off}$ (1/s) | Full $R^2$ | Full $X^2$ |
|---|---|---|---|---|---|---|
| Her2-His | TZM HC-MTf | <1.0E−12 | 4.94E+04 | <1.0E−07 | 0.999074 | 0.002797 |
| Her2-His | MTfp NH-TZM | <1.0E−12 | 9.06E+04 | <1.0E−07 | 0.997464 | 0.014593 |
| Her2-His | TZM HC-MTfp | <1.0E−12 | 1.21E+05 | <1.0E−07 | 0.997177 | 0.019048 |
| Her2-His | Human IgG1 | <1.0E−12 | 1.04E+06 | <1.0E−07 | 0.997389 | 0.010269 |

MTf-trastuzumab fusion proteins demonstrated tight binding to human Her2, as shown by the equilibrium dissociation constant ($K_D$), association rate constant ($K_{on}$), and dissociation rate constant ($K_{off}$).

Example 2

ADCC Cell-Killing Activity of p97-Trastuzumab Fusion Proteins

MTf-trastuzumab fusion constructs were tested for Antibody-dependent cell-mediated cytotoxicity (ADCC) in BT-474 breast cancer cells compared to Herceptin® (trastuzumab) and human IgG1 Fc as positive and negative controls, respectively.

BT-474 cells were purchased from ATCC and grown in Hybri-Care Medium supplemented with 1.5 g/L sodium bicarbonate and 10% fetal bovine serum. Human peripheral blood mononuclear cells (PBMCs) were freshly isolated by Histopaque centrifugation and incubated with carboxyfluorescein succinimidyl ester (CFSE)-labeled target BT-474 cells at a ratio of about 30:1.

Test samples were co-incubated with the effector: target cell mixture for four hours at ten different concentrations (up to 100 µg/mL). Negative controls included effector:target cells only as no antibody control, and 100 µg/mL IgG Fc. Each treatment was performed in duplicate. After the 4 hour co-incubation, cells were stained with propidium iodide (PI) and analyzed by flow cytometry (FACS). The percentage of PI/CFSE+ cells was quantitated as an indication of cytotoxicity. A dose-response curve was generated by plotting the mean±range of the data points for all ten different concentrations, and the $EC_{50}$ was calculated. The results are shown in FIGS. 3A-3B.

Figure 3A:
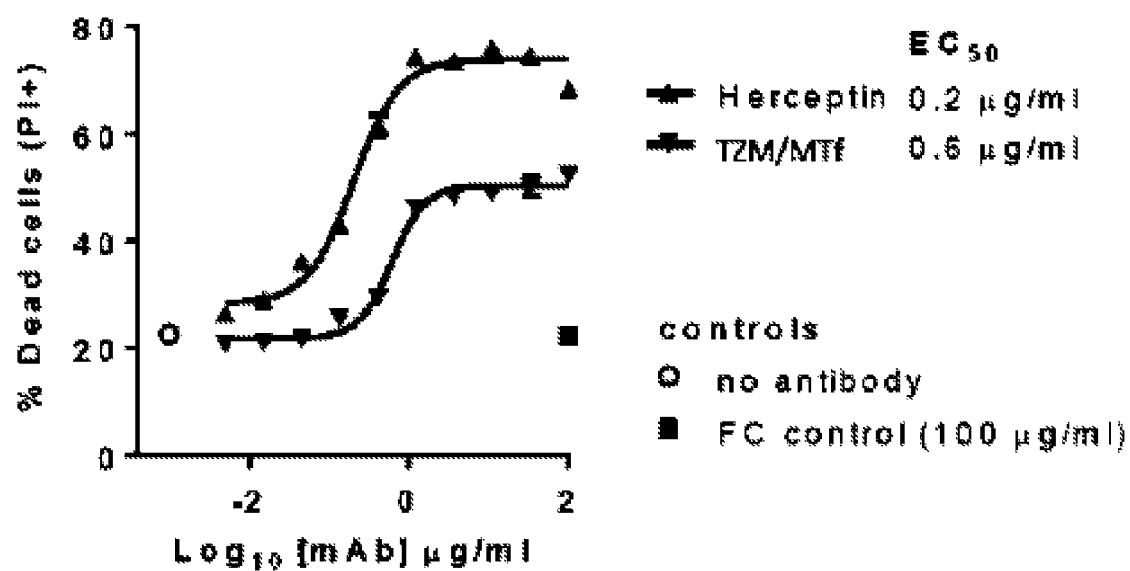
FIGS. 3A-3B show antibody-dependent cell-mediated cytotoxicity (ADCC) evaluation of antibody fusions in BT-474 breast cancer cells compared to Herceptin® and human IgG1 Fc controls (see Example 2). These data show that the p97-trastuzumab antibody fusions induced significant antibody-dependent cell-mediated cytotoxicity in breast cancer cells.

FIG. 3A shows the ADCC evaluation of TZM/MTf fusion in BT-474 breast cancer cells compared to Herceptin® and human IgG1 Fc. Here, the TZM/MTf homodimer fusion induced ADCC with an $EC_{50}$ of 0.6 µg/mL compared to that of Herceptin® at 0.2 µg/mL.

Figure 3B:
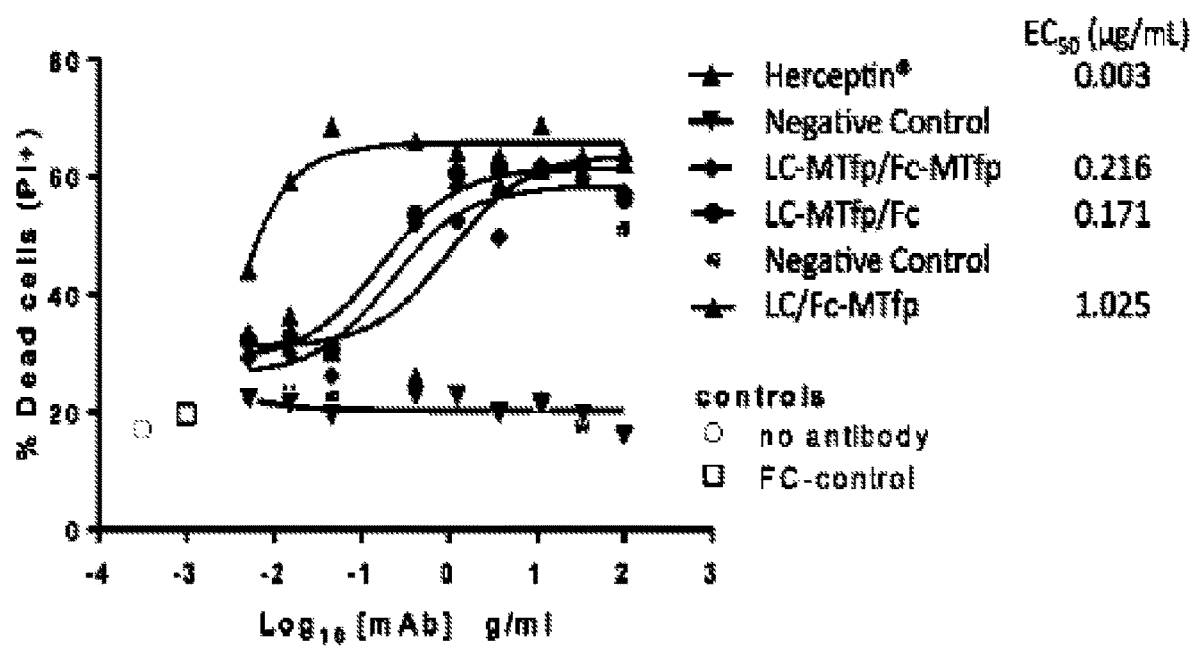

FIG. 3B shows the ADCC evaluation of LC-MTfp/Fc-MTfp, LC-MTfp/Fc, and LC/Fc-MTfp fusions in BT-474 breast cancer cells compared to Herceptin® and human IgG1 Fc. LC-MTfp/Fc-MTfp, LC-MTfp/Fc, and LC/Fc-MTfp induced ADCC with an $EC_{50}$ of 0.216 µg/mL, 0.171 µg/mL, and 1.025 µg/mL, respectively. These data show that MTf-trastuzumab fusion constructs induce significant antibody-dependent cell-mediated cytotoxicity in breast cancer cells.

Example 3

In Vivo Anti-Tumor Efficacy of p97-Trastuzumab Fusion Proteins

The p97-trastuzumab fusion proteins are tested for anti-tumor efficacy and effects on survival in mice that are intracranially injected with human BT-474 breast tumor cells. Specifically, the fusion constructs TZM HC-MTf and MTfp NH-TZM are tested relative to Herceptin® (Trastuzumab, AMM: 5621037, ROCHE).

Test Compounds.

The stock solutions of TZM HC-MTf and MTfp NH-TZM constructs are diluted in PBS and administered respectively at 60 mg/kg and 30 mg/kg (equivalent dose of 30 mg/kg Herceptin®). Herceptin® is prepared as follows: one vial containing 150 mg of Herceptin® is diluted in NaCl 0.9% (Aguettant, Lyon, France) to a final concentration of 20 mg/mL. The stock solution is stored at 4° C. for the duration of the study. Each day of administration to mice, the stock solution is diluted in NaCl 0.9% to reach 3 mg/mL final concentration. Herceptin® is administered at 30 mg/kg.

All compounds are administered by intravenous injection (IV, bolus) into the caudal vein of mice at a dose volume of 10 mL/kg/inj (i.e., for one mouse weighing 20 g, 200 µL of test substance is administered).

Cancer Cell Line.

The BT-474 cell line is purchased from ATCC. It was originally isolated from a solid, invasive ductal carcinoma of the breast from a 60 year old Caucasian female patient (Lasfargues et al., J Natl Cancer Inst. 61:967-78, 1978). Tumor cells are grown as monolayer at 37° C. in a humidified atmosphere (5% CO2, 95% air). The culture medium contains DMEM supplemented with 2 mM L glutamine (ref: BE12-604F, Lonza, Verviers, Belgium) and 10% fetal bovine serum (ref: 3302, Lonza). The cells are adherent to plastic flasks. For experimental use, tumor cells are detached from the culture flask by a 5 minute treatment with trypsin-versene (ref: BE02-007E, Lonza), in Hanks' medium without calcium or magnesium (ref: BE10-543F, Lonza) and neutralized by addition of complete culture medium. The cells are counted in a hemocytometer and their viability is assessed by 0.25% trypan blue exclusion assay.

Animals.

Sixty-one healthy female Balb/C nu/nu (CByJ.Cg-Foxn1nu/J) mice, 5-6 weeks old, are obtained from CHARLES RIVER (L'Arbresles). Animals are maintained in housing rooms under controlled environmental conditions: Temperature: 22±2° C., Humidity 55±10%, Photoperiod (12 h light/12 h dark), HEPA filtered air, 15 air exchanges per hour with no recirculation.

Animal enclosures provide sterile and adequate space with bedding material, food and water, environmental and social enrichment (group housing) as described: Top filter polycarbonate Eurostandard Type III or IV cages, Corn cob bedding (ref: LAB COB 12, SERLAB, France), 25 kGy Irradiated diet (Ssniff® Soest, Germany), Complete food for immunodeficient rodents—NM Extrudate, Complete food for immunocompetent rodents—R/M-H Extrudate, Sterile, filtrated at 0.2 µm water (supplemented with 2.5 µg/mL estradiol), Environmental enrichment (SIZZLE-dri kraft—D20004 SERLAB, France).

Induction of BT-474 Tumors.

For stereotaxic injection of tumor cells, mice are anesthetized by an intraperitoneal injection of Ketamine 70 mg/kg (Ketamine500®, Ref 043KET204, Centravet, France) and Xylazine 5 mg/kg (Rompun®, Ref 002ROM001, Centravet, France) in 0.9% NaCl solution at 10 mL/kg/inj. Tumors are induced by stereotaxic injection of $1 \times 10^5$ of BT-474 cells in 2 µL of RPMI 1640 of 52 female animals. BT-474 tumor cell implantation is performed 24 to 72 hours after a whole body irradiation with a γ-source (2 Gy, $^{60}$Co, BioMep, Bretenières, France).

The tumor cell suspension is injected into the caudate nucleus of the right cerebral hemisphere at a rate of 0.5 µL/min. Five minutes after the end of the injection, the needle is slowly withdrawn by 1 mm every minute. Carprofen (dose: 5 mg/kg) is injected subcutaneously at the end of the surgery and 24 h post-surgery. The day of tumor cell implantation is considered as day zero ($D_0$).

Treatment Schedule.

The treatment is started on day five ($D_5$). Forty animals (40) out of fifty-two (52) are randomized according to their individual body weight into 4 groups each of 10 animals using Vivo Manager® software (Biosystemes, Couternon, France). A statistical test (analysis of variance) is performed to test for homogeneity between groups. The treatment schedule is as follows:

Group 1 mice receive two weekly IV administration of vehicle for 6 consecutive weeks.

Group 2 mice receive two weekly IV administrations of TZM HC-MTf at equivalent dose of 30 mg/kg Herceptin® for 6 consecutive weeks.

Group 3 mice receive two weekly IV administrations of MTfp NH-TZM at equivalent dose of 30 mg/kg Herceptin® for 6 consecutive weeks.

Group 4 mice receive two weekly IV administrations of Herceptin® at 30 mg/kg for 6 consecutive weeks.

The treatment schedule is summarized in Table E3 below:

TABLE E3

| Group | No. animals | Treatment | Dose (mg/kg/adm) | Adm. Route | Treatment schedule |
|---|---|---|---|---|---|
| 1 | 10 | Vehicle (PBS) | — | IV | TWx6 |
| 2 | 10 | TZM HC-MTf | 60 | IV | TWx6 |
| 3 | 10 | MTfp NH-TZM | 30 | IV | TWx6 |
| 4 | 10 | Herceptin ® | 30 | IV | TWx6 |

Monitoring.

All study data, including animal body weight measurements, clinical and mortality records, and treatment are scheduled and recorded on Vivo Manager® database (Biosystemes, Dijon, France). The viability and behavior is recorded every day. Body weights are measured twice a week.

The following Human endpoints are measured (Workman et al., Br J Cancer. 102:1555-77, 2010).

Signs of pain, suffering or distress: pain posture, pain face mask, behavior
20% body weight loss remaining for 3 consecutive days
Poor body condition, emaciation, cachexia, dehydration
Prolonged absence of voluntary responses to external stimuli
Rapid labored breathing, anemia, significant bleeding
Neurologic signs: circling, convulsion, paralysis
Sustained decrease in body temperature
Abdominal distension Necropsy (macroscopic examination) is performed on all terminated animal in the study, and, if possible, on all euthanized moribund or found dead animal.

The following evaluation criteria of health are determined using Vivo Manager® software (Biosystemes, Couternon, France).

Individual and mean body weights of animals

Mean body weight change (MBWC): Average weight change of treated animals in percent (weight at day B minus weight at day A divided by weight at day A) is calculated. The intervals over which MBWC is calculated are chosen as a function of body weight curves and the days of body weight measurement Magnetic Resonance Imaging (MRI).

Imaging experiments are performed on a 4.7T horizontal magnet (PharmaScan, Bruker Biospin GmbH, Germany) equipped with an actively shielded gradient system. For image analysis, mice are positioned prone in a dedicated mouse body cradle which is slid in a volume coil (38 mm internal diameter) within the Pharmascan and images are acquired under ParaVision (PV5.1, Bruker Biospin).

During all the image acquisitions, mice are continuously anaesthetized using isoflurane (Minerve, Bondoufle, France) in a mixture of air via a nose piece. Body temperature of the animals is maintained within physiological levels by a flow of warm air. Breathing rate is continuously monitored using a pressure sensor taped on its abdomen. Physiological signals are monitored via a laptop placed next to the MRI workstation and connected to the sensors by fiber optic cables (SA Instruments, USA).

The contrast agent Gadopentetate dimeglumine (Gd-DTPA, Magnevist, Bayer Healthcare Pharmaceuticals, Germany) is injected intravenously (IV) at 0.4 mmol/kg via the caudal vein of mice.

Images are transferred to a workstation to be analyzed under ImageJ (4). Regions of interest (ROIs) are drawn manually on anatomical images. Tumor volume is computed from the ROIs by multiplying the number of ROI voxels by the voxel volume (in $mm^3$). Tumor volumes in $mm^3$ are tabulated at each time point and for each animal.

Sample Collection.

All mice are euthanized fourteen days after the last treatment. Intracardiac blood collection is used in terminal procedures under deep gas anesthesia. Approximately 200 µL of blood from ten animals per group is collected into blood collection tubes with clot activator. Tubes are centrifuged 30 minutes after sampling at 1300 g for 10 minutes at room temperature to obtain serum. The serum samples are stored in propylene tubes at 80° C. until analysis. Immediately after termination, samples from the brain, heart, lung, liver and kidney of each animal are collected, weighed and stored for analysis.

Efficacy Parameters.

The treatment efficacy is assessed in terms of the effects of the test substance on the tumor volumes of treated animals relative to control animals, as measured by MRI (see below). The efficacy parameters are expressed as a percent treated over control survival (T/C %). T is the median of the survival times of animals treated with test substances and C is the median survival times of control animals treated with vehicle. Survival systems indicate a degree of success when T/C percent exceed 125% (7). T/C % is expressed as follows:

$$T/C \% = \frac{T \text{ (median survival time of treated animals)}}{C \text{ (median survival time of vehicle} - \text{treated animals)}} \times 100$$

Survival curves are drawn, and mean and median survival times are calculated.

Statistical Tests.

Statistical analyses are performed using Vivo Manager® software (Biosystemes, Couternon, France). Statistical analyses of mean body weights, MBWC, mean tumor volumes V, are performed using ANOVA and pairwise tests are performed using the Bonferroni/Dunn correction in case of significant ANOVA results. The log-Rank (Kaplan-Meier) test is used to compare the survival curves. A p value<0.05 is considered as significant.

The invention claimed is:

1. A fusion protein, comprising: a binding domain of an antibody binding to human Her2/neu receptor, wherein the binding domain comprises a trastuzumab heavy chain sequence comprising the amino acid sequence of SEQ ID NO:29 and a trastuzumab light chain sequence having the amino acid sequence of SEQ ID NO:36; and a peptide fragment of a mammalian p97 protein, wherein the peptide fragment comprises the amino acid sequence of DSSHAFTLDELR (SEQ ID NO: 14); and wherein the trastuzumab heavy chain sequence is fused to the N-terminus or the C-terminus of the peptide fragment via an optional linker in between; and wherein the peptide fragment has no more than 20 amino acids, wherein the fusion protein has the ability to cross the blood-brain barrier.

2. The fusion protein of claim 1, wherein the linker is a Gly, Ser and/or Asn-containing linker.

3. A pharmaceutical composition comprising the fusion protein of claim 1 and a pharmaceutically acceptable carrier.

* * * * *